US007868155B2

(12) United States Patent
Lu et al.

(10) Patent No.: US 7,868,155 B2
(45) Date of Patent: Jan. 11, 2011

(54) PROMOTER, PROMOTER CONTROL ELEMENTS, AND COMBINATIONS, AND USES THEREOF

(75) Inventors: Yu-Ping Lu, Camarillo, CA (US); Roger Pennell, Malibu, CA (US); Jack Okamuro, Oak Park, CA (US); Richard Schneeberger, Carlsbad, CA (US); Yiwen Fang, Los Angeles, CA (US); Shing Kwok, Woodland Hills, CA (US)

(73) Assignee: Ceres, Inc., Thousand Oaks, CA (US)

( * ) Notice: Subject to any disclaimer, the term of this patent is extended or adjusted under 35 U.S.C. 154(b) by 574 days.

(21) Appl. No.: 11/603,542

(22) Filed: Nov. 22, 2006

(65) Prior Publication Data

US 2008/0044898 A1 Feb. 21, 2008

(51) Int. Cl.
*C12N 15/82* (2006.01)
*C12N 15/63* (2006.01)
*C12N 15/11* (2006.01)
*A01H 5/00* (2006.01)

(52) U.S. Cl. .................... 536/24.1; 536/23.1; 800/278; 800/287; 435/320.1

(58) Field of Classification Search ....................... None
See application file for complete search history.

(56) References Cited

U.S. PATENT DOCUMENTS

| | | | |
|---|---|---|---|
| 5,362,865 A | 11/1994 | Austin | |
| 5,424,412 A | 6/1995 | Brown | |
| 5,659,122 A | 8/1997 | Austin | |
| 5,754,888 A | 5/1998 | Yang et al. | |
| 5,764,903 A | 6/1998 | Yu | |
| 5,857,208 A | 1/1999 | Ofek | |
| 5,974,563 A | 10/1999 | Beeler, Jr. | |
| 6,092,066 A | 7/2000 | Ofek | |
| 6,448,476 B1 | 9/2002 | Barry | |
| 2003/0226166 A1 | 12/2003 | Falco | |
| 2004/0163144 A1* | 8/2004 | Kriz et al. | 800/279 |
| 2005/0048556 A1 | 3/2005 | Heck | |
| 2005/0086718 A1 | 4/2005 | Heard | |
| 2006/0008816 A1 | 1/2006 | Lu | |
| 2006/0041952 A1 | 2/2006 | Cook | |
| 2006/0137034 A1 | 6/2006 | Schneeberger | |
| 2006/0150283 A1 | 7/2006 | Alexandrov | |
| 2006/0150285 A1 | 7/2006 | Nadzan | |
| 2006/0168696 A1 | 7/2006 | Feldmann | |
| 2006/0195934 A1 | 8/2006 | Apuya | |
| 2006/0195943 A1 | 8/2006 | Feldmann | |
| 2006/0236421 A1 | 10/2006 | Pennell | |
| 2007/0006335 A1 | 1/2007 | Cook | |
| 2007/0006345 A1 | 1/2007 | Alexandrov | |
| 2007/0199090 A1 | 8/2007 | Apuya | |

FOREIGN PATENT DOCUMENTS

EP 1033405 9/2000
WO WO 01/98480 12/2001

OTHER PUBLICATIONS

Kim et al., "A 20 Nucleotide Upstream Element is Essential for the Nopaline Synthase (*nos*) Promoter Activity," Plant Molecular Biology, vol. 24, pp. 105-117, 1994.
Donald et al., "Mutation of Either G Box or I Box Sequences Profoundly Affects Expression From the *Arabidopsis* rbcS-1A Promoter," EMBO Journal, vol. 9, No. 6, pp. 1717-1726, 1990.
Dolferus et al., "Differential Interactions of Promoter Elemtns in Stress Responses of the *Arabidopsis* Adh Gene," Plant Physiology, vol. 105, pp. 1075-1087, 1994.
Database Genbank [Online] Feb. 14, 2004, "*Arabidopsis thaliana* genomic DNA, chromosome 5, P1 clone: MNC17." retrieved from NCBI accession No. AB016890 BA000015.
Database EMBL Nov. 24, 2004 WiscDsLox 262D09 *Arabidopsis thaliana* T-DNA insertion flanking sequences XP002372669.
Database EMBL Mar. 21, 2002 *Arabadopsis thaliana* cDNA clone: RAFL09-89-K19,5-end. XP002372670.
Database EMBL Apr. 23, 2002, *Arabidopsis thaliana* putative photoassimilate-responsive protein PAR (At5g52390) mRNA, complete cds. XP002372671.
Database Geneseq Oct. 18, 2000 *Arabadopsis thaliana* protein fragment SEQ ID No. 62052, XP002372672.
Shahmuradov I A et al., PlantProm: a database of plant promoter sequences, Nucleic Acids Research, Oxford University Press, Surrey GB vol. 31, No. 1, 2003, pp. 114-117 XP002993034.
Database EMBL Nov. 16, 1998 *Arabidopsis thaliana* genomic DNA, chromosome 5, TAC clone: K24M7 XP002372668 retrieved from EBI accession No. EM_PRO: AB019226 Database accession No. AB019226.
Benfey, et al, Science, (1990), vol. 250, pp. 959-966.
Sato, et al, NCBI GenBank Sequence Accession No. AB022216, pp. 1-31 (Dec. 27, 2000).
Tyagi, et al, Current Science, (2001), vol. 80., pp. 161-169.
Maniatis, et al, Molecular Cloning: A Laboratory Manual, Cold Spring Harbor Laboratory (1982).
GenBank Accession No. NM 112618 (Apr. 20, 2007).
Goto, et al., Genes Genet. Syst., (2002), vol. 77, pp. 89-95.
Shen, et al., Plant J., (2002), vol. 29(3), pp. 371-380.
Doerks, et al., TIG, (1998), vol. 14, pp. 248-250.
Smith, et al., Nature Biotechnology, (1997), vol. 15, pp. 1222-1223.
Bork, et al., TIG, (1996), vol. 12, pp. 425-427.
Guo, et al., PNAS, (2004), vol. 101, pp. 9205-9210.
Keskin, et al., Protein Science, (2004), vol. 13, pp. 1043-1055.
Thornton, et al., Nature structural Biology, structural genomics supplement, (Nov. 2000).
Wells, Biochemistry, (1990), vol. 29, pp. 8509-8517.
Miyoshi, et al., Plant J, (2003), vol. 36, pp. 532-540.
Ngo, et al., The Protein Folding Problem and Tertiary Structure Prediction, K. Merz and S. LeGrand (eds.), (1994), pp. 492-495.
Office Action dated Jul. 28, 2008 in U.S. Appl. No. 11/058,689.
Office Action dated May 7, 2009 in U.S. Appl. No. 11/097,589.
Office Action dated May 13, 2009 in U.S. Appl. No. 11/058,689.

* cited by examiner

*Primary Examiner*—Michele K Joike
(74) *Attorney, Agent, or Firm*—Birch, Stewart, Kolasch and Birch, LLP

(57) ABSTRACT

The present invention is directed to promoter sequences and promoter control elements, polynucleotide constructs comprising the promoters and control elements, and methods of identifying the promoters, control elements, or fragments thereof. The invention further relates to the use of the present promoters or promoter control elements to modulate transcript levels.

10 Claims, 2 Drawing Sheets

SEQUENCE LISTING

<160> NUMBER OF SEQ ID NOS: 68

<210> SEQ ID NO 1
<211> LENGTH: 1952
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 1

```
ctgcattcac acatattttg ggctctcacg tgtttgtgaa tttaatatat ttgactacac      60
gatctttcaa cgtatgaaaa agttttatac tactattttc gtttgagtgg gaaataaaca     120
aatgatagct acagttatct atatggtata attttacact tttataacta ataatgatga     180
gtgatgacaa tcgagtgtcg gatataacag gccaacaagt ggaatggact tatgtaactt     240
tttaatcacg ggattaaatc acgtaaccca atgtcctaat tggtatttaa ttttgattat     300
ctcgatgcta catattgtca taggactcat atctttgatc acgtgccgct accaatccag     360
acattttagt atacaaaaaa aaagaagata caaacttaag atatggaata tatatcagaa     420
ctatcagttt tagactttaa taattcgaat tgaataacta cgatcaatat ataaattggc     480
```

```
aaatagattg gtcaattgta gtgcaagaaa tttgtgaact ttattacagt acgaagagag    540
taagagaagc aagatccggt ttttaggcaa caagtaacat ttttgagttc agagagtttg    600
cttcttactt taagttacgt cactacaaaa gccaagttcc tacttcttag gtctaaagtc    660
aattttcgaa tattcagaaa aattgtactc tactagatcg aatagttttc accggtgaaa    720
cgatatataa atgaagacta caatatttt taatttttt aagcgtatga gttctagacc    780
tttggcacgt aaatttctcc ggtacctggg accaatcgtt gataatatca cgtttaagat    840
ttaatcatcc atcccaagta gagttgaact agtaaccttg agcactttt ctcgagacaa    900 ctaaaccatc atccacttag tgcaataaag cgtcattctt ttttttcttt tcaaaaattc    960
gtatttaatt ttaatttatt aaaaatattt cttttgtttt aaattgggac agaattatca   1020
tttaacatat ttaaaattta tattttaat taaaaatagg gtaaaatata ttttcaaac   1080 aaaaattcaa aaatagggca attttcaaaa tcatccattc ttaaatctaa agtcggctac   1140
agtcttttcg ttgttttgtt gctaatttca atttatatac atgcaaatta caaaatataa   1200 tagttttgg gggataatta tcttcttgcg cctttttatt aaattaatat gctcatatag   1260
cagttcttac aattaatata actagggttt taaatttcaa tatcgagttg acaaaatgaa   1320
ttgtttacaa gttttttct tttcaatatg cattgttcat cacgtattcg tagtgatgca   1380
aaaacaaact ataattata attgcactag tgagattagc aagaagtgtt ataaattaga   1440
ataaacggaa ctatcaaact gtgttatgta caccatttat ttttgttaaa gaatatgtgt   1500
agtagttaga aaactgatca aattaaactg aaaattcaca ttacggagat caagttacat   1560
tgtctattga tgaaaaaaac aaaataaatc caaatggcac taaaagttgt agaaattgaa   1620
agaagaaaat agatttttgt ctaggaataa aagtcaaaat gggaaagaca aaaaaaagag   1680
aggcaaataa gcagtgatgg agctaaagca acgctttact cttttaatta tgaattattt   1740
gatttgacct ccactcgcct ggcttttttt ggttgttctt tatagaaaag taaaataaca   1800
caattagcac ataacatgag ttatcgagaa accaattctc tttgtggtgt tttagttaat   1860
ttctataact tatgaaacca ttttctcagt ttatcatgat aattgatcct ctatttaaaa   1920
ccctaaagtt tatattttgt ttgttcaaac ac                                 1952
```

<210> SEQ ID NO 2
<211> LENGTH: 1033
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 2

```
agcagaacaa ctatatttat tgtgtcacat aaatctgaga tcatttataa ccaccaaaga     60
acctatacac agtaaatgac aaatgtatct ccctctatct ctattgccca tatgtagatg    120
ctaaagtaag atttctcttt tttttaatgt actttttttt gtataaagta tattccataa    180
gaaaaaggaa aagcttgttt atggatcaat tgaccccaaa aaaagttttt agatcaaagc    240
ccaatataaa aaaaaaacac agtagtgaca caaaggaact taaataaacc atgaattgat    300
ctataaacag tagagatcga taaggcgaac attttccatg tgaagtgtct tctttcatct    360
ataatatttt tgacatccaa taatttcctc tataatatca ttcacataat tgatagaaac    420
attatgttag aattgtccac atcatttgag ctgtaatata ttctgtttta acaaattata    480
tggtagttgc ttaatcttat gtccatcttc ttctatgcat cgttttcgcg cctagttgtc    540
```

-continued

| | |
|---|---|
| cagtccattt caactaccta cctctaattc ttatcttaaa acaacatttt ttaatttaag | 600 |
| tattatgctc aaagactaac tagatagaaa accgttatta acattaaac gaattaaaag | 660 |
| tcttacatgg aaaatgtagg tttataaacc acgagttatg attgacaata aaaaaaatgc | 720 |
| aaatcatcaa tcaaaagaga cttgagtgcg actctatatc aaccattgca attaaaatta | 780 |
| tctatcacaa aaattttaga cagattaagt taatttagtc taaattcact aatttatttt | 840 |
| ctataattag taattaacta tatttattta tttacacatt ttctgataat ttagaaattt | 900 |
| gcatgaataa caaatataag attttggaaa ttagtagcaa atttaattaa taattatttt | 960 |
| tgcctaaatg aaccaaacta taaaacctcc acatacacca gtcatcaaat ttacagagac | 1020 |
| aacaaactaa agt | 1033 |

<210> SEQ ID NO 3
<211> LENGTH: 999
<212> TYPE: DNA
<213> ORGANISM: Unknown
<220> FEATURE:
<223> OTHER INFORMATION: Promoter and/or promoter control element
identified from Arabidopsis thaliana or Oryza sativa.

<400> SEQUENCE: 3

| | |
|---|---|
| atcttgtgat acacaattta ttactatttg gtacattttg aagtatttgt ttttgcatga | 60 |
| tatatgacgt taatttgaac tgatattagt caatttatgg gtacaaaagt tgaaagttta | 120 |
| gagcactatg ttggatttat taaaaatgat atcatacaat ggttcaatat atatatattt | 180 |
| ttttccacgt ttttaataac attttttgtaa acaagtcttc tactattgtc tttattgtta | 240 |
| atgagtttct agtacctaat taggaatttt gaggatatac gatacattaa tgagttacat | 300 |
| tatcccgaaa acaaaatctt gaaaacgaac aaagataatt tggacattac tcgttatgta | 360 |
| tacgtatgga attggataga gccgttgaac catcaagtgg gtcttcaagt caacgaactg | 420 |
| aatttgatt tacactcatg tacatcggcc acaattttat tcacacacta ctaacacctc | 480 |
| tggtgtccac ttttttcttt ctctagattg atgtgttaag attttgttg caattcattt | 540 |
| attcaggtat tttatatat atatatatat aaattagaat aaaactaattt aaagaaagat | 600 |
| atagcaatta tgtttcacat tttaacattc tcaatcattt ataaaactaa tgtggtgatg | 660 |
| aatggtatat atatatatat atatatatat atatatatat attttgttgt gaactaatgg | 720 |
| taaatattta aaataagaca tacgtacata aatccacgga ctcttaaagt catgatgcgg | 780 |
| ttaataaatg ttcacataac ggtaaccaag tggctcaaaa tcatgaaaca acgtcacata | 840 |
| atttatctta taatgtggat aattagtacc gcattatttg taagaaaatt aaattaatta | 900 |
| tagattcaca gctaagaaaa tacgaaaaga cagctcaaca cttttccact tctattcccc | 960 |
| actgtctata aactctgata ataatctct gatctctcc | 999 |

<210> SEQ ID NO 4
<211> LENGTH: 1000
<212> TYPE: DNA
<213> ORGANISM: Unknown
<220> FEATURE:
<223> OTHER INFORMATION: Promoter and/or promoter control element
identified from Arabidopsis thaliana or Oryza sativa.

<400> SEQUENCE: 4

| | |
|---|---|
| ttcatcttta tatttaagag tttaaaaact gcaactttg tttttctttc actaagtctt | 60 |
| atggccacag ttaattaaaa gcagatgaaa ggtggtccaa tggaaaagga gaatgtgatt | 120 |

-continued

```
gggctagttg ggagagttct gatgtctagt gttgggtaca cgtgtccgtc agttacacat      180
agcattaaat cagacggcat gtcattattc aaatctagtt cacatagtac gactaatagc      240
tgataaatta atgattatac agcatatgaa ttatgaattc aaaaaaaaaa aaaaattgaa      300
aatgttaagg agatgctata ttttacaaaa ttcatcgcaa tgctttctac taatttgcta      360
agtggtcttc tccagttagt cttgtcgatt ccaagcgata ttattaaatc ttgaagcatc      420
gctcaaagca ttatagctta agataaccaa attgttatta aaacaccta gtgaaatttt       480 taaattaaaa caattttgat atctttgtaa tatctaatac tactctttct gtgtctaaaa      540
ggattaattt tcaaaaattt cacacatatt aaaaaaaaaa aaaattact agctaaacaa       600 ttttcaataa tcataaaaca atagtaactt ataattttt ttttatttc aaaatagtcc        660 ttcaagttta caattcattt tagtattata atcaacaaaa tttgtattaa aaagttggaa      720
aattaatctt tgtggaacaa aaaaatctag aaatcattt ttagaattag agagaggttt       780
gataaaaaaa aataaaaaaa aatagagaga ggtagtacat actaaacgat gtgatactac      840
tattgacaaa atcttaattc tcagtttagt agaataaact agaaggaatg aatgaagtaa      900
atgcgaatcc aactactaac aaaccctact tagtcatcat attttcccat atgaaatccc      960
tatataaacc catcatcatc tcccactttt ttcatatcca                            1000
```

<210> SEQ ID NO 5
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 5

```
tatatagttt ttatgcattc tcctcttgtg taatacataa accaaatatg agataggtta       60
atctgtattt cagataatat taaattccaa acaatatttt tacttgttat aagaaggcaa      120
ttaatatctc tctgttaatg gcaagtggta ccaagtagta ttaaactatt aatgcaatgg      180
aagagtactg ttggaaatta taatcctcta tcacacattc aaacagatct cctgaaatct      240
tctcttccaa acttgtactt ctctgatcca aatgtaggct ccaaaatata gacatttacc      300
atttactaag tccacaactc cttttcttgtc tccttcaaaa atgactcttg tgtaaccatc      360
atatgactcc gacagttcgg cattgccatg atgagagctt aaaaattcac cttcctgagc      420
atttcaagtc ttcactccct tagcttgacc tgaaccaaga taaatgcct tgtcgtccc       480 gtaatatcca tcctgctttg gacggcatca tagttacatt cgatccatcc tatttacaat      540
gttattttag tattaaaaac atgacaataa atttgttgtt aaacatattc aaatacaata      600
tgattggatt tataagtaat tgtaatatga aatgtcctta gtaatatgtt aaaaaataca      660
tagatacaca cacgtactaa aagaggcaac gcgggagatg tcattagagg aagaactagg      720
aagcagagcg ttcatgcaaa atgctaccaa aaacgttaat gcaatatctc aactaatcag      780
cacagtccat ttcatactga gaatgtaaaa accaatcagc atcgtccatt ttttcatcta      840
attatttgtt aactcttaat tggccacaac ttccaaccac atgacgctct ttctattccc      900
tttatatatt cccatctcaa atgttcttgg agacacaaaa tatcataaac atataaacat      960
aaacgccaat cgcagctttt gtactttggg cggtttaca                             999
```

<210> SEQ ID NO 6
<211> LENGTH: 999
<212> TYPE: DNA

<213> ORGANISM: Unknown
<220> FEATURE:
<223> OTHER INFORMATION: Promoter and/or promoter control element
    identified from Arabidopsis thaliana or Oryza sativa.

<400> SEQUENCE: 6

```
tttattttat ttttgaatg aaaatgtctt ctttattcgt aattttaaac tcactggtgg      60
tggatatatt gttatgtccc caattcgtct ggcaactctc gtatattagt gagaaaaatt    120
tgtccattat ttactgcact attaccctgt gttaattttt tgtattgaaa ttgttttta    180
gtaattcacg tcatatagcg aatgattctt taattttaaa aattcagtct taagtttaca    240
aattaaataa cgctactgta accaactctg tacgaccaac atgttcgagt ttttgtatat    300
acggccatat atgtacatat tttactataa agcgaaaaaa tccataaatt atttaattaa    360
tatataaagg tgccattcta tttccaatgt gcttaggaaa atgcagaacc tcgtgctata    420
tctctgtcgc cacgtgcaaa tataacaata tgaaatagaa ctagcaaatc ttgaaatcta    480
actcttaaga ctaattcaag cacatacgta gagaaagttg accaacggtt atcagcattt    540
taacatggac cttatcaaca ttttaacaaa gtccacaaac aaccagtctt acaatcgcat    600
tggtacaaga taatcgaatt catcttccat ataacaaaac ctaaaccttg gtgtgaaaag    660
gagaagatat gtatgttaaa ggccgcctat gcctctggtt tggggtatat gattctaaga    720
ttagggtttg aatattttcg ttagcctgcc atgagatata tttatgtgat aattagagcc    780
tcttatgcat taatgcataa ccgactagat catgtggtat tcagctaatc agtacacaca    840
agacaaagta gtaaatgagt ttgatgaaga ctgtggtctg ataattccta tcaacgttaa    900
atctgtcggg gccaggcagc cagcaacatt ttgcctaaca acgctctgaa ttcaattgaa    960
cctaggctat ataatagcag gctaacttaa ctaagagtt                           999
```

<210> SEQ ID NO 7
<211> LENGTH: 1000
<212> TYPE: DNA
<213> ORGANISM: Unknown
<220> FEATURE:
<223> OTHER INFORMATION: Promoter and/or promoter control element
    identified from Arabidopsis thaliana or Oryza sativa.

<400> SEQUENCE: 7

```
tggattacaa atcattaagc taatatcttc gatgaattaa gaagataagt ggataacaag    60
tacctaaccg caatagtcca taaattaaaa cattaatgta tttgtcgttg aaaatttggc   120
cgacttttat ttgttattct agtttccaca tcaaaaatgt ttgtacttcg tagcaatcca   180
tccacctaaa ccccaaatct taattttat ttgttgcgtt taaatttggg tgagatttga    240
ttctaagtag ttgagataaa ttgatattct attcattagt aaaatgatag agaaattggt   300
ttataataat tttaccctag aacatgacat gatattggta accattaatc aaagaaagag   360
caaagcattt aatttaccct actctccaac cactccagcc tttattagtt gcagttggga   420
atcatttctt tatgattctt atgtcattgt ctcctaaatc aatgaagtgc cttgaccttg   480
ttactaattc gaacatagca aagccaacta catagatcct ttacaaagtt ctaaaaacag   540
gttgtttagg cgtctagaca aacaaaacca ttttgtacga ttcaacaaat tggtccatag   600
aatgttattg atctttcttg tttaggcatt cgataaatcg gctaatacat tatttttttg   660
ttttgctttt tccttattaa aaatatgcaa agtattatga tgtttaacct gaactgaatt   720
ttacattaa ctggatatag gaaaatattg ggttgaattt aataattaag caattgtcac   780
gtaaatcaaa ttgggcttaa tatatattgt tgatttcagc aaagacaaag ttgggccgtt   840
```

```
tcaatagtct tcacgcgatg taagcgttca ctaaccaact agagaagaca atcaaatgaa    900
tacgttccac gtgacgctta cgaacttgtc agtcactttg gtaatatgac agacagtaac    960
cagtaaacta ctaatctctt tcgctaacga acacacaaaa                         1000

<210> SEQ ID NO 8
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 8
aaacatgttt tatgtaacta ctttgcttat gtgattgcct gaggatacta ttattctctg     60
tctttattct cttcacacca catttaaata gtttaagagc atagaaatta attatttca    120 aaaaggtgat tatatgcatg caaaatagca caccatttat gtttatattt tcaaattatt    180
taatacattt caatatttca taagtgtgat tttttttttt tttgtcaatt tcataagtgt    240
gatttgtcat ttgtattaaa caattgtatc gcgcagtaca aataaacagt gggagaggtg    300
aaaatgcagt tataaaactg tccataatt tactaacaca tttaaatatc taaaaagagt    360
gtttcaaaaa aaattcttt gaaataagaa aagtgataga tattttacg ctttcgtctg    420 aaaataaaac aataatagtt tattagaaaa atgttatcac cgaaaattat tctagtgcca    480
ctcgctcgga tcgaaattcg aaagttatat tctttctctt tacctaatat aaaaatcaca    540
agaaaaatca atccgaatat atctatcaac atagtatatg cccttacata ttgtttctga    600
cttttctcta tccgaatttc tcgcttcatg gtttttttt aacatattct catttaattt    660
tcattactat tatataacta aaagatggaa ataaaataaa gtgtctttga gaatcgaacg    720
tccatatcag taagatagtt tgtgtgaagg taaaatctaa aagatttaag ttccaaaaac    780
agaaaataat atattacgct aaaaagaag aaaataatta aatacaaaac agaaaaaaat    840
aatatacgac agacacgtgt cacgaagata ccctacgcta tagacacagc tctgttttct    900
cttttctatg cctcaaggct ctcttaactt cactgtctcc tcttcggata atcctatcct    960
tctcttccta taaataccctc tccactcttc ctcttcctcc                        1000

<210> SEQ ID NO 9
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 9
taaagatcag aagaggaagg tttcgccgcg gcggttgcat cttcaccgtc gatttcatcg     60
ttacagcgac gccggtaatt cctaggttgc ttagttccca ttctctctct aaaattaggg    120
ctcgaaatga attgttgaac aagatagaga tcttttctg atccccgtcg aacatttatt    180
caaggccaaa aaaagcacac gggaatttag agtaccaata catatcaaaa cctaatgggc    240
tttgaatggt tgcatgtgtg tgtttatttc tgatatgcaa agcgatcgat agtctttcc    300 atacaagtgt aaactgtaaa caacgtaatt aagcataaca atacaactct ttcttctctt    360 ttttttgta aacacaaaat aaaattacat caattcatgc ttttcctagt tcatctgaca    420
ttttccaaaa ttcatgttcc attgagtccc taatacttgt tcatattcat attagggtac    480
```

| | |
|---|---|
| atgaataaaa gttatcattc ttgaaactac taaattttca tagtttattt ttcttctttt | 540 |
| cgtttcactt tcgaacaaaa cactacgcgt ggcatttgca atgaattcca cattatatgg | 600 |
| aataacacca tgatgaacat tctacatata taattattat gtttaagcac ttagacagca | 660 |
| taaattcttt ctaattatat aaatctaacc ttgttacatt gtacatctat aaattacttg | 720 |
| aagaaataac gagttctatt tcttttttaaa aattaaaaat actataccat atctcagtga | 780 |
| ttaagttgaa ccaaaaggta cggaggagaa acaagcattt gattcttcct tattttattt | 840 |
| tattcatctc tcactaatga tggtggagaa aaaagaaaa tacctaacaa acaaatatat | 900 |
| attgtcatac aaaaatattt ctatattttt agttaattag tttatattcc tcacttttca | 960 |
| gggcttatat aagaaagtga gcaaacacaa atcaaaatgc | 1000 |

<210> SEQ ID NO 10
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 10

| | |
|---|---|
| aaacttccaa atttctaaac ggatgcaata agaacttaca tattctcttt cattagtcat | 60 |
| ttattggcca gatttattaa aaaaagttttt actcaatgac caaggattag agttaaagat | 120 |
| aatatagatt attacatata ttattcgaaa aaatatacgc atgtccgact tttaaacct | 180 |
| caaaaatatc aaaaccagaa aagatgatac cacacaaaaa aacaataaaa taataagtgg | 240 |
| aagagatatc atcggacaac agtacaagta cagcaccagc tctgccaaaa gccaaaacca | 300 |
| tttgtcaatt acagaaagat actattgttt gcaattacta aattacccct cggactttac | 360 |
| aaaagcatct ctaacttatc cacgtgtcag tcatctattg attgtttcaa taccaccttg | 420 |
| tattaacgcc ccacgattcg tggttgggta cacctgatag tccgaggata tttaaatctc | 480 |
| acgcgctcgt gtctataatt cgactgtact cgcttttctt gtcgtgattt tagcaattta | 540 |
| cgaagtcaaa tgtttgactc aatcagactt gcgcataaga gagcgagtat aaatgtttac | 600 |
| tatactcacg caagtggggc tttattgaaa ctactctttt gtaataaaac cagcagtggt | 660 |
| tttgttctga atccgctctc ttgccatata taccacaaac agaaaccaca gaagatatct | 720 |
| tttgagaagg aaaaaaaaaa agaagcttct cctcttcctc tgccttcttc tttccattta | 780 |
| ttgcaaaccc tgatcaagta agtcaaatct tcacgaacac atatgtatat aaattcaatc | 840 |
| caagaaacta ggagaaatct atgaaagagg acaaatctaa gtcaagtttg aatcaggaag | 900 |
| attatctaga tttgatcatt ttgacattta cgatgtgctt acttattctt gataaacttt | 960 |
| gatgcagttg gttttggtgt tagtcttttg gggagagag | 999 |

<210> SEQ ID NO 11
<211> LENGTH: 915
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 11

| | |
|---|---|
| acatcaattt gcctgcttgt agggtgattc gtcaaatcta ttatcaggtt ttaaatatac | 60 |
| tcgaattgac ttccaaattc ttagtctcta gtgtaatgat tttgagaatc acttaactcc | 120 |
| aaaaatataa tccacgatcc cgtgttaatt attgaagaat caatcgttttt taatttctca | 180 |

```
ccaatagatg ttgctcttat tacttaaaac aaattgttta gacaaatgta gcaagtgtga      240
tacttagtgg gatcttaaag acgatttctc ctataacaga ggacaaacag gtcggtcaat      300
tacaatgtca tccctctta ccctgtcttt ttttttcttc ttaaaaccta accatttgat       360
tgtttctaaa ggtatttcaa gaatatatga tcaatctaga tgaatactat accgacgatg     420
actacacaca caaggaaata tatatatcag ctttcttttc acctaaaagt ggtcccggtt     480
tagaatctaa ttcctttatc tctcattttc ttctgcttca cattcccgct agtcaaatgt     540
taataagtgc acacaacgtt ttctcgaagc attagaatgt cctcctctta ttaatctcc      600 ttctgattag attctcaata gagtttaaat ttgttaatgg agagatatat tgggaccctc     660
aaggcttcta attataccac gtttggcata attctctatc gtttggggcc acatctttca     720
cacttcatta ccttatcacc aaaacataaa atcaatcaac ttttttttgc cttattgatt     780
gtgttggatc cctccaaaat taaaacttgt gttccccaca aaagcttacc caatttcact     840
tcaatcttaa caaataggac caccactacc acgtacggtt tgcatcatac aaaccacaaa    900
ctccttcttc attac                                                       915
```

<210> SEQ ID NO 12
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 12

```
tggagcttta ttgaaatgca agaaagtaaa caaaggaaga tctttagatt gtcaccaaga      60
gtggtctgaa actctcataa cactcaatcc tcctcctcct catcaccacc actacaaaat     120
attatattct ctatctctca atctatgagg agatgtattc tatcaagcat ttgaaatgat     180
aagaaactgg cgatcatcct ctacgtcacc atcactccaa aattatcctc tttctaggtt     240
taagttttgt aatgatcgcc tttatttgtt gagatctcta acttctcgca tttccaaaat     300
gttaagtcca ataactgcat tggttaagtt ggggcgttac tagtcggctt aaatccaaat     360
atggatttga ttccatatgt atgtgacagt ttcttaacgt tcatattaca atgaatgatg    420
gatccttgac tagacaaaga gaaatggat tgtcacttcg taggaaaaat agaaattctc     480
cacgaaggct ggtctccttt atttaacgac aaattcactc atagtctcat tcacaatttg     540
aacttgtcta acacaatgtg ttatatactc gcgaaaagaa gcataatagg ctcttaaggg    600
taatccacga aaccaaaaca catataaaac attaatattt ttctctaaat ttattcatat     660
caataataaa gtttacaaaa aatataaaac aataatccat acttagccca tagcttcgtg    720
tggaagaaga cttgattttt gactagtcaa cgaaaatgag taaatgacgt attcagctat     780
agtaaaaggg atcataagcg gaaattacaa agaagctttg agggtaaaat agtcaaaaag    840
cataatcaga ataacttag gcccaaagca aaaggaaag gactctggat ccagccgcaa     900
atcagaatct ggtaagttcg aacgccacgt catcacctaa atatctgaaa tatctaatta    960
agacttgtct atatataaag gcttctcctt tcacaatccc                           1000
```

<210> SEQ ID NO 13
<211> LENGTH: 1000
<212> TYPE: DNA
<213> ORGANISM: Unknown
<220> FEATURE:
<223> OTHER INFORMATION: Promoter and/or promoter control element identified from Arabidopsis thaliana or Oryza sativa.

<400> SEQUENCE: 13

```
aaagattgag ttgagagaga tggtggagac gcagaacaga caaagggagt ttaccatata      60
gtgctctaaa gggcaatgag attgcagtga tgtggctatc cggggaatca tcgcaggtta     120
ttccttccca tgagcaacaa tcaatggatg ggttccaatt cagaggagaa acagaagaag     180
aaacgtttcc agagaaccac agtagggatt ctcgatcttg cgagttgcag agagcctctg     240
aaactgcaat agaaaggaca ctgatgaaaa gaacacactg aaggagtatg ccaatcatgt     300
gaaaactcag agcttgtatt ggtcttgtgg ttgatgaagt tctcacaaaa cctttggctt     360
tgaatctccc ctcattagtc atggtgagaa caagaacaag acgagaaaca gacaaagaag     420
atgaaaaaac ttgttggcca gtgttgacta aggggggaata gcccagacat aacaaaatta   480
gacttgtcgt acatctttaa tatttttttt atctgtttct ttgtcctgac gctttcatta     540
ttcctgtgat caattttctc ataccattgg tccatcgtta atcctttctc aatttcattt     600
tctacgtaac atgagaggag accaagtcct atgagaacag ttgacgtaac agtggttgtt     660
aagttaagtt aaaagagga agctagtgag agtgaccgtt aggtagagaa gtgagatctt      720
taaccactct tctttctctc tctctctgct tttttcgtcg tctttcacat ctactgttcg     780
caaactctct tatgcttcca ataatggtga taccaattga gacttgcagg agaatctcct     840
cttctccaca ctctatcaac tggtcagcca tggaatggtc gtttcagttt caatattcct     900
ggattctttt taaggattcc tgtttctctt ctgttcctgg tatattctta acgacgaaat     960
tagtatcgga tcctggtaat acattttgaa gcttttaagt                            1000
```

<210> SEQ ID NO 14
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 14

```
tatgaagaaa ttataataga ctctcataaa aatagtgtta caacttacat tctcttatat      60
agaaattagg ataaacagaa atgtaaataa tatatttcga aataatgtta aatttcctaa     120
attctaatat taatatttat aaatggtcat ttaacttttt cgtaccggtt cgatgggaca     180
tgtgttatat tcagttaagg ttaccaccat gcgccaactt ggcctctacc aagtcaacat     240
ggatatggac cttatggtta catgccgcct ccgcctccac cgctaccggg atatggatac     300
agaggtccgc cacctcagca accgacgagg aatgaaacaa ggcaataata tattgatgct     360
attgtggatt tagttactga taattagtgc cttagtgaca gttcaaaaat gttgttcatc     420
aataatctac aatttaaggt ttgtgttgtg aatgtttca tgattttatg aagtcttgct      480
tatcaaaaag tatgatgatt aagaatttga cttcatggca tattcatttg agttagcaaa    540
acttttttgt gttgcacctt caaatttata aatttatgat ttttaaccat cgaaattata    600
tatttgaaaa gactatctct acaagccaaa cccactgggc caccaatatg ggtttatctg    660
cgaaatctgt gaaccttaga aaatcaaagc ccatatccac tttgctgaa cttgctgga     720
atgtaggtta gacaaaacct taagacgcag ctacaagtct cttatgtggc agatgtcaaa    780
attaatgagc acgtataatt tacccaagag gagcaaaata agattagcag cttaaattaa    840
ttgtgttgga ttaaatgaaa cttgcactat gaatggcaaa aaagaggtta caatctagca    900
```

| accacctcat aaaccctcat taatgagata ctgactcgtg aaccaatcaa atctcaagtt | 960 |
| tcgtagttta aataagtagt aaacacctcc tgatcaaagc | 1000 |

<210> SEQ ID NO 15
<211> LENGTH: 999
<212> TYPE: DNA
<213> ORGANISM: Unknown
<220> FEATURE:
<223> OTHER INFORMATION: Promoter and/or promoter control element
    identified from Arabidopsis thaliana or Oryza sativa.

<400> SEQUENCE: 15

| ttcctcgacc atgccgttgc cggaaccggc tagcgcggcc ggccggcggc ggcggggagg | 60 |
| ccgcagtggg acgacgggtg aaggatcctc cagctgcgga aggaggtggt cctcgaggcc | 120 |
| gaagggaga ggctacggag atggagggaa gccgaagaga agggaggctg ctgctgctgc | 180 |
| tgcatttggg agacgagaac tcgactcgag ccatggcggc agattggtgt tcacggcgg | 240 |
| aatgctaact agatccagca tctccatagc aaaggtagaa tggtagattg aggtgagttt | 300 |
| ttttccct cttctgcagt tttgatgtat tattactgcc ctcatctgat ctgggtaaca | 360 |
| tatttctgag ctcagtagaa ctgttaaaaa aaggcagaaa tgcacaaact cttctcacaa | 420 |
| aacaacatac aaatgcttat attttggagc ggaggcaata catggtatat tttttaaagt | 480 |
| gaaaaaaaca atcagacaca tggtattgag tgatagcaaa gctgggtgac cacagaaaat | 540 |
| acctcctgct ttaaatactt tatacctggg ctgtcaatcc tcggagttcc tcccaatgta | 600 |
| atgtctgagg aagaagtatt gcagctaaat tttaagggtt tcttgtacga aacagggaca | 660 |
| atcagagatt aagaaactct atgtggaaaa ggccatgcgc attttgttat gtgattcaac | 720 |
| aaataagatg aggaggcaaa gtcatggttc tgttctaatt aacaaatcta ctatgggggc | 780 |
| cgttgctccc tattgtccac gctccttttc ttcatttctc tcctgcagga tatcttgtct | 840 |
| tttgattctt catttaggt cttataaata tcacgtggtt caggcctcca atgtcaaatt | 900 |
| atcattacgt ggaactctct tagatgcttg agaaaagtta gctcttacct gtccatagaa | 960 |
| gctccaagga agcgagaata gtagatactt tggttggcc | 999 |

<210> SEQ ID NO 16
<211> LENGTH: 1000
<212> TYPE: DNA
<213> ORGANISM: Unknown
<220> FEATURE:
<223> OTHER INFORMATION: Promoter and/or promoter control element
    identified from Arabidopsis thaliana or Oryza sativa.

<400> SEQUENCE: 16

| atttggttga taacgttttc actcgactaa ttatatactt cagaaggata gtaatagaat | 60 |
| accaaaataa ttaaatgatt ggttagtgcc ttagtggaga ctttttaacc gattctaata | 120 |
| gactaatgat gtagctaagc atttatttgg gatcatcact gtttgaaaac gtgaaatgtg | 180 |
| ataaaagtta tgaaacgatt aaaatataaa ataccgtac aaaacattat gtaccgtttt | 240 |
| tttctctgtt cttttggcga tttggttag ttcgttacac tctaaatgtt attgcagata | 300 |
| tatatataat gatgcatttg catctgagga acatataatt ccggttaaca cttccaaatc | 360 |
| ttatatccgt ctaggtaggg attttataaa tcatttgtgt catcatgcgt tatgcttgtc | 420 |
| ggctttgacc ataacgcaga gatatagaac tagcttttac ttaactttta gatttattat | 480 |
| ttgatctaga gttaagtgga gatatatagt gttttgtta gattattggt ggatgtgaga | 540 |
| gtttgtcttt agtttcaagt tgagaatata aggcaagagg agactctgag gcaatcagag | 600 |

| | |
|---|---|
| gttttgattg gcaaaatatc caaaaggccc aaaccaagtc gaagcccatc tcgtacaaaa | 660 |
| aaagaaagag atctgtaaga aaaaatattc tttgatattc ttacaaaaat aagtgtaaaa | 720 |
| cttttattag tcaaaatctt caatctttaa aaactctcat cactcctacg aaagcgcgtg | 780 |
| agagttatga gacattcctt aatagcatta ctcacaagtc acaagttcaa aacgtctgac | 840 |
| tgaaacagaa acaagccttt gttgaagtct gaagaagag acattagtac tcgtcgtata | 900 |
| gccataaaag gtaatatacg aaatttcttc gctaatctct tcaccttcct ctacgcgttt | 960 |
| cactttcact ttataaatcc aaatctccct tcgaaaacat | 1000 |

<210> SEQ ID NO 17
<211> LENGTH: 1001
<212> TYPE: DNA
<213> ORGANISM: Unknown
<220> FEATURE:
<223> OTHER INFORMATION: Promoter and/or promoter control element identified from Arabidopsis thaliana or Oryza sativa.

<400> SEQUENCE: 17

| | |
|---|---|
| gttttgaaga acaatctgga tcgaaatcta acataaggtc atcgtattca agttacgcag | 60 |
| tcaaggactt gacatcatcc tactctggtc tgaggttacc acttccaaag atgggatttt | 120 |
| tcgactcggt atgcttccta agaaattcgt tttattgaac ctagcaaata tcttgtaatg | 180 |
| taagattcct gagatgatga agaaaaaaca aactttttgtt acagcaggag aacggagaga | 240 |
| aagaaaacag agaaccaaat gctcttgaag caaacagaag aagaagacac aaatccaaac | 300 |
| ttgagacttc ttctacacca gaaaaccgca gcattctggg acaacgcaaa acacgaaagt | 360 |
| gaaacgggca atgatatata tgtcttgggt gcgttacaag gcatcgtttg catgttgagt | 420 |
| tggataagtc aactgtcttc ttttcttttg gttgtagtag ctgccttttt tttcctttgt | 480 |
| tgctttaaga aatagcccga aaaaagaat gttctacatt tcggagcaga aaactaaccg | 540 |
| aatgagtttt tggtcggatc atcggatcga tcagatatat tttgagttac gaactgttat | 600 |
| aaaaaaagcc ataattttgt gttgagtttg caaaatacct tataacttgt tatttgagat | 660 |
| tgcacctcca tatatattaa ttcgtaagag tatttattaa gtaagcttta gtataaatcc | 720 |
| ttttttcctt taaagtaagt taatgttcta ctaaataata gtaaagttga agaaccgctc | 780 |
| cgttttacac catgcacgtg ttatctaaca aagaaaatat ggtacaccta atggctaatg | 840 |
| caaaggacaa cacaatgaaa ctaacttgac tctgtgttat acaaacccat agacatctgc | 900 |
| atacatccta gtatttgtat aaattggact caaattcctg aggacaatca tagcaaacaa | 960 |
| tcacatcatc gcaatataca taaacaaaag aggaagaaaa a | 1001 |

<210> SEQ ID NO 18
<211> LENGTH: 1000
<212> TYPE: DNA
<213> ORGANISM: Unknown
<220> FEATURE:
<223> OTHER INFORMATION: Promoter and/or promoter control element identified from Arabidopsis thaliana or Oryza sativa.

<400> SEQUENCE: 18

| | |
|---|---|
| taacaatcct tgggaacatt gcatccatag atatccggtt aagatcgatc tttgaactca | 60 |
| taaaaactag tagattggtt ggttggtttc catgtaccag aaggcttacc ctattagttg | 120 |
| aaagttgaaa ctttgttccc tactcaattc ctagttgtgt aaatgtatgt atatgtaatg | 180 |
| tgtataaaac gtagtactta aatgactagg agtggttctt gagaccgatg agagatggga | 240 |

| | |
|---|---|
| gcagaactaa agatgatgac ataattaaga acgaatttga aaggctctta ggtttgaatc | 300 |
| ctattcgaga atgttttttgt caaagatagt ggcgatttttg aaccaaagaa aacatttaaa | 360 |
| aaatcagtat ccggttacgt tcatgcaaat agaaagtggt ctaggatctg attgtaattt | 420 |
| tagacttaaa gagtctctta agattcaatc ctggctgtgt acaaaactac aaataatata | 480 |
| ttttagacta tttggcctta actaaacttc cactcattat ttactgaggt tagagaatag | 540 |
| acttgcgaat aaacacattc ccgagaaata ctcatgatcc cataattagt cagagggtat | 600 |
| gccaatcaga tctaagaaca cacattccct caaattttaa tgcacatgta atcatagttt | 660 |
| agcacaattc aaaaataatg tagtattaaa dacagaaatt tgtagacttt tttttggcgt | 720 |
| taaaagaaga ctaagtttat acgtacattt tattttaagt ggaaaaccga aattttccat | 780 |
| cgaaatatat gaatttagta tatatatttc tgcaatgtac tattttgcta ttttggcaac | 840 |
| tttcagtgga ctactacttt attacaatgt gtatggatgc atgagtttga gtatacacat | 900 |
| gtctaaatgc atgctttgta aaacgtaacg gaccacaaaa gaggatccat acaaatacat | 960 |
| ctcatagctt cctccattat tttccgacac aaacagagca | 1000 |

```
<210> SEQ ID NO 19
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.
```

<400> SEQUENCE: 19

| | |
|---|---|
| tcatctgcta ggcgattagg tttcatacac acatgagtaa actgcactat ctagttcata | 60 |
| tacactccat cttattgatg atatttcaat tttaaatagt aactcatata cttttcagta | 120 |
| tttaatttat tatttcctta aaccaaattt caatcttaca atttcgaatt tgcaatacaa | 180 |
| tttaaatatc tattttatga taataaaaat aaaatttaat ttgattgtat aaaattcaaa | 240 |
| tacaattcga ttttgcaata gaaaacaatt taattctata cactccatct actattaatt | 300 |
| ttccattata gttataaatt agtatatgta aatttgttta ttttttttag gttttttctc | 360 |
| ttctaagaga aaaaaaaaa gttaaaatct tttccgatac atgtcaaaat ataagatcga | 420 |
| tagatttgcc atgtgttacg atcgtatgag ttattaactt tgaaaatcat acttttatata | 480 |
| atacaaaaca tgtaaataca tgtttataca tatatttaca actaaaaaca tgtgtaaaat | 540 |
| ctaatggatt tttaaataca tgcttttagc tcgaaaaaaa tttgatacgg agaaaaaaat | 600 |
| ttgacgggaa ataacatacg taaatatctg atcaaattat ctatagtacg attttgacgg | 660 |
| gaaaaaaaat tatttttaaag gaagagctta actttgaatc tcactaaacc agatcataca | 720 |
| taatcaatcc tttctttttat ctttttttttt cttttcatta cgtgtaatcg tgttgtgtct | 780 |
| aatatatcag tttgatttgt aataatttga ataaaaaagg gagtgttgtt atctttaagt | 840 |
| ttgcccaaaa tctatagtca tgttcgatgt aaacgtatct taaacaaaat tattaaatgt | 900 |
| taaagatagt aacatacaat tattaatgaa taaatgttta actaattaaa tatcatttag | 960 |
| tgattgtcct ataaaatctc ttgttttctt gtttcatatc | 1000 |

```
<210> SEQ ID NO 20
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.
```

<400> SEQUENCE: 20

```
ttatgtgccc tgatgtccta tgcagatggt gcaactactg cttttggtga gaagcttcgc    60
gaacaagttg aggaaaggct agaattttat gacaaaggtg ttgccccacg caagaacgtg   120
gatgtaatga aggaggtgat agagaatcta aagcaaggta tttcttgtag ctgttttttt   180
ttggttgtaa tcagagtcct ctttatgatg gcaaactcag tgttttttta tctgttcctc   240
ctttagaaga ggaagggaag gagccagttg atgcctcggt gaagaaaagc aagaagaaga   300
aggcaaaggg tgaagaagaa gaagaggtgg tggcaatgga ggaggacaag tcagagaaaa   360
agaagaagaa agaagagagg aagatggaga ctgcagagga gaacgagaaa tcagagaaga   420
agaagacaaa gaagagtaaa gctggaggag aagaggagac tgatgatggt cacagcacca   480
agaagaagaa gaagaagtct aagagcgctg aatagaaagg gatgcaacat taacaaaccc   540
tgtattgtat ttttttttg agctaaatta atgtcgtctg tttttcgtag tgaacatcgg    600
agaattttg ttttggtctg gaaacgattc aaggtttggc aatatcttaa gtttgtttag    660
gttttcacta ttttgacgtt tgcaaccgtg aaggaggctc ctccatttta taaaatacaa   720
ttaccaattc cagtgctttg caaatgtttc aataatagct aaactaacta ccaaattgga   780
aaactagctt aacaagtttg tgaaaatgaa tttggagcca tatgatttat tatttttaccc  840
aaatggagta atagaagaag agcagctcgc gtttgaatgg tcagttaaca ttaacaaaag   900
gtaaaattga atagatgtta aaacttgtgt aagtaaacaa tagagctacc tccttttgag   960
aaggatagat aaactcgtga ccaaccacat tcccagtccc                        1000
```

<210> SEQ ID NO 21
<211> LENGTH: 935
<212> TYPE: DNA
<213> ORGANISM: Unknown
<220> FEATURE:
<223> OTHER INFORMATION: Promoter and/or promoter control element
    identified from Arabidopsis thaliana or Oryza sativa.

<400> SEQUENCE: 21

```
aaacgcctct tcggtccacg ctgtcgtttt attgaaggaa ttatatttta ttttaattgg    60
gcctgcaggc taaactataa gtccgtctga tatgggtcgg gttgggctta tgagttatgg   120
gtctggtagg ggtcaattag cttaatttcg atatgtgccc tactctcgac ctaacgtttt   180
gaacacgtaa gagagagttt ctaatattga gttgtctaat taactcgata ggcttataca   240
aagtgtttcc gcattttacc ttcttaataa ctcatcattc actaactaag aaaagtttta   300
ctcagaccat atcttccgct tcttgattat tgtcaatttg ttgtcactca atttatctct   360
tgcaaaattt agttgaaatc atttggtttc atctttggct cttgaatagt tgcatgtgtg   420
tatttagtaa gttcttttca attaagaagg aagaataaaa caattgtgg ccagaaacaa    480
ttatgttgag ttttatctca tacgttggct cattcatccc catctctctg cttttgaatc   540
attctactcc tcccattttt tgatcgtcct ttttcctgct tctgaacatg gatcattgtg   600
catgttcgga tgttcctcga tcgtgctgaa actcaaagtc tgaatcgatt accatagact   660
ctcaacccat cctttgatata taaaaaagag ccttaaccca tctcttctac tctccctctc   720
tagaaacaaa cacatcacgt gatgatctgt tcccccccat acttacggga tgatcagaat   780
gtggcatgag gaaaaagcca agaaataagt tgataaattt aaggtttaat ttaacaaaaa   840
tgagagatta atcttttcat tttagggtcg cacgcggtgt tttgtgcaac cgcagaaact   900
tcctataaat accgatacaa tgtgcatgct ttcta                             935
```

<210> SEQ ID NO 22
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 22

```
aatcacagtc ctttatgata aaacgaactc ataattattc caccgacaac atgcgtttta      60
aattattttt tcttaaatta tattatatta tattgatatc aacctagcta aaataattcg     120
gatggcgaaa tcggacaatt tttaatagaa aaaatgggta tgaagatagt ctatgattcc     180
gttcttagcg actagaggga cctgctcaaa tctcccgggt gatacgcgat gtcaagctca     240
atagaacccc acaaccgacg agaccgagaa atccttgatt tgggctagaa gattttgaaa     300
tgaatttaat atattctaag taacttgctt aaatttttt tcaaactcta aagacataac     360
taacataaag taaaaaaaaa aagttaatac atgggaagaa aaaaattaaa ctaatgatta     420
gctctctaac gtgtttaatc tcgtatcaag ttttttttta aaaattatat tgctattaaa     480
acattgtact attgtttcta ttttgtttag ctattattct tgtgaaatga aagttgtgt      540
ttattcaatt actaaatggc aatatttatc ttggaaaact atacctctaa ttggattagg     600
ccctagacat cctctttagc ttattgacgt taaaattatt cccaaaacta ttaaagttta     660
gtagtttgaa agatgcatca agacctactc agataggtaa aagtagaaaa ctacagttag     720
tgtgattata ttttaaaata tataaaacaa tcttattaaa ctaaatattc aagatatata     780
ctcaaatgga agataaaaac atttagtctg ttaccactac cagcctagct agtcactaat     840
agtcactttg gaactgagta gatatttgca tcttgagtta ccatggactc aaaagtccaa     900
aaagagaccc cgagtgaaaa tgctaccaac ttaataacaa agaagcattt acagcggtca     960
aaaagtatct ataaatgttt acacaacagt agtcataagc                          1000
```

<210> SEQ ID NO 23
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 23

```
aattgagaaa ggtgcctcaa tttcagtaga acctgacgca aaatttcgcg atcatgcatg      60
actcaaattg gttattcac ttaaataaaa aagttgtttc cctatctagt tgaagttctc      120
aattcaaacg caacttctta cttttttcttt ttatttatac tggaatgaat ttttcgtcaa     180
tgctagacct caatatttgg tgattaagtc caaaaaatta tagcaatatt cattagttaa     240
atcataataa tatttgttat ttctgctaaa tatattagtt ttaaattggt aaatatatca     300
gtcatcatac tttatatatg tgcacaagaa aaagaggaaa aaaaactaac ttttaataaa     360
ttgaacgcta tcctctatat ctcgtcctgg tccaaatgta aacttcaata tccttttgat     420
tttattgctg attgctttaa aaaatttcac aaacacttt atcattcttt tattccacca     480
aaatctacag acataatact ttgtaatttt atgtaaaaat cttcaaaatt tgggaaaaga     540
aaaatcattt aaaatcaatt tgcattaact ggatttattt ccaaaggtgt ggtattgtgt     600
ttatatatgt ggagttgttg gctagtaata taataaggaa aagagtgaaa catatgtagt     660
```

```
ataacgtatt tctagttttt ttctctgtat taatgaatca ctaattaagt agtatgcatt    720
aattgaatta tcagaagctg gtcacaaaag tctaccaaaa aaacaaaaa aattggtcag    780 aagaaaatga aaataatgag aataaaaaag ggaaaaaaaa taagaagcta gcaaacaaag    840
caattaacat ttcaaggcag ttaattcatc atgcaaggtg cttatgtgtg acaacgtcat    900
gcgttacttt ttgcgtctac actcatctct ctaacgcaat ccactaattc tggtaatgga    960
ttctgctatt tagaccagcc agtttcttcg tctctcaatc                         1000

<210> SEQ ID NO 24
<211> LENGTH: 1000
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 24
cattgtatct gagatgtgac tgtgaagaac aaagattcat gacatggtat tgttaagccg     60
cccattggat gatcataacc aaactcttcc tcagatttac tcaacagttg ttgaaacaaa    120
ggctggttta agtatgaaac cggcaccaca tatctcttct tcttctgatc attctctcct    180
acatagaccg ccatgaatcc tcttggtgtc gacgatgatt ccttcgaat aatttgctta    240 gcacccaaga aactcctcaa aaaagccata ttttcccta tgttttcctg aagcttaaat    300
gtttcttagt cttggagaaa gctttgagat tttaaaattg gatcttcttt agtttgtgaa    360
tctaaagggg tttagttact tgttatataa acgaacgtat gaaagaaatg attaagtatt    420
tttgaggttt ttcttttaa ttacagagca catggctttg ggttgtagat actaaaccaa    480
gaacaaatca ataaatggtg tctgagaagt tagtgtctaa tgatgtccta catgataact    540
tcattggggc ttatttgtct caaagacatc acatgccaaa tctctctata gattatgtag    600
ggacatgaag ttgtgtacct aatgaaccac aagtctctat cactgattaa gtcataacctt    660 cttctcaatg atattcaaaa gacaggacca catgatttga ttatatactg acaaagtcac    720
aaaagccttc aaaaaaattc tgtggcaaga aggaaaatt tgactagtta tagtgtctat    780
ctaacaaaca agtggtcata ttgatttctg tcttcacatc agaaatcatg aagattgatc    840
actatagggc ccttacttat catgccgtgg tccggcaaag ccatgtgctt gcttgttggt    900 gtaaaattt atgagctgaa acttttgaaa ccaataaagg gttatctaca agtaatgttc    960
ttatctatat atactcatca ctgactcctt tctgctctgc                        1000

<210> SEQ ID NO 25
<211> LENGTH: 1041
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 25
acgtttaaag ttgagacata aaacagtgat ttcaaatttg tattagggtg gtcttattgt     60
gtgtctagct actagctaga gaatactaga agaagaatac gtagcaagat acgcacaaca    120
tttggtcctc tctttttttt actttctttt aacacattgt cctcttatga tttgcttatt    180
gatttcagta tcttttgta tcaataattc cctccaaatg attaaaccct aaaaaaatgt    240
gattcattca ccaccgaag attagcatca tcaagtaaca cacaataact accaataacc    300
tagttttcat ttttctatac taaaatccta aacatcccat aaaaatacaa acaactctga    360
```

-continued

| | |
|---|---|
| accaataatt tcctctaatc cacgtgcacc ccatcgtctc ctgacgtaag atttgtctat | 420 |
| aacttatcaa atcccaaatt cagctttgtt ttcattatat agtacgtact cttataaaaa | 480 |
| agagaagagt acacatcttt aatactttaa cttaaaagaa gaaagtaata ctaatataag | 540 |
| aggagtctga gtcagcgaca agtgttcgcg gagaaacgga aacgctctct ttctctctct | 600 |
| tcccccaacg ccaataccttt tggaatccct ccctaactct gtcctgtcct ttcgtcctca | 660 |
| ctttctctct ttttacattt tctacacacc aataaaattg aaaccagcaa cttataaatc | 720 |
| aactcaagtt tgaattaatg atcgaaaaac tagtttattt gtgtcaatat gacccattct | 780 |
| ttattcacat aagtatttta acttttcaaa atgttatctc aatctccttt gagtttctgt | 840 |
| cttcccata ataaatttca ataattaat acacatggtt ttttaattag aaataatgga | 900 |
| aaagaaagga caaggaata aaaagaaac acaagttggc acactctctt tattattcac | 960 |
| tccctctat aaatctcata ctatcttctc tcatcttctt aaatattgga tatatttctt | 1020 |
| tttcaaattt cggaaaagaa a | 1041 |

<210> SEQ ID NO 26
<211> LENGTH: 975
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 26

| | |
|---|---|
| gataaactga taatggaaaa gaacaaagaa accagttttt aactatttgc atatgtaatt | 60 |
| tatttgttgc aaattatatt tagttaaaat gtttcctcta tttatatata tatcagtcaa | 120 |
| gcactatgta taagaaatgt caatttataa attttttacat gtcctttaac agaaagaaaa | 180 |
| tgaattttta catgtcattc atagagagtc actcgtttat ttcttatata gagaataaca | 240 |
| cactcacatg catatgcatg caatatgata cattttatga caaagataat caacggaaac | 300 |
| ggtcaagaca taatttgata aacaacttgc acgatgcaca gatctgatca aatatataac | 360 |
| tctttaacat atccaaaata ttcaaaaaga aaaactcgat ccaaactagc aacatcacgc | 420 |
| tcacgcgtag gctaaaaatt tattaatctc caaaagtctt tcttatgaac actgcaaaca | 480 |
| caacaacttg aaaagtcata taggtttaga tgatgacgcg tattggctat cgcttaccgg | 540 |
| agtggctcat aaatacaata aacaatacgt aaaagtcaaa gtcaaatata tttagtcaac | 600 |
| tataaccatt aatcgggcaa aacctttagc tgtcaaaaca acgtgaaaac gatatttgta | 660 |
| tatatcatca agaatcagta gataagagaa tgatttaatc ccctgactat tacaattttg | 720 |
| gtgtaataaa cagtctctat tggttttat tctttgtttt aatttctcat gacctataga | 780 |
| gagaattagg tagtttcgaa aattggctaa tcaacttttg aaaactactg tctactttgc | 840 |
| ttaaattctc tacacttagt ttcggataag ataattgtcg gactaatagt taatcccttg | 900 |
| acaatctttg atattataaa aggtttagtt aatctcttct ctatataaat attcatacac | 960 |
| cagctttcaa aaata | 975 |

<210> SEQ ID NO 27
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

```
<400> SEQUENCE: 27
cagagcagtg catattttttt tttttttttt tttggtgtta gtgcatatct atatatatag    60
tactattata atatatttca atatatatat tttaagaaaa tatctgattc ttaagtttgg   120
acttatttgt caacaatagc cagtaaaaaa caaaagcgaa gtttcactaa cttaaaaat    180 aaccacattt gtatatttcg aatacatact ataaattaat aaatttatca aaacaactat   240
agaaactgtt atttccaatc aatttcttta tcaagattat atctgaaata tatttattaa   300
aattaatagt tatttacaag aactattttt atgaaagtgt aagaactctc tgaaaacttg   360
ataagtcaat attttttcta acatcgtaaa cataaactag attcaaattc gaatctagtt   420
attcaaaaac ttataaaaac ataaaaatga aatactgtta cttcaacaaa aaacattat    480 tattattttg tttaaatatc taaatttatt catcaacagc aaaatattta aaagagtggg   540
aaacaaataa aaattaaact ctgttttggt atgataaaat tatttactaa actaaactca   600
atttttttta gtatcacggt tataactata acaataatcg aactttgtta ttttcttggt   660
actggtttta gtagtataga tagatatttt agtcataact cataagatac atgtacaaat   720
atttgctata tatgatcagt gataactgaa tttcgtgctg aaaattgcca tagtttgctt   780
attttactct tgaaacaata acgatatggt cgttacttaa aacaacattt taaaaacgaa   840
gaaaattaaa cagagtttgt taaaataaat taaataccat aaatttctct ttgactcttc   900
ctatatagta aaatctctca tccccttctc tctctctctc atagcatgtt ggtctttagg   960
ttcctatata aacaacgcca cacacaccca tttagtccc                          999

<210> SEQ ID NO 28
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 28
tagttccatt acaatttcca aatgattgt tacaaagcta caagattatt cgaaatagga     60
tttcatccat aagagagaat ggtgtggtcg acgctacaat gttgatttat tggttgtggt   120
ttgcatcttg gggatgtcaa atcctaagtt tcaagttctt gtaaaaacgt tttcaggttt   180
ctttaatata ttttaatatt aatgtaaaaa gaaaagatat agcttttgta caaaaaaatt   240
tgtttaatca ctatgtagga ggatgcgatc aaattcatgg aatgatgtat tattagcttt   300
tctatcctca ctctaaaaac aatactatag tgagttaaat aatttgatca tttcaatgta   360
gattaaaatt ttattaaaag aagaaaaatt taaaagccta taacaaaata aaaaaggagg   420
ctcgaggtat gatgggtgta gcagaagagc tggcaacagc tatcgactga gtgattacga   480
actcagtact cagtgttctc agctcacaca ctctttttt gttctctttc ttttggacag   540
ctttcatttt ctcttttctt tttctatttt tgtttcaaaa ttccatccat attaaaatag   600
gcctgatcat gagaataaag gaaatactaa tgatgagttt ctcaataatg caataagatg   660
caattattat gagctatttta ctattgaaaa tgagcaaata aatgtcaaaa cacaatctgg   720
ttaagttaga gcaactccat tgtataggat tcatgtagtt tctaagaaaa caaaatgtat   780
taatatttta cttttacatc caaaaaacca acttatatga gtaatagaaa cgatcctaat   840
attaggaatt ttagagattt tctctcatct gtttcttaac ttttcaatat ttttattttt   900
taaaattgta tgagtttcta ctaagaaact actgctggag ttggtcttag cttcccaatg   960
```

-continued

| | |
|---|---|
| cttctccacc tatatatatg catatctcct tcttaaaac | 999 |

<210> SEQ ID NO 29
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 29

| | |
|---|---|
| tgttaaggga aggtttgcac ctaagaattt tgaaggaatt ttgcggcgat atatcagtaa | 60 |
| gtaactttct tcttagtctc aaaatttaag ttgccataaa agtatatcag tttggagttg | 120 |
| ttaacctctt gttttattat ttctcagctg actacgtcat ttgccttggt tgcaagagcc | 180 |
| cagacaccat tctctccaag gagaaccgtc tcttctttct gagatgtgaa aaggtataag | 240 |
| ttaatctaat tagtcctgat cttgatatgc attcctttgt ttctgttta cagtttact | 300 |
| ttctgcgcaa caaagtaata agtattttg tgtgtttgaa tttgctaatg tgattaacga | 360 |
| gtgggctaca tggttttgc agtgtggatc tcaacgatct gtggctccga tcaaaacagg | 420 |
| gtttgttgct cgtgttagtc gcaggaagac ttgagaaatt agaaggtgaa gtgaccttgg | 480 |
| tatggagttt ggagctattc tactgcttct gtatgagttt atgagttgaa gaaatacttg | 540 |
| tcttgttttt tttattttgt tttggaatat gattatgact tgacttttaa aatgggatag | 600 |
| gatcaaaacc ttttactctg tcaggttcat gtggtcacct tgaaggttga tttagtaaat | 660 |
| ccatggactt cttttttgtg ttaagattat tcttagttca aaattaatag actaatgata | 720 |
| ttaacgtcca caggcattgc gttcaacatc tcaaattaaa gcgtggaagg ctcagaaagt | 780 |
| ccaatataca ctatgtttat ctacagttac aatcatacta caaaaaacaa ataatgtata | 840 |
| cggtttggtc taatatagcc gcatacgatt tagtatttac caacaaaaaa ttggtctcaa | 900 |
| accaaaccga acaattggta attaacaatt gttcttttgg tcttgaaccg aaccaaaccg | 960 |
| aactgaacta tattaaccga ccgacttcgt cctttcctc | 999 |

<210> SEQ ID NO 30
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 30

| | |
|---|---|
| tagtacttga aacacttggt tggtttcatg tatttggcct atatataaac aaacatcgta | 60 |
| attatatacg gatttttttc ggaattttac gccatatctg taagtatata taacatgcat | 120 |
| gtcgttttca aattcatatg atgaacgatc cacgtaagtg ctactactcc tacaatattg | 180 |
| catgagagag atatgtattt ataattttta ttttgaagaa gaaataagag ggaaggttac | 240 |
| ttgggtggat cgatgtgaaa acaaagaag aaaaagcgaa acccactaag ccattacatg | 300 |
| atatcgacct tcttatcttt ttcctctta ttttattttt ctcaggactt ttttctactt | 360 |
| aatgaaacct ccaaactatc taactaatac actcccatgt agaataaaga aaattatata | 420 |
| agatattgtt gatattttgt aactagaaaa tatatttgct ctgtaattt tcgtaagtta | 480 |
| aatcaacatt tttcagtaga aacaaatatt actgcaaaaa gtaggatcat tattttgtc | 540 |
| caaaatctca gttagctata gggttgtagt aaaaacaaaa cacattcttg atttgcccca | 600 |
| aaaaataaag agagagaaga atattgttca aaagtggtct cttctctctc taattatgtt | 660 |

-continued

```
ttcactaaac ccaattagat tcaaacagtc tacaaagtcc aaaagataaa catgggacaa      720
caattcgatg caaaaaatcc tcttttcatg ctctttttt attctctagt cttttaaatt      780
actaataaaa actcacaaat ccaccaaacc cattctctac aactcacctt catctagatt      840
tacccactcc caccgagaaa cacaagaaaa aaaatataca tatataaata tacaagacaa      900
cacatgatgc tgatgcaata tacacaacaa agtattaaat cttagatatt gtgggtctcc      960
ctttcttcta ttcatttct tattcattaa aaaaaaaa                              999
```

<210> SEQ ID NO 31
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 31

```
tacttgcctc atgtgtttgg atacgagatt actgaacgtt gtggtgtatt ttatagtcat      60
gggtttgtta attgttatca tgcttgccta cttaactagc gtaattatgt ttttttgtac     120
tacctcggaa gtagctattt tgtcgcttat tgacaacgag atactttaag atgttccaca     180
tccacgtcgt aatcggttga tcgaatggtg cctaatagat caaagttatc ctcaacaaat     240
atcgatgtgt agtatatacg tgaatatata gtagtctctt gcatgcatat catatacaac     300
ttaaatactc ttttgtttc aaaataaata atgttttagg aaaaagatta ttgtgtcaaa      360
ttaagtgttg gtctattcat ccaaacaaga agaaaaaaa atacgaattt gttttatata      420
tcattgacga acaatgttta gctaataata ataattatt tatttataaa aattaaaagt     480
tagatagttt cttaatttag gtgcatataa gttctttaac aaaaaaaaca tttaggtgca     540
taagtcttaa atatcaaata ttttggaaca gtaattttat gtataacttt tttcgtacct     600
atcttcacac cgcataaatt gccaaagtca accttttgat atttcattcc tcacaaaacc     660
atattaattt atacacctca atattgttta atagtattat catgttggct ttcgctgaat     720
ttatcaaagt gcaacatgtt ttatcttaca aaaaaataaa aagaaattca cgttgtgtga     780
tcttgagagt tgactttaa atatatcaca acttatataa atacgcagca acattccaat     840
ctctcaagaa aatctacagt tcctccaaat aataatacc tccctctaag gtttaaaact     900
atacctcatt aacacattaa gaagctagtc attacttcat ttctatattt taaataatgt     960
ttattgataa caattgcagg caactaattt tcagcaatc                            999
```

<210> SEQ ID NO 32
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 32

```
agcttatttt gttctattct atcgtatttg attcttcttt cgttttttt ttgtttgact      60 taagaaaccg attgtttata gtagtaaaca tttgttttta atgttgctcg attccagtgc     120
acatgtccag gctagacact tgtcgttata aaggttgctt tggttcaata ttgatccact     180
agagatgtta caactattgt tgacatctga gattgtgtga taagaaaata tgaaactgga     240
tttagtgaaa gttacaatat ataatcatac atcatagata ggaaataagg aaatgtcaga     300
```

-continued

| | |
|---|---|
| tatacttgaa gaatacatca aatagacaag gtccttttc ttattgtcga ctattataga | 360 |
| gccgtacaga accttttcac gtctttagta attagtacat tctccatttc ggctctctct | 420 |
| tatttttttt ccatctcttt tacttctcca aataataaca ataaaagctt cgattttgtg | 480 |
| tgtgtttgta tttacatctt gacatcgata ttcttttcat caattttta ccaaaaatgt | 540 |
| aataaaaaca aaaaaaaacc aacgctgaac acagacatgg tttctccatc cgtttatatt | 600 |
| catcgtttgt atgtttactt aacaacttat ttcaaaatag tacatatcat ggttgtgttt | 660 |
| ttaaaaaaag tatacagaac agaaaagcac atggtagaca aaataatgaa gccaaaatta | 720 |
| atacaaagaa gaagttcaac ttgtatttat taacacattt tctttccttg tcaaagacat | 780 |
| gcaaattggt tttgttttct tattcccatt ttttttttat aataaaaga agaagagtaa | 840 |
| aacaaaaaaa ctatcatttc ttcttatcgc aaaactctta tctaagcaag aaaccgacaa | 900 |
| aacctatatc tacatatatt ctcatcaaca tctcttgaga catattcatt ttggttaaag | 960 |
| caaaagattt taagagagaa aggggagaa gtgagagag | 999 |

<210> SEQ ID NO 33
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 33

| | |
|---|---|
| tacttgaggg aaacatcata tttttaaacc ttgtctcagt aagctaacac acacccttg | 60 |
| tgattactta tccatgttta tccacaagaa tgcagttgga ttgagatatt ttcttctttg | 120 |
| ttgaaatcag gcctcaaggt gttcatgtgg tctgcaaaaa aattcccaaa aataaagata | 180 |
| gtgacatctg aaatcgataa tggattagac gaagagtttc gtgttattcc ttggtatggg | 240 |
| cgggtttggg gacagatatt ttggcacaga cgaggactag gccactgtgg tcctgcagca | 300 |
| ttaggtgtcc cttccatgtc ctgcattaca ttttattgat ggattcatca ccctatctac | 360 |
| tacaacggct acacaaacta tgaagagttt tgtttactaa taaatgccca agtgaggggt | 420 |
| cgatcgaacc cgggacacgt ttttcagttt accatataga attatccttg gaacccttga | 480 |
| tactccataa aacatcacca cctctgttgt catctcatga atccaggttc aaacctagtc | 540 |
| tctctctccc tagtgggagg tatatggcca ctgggccaat gatgacaaaa tgcaaaaaaa | 600 |
| ataaaataca tttgggttca ttatctaaaa tatctcttgt gtttgtaagt tttggttgca | 660 |
| cactcgtgtg gttgaagtgt gtgtgagagg tactatacaa tacactctgc ttttgttttg | 720 |
| tacctatctc tttctcttct ccacatatcc aagactttgg ggataaagct gagatcattg | 780 |
| gttgccattt ggttgtgtag aagcaatcac ccatttgctt tatccgaggt tgataaattt | 840 |
| cctcgggttc tccttctgac acgtatgaca aattctaata gtatattcct cgtagatatt | 900 |
| acctatatat tctcaatagt tgcaggtact taaggctttg tcttggcatc ctcgtcctct | 960 |
| tcagcaaaac tcgtctctct tgcactccaa aaagcaacc | 999 |

<210> SEQ ID NO 34
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 34

-continued

```
cccatcacat gtaacatcat tgggctatcc aaaagtctaa ccaataatgt caatctataa      60
accacattaa gtagttcatt ttttttgtag tcgtgtttag cttgttaaac ctcataaaat     120
atgtttccac ttacgttaac aaaacaaata tcttcacgaa aaaaaataaa ataaaatatc     180 ttttgatac cgaaaaaata aaataaaata attttcccct tcgatcataa aatgcgtaga      240
taagagaaac tgtgtttgag gctccatttc atgttcacct accagtctac cacgtcattt     300
ctcaaagacg caaattttct aattagggat gtgctctttt tacatataga tcaatatcct    360
aaaaaaattt aagatattca tattttcgta catatatatc gagtttcccg aaaaatccat    420
aaaatgggta taatgatagt ccttttttcac ctttaataat aatttctgaa caaaattata   480
tcataataaa cttgtgatttt tatacaaaat ttatttgtat atataatttt actaaccaac   540
gtgaacgata aaaataatat tctcataaaa tgttgattaa aaattactta aaataaataa    600
ttatttagga ttatgtatta gtagtactcg aaccattttt ttagttatct gcatgaagac    660
cctaattttt cacatatatc gaaactaaaa ctttggatat acactgtaat ttgaaaacgc    720
ttggaacgga taatgtagtt acctcacaag attttgtaca tccctgacat tttatattca    780
ttaaagtgtg ttttttttctt cagaaaagaa aacactttttt tttttttgtgc ttttagttta  840 aattaacaaa aaaatggaca ccatgagatt ccactaactc atgtgtatat aacattaggg   900
aagcagtcaa ttcatttcag catccacaca cacttttgaat gctcaatcaa agcttcttca   960
tagttaaact tccacacaac gtcaaaactc gagaagaag                          999
```

<210> SEQ ID NO 35
<211> LENGTH: 999
<212> TYPE: DNA
<213> ORGANISM: Unknown
<220> FEATURE:
<223> OTHER INFORMATION: Promoter and/or promoter control element identified from Arabidopsis thaliana or Oryza sativa.

<400> SEQUENCE: 35

```
ataggaatct gcttcggtag aagattcgag agaggagagg aagcatcggt ggttttggag     60
ttccttattc ttctcttctt tccaaagttt tgtcattcgc caagattcct taaaaacttg    120
ttcacacatc ataattatgc accaataggt tataaatcat aatccaacaa gttagtcatt    180
ggctttaatt ttaaaaaatc ccataagagt aaaatctttt agaaagttaa tcaacccaca    240
catgggctag aaaaccaaaa accccacgaa cattgagatt acaagaaaca ttttttaagtc   300 ctaaatgagc ccaagagcat tgcttaatga agaagaactg atattaatta actaatatta   360
ggacacataa aaaaatacga aaacaccaat cttcatgcca caaatcaaa caaaaacgaa   420 aaaatcaatt tcatgaaat ggataaagag agagcgtaat tatcaggaat ttgattgagt  480
acggttgtta tgatgatcat tcacaattat ctttgatctt gagatttagc aatagttaat   540
tttcggatgt tttttttgtta cttgctgctc acttcttgta tgcagattaa tttataagag   600
agaccagtta caactctttc ttatttgaat aagatttat aagatgtagt gtggccatgt   660
gggtttattg catgcagctc tctgcgttgg tcccaagtcc acgacaatag agagtttctg    720
cacttcacgg tatcgtcgtc gtcacaagtt ctttaccttta tcattggcac aagttagcca   780
ccgtctttgc gcaagttagc atgttgtgct acatacgtgt catgaactga ttggtcaaat    840
ttggatatat tttattcccg tcggttatgt ttggataaaa atataaaacg gaaatttctg    900
tttcagcctt ccttggtccc aaagaaaaat acgcacacct actcccttca ttctctatcc    960
tctccactca taatatatac atctaaatgc aatctctcc                         999
```

<210> SEQ ID NO 36
<211> LENGTH: 998
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 36

```
aaattgggga gtggggagat gtttggttat attcccttct catcgatggt ctagatgtgc    60
gaggtgactc tcatggaggt aaagaacaat ggtgattttg tgaagaaccc aacgtaatgg   120
taattcctaa aaaggttaga agttttttca gcttgttgta ttgctaaaat ggggttgatg   180
tactcaacga catccaagtg tacttgagtg agcttttttg gggttgagta cctcgaccca   240
ttattcaaac taatgtaaat ggtgaatgca gcagtgactt tgttgccttt tgcaagaact   300
aaagaagaca gaaacaggtt gtaaaagaga gccaagtgtg tgtttatggt agaaagagca   360
aagtgaacga aaggtgtacc tttttgactt gttgtcactg gttttctccc acttcatccg   420
tttcatgctg catcagaaaa caacataagg aatgaatgac gtaacgcgaa gcattaggag   480
ttgcttgtaa attaatacat tgccattact aacgtaattc agtagattct aactacaaat   540
gaagtcaatg tatctatttg tctactttag ccaatgtatg ataagaccaa atagtcttct   600
cttttttcag aaactctcta ggattaaaaa gtttgtgggt gaaagaaata ttatcgtgtg   660
gatgataaga ataattgatc ttgtgttagt aaattaggaa tagatataca agtaggtttc   720
tctctaaata aaaaataaaa gagtttaaat tgcatgcgta taaagaaaaa aagtaagaag   780
aaaatatgtt ccggttaatg gttgggtgca tccgaatcga accggcgcaa accaaaaaat   840
ctaaaggaga tttgaggtga taaaaggaaa tcagacattg aaccaaaaaa acaaaagcga   900
gacggtggaa agaaaaaact ggaaaagaca gttttagccc ctcctaaaag caaagaaaaa   960
aaagataata aatagcttcg tcgtcgtgat cgacctct                           998
```

<210> SEQ ID NO 37
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 37

```
tgtccttaag actcttatag taaagctgga attatatggt tcaaggaatc gtctagtcta    60
tatacactgg tttgaacaat tgtgatatat aatatagtta ggggtatatt atatttaatc   120
tgttagataa cggttggggt acttgaagat ctgtaggagt tgacagcacg tagaggcaga   180
ggtaagaaca cttctgcatg tagtgtgtct acataataaa atatagagtg tatttttttac   240
acacaccaaa aagagagatt ataattaatg tattatgtca aagcatatat gaaggtcagc   300
ttagctagag acacgtcttt tgtttatctc tcgactaaac aacatggcgt tttaataaaa   360
tcaaaactta aaaggtccaa ttcagaacgg ccccatagta tatagtctac gttgaataaa   420
taaacctcaa gatagcgtca aactctttag tctttaccca aaaatatttt ttttttaaata   480
acgtcaaaac tctaagtctt gacctcaaca ccaatatata tttgccttct ccaatatctg   540
attttttttaa ttgtttatcc gagtcttctt ggtcttttcg aatgtttgcc cgaaccagac   600
cttcccacgt tcggtggttg gtggccgcct cggcctttgg ttgatttctg tccacatttt   660
```

```
ggtcctttc attcatgtac catgttctag ggtcatttga cttgttgacc ataaatctac    720
taaaacaggc ctaataccga tgggccgtag cccgttaata aacaagacaa tttatatttg    780
tttcacttag cttgggagcc acggatctct agaaacatcc agagaaatat caatctcccc    840
acttctccag aacattcact cactgacaat atcccacctt caacacttaa ctcctgtata    900
tagtcctccc ctgtctccag tttcgtcgca cacagttctc agataaatac taaactcact    960
gttaaaactt tctcaacaaa gcttcctgtt tctctacaa                            999
```

<210> SEQ ID NO 38
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 38

```
ttacgcggcg ctacactctt atcaaagttt gaagattttt caagagacac aacagattca     60
agattttctg gtggctaaac ttacaatgac agtacatgga ggatctccgc gaatggactt    120
ctgcaatgta ctagcgtaga acaaacactt tttgttaaag tcatcaacca acatagcata    180
gagttgttta tctgaacaga acactgaaag tcttggtttt gtttgtgttc cagtaaactg    240
tttcaaaatg aaagaaaata cttattaaca agttcggcaa aaaaaattca aacttttgtg    300
cattattata tgaaagcact tctagaaagc taccttcttc ctgctcctcc tgttcctagt    360
tttcggactc tccactcgag tgttccctct cgcttcaatc acaaacggct ttactacaga    420
catagctgat aaaagggtcg aaaaatcatg aaccaagtaa gcgaaacaga ggataataaa    480 catgaagaa gaacagagta agacgaatta ccactcac ttgttattcg aattggaaac      540
tggggataag gtttcaaacg agttccgaga atgtcagaga ctctaaactg aacagtagaa    600
agagaagtca aagcagccat gccaagtatc attcgtaaag catcgaaagt cagaacatta    660
ccctcagcgg aatttaatca aacaccttct gtgcaggaat aatctctggg ggttttatca    720
acactccaaa aaaactggaa cttttgtaaat aaaattataa atgttcgtac ctttatgcaa    780
aatttctcac agcgtaatta tctatttcct ttttgtcctt tatgaaagag gataaggttt    840
ttaaataata aatactaaat tgtttttaaa agaaactaaa aataaatgga aagtcttaag    900
cgtcgtcaat ggttctagag tcttctgcaa cttttctttc atgaaactac tgtaatcttc    960
tgctaacata tataatctca aacactatct tctccaatt                           999
```

<210> SEQ ID NO 39
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 39

```
tgaattgagt aaaatgtgtt ttcaaacagt taggtggtag aaggtaaagg taataacatc     60
atgatcttac taaagaatt gttgcatact aactatcaat attctcaaca acataatata    120
atgttttttt aggtaatttt ccatttaat tttttgtgat taaacaatta aacaactcga    180
atgatgatga taaaaaaaaa aaattaacaa ctcgaataag ttaaagtagc aatacacatg    240
tcgttcaatt caaccaataa agtaagactt atattttaa gaagttgact aatagcttaa    300
taagttggaa aacttgtgta gtttcttaat tcccacgtgc agtaagaaat aaaaatgaaa    360
```

```
aaaattatta tatccttccc actctgcgac ttttctttta ttttatcaaa tattaaaaag    420
attcatatca cagtttacac attgaaatca taaacgataa ttatgtattt tgtaataaaa    480
agttagttct gaagctcata ctttggatag tcgctagtcg ctaatatgct ccttgtaata    540
attaaagtca ctacgacgca cgtcaaagcc gatatttagg gcttaattga tgcgtgtttt    600
tcttttcata taatagtaat ataaattagt actaataaag tatgatggat ggttgagaca    660
gaaaagaaaa aagatgactg tatggtcatc attacaaaga agaatgtatt cttcatgttc    720
ttaagaataa taaaatgtca cttgtaaatc aagttggtaa gcattttgag aactttgttc    780
gatgcaacgt atgatgattt atgtagacaa aagataaaac cgtatcttca actattgcca    840
agaaaagata aaacctaatc tagtcagtct ctcaacataa atacaaccca atagccaaac    900
tgtgtccaat tcggagagaa actaaactaa aacaaaacac aaaagcccaa cataagccca    960
ataaaaccca ttttataaac agaacattac taacactca                          999

<210> SEQ ID NO 40
<211> LENGTH: 990
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 40
ttattgttga aacggatggt atccagattc atagagttat agttgttgac ctcgtaagga     60
tgaattcatt atcttcttct tcttttgcag catggaggtg atcgatggta tgactttgat    120
gatagccatg tccaccaaat cagccaagaa aagatcaaga cctcggctgc ttacgttctg    180
ttctataaac gccttgtaga ctaaagaaac tgaagcggaa aagacaagaa agtggtattt    240 gcattttgc cgggtttggc ttatttaaaa acatcattgg cttgattcta attcactaca     300
agatcaagat gaaagcagct ctgcgttgag gctaatttac agaagagaga gagagagttg    360
ggaagaagag caaaagaccg agaggacatg ttgcggggaa tttatttttat tcttacaaaa    420 attggtatct gattatttta ttaaccatat tcaattagag aatagaagaa tagagaaaag    480 ccctttgtg ggatatggtt ctaaattgtt gtttagttct tgtgtgtcag ttttggctct     540
cgtcgaccaa agaagattaa agaaacctct accttatttt aactcaattc ttttgttttt    600
gcaatgtcct ttgctttcca aaattgttag tcttacttt cactactttg atagacattg     660
cctttgcgtt tccctgatta ataagccaga gtacttaaat caaaattgac tgttttgtgc    720
atcctgcatc acgtttccaa tcagaaccat agtgttgtcg ttgtgtcatt atccgaattt    780
aagtggagac attggtaagt tatttataaa ctaattacaa tctatttttc taattatttc    840
aaataacata tttaagctct gtagcttcca ctagacggtg aagatttgaa gtgagagctc    900
tctttgcatt gctcacccac caatggatct acctacccct cttcttcttc tcctcctttt    960
aaaccctaaa agtttctctt tccttcaaca                                     990

<210> SEQ ID NO 41
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 41
```

```
tggacaatta ctcttgtgtg tatccttgga gttgctgttt catatgtaag tggacaatta      60
ctcttgtgtg tagccttgga gttttttat  ttacgttatt ttggtcagcc tttaattatt     120
ttgcaaaaaa tgtatctgtt tttgccacat gcccacataa tacatttcgc aaatttgata     180
cattatgctt tggcccttgt atattcggta aaaaaaaaag ctcaggctac tctcaaaacc     240
ggctctgagt attcgtaggc cacaatcgaa gaaaaaagt  gccgatttac atatttttca     300 tacaaaaat  taaaactgtt atgtattatt caaaagctat ttacatatgt tttactaaca     360
cgttttcaat attttcttaa tccttttcaa aatttaacta agtataatac ttttttttgtg    420 tgttatttcg ttgttttggt taagaaaaa  cgaaaaaag  agagagttat tcatccttgc     480
agataaggct agggttggtt gaataaagat gtgcatatct tataccacta gaccaaagaa     540
acagtcacaa gtaaaaggcc gaatcctttt tataaaatat aaacagacga aagctaatgc     600
ttcatgggct tggcccaagt gcaggctctc gctagtcgct acgctacaac tatcccatat     660
ttaattagtg aagagtattt tattattttg gtcaacgggc tatctttgtt gacaaaacta     720
tcccattggt aaagaaatag caaaataggc gtttcattct ctatatttaa acttgatttt     780
atgaagagtt gaatagctga accaggaaga tatttaagaa gcccgtactt cacgctttaa     840
ctgtcaatcg atagatcata ataaatgact atctatggat aggaactata actgaattca     900
gaaagaatct actactacta taaatactaa aagagtatta atacaacgga aaaaacaaaa     960
caaaaaaaag ggggaacaag ggagtttcat gttaaaaag                             999

<210> SEQ ID NO 42
<211> LENGTH: 996
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 42
ttggattttt ttttgttga  gtcagcagac catctaatct ctcttttcc  accacagcct      60 gctttctatg aagcatttgg gcttacggtt gtggaatcaa tgacttgtgc actcccaacg     120
tttgctacct gtcatggtgg acccgcagag attatcgaaa acggagtttc tgggttccac     180
attgacccat atcatccaga ccaggttgca gctaccttgg tcagcttctt tgagacctgt     240
aacaccaatc caaatcattg ggttaaaatc tctgaaggag ggctcaagcg aatctatgaa     300
aggttggccc attctccttg acaggcttaa caatacaact tgtatcgctt caacaagatg     360
atggcttaat aaggattttt gcatgtatag gtacacatgg aagaagtact cagagagact     420
gcttaccctg gctggagtct atgcattctg gaaacatgtg tctaagctcg aaggagaga      480 aacacgacgt tacctagaga tgttttactc attgaaattt cgtgatttgg ttagtgtaac     540
ccactgttat tcttttgatg tctacatcta ctttacttac attattcttt tcttcggttt     600
gcaggccaat tcaatcccgc tggcaacaga tgagaactga tcatgacagg gtaggatttt     660
atttcctgca ctttctttag atctttgtt  tgtgttatct tgaataaaaa ttgttgggtt     720
ttgtttcctt cagtggtttg attttggact tatttgtgtt aatgttgttt tggctgttct     780
cttaatatca ataacaaata aatttactgg ttggtatcta agatctaaca atagttacta     840
tttttagagg taaagacacc aaccttgtta tattggtcag agagctaaaa ccttgacttg     900
ttgggaaaac aaaactctaa tgacagaaaa tctgacatga tgccttataa ttagcctcat     960
gttctacata aatcctaaca atagcacttt gtttct                                996
```

<210> SEQ ID NO 43
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 43

| tgcaaaattg aaaaattgaa gggtgagaca aatttaaaga taatatctat taaatcctct | 60 |
| aattttaaaa atttagcaaa aattgtattt tcttatggat cagttagttc acacgtatct | 120 |
| tagttagtat caaatcatat ctaatgatta gtgataaaac tagttagata tctatatgtg | 180 |
| tctttaccat ttaacttgaa tccttcttct ttttttacgt aaacaacttg aatccttcgt | 240 |
| taatatataa atttaaagca tttttctctt aattctattg atcggtatat atttactata | 300 |
| agttttagct catatgcaat ttcaaatgat atgcttttaa attttgtcta ggtgtgatag | 360 |
| ttgtatcttt aacataaatc ttatagcaaa actatacttg atattctaaa tttatctatt | 420 |
| tgctcttgtg aacctcatat tagtctagag aaactttgaa atcctttcaa ttagttgtat | 480 |
| gtccaataca ttttactaa catttattag tcttttaat taagattatt gttagaaaaa | 540 |
| aaaagatttt ttaaaaataa ataatatgtt ttagatacaa tgtgagttag gcttcttata | 600 |
| ttttaaaaaa taaatttatt tcatacttaa aaatagtttg gaatttcaat ttatttggct | 660 |
| gaataccata aaatatgtca atttgaacct tatacccatt gactatttgg tgttagaaac | 720 |
| cctttaacaa aaaaaaacta tttggtgtta gatatcaaaa taaaaaaaaa ttaaccattg | 780 |
| gtttcttata ttgaattgga tattgttaca tgtattaaag ttttttttggt ttaatttga | 840 |
| aacgttgata gaaactatta agtttaagtt tggtagtata tttatttgtg gaaaatttaa | 900 |
| ttgccattaa atataacgtc aactttttt gtttttttt gagaagttac gttgtgattt | 960 |
| tgatttccta tataaaagtt agattacgtc attttttaa | 999 |

<210> SEQ ID NO 44
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 44

| tattttata aattatctta gtaaaagtat gtattttcta atagatctgt tagttcatac | 60 |
| atatcttaat tagtgttaaa ttagatctaa tgattagtga taaagttttt agatatcgat | 120 |
| ataggtgtct ttaccattta acttgaatcc tttgttaatg taaaattta aaatattttg | 180 |
| ctttgattct acttattggt atataatttt aacatatcaa tccaatgcca ctcttaaatt | 240 |
| atcatgtact tttcgatata tgttatgact cacttgttat gaaacgatgg attttcacca | 300 |
| attttggtta tttattaact agaagtttta gctctagtgc aattttaaat aatatgcttt | 360 |
| taaaattggt ctagttataa tagttgtatc tataacataa aacttataac aaaactatac | 420 |
| ttgatattca aaattattg attttctctt gtgaacttca tattagccta gagaaacttt | 480 |
| gaaacctttt caataaattg tatgtcgaat aaagttttac aaacatttat tagccatttc | 540 |
| gattaagact attgtgagca aaagttttt ttattataaa ataaataatt tgtttaagat | 600 |
| aaattgtgaa ttaggcttct tatatttta aaattatata aatttatact gaaaaattgt | 660 |
| tagaattttc aaattttaaa tttatttggc ttaagaacat aaatatgtca atttgaacct | 720 |

| | |
|---|---|
| tatacccact aaatattcca tgttagatat ctaaataaaa gaaaattaac tattgatttc | 780 |
| ttatattgaa ttggatattg ttacttgtat ttatgttttt tgtttcattt ttaaacgttg | 840 |
| ataaaatcat taaactaaag ttttgtagta tatttatttg tcgaaaattt attcccatta | 900 |
| aatataacgt taaatttatt tgtctttatt aaaaaagtta ctttgtgatt ttgatttcct | 960 |
| atataaaatt tagataactt caattttcaa ataaaaaat | 999 |

<210> SEQ ID NO 45
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 45

| | |
|---|---|
| ttagctgaac caggaaattg atctcttata ccagtttccg ggtttagatt ggtttgatgg | 60 |
| cgatttgatt aaaccccga aattttatgt cgtagttgtg catagtatta ttattctttg | 120 |
| cggacaatag acgtatcggg accaagttct gtagcaaaat tgtataagct taagtttgat | 180 |
| gaaatttaaa ggtaatcact aaaacccaaa tgggacaata aaccggtgaa gatttagagt | 240 |
| ttttaatttt gactcatgaa tctggagaaa gagccctcgt taaaggagt gaatcaatcc | 300 |
| atagggaaa aagttttgtc ttttttaaaa ctaaagaacc aaaccttaat agaagcagct | 360 |
| caatgtgtga caactttcca ctggcactaa gataaagtga ctagcgatga gtgcaattat | 420 |
| tgaaatagta gatggtaaat attacataca agagtaaaaa tatctttatg tcaatgctta | 480 |
| attcagtgtt tctggttaac aagagaaact tctctaactt tcgtaattgg gtcttataaa | 540 |
| attttatgca attatgattt tacccttta ctactttca ttagctttca cgaatctatt | 600 |
| ttgacaagag aaatcattag aggtaaacat gcttttggt caagggcctt aacagttcca | 660 |
| ccaatcaagc tcaaaagttg tacttaaccg acatcttctg tgaaaacata taattacatg | 720 |
| tacaaatcaa aactaccta tgaaataaat agaaatattg cagttcattt ctaatttaac | 780 |
| ctcttcaact tttaaaacta tttacatttc tttatgtcat ttctagtcat tttgatgcaa | 840 |
| attgtaccat ttatggatta tcttcacaaa ttttaagtt ggtgaaaact ttttggtggg | 900 |
| tagttaaaac ttgaaataga aatttacttt accaaaataa actaatgaaa agtaatcact | 960 |
| ccactcccta aataagatt tccaacgttc ccactaagc | 999 |

<210> SEQ ID NO 46
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 46

| | |
|---|---|
| cctactttag gcttaaacaa gaagaaaata tgactgctaa gtcatatttt tcaactctca | 60 |
| tgagcaaccg taaagttgca ccgcaatatc caacaaatga cattcgtgtt atctacaatc | 120 |
| taatgttgaa aatttggctc atctaataaa ggagacaaaa gttatatctc tttcacacac | 180 |
| acgttaatgg aagtgtaaag gcggtgagag tgtgggagag acttggggaa caagaagaag | 240 |
| gacgcggtca aaaagtgacg gtgggctacg gcttttcttg gtagcagttg gaaattccat | 300 |
| taatgactta aaaagtgtaa atcttatctt ctttttattt tgtgatttga tatgcacatt | 360 |

| catttcatga aaatatttgt atagtttgat gatcatacga caaacttata gggttcacaa | 420 |
| agtagatgca atagttgcat acctctgttt aaatgttctt gttaatatta tacttgatga | 480 |
| tgaaactcgt gaatgttatt caaaatgtcc atgtaataca agatcatgca ctataataag | 540 |
| taatctatca atttcagcac aacaattttg acaaaaagta aaaataaaat aaaataaact | 600 |
| gatatcatat ttccgaatta tatgtaaacg ttttctgttt ctcaatggtc tctttcactc | 660 |
| ttgtgttttc taatatttca tttaaaccta tttctaaact aagcacatct ttgttgattg | 720 |
| attgcatttc aaccaaaatc gataaccgaa tcattgttt tttatgtttt atttcagctt | 780 |
| accacacacg tttagaattt taaaaataaa acaaaaaaaa gttaactcgt tacaaatgaa | 840 |
| aatgatattt ttaattggac tcgatggaaa ggaccaattt attcaacact attgtttagt | 900 |
| ccgaacactt gccgcgtaag ttttccaact cccccccattg acctttcgca ctttcacaaa | 960 |
| ctccgtatat atataatgga tacactctct ctttgatct | 999 |

<210> SEQ ID NO 47
<211> LENGTH: 999
<212> TYPE: DNA
<213> ORGANISM: Unknown
<220> FEATURE:
<223> OTHER INFORMATION: Promoter and/or promoter control element identified from Arabidopsis thaliana or Oryza sativa.

<400> SEQUENCE: 47

| tgtgtgtcct aaatagtttc ttttaaaat ttgtaaatac caagacgcgt atttaagagt | 60 |
| attttgaaaa gatatttgat tataaaaaga aagaaaaaga gaaggctgag gattaactgc | 120 |
| aacgtctacc gttggaaaag aaaaacgatc agaaaacaca gaattaata aaaagagaga | 180 |
| aaaaaaaata gagtatgaga gatgcacatg ggtgcctgca aaaaaaggt agaagaaatt | 240 |
| tgtctgaaag tgtcacaggc acactctctc gaaccacatt taacaacact ccaaacactc | 300 |
| ttcttctact ttgtaccctt cagtacatta ctctttccaa agtccgtgat ttacgctctt | 360 |
| cgatgacacc tctcaacaga gagagactac atgtgtacat tttcttctac cattaaattt | 420 |
| tgaagatttt cgatgattca atttagtata tatatgaag ataaaatttt cattgtcttt | 480 |
| ctacatgata gtaacggttt tagaagggtg gttatcactt atagtatttg agttaagaaa | 540 |
| tataaaaata tacgtgactg ttttttccttg taaactattt ttaggcccctt attttttattc | 600 |
| aagtagtcac atacgtgttt gaagtgtatt taactaagaa aaagaaagta ggaaatgaaa | 660 |
| aggatatagt atttatggtg taatcttggt aaggaccagg agatcagaag gggccacaat | 720 |
| gtcacaaaga ggaccaacaa tgaaattaaa tcctcagctg gcctttaaca ttttggctcc | 780 |
| caccatctcc ttccacacat atgcacatgt cttcatgtct ctctctctct atacgttacc | 840 |
| tacacaaata tgtacagaca aatagcccat tacaaaatct ttatttataa atatatactc | 900 |
| ctcaactccc tcaatatcca cccatctcct tctccataac tctctctctc tctccctaaa | 960 |
| cacaaccaaa gacttttatc tctcaggaac cccaaaaac | 999 |

<210> SEQ ID NO 48
<211> LENGTH: 999
<212> TYPE: DNA
<213> ORGANISM: Unknown
<220> FEATURE:
<223> OTHER INFORMATION: Promoter and/or promoter control element identified from Arabidopsis thaliana or Oryza sativa.

<400> SEQUENCE: 48

| tcctcctact gtctgctacg tcaacaagtg gattgcaatc agacggtgat tgtgtctctt | 60 |

```
ttcattctct ctcttttact aatttctctg ataattaaac tgagaatgta tattaagaaa      120
aaaaaacaaa aacaagagag gaattttcat acacactaac ttaagactct tgtaagtttt      180
tcccaaatat ggattttcta gtataaatat gagttcatta gtttcaccaa gcctacaagc      240
atctctccat ctcaaatcat attcacctaa aaatcaggtc ccctctcttt atatctctaa      300
cattcttata tcagatcata ttttttggat ttcttgttaa gtaacaccaa tcttttaaaa      360
gtgttttcag gttaatataa aagaataatg atgttttcgg tgacggttgc gatccttgtt      420
tgtcttattg gctacattta ccgatcattt aagcctccac caccgcgaat ctgcggccat      480
cctaacggtc ctccggttac ttctccgaga atcaagctca gtgatggaag atatcttgct      540
tatagagaat ctggggttga tagagacaat gctaactaca agatcattgt cgttcatggc      600
ttcaacagct ccaaagacac tgaatttccc atccctaagg ttcactctta ttctcaatat      660
taactctcgt acatgtcaca tgcccatttt caccatttta gatatacagt tttgatactt      720
tactttgcat ttattttgct atatgtaatt gaggatattg ttttaatttc tttgggtttt      780
ttttttggct aaatgagaat tcagtgtctt tggttcttaa aaaaaaagta tttgttaatg      840
gtaaacgcta aacgctattt gagtttatgt tttttcaaga actgaaaacg ttttattgaa      900
aatatacact tttttgcta tttatagaaa ggcatatcac atctagacgc aaacgcaaaa       960
ttgacttttg aagcaaccac aatcttaaat gcaatgaaa                             999

<210> SEQ ID NO 49
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 49
aactaattag gtcgttaatt gtccaagggt ttttcatagt tgatatagtt ctgttcaaat       60
atagccatcc ttaatcgatt catgggatcg taaattacta cttcgagtgt tgtaaaaaaa      120
aatgaaactt ctacattaca aactcgaatt taatgcatct ggagtgatac tataaaagta      180
gggatgctct caggtcgcat ttgagagaca cagaaatgat tttaatggaa ttaatatatt      240
ttcagttttt cacaaaaaaa aattgtgttt ataacaactg cagattcaat gctgatttta      300
tgagtctcac ctatagaatt tatatttcta tattcataga ggcagtatag gtgttgaccc      360
aacatcgaaa gaacacttcg taaaaaattc tttggaacaa ggctgaaaat ttactcccaa      420
atttagctat ccgatgaaga taaatcattt accgtttatt aaagaattat cgagattta       480 gtccaaacca aaagagatta tgagcctaag attttgaatt tgtattggta aaagaaattg      540
aacgaaaatt tcagaaaaaa atattaataa attgaacgat agagttcact tactacatag      600
tcaactagtg cctagctata atagtttcaa aagacaaaaa aaaacaaaat cggttaacta      660
cttccgtgac ataattctca ttttgatttt tgaatccagt ctaatttgaa aagtatattc      720
aaaatcttta aatccattaa tgataacttt tataatacgt tgcacacgc aattgtatat       780 acaatattct tgaattttaa atgtaaattc tagaatatat tgcgatcacc acactaatca      840
aaatctttgg gacaacttga acccacattt gacttttctt ggtcaaatat tttggcatca      900
tgcatgatct tctctataaa aaccaaaagg cctcaacgac attcataaac tcagtcatta      960
tatttatttt tgttgtattt caacgttcaa tctctgaaa                             999
```

<210> SEQ ID NO 50
<211> LENGTH: 1823
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 50

| | | | | | |
|---|---|---|---|---|---|
| gtctcttaaa | aaggatgaac | aaacacgaaa | ctggtggatt | atacaaatgt | cgccttatac | 60 |
| atatatcggt | tattggccaa | aagagctatt | ttaccttatg | gataatggtg | ctactatggt | 120 |
| tggagttgga | ggtgtagttc | aggcttcacc | ttctggttta | agccctccaa | tgggtaatgg | 180 |
| taaatttccg | gcaaaaggtc | ctttgagatc | agccatgttt | tccaatgttg | atgtcttata | 240 |
| ttccaagtat | gagaaaggta | aaataaatgc | gtttcctata | gtggagttgc | tagatagtag | 300 |
| tagatgttat | gggctacgaa | ttggtaagag | agttcgattt | tggactagtc | cactcggata | 360 |
| cttttttcaat | tatggtggtc | ctggaggaat | ctcttgtgga | gtttgatatt | tgcgagtata | 420 |
| atctttgaac | ttgtgtagat | tgtacccaaa | accgaaaaca | tatcctatat | aaatttcatt | 480 |
| atgagagtaa | aattgtttgt | tttatgtatc | atttctcaac | tgtgattgag | ttgactattg | 540 |
| aaaacatatc | ttagataagt | ttcgttatga | gagttaatga | tgattgatga | catacacact | 600 |
| ccttatgat | ggtgattcaa | cgttttggag | aaaatttatt | tataatctct | cataaattct | 660 |
| ccgttattag | ttgaataaaa | tcttaaatgt | ctcctttaac | catagcaaac | caacttaaaa | 720 |
| atttagattt | taaagttaag | atggatattg | tgattcaacg | attaattatc | gtaatgcata | 780 |
| ttgattatgt | aaaataaaat | ctaactaccg | gaatttattc | aataactcca | ttgtgtgact | 840 |
| gcatttaaat | atatgtttta | tgtcccatta | attaggctgt | aatttcgatt | tatcaattta | 900 |
| tatactagta | ttaatttaat | tccatagatt | tatcaaagcc | aactcatgac | ggctagggtt | 960 |
| ttccgtcacc | ttttcgatca | tcaagagagt | ttttttataa | aaaaatttat | acaattatac | 1020 |
| aatttcttaa | ccaaacaaca | cataattata | agctatttaa | catttcaaat | tgaaaaaaaa | 1080 |
| aatgtatgag | aattttgtgg | atccattttt | gtaattcttt | gttgggtaaa | ttcacaacca | 1140 |
| aaaaaataga | aaggcccaaa | acgcgtaagg | gcaaattagt | aaaagtagaa | ccacaaagag | 1200 |
| aaagcgaaaa | ccctagacac | ctcgtagcta | taagtaccct | cgagtcgacc | aggattaggg | 1260 |
| tgcgctctca | tatttctcac | attttcgtag | ccgcaagact | cctttcagat | tcttacttgc | 1320 |
| aggttagata | ttttctctct | ttagtgtctc | cgatcttcat | cttccttatga | ttattgtagc | 1380 |
| tgtttagggt | ttagattctt | agtttttagct | ctatattgac | tgtgattatc | gcttattctt | 1440 |
| tgctgttgtt | atactgcttt | tgattctcta | gctttagatc | cgtttactcg | tcgatcaata | 1500 |
| ttgttccctat | tgagtctgat | gtataatcct | ctgattaatt | gatagcgttt | agttttgata | 1560 |
| tcgtcttcgc | atgttttta | tcatgtcgat | ctgtatctgc | tctggttata | gttgattctg | 1620 |
| atgtatttgg | ttggtgatgt | tccttagatt | tgatatacct | gttgtctcgt | ggtttgatat | 1680 |
| gatagctcaa | ctggtgatat | gtggttttgt | ttcagtggat | ctgtgtttga | ttatattgtt | 1740 |
| gacgttttgg | ttgttgtata | gttgatggtt | gatgtatttt | tgttgattct | gatgtttcga | 1800 |
| tttttgtttt | tgttttgaca | gct | | | | 1823 |

<210> SEQ ID NO 51
<211> LENGTH: 1539
<212> TYPE: DNA
<213> ORGANISM: Unknown
<220> FEATURE:
<223> OTHER INFORMATION: Promoter and/or promoter control element -continued identified from Arabidopsis thaliana or Oryza sativa.

<400> SEQUENCE: 51

| | | | | | |
|---|---|---|---|---|---|
| aagcttatgt | caaaaatatt | taattaaaat | atatgtaatt | tatatgttga | ttgagttatg | 60 |
| agtatcaagt | aaaaacccta | atccgttatt | aaaatatcaa | tgattataac | gtatttataa | 120 |
| acgaaaaaaa | aaagaacatc | tagaattttc | gatatttgat | cctcaagtta | aacttggaaa | 180 |
| aatttggatg | tatgaaatat | tttgtcgtcc | acttatacaa | taaagtatga | aacatggatg | 240 |
| catgaaggct | agacatccaa | tgtctaaaaa | tactatatat | aatgcttttg | gtagggtctt | 300 |
| ttctttatca | tgtctcactt | ctgtttctat | ccctcattt | aaatagccaa | tataatttca | 360 |
| ctctttacta | taaaattatt | atataaacat | cattttgatt | gaactaccta | aaaggaagaa | 420 |
| acgtatagga | attttggag | cctcaagatt | gtaataatgt | ctcatagttt | gacttgcaaa | 480 |
| agctaaatta | aacgcctaaa | tcattaccat | taaataaatg | aacttttgta | cgcaattgat | 540 |
| tcagacacaa | ggaccgacca | attcgaaaac | aatgaatgga | tatgattcat | ccttatgaaa | 600 |
| gcttgacaac | aaactcggtt | ttggctggtt | aacctagact | cggtttattt | aaaccagaca | 660 |
| ataaatttctt | tcgtcgtcgt | tttattgaa | taggtgcgtc | aaaaataaaa | gctgaaattc | 720 |
| ttggttgcaa | aagcccaaca | ggcctgtgga | gatagctttt | tagattgatt | aaatgggccg | 780 |
| aattgggctg | acacatgacg | agaatgtggc | tatagaaatt | gttagtgaga | gggtccgggt | 840 |
| ccaaaaatgt | tgcagaagtg | atatagtatt | tatttaatta | aaaacatatt | attcgacgta | 900 |
| tttttaacgc | tcactggatt | tataagtaga | gattttttgt | gtctcacaaa | aacaaaaaaa | 960 |
| tcatcgtgaa | acgttcgaag | gccatttttct | ttggacgacc | atcggcgtta | aggagagagc | 1020 |
| ttagatctcg | tgccgtcgtg | cgacgttgtt | ttccggtacg | tttattcctg | ttgattcctt | 1080 |
| ctctgtctct | ctcgattcac | tgctacttct | gtttggattc | ctttcgcgcg | atctctggat | 1140 |
| ccgtgcgtta | ttcattggct | cgtcgttttc | agatctgttg | cgtttcttct | gttttctgtt | 1200 |
| atgagtggat | gcgttttctt | gtgattcgct | tgtttgtaat | gctggatctg | tatctgcgtc | 1260 |
| gtgggaattc | aaagtgatag | tagttgatat | ttttccaga | tcaggcatgt | tctcgtataa | 1320 |
| tcaggtctaa | tggttgatga | ttctgcggaa | ttatagatct | aagatcttga | ttgatttaga | 1380 |
| tttgaggata | tgaatgagat | tcgtaggtcc | acaaaggtct | tgttatctct | gctgctagat | 1440 |
| agatgattat | ccaattgcgt | ttcgtagtta | tttttatgga | ttcaaggaat | tgcgtgtaat | 1500 |
| tgagagttttt | actctgtttt | gtgaacaggc | ttgatcaaa | | | 1539 |

<210> SEQ ID NO 52
<211> LENGTH: 1954
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 52

| | | | | | |
|---|---|---|---|---|---|
| gtgggtaaaa | gtatccttct | ttgtgcattt | ggtattttta | agcatgtaat | aagaaaaacc | 60 |
| aaaatagacg | gctggtattt | aataaaagga | gactaatgta | tgtatagtat | atgatttgtg | 120 |
| tggaatataa | taaagttgta | aaatatagat | gtgaagcgag | tatctatctt | ttgactttca | 180 |
| aaggtgatcg | atcgtgttct | ttgtgatagt | tttggtcgtc | ggtctacaag | tcaacaacca | 240 |
| ccttgaagtt | ttcgcgtctc | ggtttcctct | tcgcatctgg | tatccaatag | catacatata | 300 |
| ccagtgcgga | aaatggcgaa | gactagtggg | cttgaaccat | aaggtttggc | cccaatacgg | 360 |

```
attccaaaca acaagcctag cgcagtctttt tgggatgcat aagactaaac tgtcgcagtg    420
atagacgtaa gatatatcga cttgattgga atcgtctaag ctaataagtt taccttgacc    480
gtttatagtt gcgtcaacgt ccttatggag attgatgccc atcaaataaa cctgaaaatc    540
catcaccatg accaccataa actcccttgc tgccgctgct ttggcttgag caaggtgttt    600
ccttgtaaag ctccgatctt tggataaagt gttccacttt ttgcaagtag ctctgacccc    660
tctcagagat gtcaccggaa tcttagacag aacctcctct gccaaatcac ttggaagatc    720
ggacaatgtc atcattttg caggtaattt ctccttcgtt gctgctttgg cttgagcacg    780
gtgcttcttt gtaaagctcc gatctttgga taagagcgga tcggaatcct ctaggaggtg    840
ccagtccctt gacctattaa tttatagaag gttttagtgt attttgttcc aatttcttct    900
ctaacttaac aaataacaac tgcctcatag tcatgggctt caaatttat cgcttggtgt    960 atttcgttat ttgcaaggcc ttggcccatt ttgagcccaa taactaaatc tagccttttc   1020
agaccggaca tgaacttcgc atattggcgt aactgtgcag ttttaccttt ttcggatcag   1080
acaagatcag atttagacca cccaacaata gtcagtcata tttgacaacc taagctagcc   1140
gacactacta aaaagcaaac aaaagaagaa ttctatgttg tcattttacc ggtggcaagt   1200
ggacccttct ataaaagagt aaagagacag cctgtgtgtg tataatctct aattatgttc   1260
accgacacaa tcacacaaac ccttctctaa tcacacaact tcttcatgat ttacgacatt   1320
aattatcatt aactctttaa attcacttta catgctcaaa aatatctaat ttgcagcatt   1380
aatttgagta ccgataacta ttattataat cgtcgtgatt cgcaatcttc ttcattagat   1440
gctgtcaagt tgtactcgca cgcggtggtc cagtgaagca aatccaacgg tttaaaacct   1500
tcttacattt ctagatctaa tctgaaccgt cagatatcta gatctcattg tctgaacaca   1560
gttagatgaa actgggaatg aatctggacg aaattacgat cttacaccaa ccccctcgac   1620
gagctcgtat atataaagct tatacgctcc tccttcacct tcgtactact actaccacca   1680
catttcttta gctcaaccttt cattactaat ctccttttaa ggtatgttca cttttcttcg   1740
attcatactt tctcaagatt cctgcatttc tgtagaattt gaaccaagtg tcgattttttg   1800 tttgagagaa gtgttgattt atagatctgg ttattgaatc tagattccaa ttttttaattg   1860 attcgagttt gttatgtgtg tttatactac ttctcattga tcttgtttga tttctctgct   1920
ctgtattagg tttctttcgt gaatcagatc ggaa                                1954
```

<210> SEQ ID NO 53
<211> LENGTH: 999
<212> TYPE: DNA
<213> ORGANISM: Unknown
<220> FEATURE:
<223> OTHER INFORMATION: Promoter and/or promoter control element
    identified from Arabidopsis thaliana or Oryza sativa.

<400> SEQUENCE: 53

```
tagaaacctc aacttgaata taatagtttg tttgtttgct tgaagttaat ctctctcttt     60
tttatcagct aaagctgcat ttataaaaat tctagtttaa cttttaccat ttgctataat    120
ttagagattt taacaagaaa tctggcctag tccgcaaaac ttatagaata aatcaaacat    180
tcttcaatat tttacacatc cacaataccc aatccaagaa atggattgca gttgcaccag    240
agattacatg tctcgtttta gtttgctagt cactcaaact cacaaagcat aaattgtaat    300
agaaaataga actttattta aatctgaaga aagatatata taaaaaaaaa aaaaaagaa    360 gaagcaggct ccagttttga tgggagaaga aaagagagct ggcaacagct attcactgat    420
```

```
agaccgatca ctctcttctg tcccgcactc ttttcttctt ttgtttcttt cttttcgaca    480
gctttcattt ttcctccatt tttaaatttg aattatttta cagtcataaa agtacttcaa    540
acgtatatgt aaataacgag caacaaaaca attaactaca acaaaactag ttctagctaa    600
gagaattagt tagaaatttt tattataata gttagtatat gtttattcat aacacaatta    660
attaacacac aaaatacatg taatttcctc tataccctct tcacatataa ttagagtagt    720
gctttaattt aagattaatt atcgatttac atcattaatg atcatctagt cttacacaga    780
gagtttcagt atctgcatga gattatataa aggaatgtat tcatgttttt acttcttttt    840
attcatggtt aaggatgata cattataatt ataaatccat aatctatgaa ctcaactatt    900
ctttataaaa aaggaattaa attctgaaaa taaacaactg tagttggctt cccaaggctg    960
ctgcttcacc tataaatacc ctatcctctt tgaaaactc                          999

<210> SEQ ID NO 54
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 54
ataggcccta cttctaatta aagcccattt acttctctcc ttgtcttctt attcctcttt     60
tctccccatc acgtgacgac gatgctataa acgccgtcgg attatataac tggtgccgtt    120
gacaagacgg cgacagaaga aagaaagaag aaaccacagg ctctagggaa cgtaacgtta    180
tgtcctgtct atagcattta taacggtcag atcaacgccg tttagataaa gatctgtcaa    240
tgttaaagaa gagatgcatc tctacaccgt taaatttaaa acgccgtgaa cctcttatct    300
attgattttt gtttgatgaa gccaaaacaa atcgtgtcag aagacttatc agagaagaag    360
aaaacgacga cgttcccgtt tctccatgtc taataagtgt agtagtggcg gctactaaaa    420
actctaaagt ttgactccag taaaactgcc tttctagtgt aattccagtg attttagagt    480
ttgaatagtg tgtgaccaaa tttgaaagta caatctcagc aatattattg atcactcgtt    540
ataaaagaat cgaatgtaaa aatagccaat gagagactga gacgtatgtg tttgaccata    600
agtcgtatag tttgtatcta tctacctgca agatcagcag atggttctct gatcaattgt    660
accttaatta tcttttattt tcgtaaaatt tctctattca caaatgataa atctacttaa    720
gacagtaacc ataacaagat ttacaagata atttgaaaaa tgaacacata aaagtatttt    780
ggcgcattat ttttaataat aacaatattt atgtaaagtc acataaaagt atatattcgc    840
tcacaaagtc ttacggtatt tagaacagta gtaccacatc gattctcttc atcttcttct    900
tcataatatg ccattgttca tgtctctgtg tcctatcgca taacactcac gctatcttat    960
tattttctct cgctctttct cactgagagg acactaaaa                          999

<210> SEQ ID NO 55
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 55
aagcggcaat ttagtaagaa gtactcaaag tatcatttac caaaagtata tggttttggg     60
aagagttgtt agggatgtat tctttctaaa cagatgatat gacgatgttc ttgaaaacta    120
```

```
atgttaaaga cggaatctct ggcatcttca ctcgggagat atattaaacc gttgattgta    180
gttagccatg tacttagctt agtgcacaaa taatctgctg caagaaatct ttttctatta    240
taatatctct catttaaaca ttagaacata ttgtttaact tgttcttcta gaaataaaac    300
tgctaatttc ttatggtaaa ctattttcct ttagattgca caatcgaact cgaaaatcta    360
gtggagacta tgtgactatg tttatatata tgaaacctaa atcaaattat cccaataatt    420
gggagacaca aagaaaaat tacgaaagaa acaggaaat caaatcaaaa gataaagaga     480
aggtaaaaaa aggcaagaag cactaatgtt taatatttat agttttctcc attaaagaaa    540
aagcgatgat gtgtgttctc atcttttgtg aaagtatata tattgctttt gcttttctca    600
aaagcaaaag actcatccaa caagaacaaa aaaaaaaact aaagctcaat ccaaaagacg    660
aagaatgcat tggatactac aacttctttt tcactttct ttcaaattta caattatgat    720
tttcacaata cagtttattc aaaataaat aaaaaaacga ggcatgaaaa taatgattat    780
cctcttcact tattaagcca ctcactataa gcagagcaac tccagaacat agtgagcccc    840
caaaacatta aagcatgatg atgtctaatg atgatgatct tcttcgttcc atttctctaa    900 attttttggga tttctgcgaa gacccttctt ctctttctct tctctgaact tcaagattcg    960
tgtcggacaa attttttgttt ttattttttct gatgttaca                          999
```

<210> SEQ ID NO 56
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 56

```
tagtttttga tttaatctac gttttttctta atcataaatg ggtaattatt agtttttgca     60
aaatcaaaat ccaaaaattg ttctaaacac tgcaaccatt taaggcctat atcactcaga    120
aaatttctgg tgggagaact aatcgtttgt cctttctaaa tctcacatat tagaatttag    180
aattagtgtg ctacataaaa atattagttc agctcggaac aactattttt tggtaaaaca    240
gagaacttaa acaaatgcat tatttttatca acatgcattt tgaattgaat ataaaatttc    300
ataattgtaa agacataaat tacataaaat tttacatgaa aaaatagata tagaaagaaa    360
atgaaactaa ctgatgatat gctctctaaa ttttttaatc tcataacaag aattcaaatt    420
aattagttca tattttttggt taatataaca tttacctgtc taagttggaa cttccatttt    480
ttttctgttt tgtttagtca gtattcttaa tgtgaaacgg aaagttgaat ttattcaaac    540
ttaaattcaa tagcattaat taaaggcgaa agctattatc tctacatgtg gttcaaacta    600
gacatccaat ttaattagct tattgacgtt gaaatgtttt ccaaaactac tatagtttgg    660
caatttgaaa gatgcatcag aactactcag acaggtaaaa gtagaacctc tagctgtgtg    720
aattgtatgt tagtccataa agaacatctt gtaaacttca tacttaagat atatattaca    780
atatatactt gaatggtaga taaaaacgat tagtctgatt gctagcatac tcacaactat    840
ttggaaatga gtaagatatt ggcatctaga gttactacta tggagacaaa agtcgaataa    900
aagagacctc acgtgaaaat gttacgagct agtaactaaa gcatttacac taacggtaaa    960
aaaagtatct ataaatgttt acacaaggta gtagtcatt                           999
```

<210> SEQ ID NO 57
<211> LENGTH: 999

```
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 57
agtttaatta tttgttatct atccaatcaa ttttttttct aaactgtttg gaccaatgta    60
cgtacgtacc atccttttg attttttttg taaactaaat tttcgaatta gcaggttctt    120
aataattgaa cgaagaaaat aagaataga ggtagacacc tgtagtattt tcttggtcag    180
accaataatt tataattcaa cgtcaaagaa gaagaaaaat ataaaccatt atttcattat    240
gacttacgta taccaaaata cacaaattaa atgtataatt gtgaggcatt ttatatgcgg    300
gaaaaaataa aataaaaaga atattaatat ttcttttgaa aattgtaaag cattttgacc    360
cacttgtgat atatatatat atatagatat atatagagag agagattaaa acattgatgg    420
ctagctatag agtctatggc agggtcatga tcacctgtct tctgatctct gaagagatac    480
caatctgatt ttttctcttc ctaggtttaa tttttatttta ccatttttata attctttatt    540
tttgcctgta gtacaattta cagacccata ctaaaagaaa aattaaattt tgtcaaagta    600
caaaacaaag agagaggtga agccacacaa tctcttttct tctctctctc tctgttatat    660
ctcttctgtt taattctttt attcttcttc gtctatcttc tcctataatc tcttctctct    720
ccctcttcac ctaaagaata agaagaaaaa taattcacat ctttatgcaa actactttct    780
tgtagggttt taggagctat ctctattgtc ttggttctga tacaaagttt tgtaatttc    840
atggtatgag aagatttgcc tttctatttt gtttattggt tcttttaac ttttcttgg    900
agatgggttc ttgtagatct taatgaaact tctgttttg tcccaaaaag agttttcttt    960
tttcttctct tcttttggg ttttcaattc ttgagagac                          999

<210> SEQ ID NO 58
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 58
ttttgtttct aatagtttga tgtttatatc aacattatta tttactttca tttgttaccg    60
atagaaagag gagaaaattg ttgacaaaaa caaagaaaaa agtaaaatta atattattaa    120
attaataaaa ataacaaact gtaaaagcta ttttttaaaaa ttttcttgt aaaacatcta    180
aaaattattc ttgtagaaac agaggaatat cattgaagat aatagtgtga aattatatat    240
atatatagaa atatataaag taggatttt ttctgtatac aaatatacgt ttccaattt    300
atcaaaaact gtaaagattt ttttctttgt cagtacctgc taaacttgtt aattttttta    360
ttaaaaaaaaa atcaaattac aattcttcta taatcattt aaattccatt tctttatacc    420
acaaagatt atattgcctt tatcgtcttt ggtatgtatg cgtgaatata tttatttatt    480
ttctttctt tcattttctt tttaaagaac tttataaatg aaataaggaa caaacaatat    540
acacatgtac taacgtatat aaataatatc atcaatatct atccaaaact tggatttcat    600
ggttgacgtg gcccaaccaa aatctcaagt tctctgcgga tgacgaacca tctcaccatc    660
tcttttttc tctctcttt tttttttaa tatcatcagc acggttacat aaaattcgtg    720
atccatgaag ttggctttct tgtcgttta cttcatcacc ccatttttt aaagtctcca    780
```

```
tctttatact tcttcaactc tccaccacca ccattgtcac caccacattt aaacacacac    840
tttcacttgt agtgggattc gaaagtgcgt tttattcatt tgttttactg tttttgataa    900
cctcaaaatt tgcctaaatt ttattctcta taaatccttta tatgttttac ttacattcct   960
aaagttttca actttcttga gcttcaaaaa gtacctcca                            999
```

<210> SEQ ID NO 59
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 59

```
ataaaattat ctataaatca ttaaatcttt gatgagaaat atccaatcta ctaatgtata     60
tcgatgattt aaatgaaatt acttatttga acacaaaaat aaatgaattt actaataaat    120
aaatagcgta gttggagcaa gtggctaaaa aaattacaaa tctagtttcc attctcagcg    180
tcggctgctt ggaacgtcac cgttttctgg aaaacgcaat cttctcccct ccgtgacgtc    240
tcaccggaat tttctcgctt ttgtctactc tcctccatct ccgaggttct ccaagctcag    300
ctcctcttcc catcattcat ccgaccgcct tatccggtca gatcctttac gtatttctat    360
tttcctgatc gtcgattttt gagaaatgta aaaacagatc gtataaggcc tcgaagtttt    420
taatttgaaa gtggtatcga aattttttgg tctttgatta ggttagggca ccgtagctct    480
gggtattgaa tttgtagggt tttcctctgg ttattggtct ttggagcttg gtaatttctg    540
ctgaattgat tgatcccttt tccatctttt gaagtaaagt ctcgagcttt cgtgtctcga    600
tgtagatgaa ttctattttg aatatgagat ttgataagac gtcaattgct gataatttgg    660
agtctttgtg tctgaatttg ttcatatgaa gttttctgag ggatgtgaat tttattgtct    720
gctaattttg aaacgttcct tttggaattt ggtttgtgag gagtcctaga tcttttttctg   780 tgaagtttct tgcttgtaag tttttctggat cacttgattg agtctagaat ctagatagat   840
tacatgtacg gtttgattcc tttggctgat tttccaaagt tttgttcaaa tttcaggaga    900
actacaaaga ggaaaccaag attgttttgt tttgttagac tctacccctt ttccgattca    960
catggtaagg acattgaggt agagaataat actaaaaag                            999
```

<210> SEQ ID NO 60
<211> LENGTH: 998
<212> TYPE: DNA
<213> ORGANISM: Unknown
<220> FEATURE:
<223> OTHER INFORMATION: Promoter and/or promoter control element
      identified from Arabidopsis thaliana or Oryza sativa.
<220> FEATURE:
<221> NAME/KEY: misc_feature
<222> LOCATION: (489)..(489)
<223> OTHER INFORMATION: n is a, c, g, or t

<400> SEQUENCE: 60

```
gtcgattggt tgtaaattag ttttatcgta gaagtaccaa atcaagtgat tcaatggtta     60
aattaaggta ttaagttaca tttgatattt aaaagtatcc agaccttcat tatagctcat    120
aagggttaaa attttgtcgt tcttttgtat attcatggca agctctaatt catgactaag    180
tcacattttt caaatatgtt tttagttttt acttatgttg gtaattagtg gatttatagt    240
taagttaaaa agttggcgag ttctagcttt gaaactcatt tagaaatata tatatatata    300
tatatattca attttagtaa attgttaatc tattctaatg gtgtaactgt aacaaatgag    360
```

```
aatgaaaaaa atatactatt gtgaataaaa ccccacacaa cacattacta taataagtta      420
aacttctttt tttataggcg cctggaaaaa aaagaaaagc aacaagaggg stgtgaggac      480
gcatcaccng gtttcgtagc acacatgtgc atttgtctct ttgcttttc ggtttttc        540 ttgccaatca atttattttg ttcctcagaa aaagaaaat ctaaaaccaa aatatatatt      600
ataacctcat ttaataaaca acaaaaatgt ttgttgaaaa aaaaaaagtt tttatttatc     660
ttgaccttat ttctttgaag aaaataaagc ttggttatta aagaagtcca agttagttgc     720
caccatcagt ggcataacgg taaattaaag ccaacttcct ctaactaaag ttttctataa     780
attcaaccac tcacctccca ctctaaaacc caacaacata atttcacata tctctctttc     840
tttctcttga aggaaagacg aagatctcca agtcccaagt acgtaactac tttctccatc     900
tacattcaat tgtttctcct taatttctct agtacatatt tacttgtgct ataagtaatt     960
gattttatat cacccatgtg caggttgtta acacaaga                              998
```

<210> SEQ ID NO 61
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 61

```
tattatatat acgattaaat aaataaaaaa attgtaatgt gaaatatca tagtcgagag       60 gggaactgac aagtgtacat atgtatctag ctgtggattc caccaaaatt ctggcagggc     120
catgatctaa aaactgagac tgcgcgtgtt gttttgcagt gatttgtatt tcatatttgc     180
accatcctac acagtccact tggtatcgta accaaacata aggagaacct aattacatta     240
ttgttttaat ttcgtcaaac tggttttac cttttagtta catagttgat tcttcatttg     300
ttttagtagt tatggagcac aataatgtgc aacaagaaa gatcatagtg gattaatatg     360
ttgagaggtc agaaattctt ggttaacaaa aaaaaaaag ttacaaggac tgagattttg     420
ggtgggagaa agccatagct tttaaaacat gattgaactt aaaagtgatg ttatggtttg     480
aggggaaaaa ggttgatgtc aactaagata gttgaagtaa tgtcttaaac taaagtaaac     540
caccggtcca aacgtggtcc ggaagcatct ctggtatgat ttatcctaaa aatcaaaata     600
gtagaaacat actttaaata tatacattga tcggacgaaa attgtaaact agtatagttt     660
caaaaactag ttgaacaggt tatgtacctt aaacatttat ttcaaactta aacactaaag     720
aacatatatg aatagaagtt tatataaatt actatatatc taccataaat ctcttataat     780
tatgatgtca cgatgaggaa gtgttgaaac gttaaaatgc caaaatataa gcatgcgacg     840
gaattttggc agaagattgt agagttgtaa tctgtcgcaa tcattactca tgctagcatt     900 tttcatttc ccttcatttg tggataacgc acgatataac attctacaca ccaacaagat      960
tctataaaaa cgcaaaggtt gtctccatag aatatcgtc                             999
```

<210> SEQ ID NO 62
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 62

```
atctctgatt ttttttatca ggaacaagta aataaatagc tttgagtttt tgttttttt      60 ctacattctt cgcccaaaag atgtaagaaa ataaaggatt tgaaaccttg ttctgttgtt    120
actcctttaa attcttaaaa actataaatc attatatctt tgatctgttt cacaaactaa    180
tcatattcgt tgcaaagtga gaattcgtcc cactttactc tttacaccga tactagtatt    240
atagatgtac agcatagtat tccatatcta gttatttagt caaaactcta tatattaaga    300
ggtaggttaa ttaattaagg agtaattgaa gattatagaa agaataaaaa ataccattta    360
atggacagaa ccaaagataa ctaactatca tactataatg ttgaatttct tccacgatcc    420
aatgcatgga taacaacatc aatcaaatca tacattcatg ctatataaca tagttttcag    480
ttacaaactc tcttttttat ttatttcagt tgttccttt catgaccata ttaacatcaa    540
ataatgcatt tttttcaacg tctcttgact tacacccact aatattgaca aattgaacat    600
ctatacgact atacacacat aagttaaaaa tgcatgcaag tgctaaggga atttataaca    660
tctaaggtta ataagactaa gaaagtataa aataagaata cgtattatga atttatgata    720
tactttacta atctttttga aaaatacttt aatttaatct actataggggg gtaaaaagta    780 aaaaagaaat aaagatacgt ttatccgcat atagtacctg gaaataacag aaaataaaaa    840
cacaggtaag tactttgcct gagctagtat atgaacacta aagagataca cacacacaaa    900
aagagagcag aaacaaaaca cacacactta aagcttcgt ctttacctct tcccttctct    960
ctctctatct aaaaagagtt ccgagaagaa gatcatcat                          999

<210> SEQ ID NO 63
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 63
cgctttatta taggtttaac aattgatttt tcattatttt gttttcaatc tccaaatcat     60
ttctcaataa ctctcaaaca ttgtttaaag cttttttct taattaacat tataacaaaa    120
aaataaatag agaaatttac tttgattcaa acaccagtca ttgtagatta gccaagagtt    180
ttcagtaaca aaatttacct tataaaacctt ttgaatggct atttctgaaa tggaatagaa    240
atctttagtc gtggaagtat ctctatccat aagaaaactc gttttacaaa gtaattttaa    300
atcaatacaa aaagtgaaaa aatccactgg tggaccccat tcattccaga attgccgatt    360
acgagctatc ttgtcccttc ttcaccattc gctcactctc tctctctctc tctcgtcttc    420
ttcttcccac cactctctct gtttctccac aacttctctt ctcaaagtta aaattacccc    480
taaaccaaaa aaaaaaaaaa cgctcttcac tatttattta ctaaactctc ctttgtttgt    540
tactaagctc tcactaaaac cctaatcttt tcctcttat atatctcgtg actcttcttt    600
ctcctccaat ctctctctcc ctcttcacaa accaattagc ttctttctgt aaaacctcac    660
tcgttggcca attctttggg ttttcataca cataaatctc agattccaaa tgggttttct    720
tagctctttc tttcaaatga tgaacatttg ttagcagaat cttcctcttt ccctaaagtt    780
ttgatctttt tttccccctt caattttgta ttttctcacc aaataaaaaa aggtttcttc    840
agtgggtttt aagggtttat tattatctta aaattaaaca caattcttta atcaaaaggc    900
aaaaatctta atttcatcac tctcttctca ctcacaaaag ttcttacaat cttcaaagtt    960
ttggtcttgt ttcttttccg atttcaccgg acaaaaaaa                           999
```

<210> SEQ ID NO 64
<211> LENGTH: 999
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 64
gggattatat atgatagacg attgtatttg cgggacattg agatgtttcc gaaaatagtc      60
atcaaatatc aaaccagaat ttgatgtgaa aacactaatt aaaacatata attgacaact     120
agactatatc atttgttaag ttgagcgttg aaagaaaatg aaagagtgta gactgtagta     180
tgtatgagtt tcccaaagga tggtgcttga atattattgg gaagagactt tggttggttc     240
ggttgaatga agattttttac ctgccatgtt gatagagaaa ggcaaataaa tgtaggggtc     300
gatgtctaac gtaaagactg gatcaaccaa gagtcctcct cctcgtcttc accaaaaaaa     360
aagagtcctc ctcgtggaaa cttatttctt ctccagccaa gatctcatct catctcttca     420
ctctatgaaa tataaggaa tcttatggtt tttctaaaaa ctatagtacg tctatatacc     480
aaaggaaaca atataaaatc agttaatctg ataaattttg agtaaataat aaagttaact     540
ttgtacttac ctatatcaaa ctaattcaca aaataaagta ataataacaa agaattttta     600
gtagatccac aatatacaca cacactatga gaaatcataa tagagaattt taatgatttt     660
gtctaactca tagcaacaag tcgctttggc cgagtggtta aggcgtgtgc ctgctaagta     720
catgggctct gcccgcgaga gttcgaatct ctcaggcgac gtttcttttg ttttcggcca     780
taaaggaaaa agcccaatta acacgtctcg cttataagcc cataaagcaa acaatgggct     840
gtctctgtct cactcacaca cgcgttttcc tactttttga ctattttttat aaccggcggg     900 tctgacttaa ttagggtttt ctttaataat cagacactct ctcactcgtt tcgtcaacat     960
tgaacacaga caaaaccgcg tcacaaaaca aaactcgct                            999

<210> SEQ ID NO 65
<211> LENGTH: 882
<212> TYPE: DNA
<213> ORGANISM: Unknown
<220> FEATURE:
<223> OTHER INFORMATION: Promoter and/or promoter control element
      identified from Arabidopsis thaliana or Oryza sativa.

<400> SEQUENCE: 65
tggatctgct agatatatga gaacggaaag aaccagaagc tattagaggc gggaggagat      60
atgtggggat gatttcagtg caattccacg acgcaccatt tccactttcg taacacctaa     120
acgaccgctt cggccgtata aaatcgcaaa tgtttggtct cagtgtattt ttccaatttc     180
caaatacatc aattcaaatt atataatatc tagtggcaat tataagtata tcatatattt     240
tcaaaattaa ttaaaaagat tactaaatta tgtttgacta caactattat aatagttaaa     300
aacataaaca aaaacaaaga aactattta ataaaaaat caagtaaaca ttaaaacata     360
agcaaaaaat aatgttaaag aaattattaa ttattaattt actaataatt aatacctcta     420
taaattaatt gttagaggtt taacgtaatt tataaggaaa actaagaag actttaaccc     480 ataaagaaaa aaacaaagac tgaattgaag gcccatattt agaagaagag aaagaagacc     540
caaatatgat ataaaatcca gcccatttat atatttttat tttgtttctg gaaggaaaat     600
aagaaaatgg caaaaacgaa ataatctgaa aaagtaaggt cttttaccaa aaaggatatt     660 tttttttataa acagagcata agttttcac ttttcttctg ctcctttctc gtctctgtct     720

-continued

```
tcttcgtcct cattcgtttt aaagcatcaa aatttcatca acccaaaata gattaaaaaa    780
atctgtagct ttcgcatgta aatctctctt tgaaggttcc taactcgtta atcgtaactc    840
acagtgactc gttcgagtca aagtctctgt ctttagctca aa                      882
```

<210> SEQ ID NO 66
<211> LENGTH: 999
<212> TYPE: DNA
<213> ORGANISM: Unknown
<220> FEATURE:
<223> OTHER INFORMATION: Promoter and/or promoter control element
identified from Arabidopsis thaliana or Oryza sativa.

<400> SEQUENCE: 66

```
ttgagcctta ttgttgttat tgacttttag ccaatagaaa gagatggaaa ttcaataatt     60
atccacaaaa ttccaaatca ttggtgtaca aaaagatcta aggctgttat attttcaaaa    120
aagaaagaaa agaaatgcaa caaatatgga ttaaactgtg gtttgtaaat tgagctttgc    180
atgaaaactt tatcactatg atttcactac tccatattta ttgactaaag tggcactaat    240
gaatttctta atcatgaaat cttgtatcaa aaagtactaa aataaacatg acattggcaa    300
ttaggaaaat tctaaattag aaattagtaa aaatgaaagg tgaaagggaa agatgatgat    360
atgaattggt tggtgaccag gagaaatgta tcccgatttt tgcagacact ttcagtgtcc    420
ccattcatat aattatggcc cacctcgtta agattttca ttcaccacca taacaagatc     480
taagcttaga tttcatgtaa ttaaacatat aatatacttg ccaatactat ctaataaagt    540
atacttaagc aaaaattatt actctagtgt aaggcgatga aatataagtt tagttgaaaa    600
tttatgtcga tataacaaag tataatgaat taagaccttg gttttcgatt aacaaactaa    660
ttaaacacta gttttgccta ataaaaccgg gaatcgtatt caaaaccgaa cgacaaaaca    720
agggacaagt tgagagacaa aaccaaatca gcatctttct tccagaaatg tcatgaccac    780
atgacgtcat cttgacccct tttcattgtg atatctgtgg ataaagcgca cgtgttaat    840 tcacgaacct tcgtagtaac gaaaaatcca caactttcat attttttaat tacccactaa    900
actaaaacaa atttggaaaa acatgaaaaa cttttctctt tttccaggt tcgtgaacct    960 cgtaccctct atataaacct cttaaccacc ttccacata                          999
```

<210> SEQ ID NO 67
<211> LENGTH: 19
<212> TYPE: DNA
<213> ORGANISM: Artificial Sequence
<220> FEATURE:
<223> OTHER INFORMATION: oligo(dT)18 primer

<400> SEQUENCE: 67

```
tttttttttt tttttttv                                                  19
```

<210> SEQ ID NO 68
<211> LENGTH: 19
<212> TYPE: DNA
<213> ORGANISM: Artificial Sequence
<220> FEATURE:
<223> OTHER INFORMATION: oligo dTV primer
<220> FEATURE:
<221> NAME/KEY: misc_feature
<222> LOCATION: (19)..(19)

```
-continued
<223> OTHER INFORMATION: n is a, c, or g

<400> SEQUENCE: 68
tttttttttt tttttttn                                                    19
```

PROMOTER, PROMOTER CONTROL ELEMENTS, AND COMBINATIONS, AND USES THEREOF

Figure 1:
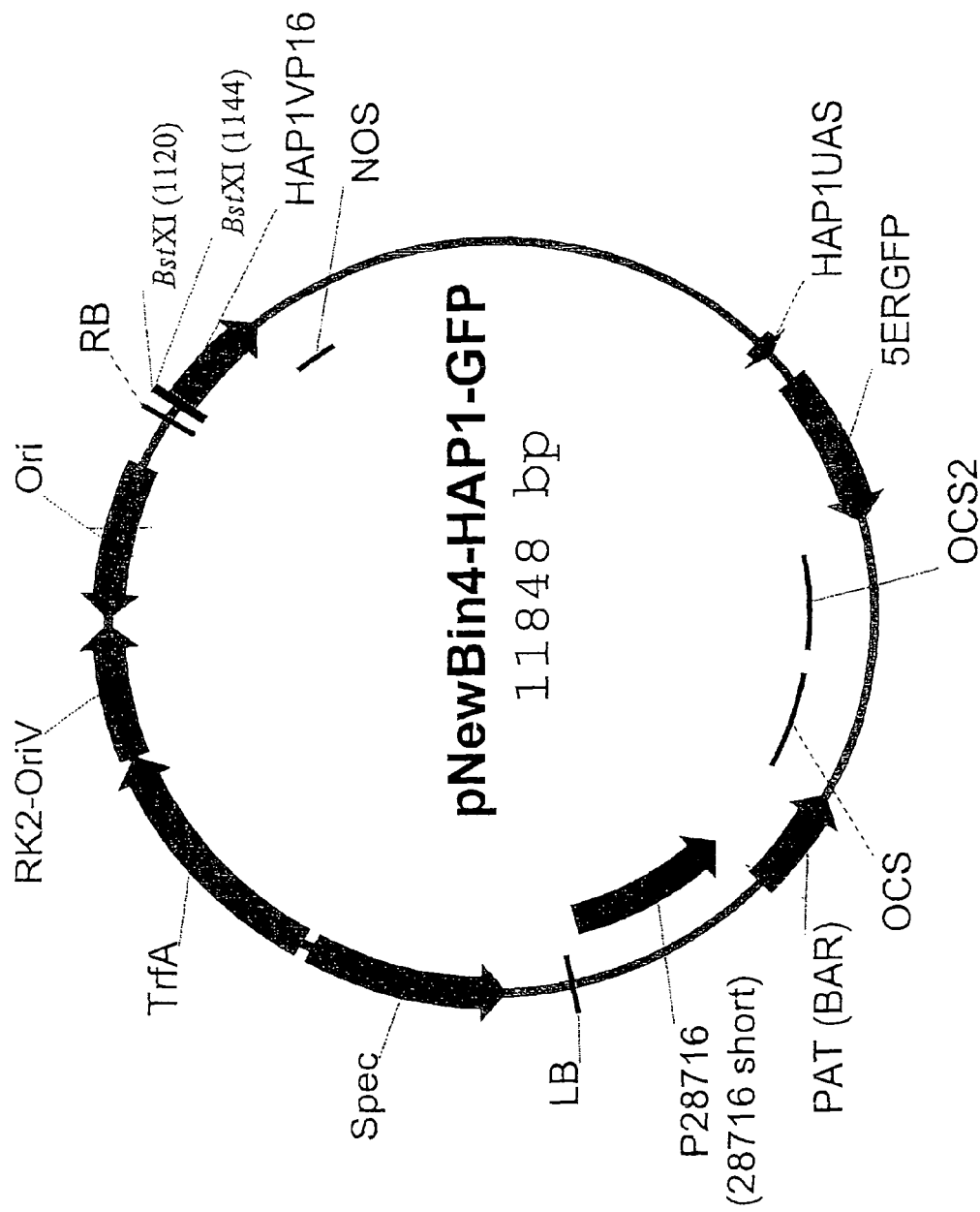

This non-provisional application claims priority under 35 U.S.C. §119(e) on U.S. to Application No: 10-981,334, filed Nov. 4, 2004, and Application No. 60/518,075 filed on Nov. 6, 2003 and Provisional Application No. 60/527,611 filed on Dec. 4, 2003, the entire contents of which are hereby incorporated by reference.

FIELD OF THE INVENTION

The present invention relates to promoters and promoter control elements that are useful for modulating transcription of a desired polynucleotide. Such promoters and promoter control elements can be included in a polynucleotide construct, expression cassettes, vectors, or inserted into the chromosome or as an exogenous element, to modulate in vivo and in vitro transcription of a polynucleotide. Host cells, including plant cells, and organisms, such as regenerated plants therefrom, with desired traits or characteristics using polynucleotides comprising the promoters and promoter control elements of the present invention.

BACKGROUND OF THE INVENTION

This invention relates to the field of biotechnology and, in particular, to specific promoter sequences and promoter control element sequences which are useful for the transcription of polynucleotides in a host cell or transformed host organism.

One of the primary goals of biotechnology is to obtain organisms, such as plants, mammals, yeast, and prokaryotes having particular desired characteristics or traits. Examples of these characteristic or traits abound and may include, for example, in plants, virus resistance, insect resistance, herbicide resistance, enhanced stability or additional nutritional value. Recent advances in genetic engineering have enabled researchers in the field to incorporate polynucleotide sequences into host cells to obtain the desired qualities in the organism of choice. This technology permits one or more polynucleotides from a source different than the organism of choice to be transcribed by the organism of choice. If desired, the transcription and/or translation of these new polynucleotides can be modulated in the organism to exhibit a desired characteristic or trait. Alternatively, new patterns of transcription and/or translation of polynucleotides endogenous to the organism can be produced. Both approaches can be used at the same time.

SUMMARY OF THE INVENTION

The present invention is directed to isolated polynucleotide sequences that comprise promoters and promoter control elements from plants, especially *Arabidopsis thaliana, Glycine max, Oryza sativa*, and *Zea mays*, and other promoters and promoter control elements functional in plants.

It is an object of the present invention to provide isolated polynucleotides that are promoter sequences. These promoter sequences comprise, for example,
 (1) a polynucleotide having a nucleotide sequence according to Table 1 or fragment thereof;
 (2) a polynucleotide having a nucleotide sequence having at least 80% sequence identity to sequences shown in Table 1 or fragment thereof; and
 (3) a polynucleotide having a nucleotide sequence which hybridizes to those shown in Table 1 under a condition establishing a Tm-20° C.

It is another object of the present invention to provide isolated polynucleotides that are promoter control element sequences. These promoter control element sequences comprise, for example,
 (1) a polynucleotide having a nucleotide sequence according to Table 1 or fragment thereof;
 (2) a polynucleotide having a nucleotide sequence having at least 80% sequence identity to those shown in Table 1 or fragment thereof; and
 (3) a polynucleotide having a nucleotide sequence which hybridizes to those shown in Table 1 under a condition establishing a Tm-20° C.

Promoter or promoter control element sequences of the present invention are capable of modulating preferential transcription.

In another embodiment, the present promoter control elements are capable of serving as or fulfilling the function, for example, as a core promoter, a TATA box, a polymerase binding site, an initiator site, a transcription binding site, an enhancer, an inverted repeat, a locus control region, or a scaffold/matrix attachment region.

It is yet another object of the present invention to provide a polynucleotide that includes at least a first and a second promoter control element. The first promoter control element is a promoter control element sequence as discussed above, and the second promoter control element is heterologous to the first control element. Moreover, the first and second control elements are operably linked. Such promoters may modulate transcript levels preferentially in a tissue or under particular conditions.

In another embodiment, the present isolated polynucleotide comprises a promoter or a promoter control element as described above, wherein the promoter or promoter control element is operably linked to a polynucleotide to be transcribed.

In another embodiment of the present vector, the promoter and promoter control elements of the instant invention are operably linked to a heterologous polynucleotide that is a regulatory sequence.

It is another object of the present invention to provide a host cell comprising an isolated polynucleotide or vector as described above or fragment thereof. Host cells include, for instance, bacterial, yeast, insect, mammalian, and plant. The host cell can comprise a promoter or promoter control element exogenous to the genome. Such a promoter can modulate transcription in cis- and in trans-.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free system of transcription or host cell. This method comprises providing a polynucleotide or vector according to the present invention as described above, and contacting the sample of the polynucleotide or vector with conditions that permit transcription.

In another embodiment of the present method, the polynucleotide or vector preferentially modulates
 (a) constitutive transcription,
 (b) stress induced transcription,
 (c) light induced transcription,
 (d) dark induced transcription, (e) leaf transcription,
(f) root transcription,
(g) stem or shoot transcription,
(h) silique transcription,
(i) callus transcription,
(j) flower transcription,
(k) immature bud and inflorescence specific transcription, or
(l) senescing induced transcription
(m) germination transcription.

Other and further objects of the present invention will be made clear or become apparent from the following description.

BRIEF DESCRIPTION OF THE TABLES

Table 1

Table 1 identifies nucleic acid promoter sequences using the headings "SEQ ID NO" and "construct." The "SEQ ID NO" is a number that identifies the sequence of the candidate promoter used in the experiments, while the "construct" text identifies the construct used to produce a specific plant line.

Table 2

Table 2 consists of the Expression Reports and provides details for expression driven by each of the nucleic acid promoter sequences as observed in transgenic plants. The results are presented as summaries of the spatial expression, which provides information as to gross and/or specific expression in various plant organs and tissues. The observed expression pattern is also presented, which gives details of expression during different generations or different developmental stages within a generation. Additional information is provided regarding the associated gene, the GenBank reference, the source organism of the promoter, and the vector and marker genes used for the construct. The following symbols are used consistently throughout the Table:
T1: First generation transformant
T2: Second generation transformant
T3: Third generation transformant
(L): low expression level
(M): medium expression level
(H): high expression level Table 3

Table 3 lists the co-ordinates of nucleotides of the promoter that represent optional promoter fragments. The optional promoter fragments comprise the 5' UTR and any exon(s) of the endogenous coding region. The optional promoter fragments may also comprise any exon(s) and the 3' or 5' UTR of the gene residing upstream of the promoter (that is, 5' to the promoter). The optional promoter fragments also include any intervening sequences that are introns or sequence occurring between exons or an exon and the UTR.

The information in Table 3 can be used to generate either reduced promoter sequences or "core" promoters. A reduced promoter sequence is generated when at least one optional promoter fragment is deleted. Deletion of all optional promoter fragments generates a "core" promoter.

Table 4

Table 4 presents the results of microarray experiments that track expression of particular cDNAs under specific conditions. The column headed "cDNA_ID" provides the identifier number for the cDNA tracked in the experiment. Using Table 2, these numbers can be used to correlate the differential expression pattern observed and produced by the endogenous promoter with the isolated promoters of the invention.

The column headed "EXPT_REP_ID" provides an identifier number for the particular experiment conducted. The column "SHORT_NAME" gives a brief description of the experimental conditions or the developmental stage used. The values in the column headed "Differential" indicate whether expression of the cDNA was increased (+) or decreased (−) compared to the control.

Table 5

Table 5 links the "short name" from Table 4 with a short description of the experiment, the parameters and the utility.

FIG. 1

FIG. 1 is a schematic representation of the vector pNew-Bin4-HAP1-GFP. The definitions of the abbreviations used in the vector map are as follows:
Ori—the origin of replication used by an *E. coli* host
RB—sequence for the right border of the T-DNA from pMOG800
BstXI—restriction enzyme cleavage site used for cloning
HAP1VP16—coding sequence for a fusion protein of the HAP1 and VP16 activation domains
NOS—terminator region from the nopaline synthase gene
HAP1UAS—the upstream activating sequence for HAP1
5ERGFP—the green fluorescent protein gene that has been optimized for localization to the endoplasmic reticulum
OCS2—the terminator sequence from the octopine synthase 2 gene
OCS—the terminator sequence from the octopine synthase gene
p28716 (a.k.a 28716 short)—promoter used to drive expression of the PAT (BAR) gene
PAT (BAR)—a marker gene conferring herbicide resistance
LB—sequence for the left border of the T-DNA from pMOG800
Spec—a marker gene conferring spectinomycin resistance
TrfA—transcription repression factor gene
RK2-OriV—origin of replication for *Agrobacterium*

Figure 2:
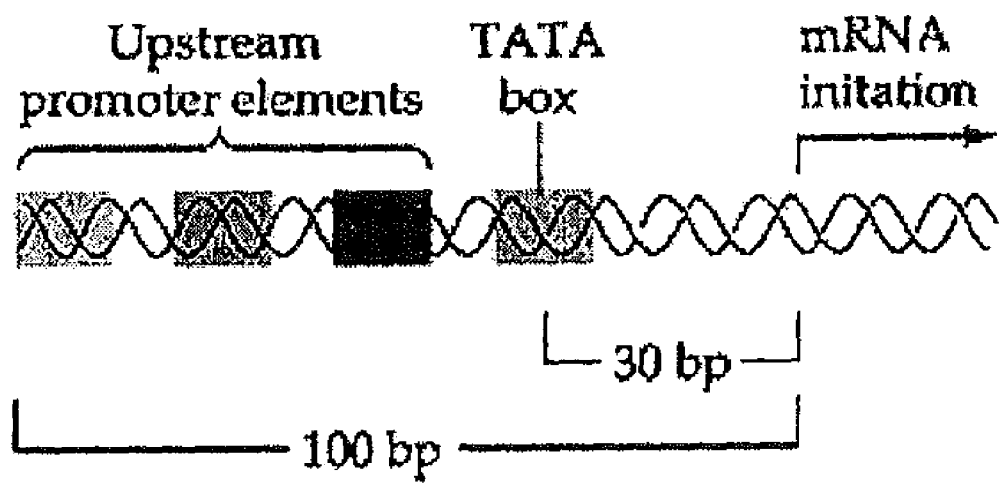

FIG. 2 is a schematic representation of a common configuration of the promoter control elements in RNA polymerase II promoters.

DETAILED DESCRIPTION OF THE INVENTION

1. Definitions

Chimeric: The term "chimeric" is used to describe polynucleotides or genes, as defined supra, or constructs wherein at least two of the elements of the polynucleotide or gene or construct, such as the promoter and the polynucleotide to be transcribed and/or other regulatory sequences and/or filler sequences and/or complements thereof, are heterologous to each other.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Core Promoter: This is the minimal stretch of contiguous DNA sequence that is sufficient to direct accurate initiation of transcription by the RNA polymerase II machinery (for review see: Struhl, 1987, *Cell* 49: 295-297; Smale, 1994, In *Transcription: Mechanisms and Regulation* (eds R. C. Conaway and J. W. Conaway), pp 63-81/Raven Press, Ltd., New York; Smale, 1997, *Biochim. Biophys. Acta* 1351: 73-88; Smale et al., 1998, *Cold Spring Harb. Symp. Quant. Biol.* 58: 21-31; Smale, 2001, *Genes & Dev.* 15: 2503-2508; Weis and Reinberg, 1992, *FASEB J.* 6: 3300-3309; Burke et al., 1998, *Cold Spring Harb. Symp. Quant. Biol* 63: 75-82). There are several sequence motifs, including the TATA box, initiator (Inr), TFIIB recognition element (BRE) and downstream core promoter element (DPE), that are commonly found in core promoters, however not all of these elements occur in all promoters and there are no universal core promoter elements (Butler and Kadonaga, 2002, *Genes & Dev.* 16: 2583-2592).

All of the references cited in this section are hereby incorporated by reference.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of domains include, without limitation, AP2, helicase, homeobox, zinc finger, etc.

Endogenous: The term "endogenous," within the context of the current invention refers to any polynucleotide, polypeptide or protein sequence which is a natural part of a cell or organisms regenerated from said cell. In the context of promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below, and include *Agrobacterium*-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

All of the references cited in this section are hereby incorporated by reference.

Gene: The term "gene," as used in the context of the current invention, encompasses all regulatory and coding sequence contiguously associated with a single hereditary unit with a genetic function (see SCHEMATIC 1). Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other.

Homologous: In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

Inducible Promoter: An "inducible promoter" in the context of the current invention refers to a promoter, the activity of which is influenced by certain conditions, such as light, temperature, chemical concentration, protein concentration, conditions in an organism, cell, or organelle, etc. A typical example of an inducible promoter, which can be utilized with the polynucleotides of the present invention, is PARSK1, the promoter from an *Arabidopsis* gene encoding a serine-threonine kinase enzyme, and which promoter is induced by dehydration, abscissic acid and sodium chloride (Wang and Goodman, Plant J. 8:37 (1995), which is hereby incorporated by reference). Examples of environmental conditions that may affect transcription by inducible promoters include anaerobic conditions, elevated temperature, the presence or absence of a nutrient or other chemical compound or the presence of light.

Modulate Transcription Level: As used herein, the phrase "modulate transcription" describes the biological activity of a promoter sequence or promoter control element. Such modulation includes, without limitation, includes up- and down-regulation of initiation of transcription, rate of transcription, and/or transcription levels.

Mutant: In the current invention, "mutant" refers to a heritable change in nucleotide sequence at a specific location. Mutant genes of the current invention may or may not have an associated identifiable phenotype.

Operable Linkage: An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoding the polynucleotide and if the nature of the linkage between the two DNA sequences does not (1) result in the introduction of a frame-shift mutation, (2) interfere with the ability of the promoter sequence to direct the expression of the protein, antisense RNA or ribozyme, or (3) interfere with the ability of the DNA template to be transcribed. Thus, a promoter sequence would be operably linked to a polynucleotide sequence if the promoter was capable of effecting transcription of that polynucleotide sequence.

Optional Promoter Fragments: The phrase "optional promoter fragments" is used to refer to any sub-sequence of the promoter that is not required for driving transcription of an operationally linked coding region. These fragments comprise the 5' UTR and any exon(s) of the endogenous coding region. The optional promoter fragments may also comprise any exon(s) and the 3' or 5' UTR of the gene residing upstream of the promoter (that is, 5' to the promoter). Optional promoter fragments also include any intervening sequences that are introns or sequence that occurs between exons or an exon and the UTR.

Orthologous: "Orthologous" is a term used herein to describe a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultrastructure of a cell).

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. All of the references discussed in this paragraph are hereby incorporated by reference.

All of the references cited in this section are hereby incorporated by reference.

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill Plant Tissue: The term "plant tissue" includes differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, proximal to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible at ncbi.nlm.nih.gov/ftp). The database at the NCBI FTP site utilizes "gi" numbers assigned by NCBI as a unique identifier for each sequence in the databases, thereby providing a non-redundant database for sequence from various databases, including GenBank, EMBL, DBBJ, (DNA Database of Japan) and PDB (Brookhaven Protein Data Bank).

Regulatory Sequence: The term "regulatory sequence," as used in the current invention, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

Related Sequences: "Related sequences" refer to either a polypeptide or a nucleotide sequence that exhibits some degree of sequence similarity with a reference sequence.

Specific Promoters: In the context of the current invention, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present invention, are: PTA29, a promoter which is capable of driving gene transcription specifically in tapetum and only during another development (Koltonow et al., Plant Cell 2:1201 (1990); RCc2 and RCc3, promoters that direct root-specific gene transcription in rice (Xu et al., Plant Mol. Biol. 27:237 (1995); TobRB27, a root-specific promoter from tobacco (Yamamoto et al., Plant Cell 3:371 (1991)). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription".

All of the references cited in this section are hereby incorporated by reference.

Stringency: "Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$-5° C. to $T_m$-10° C. Medium or moderate stringency conditions are those providing $T_m$-20° C. to $T_m$-29° C. Low stringency conditions are those providing a condition of $T_m$-40° C. to $T_m$-48° C. The relationship of hybridization conditions to $T_m$ (in ° C.) is expressed in the mathematical equation $$T_m = 81.5 - 16.6(\log_{10}[Na^{+1}] + 0.41(\% \, G+C) - (600/N) \qquad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log \{[Na^+]/(1+0.7[Na^{+1}]) + 0.41(\% \, G+C) - 500/L \, 0.63(\% \, \text{formamide}) \qquad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., J. Mol. Biol. 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

All of the references cited in this section are hereby incorporated by reference.

Substantially free of: A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene can be substantially free of other plant genes. Other examples include, but are not limited to, ligands substantially free of receptors (and vice versa), a growth factor substantially free of other growth factors and a transcription binding factor substantially free of nucleic acids.

Suppressor: See "Enhancer/Suppressor"

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present invention, a "translational start site" is usually an ATG or AUG in a transcript, often the first ATG or AUG. A single protein encoding transcript, however, may have multiple translational start sites.

Transcription start site: "Transcription start site" is used in the current invention to describe the point at which transcription is initiated. This point is typically located about 25 nucleotides downstream from a MID binding site, such as a TATA box. Transcription can initiate at one or more sites within the gene, and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

Variant: The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc) Likewise, polynucleotide variants can consist of changes that add or delete a specific UTR or exon sequence. It will be understood that there may be sequence variations within sequence or fragments used or disclosed in this application. Preferably, variants will be such that the sequences have at least 80%, preferably at least 90%, at least 95%, at least 97%, at least 98%, or at least 99% sequence identity. Variants preferably measure the primary biological function of the native polypeptide or protein or polynucleotide.

2. Introduction

The polynucleotides of the invention comprise promoters and promoter control elements that are capable of modulating transcription.

Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:
 (a) antisense;
 (b) ribozymes;
 (c) coding sequences; or
 (d) fragments thereof.

The promoter also can modulate transcription in a host genome in cis- or in trans-.

In an organism, such as a plant, the promoters and promoter control elements of the instant invention are useful to produce preferential transcription which results in a desired pattern of transcript levels in a particular cells, tissues, or organs, or under particular conditions.

3. Table of Contents

The following description of the present invention is outlined in the following table of contents.

A. Identifying and Isolating Promoter Sequences of the Invention
  (1) Cloning Methods
  (2) Chemical Synthesis
B. Generating a "core" promoter sequence
C. Isolating Related Promoter Sequences
  (1) Relatives Based on Nucleotide Sequence Identity
  (2) Relatives Based on Coding Sequence Identity
  (3) Relatives based on Common Function
D. Identifying Control Elements
  (1) Types of Transcription Control Elements
  (2) Those Described by the Examples
  (3) Those Identifiable by Bioinformatics
  (4) Those Identifiable by In Vitro and In Vivo Assays
  (5) Non-Natural Control Elements
E. Constructing Promoters and Control Elements
  (1) Combining Promoters and Promoter Control Elements
  (2) Number of Promoter Control Elements
  (3) Spacing Between Control Elements
F. Vectors
  (1) Modification of Transcription by Promoters and Promoter Control Elements
  (2) Polynucleotide to be Transcribed
  (3) Other Regulatory Elements
  (4) Other Components of Vectors
G. Insertion of Polynucleotides and Vectors Into a Host Cell
  (1) Autonomous of the Host Genome
  (2) Integrated into the Host Genome
H. Utility A. Identifying and Isolating Promoter Sequences of the Invention The promoters and promoter control elements of the present invention presented in Table 1 were identified from *Arabidopsis thaliana* or *Oryza sativa*. Additional promoter sequences encompassed by the invention can be identified as described below.

(1) Cloning Methods

Isolation from genomic libraries of polynucleotides comprising the sequences of the promoters and promoter control elements of the present invention is possible using known techniques.

For example, polymerase chain reaction (PCR) can amplify the desired polynucleotides utilizing primers designed from sequences in Table 2. Polynucleotide libraries comprising genomic sequences can be constructed according to Sambrook et al., (*Molecular Cloning: A Laboratory*

*Manual*, 2*nd* Ed. (1989) Cold Spring Harbor Press, Cold Spring Harbor, N.Y., for example.

Other procedures for isolating polynucleotides comprising the promoter sequences of the invention include, without limitation, tail-PCR, and 5' rapid amplification of cDNA ends (RACE). See, for tail-PCR, for example, Liu et al., *Plant J* 8(3): 457-463 (September, 1995); Liu et al., *Genomics* 25: 674-681 (1995); Liu et al., *Nucl. Acids Res.* 21(14): 3333-3334 (1993); and Zoe et al., *BioTechniques* 27(2): 240-248 (1999); for RACE, see, for example, *PCR Protocols: A Guide to Methods and Applications*, (1990) Academic Press, Inc.

All of the references cited in this section are hereby incorporated by reference.

(2) Chemical Synthesis

In addition, the promoters and promoter control elements described in Table 1 can be chemically synthesized according to techniques in common use. See, for example, Beaucage et al., *Tet. Lett.* (1981) 22: 1859 and U.S. Pat. No. 4,668,777, both of which are hereby incorporated by reference.

Such chemical oligonucleotide synthesis can be carried out using commercially available devices, such as, Biosearch 4600 or 8600 DNA synthesizer, by Applied Biosystems, a division of Perkin-Elmer Corp., Foster City, Calif., USA; and Expedite by Perceptive Biosystems, Framingham, Mass., USA.

Synthetic RNA, including natural and/or analog building blocks, can be synthesized on the Biosearch 8600 machines, see above.

Oligonucleotides can be synthesized and then ligated together to construct the desired polynucleotide.

B. Generating Reduced and "Core" Promoter Sequences

Included in the present invention are reduced and "core" promoter sequences. The reduced promoters can be isolated from the promoters of the invention by deleting at least one 5' UTR, exon or 3' UTR sequence present in the promoter sequence that is associated with a gene or coding region located 5' to the promoter sequence or in the promoter's endogenous coding region.

Similarly, the "core" promoter sequences can be generated by deleting all 5' UTRs, exons and 3' UTRs present in the promoter sequence and the associated intervening sequences that are related to the gene or coding region 5' to the promoter region and the promoter's endogenous coding region.

This data is presented in Table 3.

C. Isolating Related Promoter Sequences

Included in the present invention are promoter and promoter control elements that are related to those described in Table 1. Such related sequence can be isolated utilizing (a) nucleotide sequence identity;
(b) coding sequence identity; or
(c) common function or gene products.

Relatives can include both naturally occurring promoters and non-natural promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

According to current knowledge, promoter sequences and promoter control elements exist as functionally important regions, such as protein binding sites, and spacer regions. These spacer regions are apparently required for proper positioning of the protein binding sites. Thus, nucleotide substitutions, insertions and deletions can be tolerated in these spacer regions to a certain degree without loss of function.

In contrast, less variation is permissible in the functionally important regions, since changes in the sequence can interfere with protein binding. Nonetheless, some variation in the functionally important regions is permissible so long as function is conserved.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Relatives Based on Nucleotide Sequence Identity

Included in the present invention are promoters exhibiting nucleotide sequence identity to those described in Table 1.

DEFINITION

Typically, such related promoters exhibit at least 80% sequence identity, preferably at least 85%, more preferably at least 90%, and most preferably at least 95%, even more preferably, at least 96%, at least 97%, at least 98% or at least 99% sequence identity compared to those shown in Table 1. Such sequence identity can be calculated by the algorithms and computers programs described above.

Usually, such sequence identity is exhibited in an alignment region that is at least 75% of the length of a sequence shown in Table 1 or corresponding full-length sequence; more usually at least 80%; more usually, at least 85%, more usually at least 90%, and most usually at least 95%, even more usually, at least 96%, at least 97%, at least 98% or at least 99% of the length of a sequence shown in Table 1.

The percentage of the alignment length is calculated by counting the number of residues of the sequence in region of strongest alignment, e.g., a continuous region of the sequence that contains the greatest number of residues that are identical to the residues between two sequences that are being aligned. The number of residues in the region of strongest alignment is divided by the total residue length of a sequence in Table 1.

These related promoters may exhibit similar preferential transcription as those promoters described in Table 1.

Construction of Polynucleotides

Naturally occurring promoters that exhibit nucleotide sequence identity to those shown in Table 1 can be isolated using the techniques as described above. More specifically, such related promoters can be identified by varying stringencies, as defined above, in typical hybridization procedures such as Southern blots or probing of polynucleotide libraries, for example. Non-natural promoter variants of those shown in Table 1 can be constructed using cloning methods that incorporate the desired nucleotide variation. See, for example, Ho, S. N., et al. Gene 77:51-59 1989, describing a procedure site directed mutagenesis using PCR, which is hereby incorporated by reference.

Any related promoter showing sequence identity to those shown in Table 1 can be chemically synthesized as described above.

Also, the present invention includes non-natural promoters that exhibit the above-sequence identity to those in Table 1

The promoters and promoter control elements of the present invention may also be synthesized with 5' or 3' extensions, to facilitate additional manipulation, for instance.

The present invention also includes reduced promoter sequences. These sequences have at least one of the optional promoter fragments deleted.

Core promoter sequences are another embodiment of the present invention. The core promoter sequences have all of the optional promoter fragments deleted.

Testing of Polynucleotides

Polynucleotides of the invention were tested for activity by cloning the sequence into an appropriate vector, transforming plants with the construct and assaying for marker gene expression. Recombinant DNA constructs were prepared which comprise the polynucleotide sequences of the invention inserted into a vector suitable for transformation of plant cells. The construct can be made using standard recombinant DNA techniques (Sambrook et al. 1989) and can be introduced to the species of interest by Agrobacterium-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., Proc. Natl. Acad. Sci. USA 89: 8794-8797 (1992); Hamilton et al., Proc. Natl. Acad. Sci. USA 93: 9975-9979 (1996);
(b) YAC: Burke et al., Science 236:806-812 (1987);
(c) PAC: Sternberg N. et al., Proc Natl Acad Sci USA. January; 87(1):103-7 (1990);
(d) Bacteria-Yeast Shuttle Vectors: Bradshaw et al., Nucl Acids Res 23: 4850-4856 (1995);
(e) Lambda Phage Vectors: Replacement Vector, e.g., Frischauf et al., J. Mol. Biol 170: 827-842 (1983); or Insertion vector, e.g., Huynh et al., In: Glover N M (ed) DNA Cloning: A practical Approach, Vol. 1 Oxford: IRL Press (1985); T-DNA gene fusion vectors: Walden et al., Mol Cell Biol 1: 175-194 (1990); and
(g) Plasmid vectors: Sambrook et al., infra.

Typically, the construct comprises a vector containing a sequence of the present invention operationally linked to any marker gene. The polynucleotide was identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin. Vectors can also include origins of replication, scaffold attachment regions (SARs), markers, homologous sequences, introns, etc.

All of the references cited in this section are hereby incorporated by reference.

Promoter Control Elements of the Invention

The promoter control elements of the present invention include those that comprise a sequence shown in Table 1 and fragments thereof. The size of the fragments of Table 1 can range from 5 bases to 10 kilobases (kb). Typically, the fragment size is no smaller than 8 bases; more typically, no smaller than 12; more typically, no smaller than 15 bases; more typically, no smaller than 20 bases; more typically, no smaller than 25 bases; even more typically, no more than any one of the following: 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than any one of the following: 250, 200, 150 or 100 bases.

Relatives Based on Nucleotide Sequence Identity

Included in the present invention are promoter control elements exhibiting nucleotide sequence identity to those described in Table 1 of fragments thereof.

Typically, such related promoters exhibit at least 80% sequence identity, preferably at least 85%, more preferably at least 90%, and most preferably at least 95%, even more preferably, at least 96%, at least 97%, at least 98% or at least 99% sequence identity compared to those shown in Table 1. Such sequence identity can be calculated by the algorithms and computers programs described above.

Promoter Control Element Configuration

A common configuration of the promoter control elements in RNA polymerase II promoters is shown below:

For more description, see, for example, "Models for prediction and recognition of eukaryotic promoters", T. Werner, Mammalian Genome, 10, 168-175 (1999).

Promoters are generally modular in nature. Promoters can consist of a basal promoter which functions as a site for assembly of a transcription complex comprising an RNA polymerase, for example RNA polymerase II. A typical transcription complex will include additional factors such as $TF_{II}B$, $TF_{II}D$, and $TF_{II}E$. Of these, $TF_{II}D$ appears to be the only one to bind DNA directly. The promoter might also contain one or more promoter control elements such as the elements discussed above. These additional control elements may function as binding sites for additional transcription factors that have the function of modulating the level of transcription with respect to tissue specificity and of transcriptional responses to particular environmental or nutritional factors, and the like.

One type of promoter control element is a polynucleotide sequence representing a binding site for proteins. Typically, within a particular functional module, protein binding sites constitute regions of 5 to 60, preferably 10 to 30, more preferably 10 to 20 nucleotides. Within such binding sites, there are typically 2 to 6 nucleotides which specifically contact amino acids of the nucleic acid binding protein.

The protein binding sites are usually separated from each other by 10 to several hundred nucleotides, typically by 15 to 150 nucleotides, often by 20 to 50 nucleotides.

Further, protein binding sites in promoter control elements often display dyad symmetry in their sequence. Such elements can bind several different proteins, and/or a plurality of sites can bind the same protein. Both types of elements may be combined in a region of 50 to 1,000 base pairs.

Binding sites for any specific factor have been known to occur almost anywhere in a promoter. For example, functional AP-1 binding sites can be located far upstream, as in the rat bone sialoprotein gene, where an AP-1 site located about 900 nucleotides upstream of the transcription start site suppresses expression. Yamauchi et al., Matrix Biol., 15, 119-130 (1996). Alternatively, an AP-1 site located close to the transcription start site plays an important role in the expression of Moloney murine leukemia virus. Sap et al., Nature, 340, 242-244, (1989). All of the references cited in this section are hereby incorporated by reference.

(2) Those Identifiable by Bioinformatics

Promoter control elements from the promoters of the instant invention can be identified utilizing bioinformatic or computer driven techniques.

One method uses a computer program AlignACE to identify regulatory motifs in genes that exhibit common preferential transcription across a number of time points. The program identifies common sequence motifs in such genes. See, Roth et al., Nature Biotechnol. 16: 949-945 (1998); Tavazoie et al., Nat Genet. 1999 July; 22(3):281-5;

Genomatix, also makes available a GEMS Launcher program and other programs to identify promoter control elements and configuration of such elements. Genomatix is located in Munich, Germany.

Other references also describe detection of promoter modules by models independent of overall nucleotide sequence similarity. See, for instance, Klingenhoff et al., Bioinformatics 15, 180-186 (1999).

Protein binding sites of promoters can be identified as reported in "Computer-assisted prediction, classification, and delimitation of protein binding sites in nucleic acids", Frech, et al., Nucleic Acids Research, Vol. 21, No. 7, 1655-1664, 1993.

Other programs used to identify protein binding sites include, for example, Signal Scan, Prestridge et al., Comput. Appl. Biosci. 12: 157-160 (1996); Matrix Search, Chen et al., Comput. Appl. Biosci. 11: 563-566 (1995), available as part of Signal Scan 4.0; MatInspector, Ghosh et al., Nucl. Acid Res. 21: 3117-3118 (1993) available on the internet, ConsInspector, Frech et al., Nucl. Acids Res. 21: 1655-1664 (1993), available at on the internet; TFSearch; and TESS.

Frech et al., "Software for the analysis of DNA sequence elements of transcription", Bioinformatics & Sequence Analysis, Vol. 13, no. 1, 89-97 (1997) is a review of different software for analysis of promoter control elements. This paper also reports the usefulness of matrix-based approaches to yield more specific results.

For other procedures, see, Fickett et al., Curr. Op. Biotechnol. 11: 19-24 (2000); and Quandt et al., Nucleic Acids Res., 23, 4878-4884 (1995).

All of the references cited in this section are hereby incorporated by reference.

(3) Those Identifiable by In-Vitro and In-Vivo Assays

Promoter control elements also can be identified with in-vitro assays, such as transcription detection methods; and with in-vivo assays, such as enhancer trapping protocols.

In-Vitro Assays

Examples of in-vitro assays include detection of binding of protein factors that bind promoter control elements. Fragments of the instant promoters can be used to identify the location of promoter control elements. Another option for obtaining a promoter control element with desired properties is to modify known promoter sequences. This is based on the fact that the function of a promoter is dependent on the interplay of regulatory proteins that bind to specific, discrete nucleotide sequences in the promoter, termed motifs. Such interplay subsequently affects the general transcription machinery and regulates transcription efficiency. These proteins are positive regulators or negative regulators (repressors), and one protein can have a dual role depending on the context (Johnson, P. F. and McKnight, S. L. Annu. Rev. Biochem. 58:799-839 (1989)).

One type of in-vitro assay utilizes a known DNA binding factor to isolate DNA fragments that bind. If a fragment or promoter variant does not bind, then a promoter control element has been removed or disrupted. For specific assays, see, for instance, B. Luo et al., J. Mol. Biol. 266:470 (1997), S. Chusacultanachai et al., J. Biol. Chem. 274:23591 (1999), D. Fabbro et al., Biochem. Biophys. Res. Comm. 213:781 (1995)).

Alternatively, a fragment of DNA suspected of conferring a particular pattern of specificity can be examined for activity in binding transcription factors involved in that specificity by methods such as DNA footprinting (e.g. D. J. Cousins et al., Immunology 99:101 (2000); V. Kolla et al., Biochem. Biophys. Res. Comm. 266:5 (1999)) or "mobility-shift" assays (E. D. Fabiani et al., J. Biochem. 347:147 (2000); N. Sugiura et al., J. Biochem 347:155 (2000)) or fluorescence polarization (e.g. Royer et al., U.S. Pat. No. 5,445,935). Both mobility shift and DNA footprinting assays can also be used to identify portions of large DNA fragments that are bound by proteins in unpurified transcription extracts prepared from tissues or organs of interest.

Cell-free transcription extracts can be prepared and used to directly assay in a reconstitutable system (Narayan et al., Biochemistry 39:818 (2000)).

All of the references cited in this section are hereby incorporated by reference.

In-Vivo Assays

Promoter control elements can be identified with reporter genes in in-vivo assays with the use of fragments of the instant promoters or variants of the instant promoter polynucleotides.

For example, various fragments can be inserted into a vector, comprising a basal or "core" promoter, for example, operably linked to a reporter sequence, which, when transcribed, can produce a detectable label. Examples of reporter genes include those encoding luciferase, green fluorescent protein, GUS, neo, cat and bar. Alternatively, reporter sequence can be detected utilizing AFLP and microarray techniques.

In promoter probe vector systems, genomic DNA fragments are inserted upstream of the coding sequence of a reporter gene that is expressed only when the cloned fragment contains DNA having transcription modulation activity (Neve, R. L. et al., Nature 277:324-325 (1979)). Control elements are disrupted when fragments or variants lacking any transcription modulation activity. Probe vectors have been designed for assaying transcription modulation in E. coli (An, G. et al., J. Bact. 140:400-407 (1979)) and other bacterial hosts (Band, L. et al., Gene 26:313-315 (1983); Achen, M. G., Gene 45:45-49 (1986)), yeast (Goodey, A. R. et al., Mol. Gen. Genet. 204:505-511 (1986)) and mammalian cells (Pater, M. M. et al., J. Mol. App. Gen. 2:363-371 (1984)).

A different design of a promoter/control element trap includes packaging into retroviruses for more efficient delivery into cells. One type of retroviral enhancer trap was described by von Melchner et al. (Genes Dev. 1992; U.S. Pat. No. 5,364,783). The basic design of this vector includes a reporter protein coding sequence engineered into the U3 portion of the 3' LTR. No splice acceptor consensus sequences are included, limiting its utility to work as an enhancer trap only. A different approach to a gene trap using retroviral vectors was pursued by Friedrich and Soriano (Genes Dev. 1991), who engineered a lacZ-neo fusion protein linked to a splicing acceptor. LacZ-neo fusion protein expression from trapped loci allows not only for drug selection, but also for visualization of β-galatactosidase expression using the chromogenic substrate, X-gal.

A general review of tools for identifying transcriptional regulatory regions of genomic DNA is provided by J. W. Fickett et al. (Curr. Opn. Biotechnol. 11:19 (2000).

All of the references cited in this section are hereby incorporated by reference.

(4) Non-Natural Control Elements

Non-natural control elements can be constructed by inserting, deleting or substituting nucleotides into the promoter control elements described above. Such control elements are capable of transcription modulation that can be determined using any of the assays described above.

D. Constructing Promoters with Control Elements (1) Combining Promoters and Promoter Control Elements The promoter polynucleotides and promoter control elements of the present invention, both naturally occurring and synthetic, can be combined with each other to produce the desired preferential transcription. Also, the polynucleotides of the invention can be combined with other known sequences to obtain other useful promoters to modulate, for example, tissue transcription specific or transcription specific to certain conditions. Such preferential transcription can be determined using the techniques or assays described above.

Fragments, variants, as well as full-length sequences those shown in Table 1 and relatives are useful alone or in combination.

The location and relation of promoter control elements within a promoter can affect the ability of the promoter to modulate transcription. The order and spacing of control elements is a factor when constructing promoters.

(2) Number of Promoter Control Elements

Promoters can contain any number of control elements. For example, a promoter can contain multiple transcription binding sites or other control elements. One element may confer tissue or organ specificity; another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

(3) Spacing Between Control Elements Spacing between control elements or the configuration or control elements can be determined or optimized to permit the desired protein-polynucleotide or polynucleotide interactions to occur.

For example, if two transcription factors bind to a promoter simultaneously or relatively close in time, the binding sites are spaced to allow each factor to bind without steric hinderance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to hairpin or loop to permit the two elements to bind. The spacing between two such hybridizing control elements can be as small as a t-RNA loop, to as large as 10 kb.

Typically, the spacing is no smaller than 5 bases; more typically, no smaller than 8; more typically, no smaller than 15 bases; more typically, no smaller than 20 bases; more typically, no smaller than 25 bases; even more typically, no more than one of the following: 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than one of the following: 250, 200, 150 or 100 bases.

Such spacing between promoter control elements can be determined using the techniques and assays described above.

(4) Other Promoters

The following are promoters that are induced under stress conditions and can be combined with those of the present invention: ldh1 (oxygen stress; tomato; see Germain and Ricard, 1997, Plant Mol Biol 35:949-54), GPx and CAT (oxygen stress; mouse; see Franco et al., 1999, Free Radic Biol Med 27:1122-32), ci7 (cold stress; potato; see Kirch et al., 1997, Plant Mol. Biol. 33:897-909), Bz2 (heavy metals; maize; see Marrs and Walbot, 1997, Plant Physiol 113:93-102), HSP32 (hyperthermia; rat; see Raju and Maines, 1994, Biochim Biophys Acta 1217:273-80); MAPKAPK-2 (heat shock; *Drosophila*; see Larochelle and Suter, 1995, Gene 163:209-14).

In addition, the following examples of promoters are induced by the presence or absence of light can be used in combination with those of the present invention: Topoisomerase II (pea; see Reddy et al., 1999, Plant Mol Biol 41:125-37), chalcone synthase (soybean; see Wingender et al., 1989, Mol Gen Genet. 218:315-22), mdm2 gene (human tumor; see Saucedo et al., 1998, Cell Growth Differ 9:119-30), Clock and BMAL1 (rat; see Namihira et al., 1999, Neurosci Lett 271:1-4), PHYA (Arabidopsis; see Canton and Quail, 1999, Plant Physiol 121:1207-16), PRB-1b (tobacco; see Sessa et al., 1995, Plant Mol Biol 28:537-47) and Ypr10 (common bean; see Walter et al., 1996, Eur J Biochem 239: 281-93).

The promoters and control elements of the following genes can be used in combination with the present invention to confer tissue specificity: MipB (iceplant; Yamada et al., 1995, Plant Cell 7:1129-42) and SUCS (root nodules; broadbean; Kuster et al., 1993, Mol Plant Microbe Interact 6:507-14) for roots, OsSUT1 (rice; Hirose et al., 1997. Plant Cell Physiol 38:1389-96) for leaves, Msg (soybean; Stomvik et al., 1999, Plant Mol Biol 41:217-31) for siliques, cell (Arabidopsis; Shani et al., 1997., Plant Mol Biol 34(6):837-42) and ACT11 (Arabidopsis; Huang et al., 1997, Plant Mol Biol 33:125-39) for inflorescence.

Still other promoters are affected by hormones or participate in specific physiological processes, which can be used in combination with those of present invention. Some examples are the ACC synthase gene that is induced differently by ethylene and brassinosteroids (mung bean; Yi et al., 1999, Plant Mol Bio141:443-54), the TAPG1 gene that is active during abscission (tomato; Kalaitzis et al., 1995, Plant Mol Biol 28:647-56), and the 1-aminocyclopropane-1-carboxylate synthase gene (carnation; Jones et al., 1995, Plant Mol Biol 28:505-12) and the CP-2/cathepsin L gene (rat; Kim and Wright, 1997, Biol Reprod 57:1467-77), both active during senescence.

All of the references cited in this section are hereby incorporated by reference.

E. Vectors

Vectors are a useful component of the present invention. In particular, the present promoters and/or promoter control elements may be delivered to a system such as a cell by way of a vector. For the purposes of this invention, such delivery may range from simply introducing the promoter or promoter control element by itself randomly into a cell to integration of a cloning vector containing the present promoter or promoter control element. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are a preferred vector for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al., Nature 317: 741-744 (1985); Gordon-Kamm et al., Plant Cell 2: 603-618 (1990); and Stalker et al., Science 242: 419-423 (1988)). Other marker genes exist which provide hormone responsiveness.

All of the references cited in this section are hereby incorporated by reference.

(1) Modification of Transcription by Promoters and Promoter Control Elements

The promoter or promoter control element of the present invention may be operably linked to a polynucleotide to be transcribed. In this manner, the promoter or promoter control element may modify transcription by modulate transcript levels of that polynucleotide when inserted into a genome.

However, prior to insertion into a genome, the promoter or promoter control element need not be linked, operably or otherwise, to a polynucleotide to be transcribed. For example, the promoter or promoter control element may be inserted alone into the genome in front of a polynucleotide already present in the genome. In this manner, the promoter or promoter control element may modulate the transcription of a polynucleotide that was already present in the genome. This polynucleotide may be native to the genome or inserted at an earlier time.

Alternatively, the promoter or promoter control element may be inserted into a genome alone to modulate transcription. See, for example, Vaucheret, H et al. (1998) *Plant J* 16: 651-659, which is hereby incorporated by reference. Rather, the promoter or promoter control element may be simply inserted into a genome or maintained extrachromosomally as a way to divert transcription resources of the system to itself. This approach may be used to down-regulate the transcript levels of a group of polynucleotide(s).

(2) Polynucleotide to be Transcribed

The nature of the polynucleotide to be transcribed is not limited. Specifically, the polynucleotide may include sequences that will have activity as RNA as well as sequences that result in a polypeptide product. These sequences may include, but are not limited to antisense sequences, ribozyme sequences, spliceosomes, amino acid coding sequences, and fragments thereof.

Specific coding sequences may include, but are not limited to endogenous proteins or fragments thereof, or heterologous proteins including marker genes or fragments thereof.

Promoters and control elements of the present invention are useful for modulating metabolic or catabolic processes. Such processes include, but are not limited to, secondary product metabolism, amino acid synthesis, seed protein storage, oil development, pest defense and nitrogen usage. Some examples of genes, transcripts and peptides or polypeptides participating in these processes, which can be modulated by the present invention: are tryptophan decarboxylase (tdc) and strictosidine synthase (strl), dihydrodipicolinate synthase (DHDPS) and aspartate kinase (AK), 2S albumin and alpha-, beta-, and gamma-zeins, ricinoleate and 3-ketoacyl-ACP synthase (KAS), *Bacillus thuringiensis* (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon that encodes the first methionine. Thus, when constructing a recombinant polynucleotide according to the present invention for expressing a protein product, it is preferable to ensure that the linkage between the 3' portion, preferably including the TATA box, of the promoter and the polynucleotide to be transcribed, or a functional derivative thereof, does not contain any intervening codons which are capable of encoding a methionine.

The vector of the present invention may contain additional components. For example, an origin of replication allows for replication of the vector in a host cell. Additionally, homologous sequences flanking a specific sequence allows for specific recombination of the specific sequence at a desired location in the target genome. T-DNA sequences also allow for insertion of a specific sequence randomly into a target genome.

The vector may also be provided with a plurality of restriction sites for insertion of a polynucleotide to be transcribed as well as the promoter and/or promoter control elements of the present invention. The vector may additionally contain selectable marker genes. The vector may also contain a transcriptional and translational initiation region, and a transcriptional and translational termination region functional in the host cell. The termination region may be native with the transcriptional initiation region, may be native with the polynucleotide to be transcribed, or may be derived from another source. Convenient termination regions are available from the Ti-plasmid of *A. tumefaciens*, such as the octopine synthase and nopaline synthase termination regions. See also, Guerineau et al., (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. 1989) Nucleic Acids Res. 17:7891-7903; Joshi et al. (1987) Nucleic Acid Res. 15:9627-9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436,391; see also and Murray et al., (1989) Nucleic Acids Res. 17:477-498.

Additional sequence modifications include elimination of sequences encoding spurious polyadenylation signals, exon intron splice site signals, transposon-like repeats, and other such sequences well characterized as deleterious to expression. The G-C content of the polynucleotide may be adjusted to levels average for a given cellular host, as calculated by reference to known genes expressed in the host cell. The polynucleotide sequence may be modified to avoid hairpin secondary mRNA structures.

A general description of expression vectors and reporter genes can be found in Gruber, et al., "Vectors for Plant Transformation, in Methods in Plant Molecular Biology & Biotechnology" in Glich et al., (Eds. pp. 89-119, CRC Press, 1993). Moreover GUS expression vectors and GUS gene cassettes are available from Clonetech Laboratories, Inc., Palo Alto, Calif. while luciferase expression vectors and luciferase gene cassettes are available from Promega Corp. (Madison, Wis.). GFP vectors are available from Aurora Biosciences.

All of the references cited in this section are hereby incorporated by reference.

F. Polynucleotide Insertion Into A Host Cell

The polynucleotides according to the present invention can be inserted into a host cell. A host cell includes but is not limited to a plant, mammalian, insect, yeast, and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

(1) Polynucleotides Autonomous of the Host Genome

The polynucleotides of the present invention can exist autonomously or independent of the host cell genome. Vectors of these types are known in the art and include, for example, certain type of non-integrating viral vectors, autonomously replicating plasmids, artificial chromosomes, and the like.

Additionally, in some cases transient expression of a polynucleotide may be desired.

(2) Polynucleotides Integrated into the Host Genome

The promoter sequences, promoter control elements or vectors of the present invention may be transformed into host cells. These transformations may be into protoplasts or intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, Glich et al. (Eds. pp. 67-88 CRC Press, 1993); and by Phillips et al. "Cell-Tissue Culture and In-Vitro Manipulation" in Corn & Corn Improvement, 3rd Edition 10Sprague et al. (Eds. pp. 345-387) American Society of Agronomy Inc. et al. 1988.

Methods of introducing polynucleotides into plant tissue include the direct infection or co-cultivation of plant cell with *Agrobacterium tumefaciens*, Horsch et al., Science, 227:1229 (1985). Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al., "Direct DNA transfer into intact plant cells via microprojectile bombardment" In: Gamborg and Phillips (Eds.) Plant Cell, Tissue and Organ Culture: Fundamental Methods, Springer Verlag, Berlin (1995).

In another embodiment of the current invention, expression constructs can be used for gene expression in callus culture for the purpose of expressing marker genes encoding peptides or polypeptides that allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media. Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP), and β-glucuronidase (GUS), etc. Some of the exemplary promoters of Table 1 will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the cre-lox system (A. C. Vergunst et al., *Plant Mol. Biol.* 38:393 (1998)).

All of the references cited in this section are hereby incorporated by reference.

G. Utility

Common Uses

In yet another embodiment, the promoters of the present invention can be used to further understand developmental mechanisms. For example, promoters that are specifically induced during callus formation, somatic embryo formation, shoot formation or root formation can be used to explore the effects of overexpression, repression or ectopic expression of target genes, or for isolation of trans-acting factors.

The vectors of the invention can be used not only for expression of coding regions but may also be used in exon-trap cloning, or promoter trap procedures to detect differential gene expression in various tissues, K. Lindsey et al., 1993 "Tagging Genomic Sequences That Direct Transgene Expression by Activation of a Promoter Trap in Plants", Transgenic Research 2:3347. D. Auch & Reth, et al., "Exon Trap Cloning: Using PCR to Rapidly Detect and Clone Exons from Genomic DNA Fragments", Nucleic Acids Research, Vol. 18, No. 22, p. 674.

Entrapment vectors, first described for use in bacteria (Casadaban and Cohen, 1979, Proc. Nat. Aca. Sci. U.S.A., 76: 4530; Casadaban et al., 1980, J. Bacteriol., 143: 971) permit selection of insertional events that lie within coding sequences. Entrapment vectors can be introduced into pluripotent ES cells in culture and then passed into the germline via chimeras (Gossler et al., 1989, Science, 244: 463; Skarnes, 1990, Biotechnology, 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, constitutively active constructs can be eliminated by screening only bacteria that do not express the reporter gene under laboratory conditions. The bacteria selected by such a method contain constructs that are selectively induced only during infection of the host. The WET approach can be modified for use in plants to identify genes induced in either the bacteria or the plant cells upon pathogen infection or root colonization. For information on WET see the articles by Mahan et al. in Science 259:686-688 (1993), Mahan et al. in PNAS USA 92:669-673 (1995), Heithoff et al. in PNAS USA 94:934-939 (1997), and Wang et al. in PNAS USA. 93:10434 (1996). All of the references cited in this section are hereby incorporated by reference.

Constitutive Transcription

Use of promoters and control elements providing constitutive transcription is desired for modulation of transcription in most cells of an organism under most environmental conditions. In a plant, for example, constitutive transcription is useful for modulating genes involved in defense, pest resistance, herbicide resistance, etc.

Constitutive up-regulation and transcription down-regulation is useful for these applications. For instance, genes, transcripts, and/or polypeptides that increase defense, pest and herbicide resistance may require constitutive up-regulation of transcription. In contrast, constitutive transcriptional down-regulation may be desired to inhibit those genes, transcripts, and/or polypeptides that lower defense, pest and herbicide resistance.

Typically, promoter or control elements that provide constitutive transcription produce transcription levels that are statistically similar in many tissues and environmental conditions observed.

Calculation of P-value from the different observed transcript levels is one means of determining whether a promoter or control element is providing constitutive up-regulation. P-value is the probability that the difference of transcript levels is not statistically significant. The higher the P-value, the more likely the difference of transcript levels is not significant. One formula used to calculate P-value is as follows: $\int \phi(x)dx$, integrated from a to $\infty$, where $\phi(x)$ is a normal distribution;

$$\text{where } a = \frac{|Sx - \mu|}{\sigma(\text{all Samples except } Sx)};$$

where Sx=the intensity of the sample of interest where $\mu$ = is the average of the intensities of all samples except Sx, $$= \frac{(\Sigma S1...Sn) - Sx}{n-1}$$

where σ(S1 ... S11, not including Sx)=the standard deviation of all sample intensities except Sx.

The P-value from the formula ranges from 1.0 to 0.0.

Usually, each P-value of the transcript levels observed in a majority of cells, tissues, or organs under various environmental conditions produced by the promoter or control element is greater than $10^{-8}$; more usually, greater than $10^{-7}$; even more usually, greater than $10^{-6}$; even more usually, greater than $10^{-5}$ or $10^{-4}$.

For up-regulation of transcription, promoter and control elements produce transcript levels that are above background of the assay.

Stress Induced Preferential Transcription

Promoters and control elements providing modulation of transcription under oxidative, drought, oxygen, wound, and methyl jasmonate stress are particularly useful for producing host cells or organisms that are more resistant to biotic and abiotic stresses. In a plant, for example, modulation of genes, transcripts, and/or polypeptides in response to oxidative stress can protect cells against damage caused by oxidative agents, such as hydrogen peroxide and other free radicals.

Drought induction of genes, transcripts, and/or polypeptides are useful to increase the viability of a plant, for example, when water is a limiting factor. In contrast, genes, transcripts, and/or polypeptides induced during oxygen stress can help the flood tolerance of a plant.

The promoters and control elements of the present invention can modulate stresses similar to those described in, for example, stress conditions are VuPLD1 (drought stress; Cowpea; see Pham-Thi et al., 1999, Plant Mol Biol 1257-65), pyruvate decarboxylase (oxygen stress; rice; see Rivosal et al., 1997, Plant Physiol 114(3): 1021-29), chromoplast specific carotenoid gene (oxidative stress; capsicum; see Bouvier et al., 1998, J Biol Chem 273: 30651-59).

Promoters and control elements providing preferential transcription during wounding or induced by methyl jasmonate can produce a defense response in host cells or organisms. In a plant, for example, preferential modulation of genes, transcripts, and/or polypeptides under such conditions is useful to induce a defense response to mechanical wounding, pest or pathogen attack or treatment with certain chemicals.

Promoters and control elements of the present invention also can trigger a response similar to those described for cf9 (viral pathogen; tomato; see O'Donnell et al., 1998, Plant J 14(1): 137-42), hepatocyte growth factor activator inhibitor type 1 (HAI-1), which enhances tissue regeneration (tissue injury; human; Koono et al., 1999, J Histochem Cytochem 47: 673-82), copper amine oxidase (CuAO), induced during ontogenesis and wound healing (wounding; chick-pea; Rea et al., 1998, FEBS Ltr 437: 177-82), proteinase inhibitor II (wounding; potato; see Pena-Cortes et al., 1988, Planta 174: 84-89), protease inhibitor II (methyl jasmonate; tomato; see Farmer and Ryan, 1990, Proc Natl Acad Sci USA 87: 7713-7716), two vegetative storage protein genes VspA and VspB (wounding, jasmonic acid, and water deficit; soybean; see Mason and Mullet, 1990, Plant Cell 2: 569-579).

Up-regulation and transcription down-regulation are useful for these applications. For instance, genes, transcripts, and/or polypeptides that increase oxidative, flood, or drought tolerance may require up-regulation of transcription. In contrast, transcriptional down-regulation may be desired to inhibit those genes, transcripts, and/or polypeptides that lower such tolerance.

Typically, promoter or control elements, which provide preferential transcription in wounding or under methyl jasmonate induction, produce transcript levels that are statistically significant as compared to cell types, organs or tissues under other conditions.

For preferential up-regulation of transcription, promoter and control elements produce transcript levels that are above background of the assay.

All of the references cited in this section are hereby incorporated by reference.

Light Induced Preferential Transcription

Promoters and control elements providing preferential transcription when induced by light exposure can be utilized to modulate growth, metabolism, and development; to increase drought tolerance; and decrease damage from light stress for host cells or organisms. In a plant, for example, modulation of genes, transcripts, and/or polypeptides in response to light is useful (1) to increase the photosynthetic rate;
(2) to increase storage of certain molecules in leaves or green parts only, e.g., silage with high protein or starch content;

(3) to modulate production of exogenous compositions in green tissue, e.g., certain feed enzymes;
(4) to induce growth or development, such as fruit development and maturity, during extended exposure to light;
(5) to modulate guard cells to control the size of stomata in leaves to prevent water loss, or
(6) to induce accumulation of beta-carotene to help plants cope with light induced stress.

The promoters and control elements of the present invention also can trigger responses similar to those described in: abscisic acid insensitive3 (ABI3) (dark-grown *Arabidopsis* seedlings, see Rohde et al., 2000, Plant Cell 12: 35-52), asparagine synthetase (pea root nodules, see Tsai and Coruzzi, 1990, EMBO J. 9: 323-32), mdm2 gene (human tumor; see Saucedo et al., 1998, Cell Growth Differ 9: 119-30).

Up-regulation and transcription down-regulation are useful for these applications. For instance, genes, transcripts, and/or polypeptides that increase drought or light tolerance may require up-regulation of transcription. In contrast, transcriptional down-regulation may be desired to inhibit those genes, transcripts, and/or polypeptides that lower such tolerance.

Typically, promoter or control elements, which provide preferential transcription in cells, tissues or organs exposed to light, produce transcript levels that are statistically significant as compared to cells, tissues, or organs under decreased light exposure (intensity or length of time).

For preferential up-regulation of transcription, promoter and control elements produce transcript levels that are above background of the assay.

All of the references cited in this section are hereby incorporated by reference.

Dark Induced Preferential Transcription

Promoters and control elements providing preferential transcription when induced by dark or decreased light intensity or decreased light exposure time can be utilized to time growth, metabolism, and development, to modulate photosynthesis capabilities for host cells or organisms. In a plant, for example, modulation of genes, transcripts, and/or polypeptides in response to dark is useful, for example,
(1) to induce growth or development, such as fruit development and maturity, despite lack of light;
(2) to modulate genes, transcripts, and/or polypeptide active at night or on cloudy days; or
(3) to preserve the plastid ultra structure present at the onset of darkness.

The present promoters and control elements can also trigger response similar to those described in the section above.

Up-regulation and transcription down-regulation is useful for these applications. For instance, genes, transcripts, and/or polypeptides that increase growth and development may require up-regulation of transcription. In contrast, transcriptional down-regulation may be desired to inhibit those genes, transcripts, and/or polypeptides that modulate photosynthesis capabilities.

Typically, promoter or control elements, which provide preferential transcription under exposure to dark or decrease light intensity or decrease exposure time, produce transcript levels that are statistically significant.

For preferential up-regulation of transcription, promoter and control elements produce transcript levels that are above background of the assay.

Leaf Preferential Transcription

Promoters and control elements providing preferential transcription in a leaf can modulate growth, metabolism, and development or modulate energy and nutrient utilization in host cells or organisms. In a plant, for example, preferential modulation of genes, transcripts, and/or polypeptide in a leaf, is useful, for example,
(1) to modulate leaf size, shape, and development;
(2) to modulate the number of leaves; or
(3) to modulate energy or nutrient usage in relation to other organs and tissues Up-regulation and transcription down-regulation is useful for these applications. For instance, genes, transcripts, and/or polypeptides that increase growth, for example, may require up-regulation of transcription. In contrast, transcriptional down-regulation may be desired to inhibit energy usage in a leaf to be directed to the fruit instead, for instance.

Typically, promoter or control elements, which provide preferential transcription in the cells, tissues, or organs of a leaf, produce transcript levels that are statistically significant as compared to other cells, organs or tissues.

For preferential up-regulation of transcription, promoter and control elements produce transcript levels that are above background of the assay.

Root Preferential Transcription

Promoters and control elements providing preferential transcription in a root can modulate growth, metabolism, development, nutrient uptake, nitrogen fixation, or modulate energy and nutrient utilization in host cells or organisms. In a plant, for example, preferential modulation of genes, transcripts, and/or in a leaf, is useful
(1) to modulate root size, shape, and development;
(2) to modulate the number of roots, or root hairs;
(3) to modulate mineral, fertilizer, or water uptake;
(4) to modulate transport of nutrients; or
(4) to modulate energy or nutrient usage in relation to other organs and tissues.

Up-regulation and transcription down-regulation is useful for these applications. For instance, genes, transcripts, and/or polypeptides that increase growth, for example, may require up-regulation of transcription. In contrast, transcriptional down-regulation may be desired to inhibit nutrient usage in a root to be directed to the leaf instead, for instance.

Typically, promoter or control elements, which provide preferential transcription in cells, tissues, or organs of a root, produce transcript levels that are statistically significant as compared to other cells, organs or tissues.

For preferential up-regulation of transcription, promoter and control elements produce transcript levels that are above background of the assay.

Stem/Shoot Preferential Transcription

Promoters and control elements providing preferential transcription in a stem or shoot can modulate growth, metabolism, and development or modulate energy and nutrient utilization in host cells or organisms. In a plant, for example, preferential modulation of genes, transcripts, and/or polypeptide in a stem or shoot, is useful, for example,
(1) to modulate stem/shoot size, shape, and development; or
(2) to modulate energy or nutrient usage in relation to other organs and tissues Up-regulation and transcription down-regulation is useful for these applications. For instance, genes, transcripts, and/or polypeptides that increase growth, for example, may require up-regulation of transcription. In contrast, transcriptional down-regulation may be desired to inhibit energy usage in a stem/shoot to be directed to the fruit instead, for instance.

Typically, promoter or control elements, which provide preferential transcription in the cells, tissues, or organs of a stem or shoot, produce transcript levels that are statistically significant as compared to other cells, organs or tissues.

For preferential up-regulation of transcription, promoter and control elements produce transcript levels that are above background of the assay.

Fruit and Seed Preferential Transcription

Promoters and control elements providing preferential transcription in a silique or fruit can time growth, development, or maturity; or modulate fertility; or modulate energy and nutrient utilization in host cells or organisms. In a plant, for example, preferential modulation of genes, transcripts, and/or polypeptides in a fruit, is useful
 (1) to modulate fruit size, shape, development, and maturity;
 (2) to modulate the number of fruit or seeds;
 (3) to modulate seed shattering;
 (4) to modulate components of seeds, such as, storage molecules, starch, protein, oil, vitamins, anti-nutritional components, such as phytic acid;
 (5) to modulate seed and/or seedling vigor or viability;
 (6) to incorporate exogenous compositions into a seed, such as lysine rich proteins;
 (7) to permit similar fruit maturity timing for early and late blooming flowers; or
 (8) to modulate energy or nutrient usage in relation to other organs and tissues.

Up-regulation and transcription down-regulation is useful for these applications. For instance, genes, transcripts, and/or polypeptides that increase growth, for example, may require up-regulation of transcription. In contrast, transcriptional down-regulation may be desired to inhibit late fruit maturity, for instance.

Typically, promoter or control elements, which provide preferential transcription in the cells, tissues, or organs of siliques or fruits, produce transcript levels that are statistically significant as compared to other cells, organs or tissues.

For preferential up-regulation of transcription, promoter and control elements produce transcript levels that are above background of the assay.

Callus Preferential Transcription

Promoters and control elements providing preferential transcription in a callus can be useful to modulating transcription in dedifferentiated host cells. In a plant transformation, for example, preferential modulation of genes, transcripts, in callus is useful to modulate transcription of a marker gene, which can facilitate selection of cells that are transformed with exogenous polynucleotides.

Up-regulation and transcription down-regulation is useful for these applications. For instance, genes, transcripts, and/or polypeptides that increase marker gene detectability, for example, may require up-regulation of transcription. In contrast, transcriptional down-regulation may be desired to increase the ability of the calluses to later differentiate, for instance.

Typically, promoter or control elements, which provide preferential transcription in callus, produce transcript levels that are statistically significant as compared to other cell types, tissues, or organs. Calculation of P-value from the different observed transcript levels is one means of determining whether a promoter or control element is providing such preferential transcription.

Usually, each P-value of the transcript levels observed in callus as compared to, at least one other cell type, tissue or organ, is less than $10^{-4}$; more usually, less than $10^{-5}$; even more usually, less than $10^{-6}$; even more usually, less than $10^{-7}$ or $10^{-8}$.

For preferential up-regulation of transcription, promoter and control elements produce transcript levels that are above background of the assay.

Flower Specific Transcription

Promoters and control elements providing preferential transcription in flowers can modulate pigmentation; or modulate fertility in host cells or organisms. In a plant, for example, preferential modulation of genes, transcripts, and/or polypeptides in a flower, is useful,
 (1) to modulate petal color; or
 (2) to modulate the fertility of pistil and/or stamen.

Up-regulation and transcription down-regulation is useful for these applications. For instance, genes, transcripts, and/or polypeptides that increase pigmentation, for example, may require up-regulation of transcription. In contrast, transcriptional down-regulation may be desired to inhibit fertility, for instance.

Typically, promoter or control elements, which provide preferential transcription in flowers, produce transcript levels that are statistically significant as compared to other cells, organs or tissues.

For preferential up-regulation of transcription, promoter and control elements produce transcript levels that are above background of the assay.

Immature Bud and Inflorescence Preferential Transcription

Promoters and control elements providing preferential transcription in a immature bud or inflorescence can time growth, development, or maturity; or modulate fertility or viability in host cells or organisms. In a plant, for example, preferential modulation of genes, transcripts, and/or polypeptide in a fruit, is useful,
 (1) to modulate embryo development, size, and maturity;
 (2) to modulate endosperm development, size, and composition;
 (3) to modulate the number of seeds and fruits; or
 (4) to modulate seed development and viability.

Up-regulation and transcription down-regulation is useful for these applications. For instance, genes, transcripts, and/or polypeptides that increase growth, for example, may require up-regulation of transcription. In contrast, transcriptional down-regulation may be desired to decrease endosperm size, for instance.

Typically, promoter or control elements, which provide preferential transcription in immature buds and inflorescences, produce transcript levels that are statistically significant as compared to other cell types, organs or tissues.

For preferential up-regulation of transcription, promoter and control elements produce transcript levels that are above background of the assay.

Senescence Preferential Transcription

Promoters and control elements providing preferential transcription during senescencing can be used to modulate cell degeneration, nutrient mobilization, and scavenging of free radicals in host cells or organisms. Other types of responses that can be modulated include, for example, senescence associated genes (SAG) that encode enzymes thought to be involved in cell degeneration and nutrient mobilization (arabidopsis; see Hensel et al. 1993. Plant Cell 5: 553-64), and the CP-2/cathepsin L gene (rat; Kim and Wright. 1997. Biol Reprod 57: 1467-77), both induced during senescence.

In a plant, for example, preferential modulation of genes, transcripts, and/or polypeptides during senescence is useful to modulate fruit ripening.

Up-regulation and transcription down-regulation is useful for these applications. For instance, genes, transcripts, and/or polypeptides that increase scavenging of free radicals, for example, may require up-regulation of transcription. In contrast, transcriptional down-regulation may be desired to inhibit cell degeneration, for instance.

Typically, promoter or control elements, which provide preferential transcription in cells, tissues, or organs during senescence, produce transcript levels that are statistically significant as compared to other conditions.

For preferential up-regulation of transcription, promoter and control elements produce transcript levels that are above background of the assay.

Germination Preferential Transcription

Promoters and control elements providing preferential transcription in a germinating seed can time growth, development, or maturity; or modulate viability in host cells or organisms. In a plant, for example, preferential modulation of genes, transcripts, and/or polypeptide in a germinating seed, is useful, (1) to modulate the emergence of they hypocotyls, cotyledons and radical; or
(2) to modulate shoot and primary root growth and development;

Up-regulation and transcription down-regulation is useful for these applications. For instance, genes, transcripts, and/or polypeptides that increase growth, for example, may require up-regulation of transcription. In contrast, transcriptional down-regulation may be desired to decrease endosperm size, for instance.

Typically, promoter or control elements, which provide preferential transcription in a germinating seed, produce transcript levels that are statistically significant as compared to other cell types, organs or tissues.

For preferential up-regulation of transcription, promoter and control elements produce transcript levels that are above background of the assay.

Microarray Analysis

A major way that a cell controls its response to internal or external stimuli is by regulating the rate of transcription of specific genes. For example, the differentiation of cells during organogenesis into forms characteristic of the organ is associated with the selective activation and repression of large numbers of genes. Thus, specific organs, tissues and cells are functionally distinct due to the different populations of mRNAs and protein products they possess. Internal signals program the selective activation and repression programs. For example, internally synthesized hormones produce such signals. The level of hormone can be raised by increasing the level of transcription of genes encoding proteins concerned with hormone synthesis.

To measure how a cell reacts to internal and/or external stimuli, individual mRNA levels can be measured and used as an indicator for the extent of transcription of the gene. Cells can be exposed to a stimulus, and mRNA can be isolated and assayed at different time points after stimulation. The mRNA from the stimulated cells can be compared to control cells that were not stimulated. The mRNA levels that are higher in the stimulated cell versus the control indicate a stimulus-specific response of the cell. The same is true of mRNA levels that are lower in stimulated cells versus the control condition.

Similar studies can be performed with cells taken from an organism with a defined mutation in their genome as compared with cells without the mutation. Altered mRNA levels in the mutated cells indicate how the mutation causes transcriptional changes. These transcriptional changes are associated with the phenotype that the mutated cells exhibit that is different from the phenotype exhibited by the control cells.

Applicants have utilized microarray techniques to measure the levels of mRNAs in cells from plants transformed with a construct containing the promoter or control elements of the present invention together with their endogenous cDNA sequences. In general, transformants with the constructs were grown to an appropriate stage, and tissue samples were prepared for the microarray differential expression analysis. In this manner it is possible to determine the differential expression for the cDNAs under the control of the endogenous promoter under various conditions.

Microarray Experimental Procedures and Results Procedures

1. Sample Tissue Preparation

Tissue samples for each of the expression analysis experiments were prepared as follows:

(a) Roots

Seeds of *Arabidopsis thaliana* (Ws) were sterilized in full strength bleach for less than 5 min., washed more than 3 times in sterile distilled deionized water and plated on MS agar plates. The plates were placed at 4° C. for 3 nights and then placed vertically into a growth chamber having 16 hr light/8 hr dark cycles, 23° C., 70% relative humidity and ~11,000 LUX. After 2 weeks, the roots were cut from the agar, flash frozen in liquid nitrogen and stored at –80° C.

(b) Rosette Leaves, Stems, and Siliques

*Arabidopsis thaliana* (Ws) seed was vernalized at 4° C. for 3 days before sowing in Metro-mix soil type 350. Flats were placed in a growth chamber having 16 hr light/8 hr dark, 80% relative humidity, 23° C. and 13,000 LUX for germination and growth. After 3 weeks, rosette leaves, stems, and siliques were harvested, flash frozen in liquid nitrogen and stored at –80° C. until use. After 4 weeks, siliques (<5 mm, 5-10 mm and >10 mm) were harvested, flash frozen in liquid nitrogen and stored at –80° C. until use. 5 week old whole plants (used as controls) were harvested, flash frozen in liquid nitrogen and kept at –80° C. until RNA was isolated.

(c) Germination

*Arabidopsis thaliana* seeds (ecotype Ws) were sterilized in bleach and rinsed with sterile water. The seeds were placed in 100 mm petri plates containing soaked autoclaved filter paper. Plates were foil-wrapped and left at 4° C. for 3 nights to vernalize. After cold treatment, the foil was removed and plates were placed into a growth chamber having 16 hr light/8 hr dark cycles, 23° C., 70% relative humidity and ~11,000 lux. Seeds were collected 1 d, 2 d, 3 d and 4 d later, flash frozen in liquid nitrogen and stored at –80° C. until RNA was isolated.

(d) Abscissic Acid (ABA)

Seeds of *Arabidopsis thaliana* (ecotype Wassilewskija) were sown in trays and left at 4° C. for 4 days to vernalize. They were then transferred to a growth chamber having grown 16 hr light/8 hr dark, 13,000 LUX, 70% humidity, and 20° C. and watered twice a week with 1 L of 1× Hoagland's solution. Approximately 1,000 14 day old plants were spayed with 200-250 mls of 100 µM ABA in a 0.02% solution of the detergent Silwet L-77. Whole seedlings, including roots, were harvested within a 15 to 20 minute time period at 1 hr and 6 hr after treatment, flash-frozen in liquid nitrogen and stored at –80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 100 µM ABA for treatment. Control plants were treated with water. After 6 hr and 24 hr, aerial and root tissues were separated and flash frozen in liquid nitrogen prior to storage at –80° C.

(e) Brassinosteroid Responsive

Two separate experiments were performed, one with epi-brassinolide and one with the brassinosteroid biosynthetic inhibitor brassinazole. In the epi-brassinolide experiments, seeds of wild-type *Arabidopsis thaliana* (ecotype Was silewskija) and the bras sinosteroid biosynthetic mutant dwf4-1 were sown in trays and left at 4° C. for 4 days to vernalize. They were then transferred to a growth chamber having 16 hr light/8 hr dark, 11,000 LUX, 70% humidity and 22° C. temperature. Four week old plants were spayed with a 1 µM solution of epi-brassinolide and shoot parts (unopened floral primordia and shoot apical meristems) harvested three hours later. Tissue was flash-frozen in liquid nitrogen and stored at −80° C. In the brassinazole experiments, seeds of wild-type *Arabidopsis thaliana* (ecotype Wassilewskija) were grown as described above. Four week old plants were spayed with a 11 µM solution of brassinazole and shoot parts (unopened floral primordia and shoot apical meristems) harvested three hours later. Tissue was flash-frozen in liquid nitrogen and stored at −80° C.

In addition to the spray experiments, tissue was prepared from two different mutants; (1) a dwf4-1 knock out mutant and (2) a mutant overexpressing the dwf4-1 gene.

Seeds of wild-type *Arabidopsis thaliana* (ecotype Wassilewskija) and of the dwf4-1 knock out and over-expressor mutants were sown in trays and left at 4° C. for 4 days to vernalize. They were then transferred to a growth chamber having 16 hr light/8 hr dark, 11,000 LUX, 70% humidity and 22° C. temperature. Tissue from shoot parts (unopened floral primordia and shoot apical meristems) was flash-frozen in liquid nitrogen and stored at −80° C.

Another experiment was completed with seeds of *Arabidopsis thaliana* (ecotype Wassilewskija) were sown in trays and left at 4° C. for 4 days to vernalize. They were then transferred to a growth chamber. Plants were grown under long-day (16 hr light: 8 hr. dark) conditions, 13,000 LUX light intensity, 70% humidity, 20° C. temperature and watered twice a week with 1 L 1× Hoagland's solution (recipe recited in Feldmann et al., (1987) Mol. Gen. Genet. 208: 1-9, hereby incorporated by reference) and described as complete nutrient solution). Approximately 1,000 14 day old plants were spayed with 200-250 mls of 0.11 µM Epi-Bras sinolite in 0.02% solution of the detergent Silwet L-77. At 1 hr. and 6 hrs. after treatment aerial tissues were harvested within a 15 to 20 minute time period and flash-frozen in liquid nitrogen.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 0.1 µM epi-brassinolide for treatment. Control plants were treated with distilled deionized water. After 24 hr, aerial and root tissues were separated and flash frozen in liquid nitrogen prior to storage at −80° C.

(f) Nitrogen: High to Low

Wild type *Arabidopsis thaliana* seeds (ecotype Ws) were surface sterilized with 30% Clorox, 0.1% Triton X-100 for 5 minutes. Seeds were then rinsed with 4-5 exchanges of sterile double distilled deionized water. Seeds were vernalized at 4° C. for 2-4 days in darkness. After cold treatment, seeds were plated on modified 1×MS media (without $NH_4NO_3$ or $KNO_3$), 0.5% sucrose, 0.5 g/L MES pH5.7, 1% phytagar and supplemented with $KNO_3$ to a final concentration of 60 mM (high nitrate modified 1×MS media). Plates were then grown for 7 days in a Percival growth chamber at 22° C. with 16 hr. light/8 hr dark.

Germinated seedlings were then transferred to a sterile flask containing 50 mL of high nitrate modified 1×MS liquid media. Seedlings were grown with mild shaking for 3 additional days at 22° C. in 16 hr. light/8 hr dark (in a Percival growth chamber) on the high nitrate modified 1×MS liquid media.

After three days of growth on high nitrate modified 1×MS liquid media, seedlings were transferred either to a new sterile flask containing 50 mL of high nitrate modified 1×MS liquid media or to low nitrate modified 1×MS liquid media (containing 20 µM $KNO_3$). Seedlings were grown in these media conditions with mild shaking at 22° C. in 16 hr light/8 hr dark for the appropriate time points and whole seedlings harvested for total RNA isolation via the Trizol method (LifeTech.). The time points used for the microarray experiments were 10 min. and 1 hour time points for both the high and low nitrate modified 1×MS media.

Alternatively, seeds that were surface sterilized in 30% bleach containing 0.1% Triton X-100 and further rinsed in sterile water, were planted on MS agar, (0.5% sucrose) plates containing 50 mM $KNO_3$ (potassium nitrate). The seedlings were grown under constant light (3500 LUX) at 22° C. After 12 days, seedlings were transferred to MS agar plates containing either 1 mM $KNO_3$ or 50 mM $KNO_3$. Seedlings transferred to agar plates containing 50 mM $KNO_3$ were treated as controls in the experiment. Seedlings transferred to plates with 1 mM $KNO_3$ were rinsed thoroughly with sterile MS solution containing 1 mM $KNO_3$. There were ten plates per transfer. Root tissue was collected and frozen in 15 mL Falcon tubes at various time points which included 1 hour, 2 hours, 3 hours, 4 hours, 6 hours, 9 hours, 12 hours, 16 hours, and 24 hours.

Maize 35A19 Pioneer hybrid seeds were sown on flats containing sand and grown in a Conviron growth chamber at 25° C., 16 hr light/8 hr dark, ~13,000 LUX and 80% relative humidity. Plants were watered every three days with double distilled deionized water. Germinated seedlings are allowed to grow for 10 days and were watered with high nitrate modified 1×MS liquid media (see above). On day 11, young corn seedlings were removed from the sand (with their roots intact) and rinsed briefly in high nitrate modified 1×MS liquid media. The equivalent of half a flat of seedlings were then submerged (up to their roots) in a beaker containing either 500 mL of high or low nitrate modified 1×MS liquid media (see above for details).

At appropriate time points, seedlings were removed from their respective liquid media, the roots separated from the shoots and each tissue type flash frozen in liquid nitrogen and stored at −80° C. This was repeated for each time point. Total RNA was isolated using the Trizol method (see above) with root tissues only.

Corn root tissues isolated at the 4 hr and 16 hr time points were used for the microarray experiments. Both the high and low nitrate modified 1×MS media were used.

(g) Nitrogen: Low to High

*Arabidopsis thaliana* ecotype Ws seeds were sown on flats containing 4 L of a 1:2 mixture of Grace Zonolite vermiculite and soil. Flats were watered with 3 L of water and vernalized at 4° C. for five days. Flats were placed in a Conviron growth chamber having 16 hr light/8 hr dark at 20° C., 80% humidity and 17,450 LUX. Flats were watered with approximately 1.5 L of water every four days. Mature, bolting plants (24 days after germination) were bottom treated with 2 L of either a control (100 mM mannitol pH 5.5) or an experimental (50 mM ammonium nitrate, pH 5.5) solution. Roots, leaves and siliques were harvested separately 30, 120 and 240 minutes after treatment, flash frozen in liquid nitrogen and stored at −80° C.

Hybrid maize seed (Pioneer hybrid 35A19) were aerated overnight in deionized water. Thirty seeds were plated in each flat, which contained 4 liters of Grace zonolite vermiculite. Two liters of water were bottom fed and flats were kept in a Conviron growth chamber with 16 hr light/8 hr dark at 20° C. and 80% humidity. Flats were watered with 1 L of tap water every three days. Five day old seedlings were treated as described above with 2 L of either a control (100 mM mannitol pH 6.5) solution or 1 L of an experimental (50 mM ammonium nitrate, pH 6.8) solution. Fifteen shoots per time point per treatment were harvested 10, 90 and 180 minutes after treatment, flash frozen in liquid nitrogen and stored at −80° C.

Alternatively, seeds of Arabidopsis thaliana (ecotype Wassilewskija) were left at 4° C. for 3 days to vernalize. They were then sown on vermiculite in a growth chamber having 16 hours light/8 hours dark, 12,000-14,000 LUX, 70% humidity, and 20° C. They were bottom-watered with tap water, twice weekly. Twenty-four days old plants were sprayed with either water (control) or 0.6% ammonium nitrate at 4 μL/cm$^2$ of tray surface. Total shoots and some primary roots were cleaned of vermiculite, flash-frozen in liquid nitrogen and stored at −80° C.

(h) Methyl Jasmonate

Seeds of Arabidopsis thaliana (ecotype Wassilewskija) were sown in trays and left at 4° C. for 4 days to vernalize before being transferred to a growth chamber having 16 hr light/8 hr. dark, 13,000 LUX, 70% humidity, 20° C. temperature and watered twice a week with 1 L of a 1× Hoagland's solution. Approximately 1,000 14 day old plants were spayed with 200-250 mls of 0.001% methyl jasmonate in a 0.02% solution of the detergent Silwet L-77. At 1 hr and 6 hrs after treatment, whole seedlings, including roots, were harvested within a 15 to 20 minute time period, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 0.001% methyl jasmonate for treatment. Control plants were treated with water. After 24 hr, aerial and root tissues were separated and flash frozen in liquid nitrogen prior to storage at −80° C.

(i) Salicylic Acid

Seeds of Arabidopsis thaliana (ecotype Wassilewskija) were sown in trays and left at 4° C. for 4 days to vernalize before being transferred to a growth chamber having 16 hr light/8 hr. dark, 13,000 LUX, 70% humidity, 20° C. temperature and watered twice a week with 1 L of a 1× Hoagland's solution. Approximately 1,000 14 day old plants were spayed with 200-250 mls of 5 mM salicylic acid (solubilized in 70% ethanol) in a 0.02% solution of the detergent Silwet L-77. At 1 hr and 6 hrs after treatment, whole seedlings, including roots, were harvested within a 15 to 20 minute time period flash-frozen in liquid nitrogen and stored at −80° C.

Alternatively, seeds of wild-type Arabidopsis thaliana (ecotype Columbia) and mutant CS3726 were sown in soil type 200 mixed with osmocote fertilizer and Marathon insecticide and left at 4° C. for 3 days to vernalize. Flats were incubated at room temperature with continuous light. Sixteen days post germination plants were sprayed with 2 mM SA, 0.02% SilwettL-77 or control solution (0.02% SilwettL-77. Aerial parts or flowers were harvested 1 hr, 4 hr, 6 hr, 24 hr and 3 weeks post-treatment flash frozen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 2 mM SA for treatment. Control plants were treated with water. After 12 hr and 24 hr, aerial and root tissues were separated and flash frozen in liquid nitrogen prior to storage at −80° C.

(j) Drought Stress

Seeds of Arabidopsis thaliana (Wassilewskija) were sown in pots and left at 4° C. for three days to vernalize before being transferred to a growth chamber having 16 hr light/8 hr dark, 150,000-160,000 LUX, 20° C. and 70% humidity. After 14 days, aerial tissues were cut and left to dry on 3mM Whattman paper in a Petri-plate for 1 hour and 6 hours. Aerial tissues exposed for 1 hour and 6 hours to 3 mM Whattman paper wetted with 1× Hoagland's solution served as controls. Tissues were harvested, flash-frozen in liquid nitrogen and stored at −80° C.

Alternatively, Arabidopsis thaliana (Ws) seed was vernalized at 4° C. for 3 days before sowing in Metromix soil type 350. Flats were placed in a growth chamber with 23° C., 16 hr light/8 hr. dark, 80% relative humidity, ~13,000 LUX for germination and growth. Plants were watered with 1-1.5 L of water every four days. Watering was stopped 16 days after germination for the treated samples, but continued for the control samples. Rosette leaves and stems, flowers and siliques were harvested 2 d, 3 d, 4 d, 5 d, 6 d and 7 d after watering was stopped. Tissue was flash frozen in liquid nitrogen and kept at −80° C. until RNA was isolated. Flowers and siliques were also harvested on day 8 from plants that had undergone a 7 d drought treatment followed by 1 day of watering. Control plants (whole plants) were harvested after 5 weeks, flash frozen in liquid nitrogen and stored as above.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in empty 1-liter beakers at room temperature for treatment. Control plants were placed in water. After 1 hr, 6 hr, 12 hr and 24 hr aerial and root tissues were separated and flash frozen in liquid nitrogen prior to storage at −80° C.

(k) Osmotic Stress

Seeds of Arabidopsis thaliana (Wassilewskija) were sown in trays and left at 4° C. for three days to vernalize before being transferred to a growth chamber having 16 hr light/8 hr dark, 12,000-14,000 LUX, 20° C., and 70% humidity. After 14 days, the aerial tissues were cut and placed on 3 mM Whattman paper in a Petri-plate wetted with 20% PEG (polyethylene glycol-M$_r$. 8,000) in 1× Hoagland's solution. Aerial tissues on 3 mM Whattman paper containing 1× Hoagland's solution alone served as the control. Aerial tissues were harvested at 1 hour and 6 hours after treatment, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 10% PEG (polyethylene glycol-M, 8,000) for treatment. Control plants were treated with water. After 1 hr and 6 hr aerial and root tissues were separated and flash frozen in liquid nitrogen prior to storage at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 150 mM NaCl for treatment. Control plants were treated with water. After 1 hr, 6 hr, and 24 hr aerial and root tissues were separated and flash frozen in liquid nitrogen prior to storage at −80° C.

(1) Heat Shock Treatment

Seeds of *Arabidopsis Thaliana* (Wassilewskija) were sown in trays and left at 4° C. for three days to vernalize before being transferred to a growth chamber with 16 hr light/8 hr dark, 12,000-14,000 Lux, 70% humidity and 20° C., fourteen day old plants were transferred to a 42° C. growth chamber and aerial tissues were harvested 1 hr and 6 hr after transfer. Control plants were left at 20° C. and aerial tissues were harvested. Tissues were flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers containing 42° C. water for treatment. Control plants were treated with water at 25° C. After 1 hr and 6 hr aerial and root tissues were separated and flash frozen in liquid nitrogen prior to storage at −80° C.

(m) Cold Shock Treatment

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 20° C. and 70% humidity. Fourteen day old plants were transferred to a 4° C. dark growth chamber and aerial tissues were harvested 1 hour and 6 hours later. Control plants were maintained at 20° C. and covered with foil to avoid exposure to light. Tissues were flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers containing 4° C. water for treatment. Control plants were treated with water at 25° C. After 1 hr and 6 hr aerial and root tissues were separated and flash frozen in liquid nitrogen prior to storage at −80° C.

(n) *Arabidopsis* Seeds

Fruits (pod+seed) 0-5 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques 0-5 mm in length containing post fertilization through pre-heart stage [0-72 hours after fertilization (HAF)] embryos were harvested and flash frozen in liquid nitrogen.

Fruits (pod+seed) 5-10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques 5-10 mm in length containing heart—through early upturned-U-stage [72-120 hours after fertilization (HAF)] embryos were harvested and flash frozen in liquid nitrogen.

Fruits (pod+seed)>10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Siliques >10 mm in length containing green, late upturned-U-stage [>120 hours after fertilization (HAF)-9 days after flowering (DAF)] embryos were harvested and flash frozen in liquid nitrogen.

Green Pods 5-10 mm (Control Tissue for Samples 72-74)

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques 5-10 mm in length containing developing seeds 72-120 hours after fertilization (HAF)] were opened and the seeds removed. The remaining tissues (green pods minus seed) were harvested and flash frozen in liquid nitrogen.

Green Seeds from Fruits >10 mm

Seeds of *Arabidopsis thaliana* (ecotype Wassilewskija) were sown in pots and left at 4° C. for two to three days to vernalize. They were then transferred to a growth chamber.

Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques >10 mm in length containing developing seeds up to 9 days after flowering (DAF)] were opened and the seeds removed and harvested and flash frozen in liquid nitrogen.

Brown Seeds from Fruits >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Yellowing siliques >10 mm in length containing brown, dessicating seeds >11 days after flowering (DAF)] were opened and the seeds removed and harvested and flash frozen in liquid nitrogen.

Green/Brown Seeds from Fruits >10 mm

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature. 3-4 siliques (fruits) bearing developing seeds were selected from at least 3 plants and were hand-dissected to determine what developmental stage(s) were represented by the enclosed embryos. Description of the stages of *Arabidopsis* embryogenesis used in this determination were summarized by Bowman (1994). Silique lengths were then determined and used as an approximate determinant for embryonic stage. Green siliques >10 mm in length containing both green and brown seeds >9 days after flowering (DAF)] were opened and the seeds removed and harvested and flash frozen in liquid nitrogen.

Mature Seeds (24 Hours after Imbibition)

Mature dry seeds of *Arabidopsis thaliana* (ecotype Wassilewskija) were sown onto moistened filter paper and left at 4° C. for two to three days to vernalize. Imbibed seeds were then transferred to a growth chamber [16 hr light: 8 hr dark conditions, 7000-8000 LUX light intensity, 70% humidity, and 22° C. temperature], the emerging seedlings harvested after 48 hours and flash frozen in liquid nitrogen.

Mature Seeds (Dry)

Seeds of *Arabidopsis thaliana* (ecotype Wassilewskija) were sown in pots and left at 4° C. for two to three days to vernalize. They were then transferred to a growth chamber. Plants were grown under long-day (16 hr light: 8 hr dark) conditions, 7000-8000 LUX light intensity, 70% humidity, and 22° C. temperature and taken to maturity. Mature dry seeds are collected, dried for one week at 28° C., and vernalized for one week at 4° C. before used as a source of RNA.

(o) Herbicide Treatment

*Arabidopsis thaliana* (Ws) seeds were sterilized for 5 min. with 30% bleach, 50 µl Triton in a total volume of 50 ml. Seeds were vernalized at 4° C. for 3 days before being plated onto GM agar plates at a density of about 144 seeds per plate. Plates were incubated in a Percival growth chamber having 16 hr light/8 hr dark, 80% relative humidity, 22° C. and 11,000 LUX for 14 days.

Plates were sprayed (~0.5 mls/plate) with water, Finale (1.128 g/L), Glean (1.88 g/L), RoundUp (0.01 g/L) or Trimec (0.08 g/L). Tissue was collected and flash frozen in liquid nitrogen at the following time points: 0, 1, 2, 4, 8, 12 and 24 hours. Frozen tissue was stored at −80° C. prior to RNA isolation.

(p) Root Tips

Seeds of *Arabidopsis thaliana* (ecotype Ws) were placed on MS plates and vernalized at 4° C. for 3 days before being placed in a 25° C. growth chamber having 16 hr light/8 hr dark, 70% relative humidity and about 3 W/m$^2$. After 6 days, young seedlings were transferred to flasks containing B5 liquid medium, 1% sucrose and 0.05 mg/l indole-3-butyric acid. Flasks were incubated at room temperature with 100 rpm agitation. Media was replaced weekly. After three weeks, roots were harvested and incubated for 1 hr with 2% pectinase, 0.2% cellulase, pH 7 before straining through a #80 (Sigma) sieve. The root body material remaining on the sieve (used as the control) was flash frozen and stored at −80° C. until use. The material that passed through the #80 sieve was strained through a #200 (Sigma) sieve and the material remaining on the sieve (root tips) was flash frozen and stored at −80° C. until use. Approximately 10 mg of root tips were collected from one flask of root culture.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 8 days. Seedlings were carefully removed from the sand and the root tips (—2 mm long) were removed and flash frozen in liquid nitrogen prior to storage at −80° C. The tissues above the root tips (—1 cm long) were cut, treated as above and used as control tissue.

(q) Imbibed Seed

Seeds of maize hybrid 35A (Pioneer) were sown in water-moistened sand in covered flats (10 rows, 5-6 seed/row) and covered with clear, plastic lids before being placed in a growth chamber having 16 hr light (25° C.)/8 hr dark (20° C.), 75% relative humidity and 13,000-14,000 LUX. One day after sowing, whole seeds were flash frozen in liquid nitrogen prior to storage at −80° C. Two days after sowing, embryos and endosperm were isolated and flash frozen in liquid nitrogen prior to storage at −80° C. On days 3-6, aerial tissues, roots and endosperm were isolated and flash frozen in liquid nitrogen prior to storage at −80° C.

(r) Flowers (Green, White or Buds)

Approximately 10 µl of *Arabidopsis thaliana* seeds (ecotype Ws) were sown on 350 soil (containing 0.03% marathon) and vernalized at 4C for 3 days. Plants were then grown at room temperature under fluorescent lighting until flowering. Flowers were harvested after 28 days in three different categories. Buds that had not opened at all and were completely green were categorized as "flower buds" (also referred to as green buds by the investigator). Buds that had started to open, with white petals emerging slightly were categorized as "green flowers" (also referred to as white buds by the investigator). Flowers that had opened mostly (with no silique elongation) with white petals completely visible were categorized as "white flowers" (also referred to as open flowers by the investigator). Buds and flowers were harvested with forceps, flash frozen in liquid nitrogen and stored at −80C until RNA was isolated.

s) Ovules

Seeds of *Arabidopsis thaliana* heterozygous for *pistillata* (pi) [ecotype Landsberg *erecta* (Ler)] were sown in pots and left at 4° C. for two to three days to vernalize. They were then transferred to a growth chamber. Plants were grown under long-day (16 hr light: 8 hr dark) conditions, 7000-8000 LUX light intensity, 76% humidity, and 24° C. temperature. Inflorescences were harvested from seedlings about 40 days old. The inflorescences were cut into small pieces and incubated in the following enzyme solution (pH 5) at room temperature for 0.5-1 hr.: 0.2% pectolyase Y-23, 0.04% pectinase, 5 mM MES, 3% Sucrose and MS salts (1900 mg/l $KNO_3$, 1650 mg/l $NH_4NO_3$, 370 mg/l $MgSO_4.7H_2O$, 170 mg/l $KH_2PO_4$, 440 mg/l $CaCl_2.2H_2O$, 6.2 mg/l $H_3BO_3$, 15.6 mg/l $MnSO_4.4H_2O$, 8.6 mg/l $ZnSO_4.7H_2O$, 0.25 mg/l $NaMoO_4.2H_2O$, 0.025 mg/l $CuCO_4.5H_2O$, 0.025 mg/l $CoCl_2.6H_2O$, 0.83 mg/l KI, 27.8 mg/l $FeSO_4.7H_2O$, 37.3 mg/l Disodium EDTA, pH 5.8). At the end of the incubation the mixture of inflorescence material and enzyme solution was passed through a size 60 sieve and then through a sieve with a pore size of 125 μm. Ovules greater than 125 μm in diameter were collected, rinsed twice in B5 liquid medium (2500 mg/l $KNO_3$, 250 mg/l $MgSO_4.7H_2O$, 150 mg/l $NaH2PO4.H_2O$, 150 mg/l $CaCl_2.2H_2O$, 134 mg/l $(NH4)_2 CaCl_2.SO_4$, 3 mg/l $H_3BO_3$, 10 mg/l $MnSO_4.4H_2O$, 2 $ZnSO_4.7H_2O$, 0.25 mg/l $NaMoO_4.2H_2O$, 0.025 mg/l $CuCO_4.5H_2O$, 0.025 mg/l $CoCl_2.6H_2O$, 0.75 mg/l KI, 40 mg/l EDTA sodium ferric salt, 20 g/l sucrose, 10 mg/l Thiamine hydrochloride, 1 mg/l Pyridoxine hydrochloride, 1 mg/l Nicotinic acid, 100 mg/l myo-inositol, pH 5.5)), rinsed once in deionized water and flash frozen in liquid nitrogen. The supernatant from the 125 μm sieving was passed through subsequent sieves of 50 μm and 32 μm. The tissue retained in the 32 μm sieve was collected and mRNA prepared for use as a control.

t) Wounding

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 70% humidity and 20° C. After 14 days, the leaves were wounded with forceps. Aerial tissues were harvested 1 hour and 6 hours after wounding. Aerial tissues from unwounded plants served as controls. Tissues were flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were wounded (one leaf nicked by scissors) and placed in 1-liter beakers of water for treatment. Control plants were treated not wounded. After 1 hr and 6 hr aerial and root tissues were separated and flash frozen in liquid nitrogen prior to storage at −80° C.

u) Nitric Oxide Treatment

Seeds of *Arabidopsis thaliana* (Wassilewskija) were sown in trays and left at 4° C. for three days to vernalize before being transferred to a growth chamber having 16 hr light/8 hr dark, 12,000-14,000 LUX, 20° C. and 70% humidity. Fourteen day old plants were sprayed with 5 mM sodium nitroprusside in a 0.02% Silwett L-77 solution. Control plants were sprayed with a 0.02% Silwett L-77 solution. Aerial tissues were harvested 1 hour and 6 hours after spraying, flash-frozen in liquid nitrogen and stored at −80° C.

Seeds of maize hybrid 35A (Pioneer) were sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings were carefully removed from the sand and placed in 1-liter beakers with 5 mM nitroprusside for treatment. Control plants were treated with water. After 1 hr, 6 hr and 12 hr, aerial and root tissues were separated and flash frozen in liquid nitrogen prior to storage at −80° C.

v) Root Hairless Mutants

Plants mutant at the rhl gene locus lack root hairs. This mutation is maintained as a heterozygote.

Seeds of *Arabidopsis thaliana* (Landsberg erecta) mutated at the rhl gene locus were sterilized using 30% bleach with 1 ul/ml 20% Triton-X 100 and then vernalized at 4° C. for 3 days before being plated onto GM agar plates. Plates were placed in growth chamber with 16 hr light/8 hr. dark, 23° C., 14,500-15,900 LUX, and 70% relative humidity for germination and growth.

After 7 days, seedlings were inspected for root hairs using a dissecting microscope. Mutants were harvested and the cotyledons removed so that only root tissue remained. Tissue was then flash frozen in liquid nitrogen and stored at −80C.

*Arabidopsis thaliana* (Landsberg erecta) seedlings grown and prepared as above were used as controls.

Alternatively, seeds of *Arabidopsis thaliana* (Landsberg erecta), heterozygous for the rhll (root hairless) mutation, were surface-sterilized in 30% bleach containing 0.1% Triton X-100 and further rinsed in sterile water. They were then vernalized at 4° C. for 4 days before being plated onto MS agar plates. The plates were maintained in a growth chamber at 24° C. with 16 hr light/8 hr dark for germination and growth. After 10 days, seedling roots that expressed the phenotype (i.e. lacking root hairs) were cut below the hypocotyl junction, frozen in liquid nitrogen and stored at −80° C. Those seedlings with the normal root phenotype (heterozygous or wt) were collected as described for the mutant and used as controls.

w) Ap2

Seeds of *Arabidopsis thaliana* (ecotype Landesberg erecta) and floral mutant apetala2 (Jofuku et al., 1994, Plant Cell 6:1211-1225) were sown in pots and left at 4° C. for two to three days to vernalize. They were then transferred to a growth chamber. Plants were grown under long-day (16 hr light, 8 hr dark) conditions 7000-8000 LUX light intensity, 70% humidity and 22° C. temperature. Inflorescences containing immature floral buds (stages 1-7; Bowman, 1994) as well as the inflorescence meristem were harvested and flash-frozen. Polysomal polyA+ RNA was isolated from tissue according to Cox and Goldberg, 1988).

x) Salt

*Arabidopsis thaliana* ecotype Ws seeds were vernalized at 4° C. for 3 days before sowing in flats containing vermiculite soil. Flats were placed at 20° C. in a Conviron growth chamber having 16 hr light/8 hr dark. Whole plants (used as controls) received water. Other plants were treated with 100 mM NaCl. After 6 hr and 72 hr, aerial and root tissues were harvested and flash frozen in liquid nitrogen prior to storage at −80° C.

y) Petals

*Arabidopsis thaliana* ecotype Ws seeds were vernalized at 4° C. for 3 days before sowing in flats containing vermiculite soil. Flats were watered placed at 20° C. in a Conviron growth chamber having 16 hr light/8 hr dark. Whole plants (used as the control) and petals from inflorescences 23-25 days after germination were harvested, flash frozen in liquid nitrogen and stored at −80° C.

z) Pollen

*Arabidopsis thaliana* ecotype Ws seeds were vernalized at 4° C. for 3 days before sowing in flats containing vermiculite soil. Flats were watered and placed at 20° C. in a Conviron growth chamber having 16 hr light/8 hr dark. Whole plants (used as controls) and pollen from plants 38 dap was harvested, flash frozen in liquid nitrogen and stored at −80° C.

aa) Interploidy Crosses

Interploidy crosses involving a 6× parent are lethal. Crosses involving a 4× parent are complete and analyzed. The imbalance in the maternal/paternal ratio produced from the cross can lead to big seeds. *Arabidopsis thaliana* ecotype Ws seeds were vernalized at 4° C. for 3 days before sowing. Small siliques were harvested at 5 days after pollination, flash frozen in liquid nitrogen and stored at −80° C.

bb) Line Comparisons

Alkaloid 35S over-expressing lines were used to monitor the expression levels of terpenoid/alkaloid biosynthetic and P450 genes to identify the transcriptional regulatory points I the biosynthesis pathway and the related P450 genes. *Arabidopsis thaliana* ecotype Ws seeds were vernalized at 4° C. for 3 days before sowing in vermiculite soil (Zonolite) supplemented by Hoagland solution. Flats were placed in Conviron growth chambers under long day conditions (16 hr light, 23° C./8 hr dark, 20° C.). Basta spray and selection of the over-expressing lines was conducted about 2 weeks after germination. Approximately 2-3 weeks after bolting (approximately 5-6 weeks after germination), stem and siliques from the over-expressing lines and from wild-type plants were harvested, flash frozen in liquid nitrogen and stored at −80° C.

cc) DMT-II

Demeter (dmt) is a mutant of a methyl transferase gene and is similar to fie. *Arabidopsis thaliana* ecotype Ws seeds were vernalized at 4° C. for 3 days before sowing. Cauline leaves and closed flowers were isolated from 35S::DMT and dmt−/− plant lines, flash frozen in liquid nitrogen and stored at −80° C.

dd) CS6630 Roots and Shoots

*Arabidopsis thaliana* ecotype Ws seeds were vernalized at 4° C. for 3 days before sowing on MS media (1%) sucrose on bacto-agar. Roots and shoots were separated 14 days after germination, flash frozen in liquid nitrogen and stored at −80° C.

ee) CS237

CS237 is an ethylene triple response mutant that is insensitive to ethylene and which has an etrl-1 phenotype. *Arabidopsis thaliana* CS237 seeds were vernalized at 4° C. for 3 days before sowing. Aerial tissue was collected from mutants and wild-type Columbia ecotype plants, flash frozen in liquid nitrogen and stored at −80° C.

ff) Guard Cells

*Arabidopsis thaliana* ecotype Ws seeds were vernalized at 4° C. for 3 days before sowing. Leaves were harvested, homogenized and centrifuged to isolate the guard cell containing fraction. Homogenate from leaves served as the control. Samples were flash frozen in liquid nitrogen and stored at −80° C. Identical experiments using leaf tissue from canola were performed.

gg) 3642-1

3642-1 is a T-DNA mutant that affects leaf development. This mutant segregates 3:1, wild-type:mutant. *Arabidopsis thaliana* 3642-1 mutant seeds were vernalized at 4° C. for 3 days before sowing in flats of MetroMix 200. Flats were placed in the greenhouse, watered and grown to the 8 leaf, pre-flower stage. Stems and rosette leaves were harvested from the mutants and the wild-type segregants, flash frozen and stored at −80° C.

hh) Caf

Carple factory (Caf) is a double-stranded RNAse protein that is hypothesized to process small RNAs in *Arabidopsis*. The protein is closely related to a *Drosophila* protein named DICER that functions in the RNA degradation steps of RNA interference. *Arabidopsis thaliana* Caf mutant seeds were vernalized at 4° C. for 3 days before sowing in flats of Metro-Mix 200. Flats were placed in the greenhouse, watered and grown to the 8 leaf, pre-flower stage. Stems and rosette leaves were harvested from the mutants and the wild-type segregants, flash frozen and stored at −80° C.

ii) Drought Reproduction

*Arabidopsis thaliana* (ecotype Wassilewskija) seeds are kept at 4° C. in dark for three days and then sown in soil mix (Metromix 200) with a regular watering schedule (1.5-2 L per flat per week). Drought treatment by withholding water starts when plants are 30-days-old. The control samples are watered as before. Rosettes, flowers (with siliques less than 5 mm) and siliques (>5 mm) are harvested separately on day 5, 7 and 10 post-drought-treatment (PDT). By day 10 PDT, the majority of drought plants are wilted and unable to recover after re-watering and the experiment is terminated. The samples has harvested between 2-5 PM. Plants are grown in a walk-in growth chamber under these conditions: 16 h light/8 hr dark, 70% relative humidity, 20° C. light/18° C. dark for the first 10 days, and under 22° C. light/20° C. dark for the following days.

(jj) Drought Stress

Seeds of *Arabidopsis thaliana* (ecotype Wassilewskija) are sown in pots and left at 4° C. for three days to vernalize before being transferred to a growth chamber having 16 hr light/8 hr dark, 150,000-160,000 LUX, 20° C. and 70% humidity. After 14 days, aerial tissues are cut and left to dry on 3 mM Whatman paper in a petri-plate for 1 hour and 6 hours. Aerial tissues exposed for 1 hour and 6 hours to 3 mM Whatman paper wetted with 1× Hoagland's solution serve as controls. Tissues are harvested, flash-frozen in liquid nitrogen and stored at −80° C.

Alternatively, *Arabidopsis thaliana* (ecotype Wassilewskija) seed is vernalized at 4° C. for 3 days before sowing in Metromix soil type 350. Flats are placed in a growth chamber with 23° C., 16 hr light/8 hr. dark, 80% relative humidity, ~13,000 LUX for germination and growth. Plants are watered with 1-1.5 L of water every four days. Watering is stopped 16 days after germination for the treated samples, but continues for the control samples. Rosette leaves and stems, flowers and siliques are harvested 2 d, 3 d, 4 d, 5 d, 6 d and 7 d after watering is stopped. Tissue is flash frozen in liquid nitrogen and kept at −80° C. until RNA is isolated. Flowers and siliques are also harvested on day 8 from plants that had undergone a 7 d drought treatment followed by 1 day of watering. Control plants (whole plants) are harvested after 5 weeks, flash frozen in liquid nitrogen and stored as above.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats are watered every three days for 7 days. Seedlings are carefully removed from the sand and placed in empty 1-liter beakers at room temperature for treatment. Control plants are placed in water. After 1 hr, 6 hr, 12 hr and 24 hr aerial and root tissues are separated and flash frozen in liquid nitrogen prior to storage at −80° C.

(kk) Far-Red-Enriched

Seeds from wildtype *Arabidopsis thaliana* (ecotype Columbia) are vernalized in sterile water for 4 days at 4° C. prior to planting. Seeds are then sterilized and evenly planted on 0.5% sucrose MS media plates. Plates are sealed with Scotch micropore tape to allow for gas exchange and prevent contamination. Plates are grown in a growth room (16 h light/8 h dark, 22° C.; 6 bulbs total Gro-Lux); light measurements are as follows: Red=646.4 $\mu W/cm^2$, Blue=387 $\mu W/cm^2$, Far Red=158.7 $\mu W/cm^2$. At 7 days after germination, the plates containing the seedlings are transferred to Far Red light only (Far Red=525 $\mu W/cm^2$) for various durations of exposure time (1, 4, 8, and 24 hrs). After timed exposure, tissue is flash frozen with liquid nitrogen and stored at –80° C. Control seedlings are not transferred, but are collected at same time as the corresponding far-red exposed experimental samples.

(ll) Far-Red-Induction-Adult

Wildtype *Arabidopsis thaliana* (ecotype Columbia) seeds are planted on soil and vernalized for 4 days at 4° C. Soil sown plants are grown in a growth room (16 h light/8 h dark, 22° C.; 4 bulbs total alternating Gro-Lux and cool whites); light measurements are as follows: Red=330.9 $\mu W/cm^2$, Blue=267 $\mu W/cm^2$, Far Red=56.1 $\mu W/cm^2$. At 4 weeks after germination, the soil pots are transferred to shade environment (16 h light/8 h dark; Red=376 $\mu W/cm^2$, Blue=266 $\mu W/cm^2$, Far Red=552 $\mu W/cm^2$) for various durations of exposure time (1, 4, 8, 16, 24, 48, and 72 hrs). After timed exposure, above ground tissue is flash frozen with liquid nitrogen and stored at –80° C. Control seedlings are not transferred, but are collected at same time as the corresponding shade-exposed experimental samples.

(mm) Shoots

Sterilized wild-type *Arabidopsis thaliana* seeds (ecotype Wassilewskija) are sown on MS plates (0.5% sucrose, 1.5% agar) after 3 day-cold treatment. The plates are placed vertically in a Percival growth chamber (16:8 light cycles, 22° C.) so that roots grow vertically on the agar surface. The shoots or aerials, harvested after 7 d- and 14 d-growth in the chamber, are used as the experimental samples. The control sample is derived from tissues harvested from 3 week-old plants that are grown in soil in a Conviron chamber (16:8 light cycles, 22° C.), including rosettes, roots, stems, flowers, and siliques.

(nn) Siliques

Wild type *Arabidopsis thaliana* (ecotype Wassilewskija) seeds are sown in moistened soil mix, metromix 200 with osmocote, and stratified at 4° C. for 3 days in dark. Flats are placed in a Conviron growth chamber maintained at 16 h light (22° C.), 8 h dark (20° C.) and 70% humidity. After 3 weeks, siliques (<5 mm long) are collected in liquid nitrogen. The control samples are 3-week old whole plants (including all tissue types) grown in the same Conviron growth chamber.

(oo) Cytokinin (BA)

Seeds of *Arabidopsis thaliana* (ecotype Wassilewskija) are sown in trays and left at 4° C. for 4 days to vernalize. They are then transferred to a growth chamber having 16 hr light/8 hr dark, 13,000 LUX, 70% humidity, 20° C. temperature and watered twice a week with 1 L of 1× Hoagland's solution. Approximately 1,000 14 day old plants are spayed with 200-250 mls of 100 μM BA in a 0.02% solution of the detergent Silwet L-77. Aerial tissues (everything above the soil line) are harvested within a 15 to 20 minute time period 1 hr and 6 hrs after treatment, flash-frozen in liquid nitrogen and stored at −80° C.

Seeds of maize hybrid 35A (Pioneer) are sown in water-moistened sand in flats (10 rows, 5-6 seed/row) and covered with clear, plastic lids before being placed in a growth chamber having 16 hr light (25° C.)/8 hr dark (20° C.), 75% relative humidity and 13,000-14,000 LUX. Covered flats were watered every three days for 7 days. Seedlings are carefully removed from the sand and placed in 1-liter beakers with 100 μM BA for treatment. Control plants are treated with water. After 6 hr, aerial and root tissues are separated and flash frozen in liquid nitrogen prior to storage at −80° C.

2. Microarray Hybridization Procedures

Microarray technology provides the ability to monitor mRNA transcript levels of thousands of genes in a single experiment. These experiments simultaneously hybridize two differentially labeled fluorescent cDNA pools to glass slides that have been previously spotted with cDNA clones of the same species. Each arrayed cDNA spot will have a corresponding ratio of fluorescence that represents the level of disparity between the respective mRNA species in the two sample pools. Thousands of polynucleotides can be spotted on one slide, and each experiment generates a global expression pattern.

Coating Slides

The microarray consists of a chemically coated microscope slide, referred herein as a "chip" with numerous polynucleotide samples arrayed at a high density. The poly-L-lysine coating allows for this spotting at high density by providing a hydrophobic surface, reducing the spreading of spots of DNA solution arrayed on the slides. Glass microscope slides (Gold Seal #3010 manufactured by Gold Seal Products, Portsmouth, N.H., USA) were coated with a 0.1% W/V solution of Poly-L-lysine (Sigma, St. Louis, Mo.) using the following protocol:

1. Slides were placed in slide racks (Shandon Lipshaw #121). The racks were then put in chambers (Shandon Lipshaw #121).
2. Cleaning solution was prepared:
   70 g NaOH was dissolved in 280 mL ddH$_2$O.
   420 mL 95% ethanol was added. The total volume was 700 mL (=2×350 mL); it was stirred until completely mixed. If the solution remained cloudy, ddH$_2$O was added until clear.
3. The solution was poured into chambers with slides; the chambers were covered with glass lids. The solution was mixed on an orbital shaker for 2 hr.
4. The racks were quickly transferred to fresh chambers filled with ddH$_2$O. They were rinsed vigorously by plunging racks up and down. Rinses were repeated 4× with fresh ddH$_2$O each time, to remove all traces of NaOH-ethanol.
5. Polylysine solution was prepared:
   0 mL poly-L-lysine+70 mL tissue culture PBS in 560 mL water, using plastic graduated cylinder and beaker.
6. Slides were transferred to polylysine solution and shaken for 1 hr.
7. The rack was transferred to a fresh chambers filled with ddH$_2$O. It was plunged up and down 5× to rinse.
8. The slides were centrifuged on microtiter plate carriers (paper towels were placed below the rack to absorb liquid) for 5 min. @ 500 rpm. The slide racks were transferred to empty chambers with covers.
9. Slide racks were dried in a 45C oven for 10 min.
10. The slides were stored in a closed plastic slide box.
11. Normally, the surface of lysine coated slides was not very hydrophobic immediately after this process, but became increasingly hydrophobic with storage. A hydrophobic surface helped ensure that spots didn't run together while printing at high densities. After they aged for 10 days to a month the slides were ready to use. However, coated slides that have been sitting around for long periods of time were usually too old to be used. This was because they developed opaque patches, visible when held to the light, and these resulted in high background hybridization from the fluorescent probe. Alternatively, pre-coated glass slides were purchased from TeleChem International, Inc. (Sunnyvale, Calif., 94089; catalog number SMM-25, Superamine substrates).

PCR Amplification Of cDNA Clone Inserts

Polynucleotides were amplified from *Arabidopsis* cDNA clones using insert specific probes. The resulting 100 uL PCR reactions were purified with Qiaquick 96 PCR purification columns (Qiagen, Valencia, Calif., USA) and eluted in 30 uL of 5 mM Tris. 8.5 uL of the elution were mixed with 1.5 uL of 20×SSC to give a final spotting solution of DNA in 3×SSC. The concentrations of DNA generated from each clone varied between 10-100 ng/ul, but were usually about 50 ng/ul.

Arraying of PCR Products on Glass Slides

PCR products from cDNA clones were spotted onto the poly-L-Lysine coated glass slides using an arrangement of quill-tip pins (ChipMaker 3 spotting pins; Telechem, International, Inc., Sunnyvale, Calif., USA) and a robotic arrayer (PixSys 3500, Cartesian Technologies, Irvine, Calif., USA). Around 0.5 nl of a prepared PCR product was spotted at each location to produce spots with approximately 100 um diameters. Spot center-to-center spacing was from 180 um to 210 um depending on the array. Printing was conducted in a chamber with relative humidity set at 50%.

Slides containing maize sequences were purchased from Agilent Technology (Palo Alto, Calif. 94304).

Post-Processing of Slides

After arraying, slides were processed through a series of steps—rehydration, UV cross-linking, blocking and denaturation—required prior to hybridization. Slides were rehydrated by placing them over a beaker of warm water (DNA face down), for 2-3 sec, to distribute the DNA more evenly within the spots, and then snap dried on a hot plate (DNA side, face up). The DNA was then cross-linked to the slides by UV irradiation (60-65 mJ; 2400 Stratalinker, Stratagene, La Jolla, Calif., USA).

Following this a blocking step was performed to modify remaining free lysine groups, and hence minimize their ability to bind labeled probe DNA. To achieve this the arrays were placed in a slide rack. An empty slide chamber was left ready on an orbital shaker. The rack was bent slightly inwards in the middle, to ensure the slides would not run into each other while shaking. The blocking solution was prepared as follows:

3×350-ml glass chambers (with metal tops) were set to one side, and a large round Pyrex dish with $dH_2O$ was placed ready in the microwave. At this time, 15 ml sodium borate was prepared in a 50 ml conical tube.

6-g succinic anhydride was dissolved in approx. 325-350 mL 1-methyl-2-pyrrolidinone. Rapid addition of reagent was crucial.

a. Immediately after the last flake of the succinic anhydride dissolved, the 15-mL sodium borate was added.

b. Immediately after the sodium borate solution mixed in, the solution was poured into an empty slide chamber.

c. The slide rack was plunged rapidly and evenly in the solution. It was vigorously shaken up and down for a few seconds, making sure slides never left the solution.

d. It was mixed on an orbital shaker for 15-20 min. Meanwhile, the water in the Pyrex dish (enough to cover slide rack) was heated to boiling.

Following this, the slide rack was gently plunge in the 95C water (just stopped boiling) for 2 min. Then the slide rack was plunged 5× in 95% ethanol. The slides and rack were centrifuged for 5 min. @ 500 rpm. The slides were loaded quickly and evenly onto the carriers to avoid streaking. The arrays were used immediately or store in slide box.

The Hybridization process began with the isolation of mRNA from the two tissues (see "*Isolation of total RNA*" and "*Isolation of mRNA*", below) in question followed by their conversion to single stranded cDNA (see "Generation of probes for hybridization", below). The cDNA from each tissue was independently labeled with a different fluorescent dye and then both samples were pooled together. This final differentially labeled cDNA pool was then placed on a processed microarray and allowed to hybridize (see "*Hybridization and wash conditions*", below).

Isolation of Total RNA

Approximately 1 g of plant tissue was ground in liquid nitrogen to a fine powder and transferred into a 50-ml centrifuge tube containing 10 ml of Trizol reagent. The tube was vigorously vortexed for 1 min and then incubated at room temperature for 10-20 min. on an orbital shaker at 220 rpm. Two ml of chloroform was added to the tube and the solution vortexed vigorously for at least 30-sec before again incubating at room temperature with shaking. The sample was then centrifuged at 12,000×g (10,000 rpm) for 15-20 min at 4° C. The aqueous layer was removed and mixed by inversion with 2.5 ml of 1.2 M NaCl/0.8 M Sodium Citrate and 2.5 ml of isopropyl alcohol added. After a 10 min. incubation at room temperature, the sample was centrifuged at 12,000×g (10,000 rpm) for 15 min at 4° C. The pellet was washed with 70% ethanol, re-centrifuged at 8,000 rpm for 5 min and then air dried at room temperature for 10 min. The resulting total RNA was dissolved in either TE (10 mM Tris-HCl, 1 mM EDTA, pH 8.0) or DEPC (diethylpyrocarbonate) treated deionized water (RNAse-free water). For subsequent isolation of mRNA using the Qiagen kit, the total RNA pellet was dissolved in RNAse-free water.

Isolation of mRNA mRNA was isolated using the Qiagen Oligotex mRNA Spin-Column protocol (Qiagen, Valencia, Calif.). Briefly, 500 µl OBB buffer (20 mM Tris-Cl, pH 7.5, 1 M NaCl, 2 mM EDTA, 0.2% SDS) was added to 500 µl of total RNA (0.5-0.75 mg) and mixed thoroughly. The sample was first incubated at 70° C. for 3 min, then at room temperature for 10 minutes and finally centrifuged for 2 min at 14,000-18,000×g. The pellet was resuspended in 400 µl OW2 buffer (10 mM Tris-Cl, pH 7.5, 150 mM NaCl, 1 mM EDTA) by vortexing, the resulting solution placed on a small spin column in a 1.5 ml RNase-free microcentrifuge tube and centrifuged for 1 min at 14,000-18,000×g. The spin column was transferred to a new 1.5 ml RNase-free microcentrifuge tube and washed with 400 µl of OW2 buffer. To release the isolated mRNA from the resin, the spin column was again transferred to a new RNase-free 1.5 ml microcentrifuge tube, 20-100 µl 70° C. OEB buffer (5 mM Tris-Cl, pH 7.5) added and the resin resuspended in the resulting solution via pipeting. The mRNA solution was collected after centrifuging for 1 min at 14,000-18,000×g.

Alternatively, mRNA was isolated using the Stratagene Poly(A) Quik mRNA Isolation Kit (Startagene, La Jolla, Calif.). Here, up to 0.5 mg of total RNA (maximum volume of 1 ml) was incubated at 65° C. for 5 minutes, snap cooled on ice and 0.1× volumes of 10× sample buffer (10 mM Tris-HCl (pH 7.5), 1 mM EDTA (pH 8.0) 5 M NaCl) added. The RNA sample was applied to a prepared push column and passed through the column at a rate of ~1 drop every 2 sec. The solution collected was reapplied to the column and collected as above. 200 µl of high salt buffer (10 mM Tris-HCl (pH 7.5), 1 mM EDTA, 0.5 NaCl) was applied to the column and passed through the column at a rate of—1 drop every 2 sec. This step was repeated and followed by three low salt buffer (10 mM Tris-HCl (pH 7.5), 1 mM EDTA, 0.1 M NaCl) washes preformed in a similar manner. mRNA was eluted by applying to the column four separate 200 aliquots of elution buffer (10 mM Tris-HCl (pH 7.5), 1 mM EDTA) preheated to 65° C. Here, the elution buffer was passed through the column at a rate of 1 drop/sec. The resulting mRNA solution was precipitated by adding 0.1× volumes of 10× sample buffer, 2.5 volumes of ice-cold 100% ethanol, incubating overnight at −20° C. and centrifuging at 14,000-18,000×g for 20-30 min at 4° C. The pellet was washed with 70% ethanol and air dried for 10 min. at room temperature before resuspension in RNase-free deionized water.

Preparation of Yeast Controls

Plasmid DNA was isolated from the following yeast clones using Qiagen filtered maxiprep kits (Qiagen, Valencia, Calif.): YAL022c(Fun26), YAL031c(Fun21), YBR032w, YDL131w, YDL182w, YDL194w, YDL196w, YDR050c and YDR116c. Plasmid DNA was linearized with either BsrBI (YAL022c(Fun26), YAL031c(Fun21), YDL131w, YDL182w, YDL194w, YDL196w, YDR050c) or AflIII (YBRO32w, YDR116c) and isolated.

In Vitro Transcription of Yeast Clones

The following solution was incubated at 37° C. for 2 hours: 17 µl of isolated yeast insert DNA (1 µg), 20 µl 5× buffer, 10 µl 100 mM DTT, 2.5 µl (100 U) RNasin, 20 µl 2.5 mM (ea.) rNTPs, 2.7 (40 U) SP6 polymerase and 27.8 µl RNase-free deionized water. 2 (2 U) Ampli DNase I was added and the incubation continued for another 15 min. 10 µl 5 M $NH_4OAC$ and 100 µl phenol:chloroform:isoamyl alcohol (25:24:1) were added, the solution vortexed and then centrifuged to separate the phases. To precipitate the RNA, 250 µl ethanol was added and the solution incubated at −20° C. for at least one hour. The sample was then centrifuged for 20 min at 4° C. at 14,000-18,000×g, the pellet washed with 500 µl of 70% ethanol, air dried at room temperature for 10 min and resuspended in 100 µl of RNase-free deionized water. The precipitation procedure was then repeated.

Alternatively, after the two-hour incubation, the solution was extracted with phenol/chloroform once before adding 0.1 volume 3M sodium acetate and 2.5 volumes of 100% ethanol. The solution was centrifuged at 15,000 rpm, 4° C. for 20 minutes and the pellet resuspended in RNase-free deionized water. The DNase I treatment was carried out at 37° C. for 30 minutes using 2 U of Ampli DNase I in the following reaction condition: 50 mM Tris-HCl (pH 7.5), 10 mM $MgCl_2$. The DNase I reaction was then stopped with the addition of $NH_4OAC$ and phenol:chloroform:isoamyl alcohol (25:24:1), and RNA isolated as described above.

0.15-2.5 ng of the in vitro transcript RNA from each yeast clone were added to each plant mRNA sample prior to labeling to serve as positive (internal) probe controls.

Generation of Probes for Hybridization

Generation of Labeled Probes for Hybridization from First-Strand cDNA

Hybridization probes were generated from isolated mRNA using an Atlas™ Glass Fluorescent Labeling Kit (Clontech Laboratories, Inc., Palo Alto, Calif., USA). This entails a two step labeling procedure that first incorporates primary aliphatic amino groups during cDNA synthesis and then couples fluorescent dye to the cDNA by reaction with the amino functional groups. Briefly, 5 µg of oligo$(dT)_{18}$ primer d(TTTTTTTTTTTTTTTTTV) (SEQ ID NO: 67) was mixed with Poly A+mRNA (1.5-2 µg mRNA isolated using the Qiagen Oligotex mRNA Spin-Column protocol or —the Stratagene Poly(A) Quik mRNA Isolation protocol (Stratagene, La Jolla, Calif., USA)) in a total volume of 25 µl. The sample was incubated in a thermocycler at 70° C. for 5 min, cooled to 48° C. and 10 µl of 5×cDNA Synthesis Buffer (kit supplied), 5 µl 10×dNTP mix (dATP, dCTP, dGTP, dTTP and aminoallyl-dUTP; kit supplied), 7.5 µl deionized water and 2.5 µl MMLV Reverse Transcriptase (500 U) added. The reaction was then incubated at 48° C. for 30 minutes, followed by 1 hr incubation at 42° C. At the end of the incubation the reaction was heated to 70° C. for 10 min, cooled to 37° C. and 0.5 µl (5 U) RNase H added, before incubating for 15 min at 37° C. The solution was vortexed for 1 min after the addition of 0.5 µl 0.5 M EDTA and 5 µl of QuickClean Resin (kit supplied) then centrifuged at 14,000-18,000×g for 1 min. After removing the supernatant to a 0.45 µm spin filter (kit supplied), the sample was again centrifuged at 14,000-18,000×g for 1 min, and 5.5 µl 3 M sodium acetate and 137.5 µl of 100% ethanol added to the sample before incubating at −20° C. for at least 1 hr. The sample was then centrifuged at 14,000-18,000×g at 4° C. for 20 min, the resulting pellet washed with 500 µl 70% ethanol, air-dried at room temperature for 10 min and resuspended in 10 µl of 2× fluorescent labeling buffer (kit provided). 10 µl each of the fluorescent dyes Cy3 and Cy5 (Amersham Pharmacia (Piscataway, N.J., USA); prepared according to Atlas™ kit directions of Clontech) were added and the sample incubated in the dark at room temperature for 30 min.

The fluorescently labeled first strand cDNA was precipitated by adding 2 µl 3M sodium acetate and 50 µl 100% ethanol, incubated at −20° C. for at least 2 hrs, centrifuged at 14,000-18,000×g for 20 min, washed with 70% ethanol, airdried for 10 min and dissolved in 100 µl of water.

Alternatively, 3-4 µg mRNA, 2.5 (~8.9 ng of in vitro translated mRNA) µl yeast control and 3 µg oligo dTV (TTTTTTTTTTTTTTTTTT(A/C/G) (SEQ ID NO: 68) were mixed in a total volume of 24.7 µl. The sample was incubated in a thermocycler at 70° C. for 10 min. before chilling on ice. To this, 8 µl of 5× first strand buffer (SuperScript II RNase H—Reverse Transcriptase kit from Invitrogen (Carlsbad, Calif. 92008); cat no. 18064022), 0.8° C. of aa-dUTP/dNTP mix (50×; 25 mM dATP, 25 mM dGTP, 25 mM dCTP, 15 mM dTTP, 10 mM aminoallyl-dUTP), 4 µl of 0.1 M DTT and 2.5 µl (500 units) of Superscript R.T. II enzyme (Stratagene) were added. The sample was incubated at 42° C. for 2 hours before a mixture of 10° C. of 1M NaOH and 10° C. of 0.5 M EDTA were added. After a 15 minute incubation at 65° C., 25 µl of 1 M Tris pH 7.4 was added. This was mixed with 450 µl of water in a Microcon 30 column before centrifugation at 11,000×g for 12 min. The column was washed twice with 450 µl (centrifugation at 11,000 g, 12 min.) before eluting the sample by inverting the Microcon column and centrifuging at 11,000×g for 20 seconds. Sample was dehydrated by centrifugation under vacuum and stored at −20° C.

Each reaction pellet was dissolved in 9 µl of 0.1 M carbonate buffer (0.1M sodium carbonate and sodium bicarbonate, pH=8.5-9) and 4.5 µl of this placed in two microfuge tubes. 4.5 µl of each dye (in DMSO) were added and the mixture incubated in the dark for 1 hour. 4.5 of 4 M hydroxylamine was added and again incubated in the dark for 15 minutes.

Regardless of the method used for probe generation, the probe was purified using a Qiagen PCR cleanup kit (Qiagen, Valencia, Calif., USA), and eluted with 100 ul EB (kit provided). The sample was loaded on a Microcon YM-30 (Millipore, Bedford, Mass., USA) spin column and concentrated to 4-5 ul in volume. Probes for the maize microarrays were generated using the Fluorescent Linear Amplification Kit (cat. No. G2556A) from Agilent Technologies (Palo Alto, Calif.).

Hybridization and Wash Conditions

The following Hybridization and Washing Condition were developed:

Hybridization Conditions:

Labeled probe was heated at 95° C. for 3 min and chilled on ice. Then 25 □L of the hybridization buffer which was warmed at 42C was added to the probe, mixing by pipeting, to give a final concentration of:

50% formamide
    4×SSC
    0.03% SDS

5×Denhardt's solution 0.1 µg/ml single-stranded salmon sperm DNA

The probe was kept at 42C. Prior to the hybridization, the probe was heated for 1 more min., added to the array, and then covered with a glass cover slip. Slides were placed in hybridization chambers (Telechem, Sunnyvale, Calif.) and incubated at 42° C. overnight.

Washing Conditions:
A. Slides were washed in 1×SSC+0.03% SDS solution at room temperature for 5 minutes,
B. Slides were washed in 0.2×SSC at room temperature for 5 minutes,
C. Slides were washed in 0.05×SSC at room temperature for 5 minutes.

After A, B, and C, slides were spun at 800×g for 2 min. to dry. They were then scanned.

Maize microarrays were hybridized according to the instructions included Fluorescent Linear Amplification Kit (cat. No. G2556A) from Agilent Technologies (Palo Alto, Calif.).

SCANNING OF SLIDES

The chips were scanned using a ScanArray 3000 or 5000 (General Scanning, Watertown, Mass., USA). The chips were scanned at 543 and 633 nm, at 10 um resolution to measure the intensity of the two fluorescent dyes incorporated into the samples hybridized to the chips.

Data Extraction and Analysis

The images generated by scanning slides consisted of two 16-bit TIFF images representing the fluorescent emissions of the two samples at each arrayed spot. These images were then quantified and processed for expression analysis using the data extraction software Imagene™ (Biodiscovery, Los Angeles, Calif., USA). Imagene output was subsequently analyzed using the analysis program Genespring™ (Silicon Genetics, San Carlos, Calif., USA). In Genespring, the data was imported using median pixel intensity measurements derived from Imagene output. Background subtraction, ratio calculation and normalization were all conducted in Genespring. Normalization was achieved by breaking the data in to 32 groups, each of which represented one of the 32 pin printing regions on the microarray. Groups consist of 360 to 550 spots. Each group was independently normalized by setting the median of ratios to one and multiplying ratios by the appropriate factor.

Results

Table 4 presents the results of the differential expression experiments for the mRNAs, as reported by their corresponding cDNA ID number, that were differentially transcribed under a particular set of conditions as compared to a control sample. The cDNA ID numbers correspond to those utilized. Increases in mRNA abundance levels in experimental plants versus the controls are denoted with the plus sign (+). Likewise, reductions in mRNA abundance levels in the experimental plants are denoted with the minus (−) sign.

The Table is organized according to the clone number with each set of experimental conditions being denoted by the term "Expt Rep ID:" followed by a "short name". Table 5 links each "short name" with a short description of the experiment and the parameters.

The sequences showing differential expression in a particular experiment (denoted by either a "+" or "−" in the Table) thereby shows utility for a function in a plant, and these functions/utilities are described in detail below, where the title of each section (i.e. a "utility section") is correlated with the particular differential expression experiment in TABLE 5.

Organ-Affecting Genes, Gene Components, Products (Including Differentiation and Function)

Root Genes

The economic values of roots arise not only from harvested adventitious roots or tubers, but also from the ability of roots to funnel nutrients to support growth of all plants and increase their vegetative material, seeds, fruits, etc. Roots have four main functions. First, they anchor the plant in the soil. Second, they facilitate and regulate the molecular signals and molecular traffic between the plant, soil, and soil fauna. Third, the root provides a plant with nutrients gained from the soil or growth medium. Fourth, they condition local soil chemical and physical properties.

Root genes are active or potentially active to a greater extent in roots than in most other organs of the plant. These genes and gene products can regulate many plant traits from yield to stress tolerance. Root genes can be used to modulate root growth and development.

Differential Expression of the Sequences in Roots

The relative levels of mRNA product in the root versus the aerial portion of the plant was measured. Specifically, mRNA was isolated from roots and root tips of *Arabidopsis* plants and compared to mRNA isolated from the aerial portion of the plants utilizing microarray procedures.

Root Hair Genes, Gene Components and Products

Root hairs are specialized outgrowths of single epidermal cells termed trichoblasts. In many and perhaps all species of plants, the trichoblasts are regularly arranged around the perimeter of the root. In *Arabidopsis*, for example, trichoblasts tend to alternate with non-hair cells or atrichoblasts. This spatial patterning of the root epidermis is under genetic control, and a variety of mutants have been isolated in which this spacing is altered or in which root hairs are completely absent.

The root hair development genes of the instant invention are useful to modulate one or more processes of root hair structure and/or function including (1) development; (2) interaction with the soil and soil contents; (3) uptake and transport in the plant; and (4) interaction with microorganisms.

1.) Development

The surface cells of roots can develop into single epidermal cells termed trichoblasts or root hairs. Some of the root hairs will persist for the life of the plant; others will gradually die back; some may cease to function due to external influences. These genes and gene products can be used to modulate root hair density or root hair growth; including rate, timing, direction, and size, for example. These genes and gene products can also be used to modulate cell properties such as cell size, cell division, rate and direction and number, cell elongation, cell differentiation, lignified cell walls, epidermal cells (including trichoblasts) and root apical meristem cells (growth and initiation); and root hair architecture such as leaf cells under the trichome, cells forming the base of the trichome, trichome cells, and root hair responses.

In addition these genes and gene products can be used to modulate one or more of the growth and development processes in response to internal plant programs or environmental stimuli in, for example, the seminal system, nodal system, hormone responses, Auxin, root cap abscission, root senescence, gravitropism, coordination of root growth and development with that of other organs (including leaves, flowers, seeds, fruits, and stems), and changes in soil environment (including water, minerals, Ph, and microfauna and flora).

2.) Interaction with Soil and Soil Contents

Root hairs are sites of intense chemical and biological activity and as a result can strongly modify the soil they contact. Roots hairs can be coated with surfactants and mucilage to facilitate these activities. Specifically, roots hairs are responsible for nutrient uptake by mobilizing and assimilating water, reluctant ions, organic and inorganic compounds and chemicals. In addition, they attract and interact with beneficial microfauna and flora. Root hairs also help to mitigate the effects of toxic ions, pathogens and stress. Thus, root hair genes and gene products can be used to modulate traits such as root hair surfactant and mucilage (including composition and secretion rate and time); nutrient uptake (including water, nitrate and other sources of nitrogen, phosphate, potassium, and micronutrients (e.g. iron, copper, etc.); microbe and nematode associations (such as bacteria including nitrogen-fixing bacteria, mycorrhizae, nodule-forming and other nematodes, and nitrogen fixation); oxygen transpiration; detoxification effects of iron, aluminum, cadmium, mercury, salt, and other soil constituents; pathogens (including chemical repellents) glucosinolates (GSL1), which release pathogen-controlling isothiocyanates; and changes in soil (such as Ph, mineral excess and depletion), and rhizosheath.

3.) Transport of Materials in Plants

Uptake of the nutrients by the root and root hairs contributes a source-sink effect in a plant. The greater source of nutrients, the more sinks, such as stems, leaves, flowers, seeds, fruits, etc. can draw sustenance to grow. Thus, root hair development genes and gene products can be used to modulate the vigor and yield of the overall plant as well as distinct cells, organs, or tissues of a plant. The genes and gene products, therefore, can modulate plant nutrition, growth rate (such as whole plant, including height, flowering time, etc., seedling, coleoptile elongation, young leaves, stems, flowers, seeds and fruit) and yield, including biomass (fresh and dry weight during any time in plant life, including maturation and senescence), number of flowers, number of seeds, seed yield, number, size, weight and harvest index (content and composition, e.g. amino acid, jasmonate, oil, protein and starch) and fruit yield (number, size, weight, harvest index, and post harvest quality).

Reproduction Genes, Gene Components and Products

Reproduction genes are defined as genes or components of genes capable of modulating any aspect of sexual reproduction from flowering time and inflorescence development to fertilization and finally seed and fruit development. These genes are of great economic interest as well as biological importance. The fruit and vegetable industry grosses over $1 billion USD a year. The seed market, valued at approximately $15 billion USD annually, is even more lucrative.

Inflorescence and Floral Development Genes, Gene Components and Products

During reproductive growth the plant enters a program of floral development that culminates in fertilization, followed by the production of seeds. Senescence may or may not follow. The flower formation is a precondition for the sexual propagation of plants and is therefore essential for the propagation of plants that cannot be propagated vegetatively as well as for the formation of seeds and fruits. The point of time at which the merely vegetative growth of plants changes into flower formation is of vital importance for example in agriculture, horticulture and plant breeding. Also the number of flowers is often of economic importance, for example in the case of various useful plants (tomato, cucumber, zucchini, cotton etc.) with which an increased number of flowers may lead to an increased yield, or in the case of growing ornamental plants and cut flowers.

Flowering plants exhibit one of two types of inflorescence architecture: indeterminate, in which the inflorescence grows indefinitely, or determinate, in which a terminal flower is produced. Adult organs of flowering plants develop from groups of stem cells called meristems. The identity of a meristem is inferred from structures it produces: vegetative meristems give rise to roots and leaves, inflorescence meristems give rise to flower meristems, and flower meristems give rise to floral organs such as sepals and petals. Not only are meristems capable of generating new meristems of different identity, but their own identity can change during development. For example, a vegetative shoot meristem can be transformed into an inflorescence meristem upon floral induction, and in some species, the inflorescence meristem itself will eventually become a flower meristem. Despite the importance of meristem transitions in plant development, little is known about the underlying mechanisms.

Following germination, the shoot meristem produces a series of leaf meristems on its flanks. However, once floral induction has occurred, the shoot meristem switches to the production of flower meristems. Flower meristems produce floral organ primordia, which develop individually into sepals, petals, stamens or carpels. Thus, flower formation can be thought of as a series of distinct developmental steps, i.e. floral induction, the formation of flower primordia and the production of flower organs. Mutations disrupting each of the steps have been isolated in a variety of species, suggesting that a genetic hierarchy directs the flowering process (see for review, Weigel and Meyerowitz, In Molecular Basis of Morphogenesis (ed. M. Bernfield). 51st Annual Symposium of the Society for Developmental Biology, pp. 93-107, New York, 1993).

Expression of many reproduction genes and gene products is orchestrated by internal programs or the surrounding environment of a plant. These genes can be used to modulate traits such as fruit and seed yield Seed and Fruit Development Genes, Gene Components and Products The ovule is the primary female sexual reproductive organ of flowering plants. At maturity it contains the egg cell and one large central cell containing two polar nuclei encased by two integuments that, after fertilization, develops into the embryo, endosperm, and seed coat of the mature seed, respectively. As the ovule develops into the seed, the ovary matures into the fruit or silique. As such, seed and fruit development requires the orchestrated transcription of numerous polynucleotides, some of which are ubiquitous, others that are embryo-specific and still others that are expressed only in the endosperm, seed coat, or fruit. Such genes are termed fruit development responsive genes and can be used to modulate seed and fruit growth and development such as seed size, seed yield, seed composition and seed dormancy.

Differential Expression of the Sequences in Siliques, Inflorescences and Flowers The relative levels of mRNA product in the siliques relative to the plant as a whole was measured.

Differential Expression of the Sequences in Hybrid Seed Development

The levels of mRNA product in the seeds relative to those in a leaf and floral stems was measured.

Development Genes, Gene Components and Products

Imbibition and Germination Responsive Genes, Gene Components and Products

Seeds are a vital component of the world's diet. Cereal grains alone, which comprise ~90% of all cultivated seeds, contribute up to half of the global per capita energy intake. The primary organ system for seed production in flowering plants is the ovule. At maturity, the ovule consists of a haploid female gametophyte or embryo sac surrounded by several layers of maternal tissue including the nucleus and the integuments. The embryo sac typically contains seven cells including the egg cell, two synergids, a large central cell containing two polar nuclei, and three antipodal cells. That pollination results in the fertilization of both egg and central cell. The fertilized egg develops into the embryo. The fertilized central cell develops into the endosperm. And the integuments mature into the seed coat. As the ovule develops into the seed, the ovary matures into the fruit or silique. Late in development, the developing seed ends a period of extensive biosynthetic and cellular activity and begins to desiccate to complete its development and enter a dormant, metabolically quiescent state. Seed dormancy is generally an undesirable characteristic in agricultural crops, where rapid germination and growth are required. However, some degree of dormancy is advantageous, at least during seed development. This is particularly true for cereal crops because it prevents germination of grains while still on the ear of the parent plant (preharvest sprouting), a phenomenon that results in major losses to the agricultural industry. Extensive domestication and breeding of crop species have ostensibly reduced the level of dormancy mechanisms present in the seeds of their wild ancestors, although under some adverse environmental conditions, dormancy may reappear. By contrast, weed seeds frequently mature with inherent dormancy mechanisms that allow some seeds to persist in the soil for many years before completing germination.

Germination commences with imbibition, the uptake of water by the dry seed, and the activation of the quiescent embryo and endosperm. The result is a burst of intense metabolic activity. At the cellular level, the genome is transformed from an inactive state to one of intense transcriptional activity. Stored lipids, carbohydrates and proteins are catabolized fueling seedling growth and development. DNA and organelles are repaired, replicated and begin functioning. Cell expansion and cell division are triggered. The shoot and root apical meristem are activated and begin growth and organogenesis. Schematic 4 summarizes some of the metabolic and cellular processes that occur during imbibition. Germination is complete when a part of the embryo, the radical, extends to penetrate the structures that surround it. In *Arabidopsis*, seed germination takes place within twenty-four (24) hours after imbibition. As such, germination requires the rapid and orchestrated transcription of numerous polynucleotides. Germination is followed by expansion of the hypocotyl and opening of the cotyledons. Meristem development continues to promote root growth and shoot growth, which is followed by early leaf formation.

Imbibition and Germination Genes

Imbibition and germination includes those events that commence with the uptake of water by the quiescent dry seed and terminate with the expansion and elongation of the shoots and roots. The germination period exists from imbibition to when part of the embryo, usually the radical, extends to penetrate the seed coat that surrounds it. Imbibition and germination genes are defined as genes, gene components and products capable of modulating one or more processes of imbibition and germination described above. They are useful to modulate many plant traits from early vigor to yield to stress tolerance.

Differential Expression of the Sequences in Germinating Seeds and Imbibed Embryos The levels of mRNA product in the seeds versus the plant as a whole was measured.

Hormone Responsive Genes, Gene Components and Products

Abscissic Acid Responsive Genes, Gene Components and Products

Plant hormones are naturally occurring substances, effective in very small amounts, which act as signals to stimulate or inhibit growth or regulate developmental processes in plants. Abscisic acid (ABA) is a ubiquitous hormone in vascular plants that has been detected in every major organ or living tissue from the root to the apical bud. The major physiological responses affected by ABA are dormancy, stress stomatal closure, water uptake, abscission and senescence. In contrast to Auxins, cytokinins and gibberellins, which are principally growth promoters, ABA primarily acts as an inhibitor of growth and metabolic processes.

Changes in ABA concentration internally or in the surrounding environment in contact with a plant results in modulation of many genes and gene products. These genes and/or products are responsible for effects on traits such as plant vigor and seed yield. While ABA responsive polynucleotides and gene products can act alone, combinations of these polynucleotides also affect growth and development. Useful combinations include different ABA responsive polynucleotides and/or gene products that have similar transcription profiles or similar biological activities, and members of the same or similar biochemical pathways. Whole pathways or segments of pathways are controlled by transcription factor proteins and proteins controlling the activity of signal transduction pathways. Therefore, manipulation of such protein levels is especially useful for altering phenotypes and biochemical activities of plants. In addition, the combination of an ABA responsive polynucleotide and/or gene product with another environmentally responsive polynucleotide is also useful because of the interactions that exist between hormone-regulated pathways, stress and defense induced pathways, nutritional pathways and development.

Differential Expression of the Sequences in ABA Treated Plants

The relative levels of mRNA product in plants treated with ABA versus controls treated with water were measured.

Brassinosteroid Responsive Genes, Gene Components and Products

Plant hormones are naturally occurring substances, effective in very small amounts, which act as signals to stimulate or inhibit growth or regulate developmental processes in plants. Brassinosteroids (BRs) are the most recently discovered, and least studied, class of plant hormones. The major physiological response affected by BRs is the longitudinal growth of young tissue via cell elongation and possibly cell division. Consequently, disruptions in BR metabolism, perception and activity frequently result in a dwarf phenotype. In addition, because BRs are derived from the sterol metabolic pathway, any perturbations to the sterol pathway can affect the BR pathway. In the same way, perturbations in the BR pathway can have effects on the later part of the sterol pathway and thus the sterol composition of membranes. Changes in BR concentration in the surrounding environment or in contact with a plant result in modulation of many genes and gene products. These genes and/or products are responsible for effects on traits such as plant biomass and seed yield. These genes were discovered and characterized from a much larger set of genes by experiments designed to find genes whose mRNA abundance changed in response to application of BRs to plants.

While BR responsive polynucleotides and gene products can act alone, combinations of these polynucleotides also affect growth and development. Useful combinations include different BR responsive polynucleotides and/or gene products that have similar transcription profiles or similar biological activities, and members of the same or functionally related biochemical pathways. Whole pathways or segments of pathways are controlled by transcription factors and proteins controlling the activity of signal transduction pathways. Therefore, manipulation of such protein levels is especially useful for altering phenotypes and biochemical activities of plants. In addition, the combination of a BR responsive polynucleotide and/or gene product with another environmentally responsive polynucleotide is useful because of the interactions that exist between hormone-regulated pathways, stress pathways, nutritional pathways and development. Here, in addition to polynucleotides having similar transcription profiles and/or biological activities, useful combinations include polynucleotides that may have different transcription profiles but which participate in common or overlapping pathways.

Differential Expression of the Sequences in Epi-brassinolide or Brassinozole Plants The relative levels of mRNA product in plants treated with either epi-brassinolide or brassinozole were measured.

Metabolism Affecting Genes, Gene Components and Products

Nitrogen Responsive Genes, Gene Components and Products

Nitrogen is often the rate-limiting element in plant growth, and all field crops have a fundamental dependence on exogenous nitrogen sources. Nitrogenous fertilizer, which is usually supplied as ammonium nitrate, potassium nitrate, or urea, typically accounts for 40% of the costs associated with crops, such as corn and wheat in intensive agriculture. Increased efficiency of nitrogen use by plants should enable the production of higher yields with existing fertilizer inputs and/or enable existing yields of crops to be obtained with lower fertilizer input, or better yields on soils of poorer quality. Also, higher amounts of proteins in the crops could also be produced more cost-effectively. "Nitrogen responsive" genes and gene products can be used to alter or modulate plant growth and development.

Differential Expression of the Sequences in Whole Seedlings, Shoots and Roots

The relative levels of mRNA product in whole seedlings, shoots and roots treated with either high or low nitrogen media were compared to controls.

Viability Genes, Gene Components and Products

Plants contain many proteins and pathways that when blocked or induced lead to cell, organ or whole plant death. Gene variants that influence these pathways can have profound effects on plant survival, vigor and performance. The critical pathways include those concerned with metabolism and development or protection against stresses, diseases and pests. They also include those involved in apoptosis and necrosis. Viability genes can be modulated to affect cell or plant death.

Herbicides are, by definition, chemicals that cause death of tissues, organs and whole plants. The genes and pathways that are activated or inactivated by herbicides include those that cause cell death as well as those that function to provide protection.

Differential Expression of the Sequences in Herbicide Treated Plants and Herbicide Resistant Mutants The relative levels of mRNA product in plants treated with heribicide and mutants resistant to herbicides were compared to control plants.

Stress Responsive Genes, Gene Components and Products

Wounding Responsive Genes, Gene Components and Products

Plants are continuously subjected to various forms of wounding from physical attacks including the damage created by pathogens and pests, wind, and contact with other objects. Therefore, survival and agricultural yields depend on constraining the damage created by the wounding process and inducing defense mechanisms against future damage.

Plants have evolved complex systems to minimize and/or repair local damage and to minimize subsequent attacks by pathogens or pests or their effects. These involve stimulation of cell division and cell elongation to repair tissues, induction of programmed cell death to isolate the damage caused mechanically and by invading pests and pathogens, and induction of long-range signaling systems to induce protecting molecules, in case of future attack. The genetic and biochemical systems associated with responses to wounding are connected with those associated with other stresses such as pathogen attack and drought.

Wounding responsive genes and gene products can be used to alter or modulate traits such as growth rate; whole plant height, width, or flowering time; organ development (such as coleoptile elongation, young leaves, roots, lateral roots, tuber formation, flowers, fruit, and seeds); biomass; fresh and dry weight during any time in plant life, such as at maturation; number of flowers; number of seeds; seed yield, number, size, weight, harvest index (such as content and composition, e.g., amino acid, nitrogen, oil, protein, and carbohydrate); fruit yield, number, size, weight, harvest index, post harvest quality, content and composition (e.g., amino acid, carotenoid, jasmonate, protein, and starch); seed and fruit development; germination of dormant and non-dormant seeds; seed viability, seed reserve mobilization, fruit ripening, initiation of the reproductive cycle from a vegetative state, flower development time, insect attraction for fertilization, time to fruit maturity, senescence; fruits, fruit drop; leaves; stress and disease responses; drought; heat and cold; wounding by any source, including wind, objects, pests and pathogens; uv and high light damage (insect, fungus, virus, worm, nematode damage).

Cold Responsive Genes, Gene Components and Products

The ability to endure low temperatures and freezing is a major determinant of the geographical distribution and productivity of agricultural crops. Even in areas considered suitable for the cultivation of a given species or cultivar, can give rise to yield decreases and crop failures as a result of aberrant, freezing temperatures. Even modest increases (1-2° C.) in the freezing tolerance of certain crop species would have a dramatic impact on agricultural productivity in some areas. The development of genotypes with increased freezing tolerance would provide a more reliable means to minimize crop losses and diminish the use of energy-costly practices to modify the microclimate.

Sudden cold temperatures result in modulation of many genes and gene products, including promoters. These genes and/or products are responsible for effects on traits such as plant vigor and seed yield.

Manipulation of one or more cold responsive gene activities is useful to modulate growth and development.

Differential Expression of the Sequences in Cold Treated Plants

The relative levels of mRNA product in cold treated plants were compared to control plants.

Heat Responsive Genes, Gene Components and Products

The ability to endure high temperatures is a major determinant of the geographical distribution and productivity of agricultural crops. Decreases in yield and crop failure frequently occur as a result of aberrant, hot conditions even in areas considered suitable for the cultivation of a given species or cultivar. Only modest increases in the heat tolerance of crop species would have a dramatic impact on agricultural productivity. The development of genotypes with increased heat tolerance would provide a more reliable means to minimize crop losses and diminish the use of energy-costly practices to modify the microclimate.

Changes in temperature in the surrounding environment or in a plant microclimate results in modulation of many genes and gene products.

Differential Expression of the Sequences in Heat Treated Plants

The relative levels of mRNA product in heat treated plants were compared to control plants.

Drought Responsive Genes, Gene Components and Products

The ability to endure drought conditions is a major determinant of the geographical distribution and productivity of agricultural crops. Decreases in yield and crop failure frequently occur as a result of aberrant, drought conditions even in areas considered suitable for the cultivation of a given species or cultivar. Only modest increases in the drought tolerance of crop species would have a dramatic impact on agricultural productivity. The development of genotypes with increased drought tolerance would provide a more reliable means to minimize crop losses and diminish the use of energy-costly practices to modify the microclimate.

Drought conditions in the surrounding environment or within a plant, results in modulation of many genes and gene products.

Differential Expression of the Sequences in Drought Treated Plants and Drought Mutants The relative levels of mRNA product in drought treated plants and drought mutants were compared to control plants.

Methyl Jasmonate (Jasmonate) Responsive Genes, Gene Components and Products

Jasmonic acid and its derivatives, collectively referred to as jasmonates, are naturally occurring derivatives of plant lipids. These substances are synthesized from linolenic acid in a lipoxygenase-dependent biosynthetic pathway. Jasmonates are signaling molecules which have been shown to be growth regulators as well as regulators of defense and stress responses. As such, jasmonates represent a separate class of plant hormones. Jasmonate responsive genes can be used to modulate plant growth and development.

Differential Expression of the Sequences in Methyl Jasmonate Treated Plants

The relative levels of mRNA product in methyl jasmonate treated plants were compared to control plants.

Salicylic Acid Responsive Genes, Gene Components and Products

Plant defense responses can be divided into two groups: constitutive and induced. Salicylic acid (SA) is a signaling molecule necessary for activation of the plant induced defense system known as systemic acquired resistance or SAR. This response, which is triggered by prior exposure to avirulent pathogens, is long lasting and provides protection against a broad spectrum of pathogens. Another induced defense system is the hypersensitive response (HR). HR is far more rapid, occurs at the sites of pathogen (avirulent pathogens) entry and precedes SAR. SA is also the key signaling molecule for this defense pathway.

Differential Expression of the Sequences in Salicylic Acid Treated Plants

The relative levels of mRNA product in salicylic acid treated plants were compared to control plants.

Osmotic Stress Responsive Genes, Gene Components and Products

The ability to endure and recover from osmotic and salt related stress is a major determinant of the geographical distribution and productivity of agricultural crops. Osmotic stress is a major component of stress imposed by saline soil and water deficit. Decreases in yield and crop failure frequently occur as a result of aberrant or transient environmental stress conditions even in areas considered suitable for the cultivation of a given species or cultivar. Only modest increases in the osmotic and salt tolerance of a crop species would have a dramatic impact on agricultural productivity. The development of genotypes with increased osmotic tolerance would provide a more reliable means to minimize crop losses and diminish the use of energy-costly practices to modify the soil environment. Thus, osmotic stress responsive genes can be used to modulate plant growth and development.

Differential Expression of the Sequences in PEG Treated Plants

The relative levels of mRNA product in PEG treated plants were compared to control plants.

Shade Responsive Genes, Gene Components and Products

Plants sense the ratio of Red (R):Far Red (FR) light in their environment and respond differently to particular ratios. A low R:FR ratio, for example, enhances cell elongation and favors flowering over leaf production. The changes in R:FR ratios mimic and cause the shading response effects in plants. The response of a plant to shade in the canopy structures of agricultural crop fields influences crop yields significantly. Therefore manipulation of genes regulating the shade avoidance responses can improve crop yields. While phytochromes mediate the shade avoidance response, the down-stream factors participating in this pathway are largely unknown. One potential downstream participant, ATHB-2, is a member of the HD-Zip class of transcription factors and shows a strong and rapid response to changes in the R:FR ratio. ATHB-2 over-expressors have a thinner root mass, smaller and fewer leaves and longer hypocotyls and petioles. This elongation arises from longer epidermal and cortical cells, and a decrease in secondary vascular tissues, paralleling the changes observed in wild-type seedlings grown under conditions simulating canopy shade. On the other hand, plants with reduced ATHB-2 expression have a thick root mass and many larger leaves and shorter hypocotyls and petioles. Here, the changes in the hypocotyl result from shorter epidermal and cortical cells and increased proliferation of vascular tissue. Interestingly, application of Auxin is able to reverse the root phenotypic consequences of high ATHB-2 levels, restoring the wild-type phenotype. Consequently, given that ATHB-2 is tightly regulated by phytochrome, these data suggest that ATHB-2 may link the Auxin and phytochrome pathways in the shade avoidance response pathway.

Shade responsive genes can be used to modulate plant growth and development.

Differential Expression of the Sequences in Far-red Light Treated Plants

The relative levels of mRNA product in far-red light treated plants were compared to control plants.

Viability Genes, Gene Components and Products

Plants contain many proteins and pathways that when blocked or induced lead to cell, organ or whole plant death. Gene variants that influence these pathways can have profound effects on plant survival, vigor and performance. The critical pathways include those concerned with metabolism and development or protection against stresses, diseases and pests. They also include those involved in apoptosis and necrosis. The applicants have elucidated many such genes and pathways by discovering genes that when inactivated lead to cell or plant death.

Herbicides are, by definition, chemicals that cause death of tissues, organs and whole plants. The genes and pathways that are activated or inactivated by herbicides include those that cause cell death as well as those that function to provide protection. The applicants have elucidated these genes.

The genes defined in this section have many uses including manipulating which cells, tissues and organs are selectively killed, which are protected, making plants resistant to herbicides, discovering new herbicides and making plants resistant to various stresses.

Viability genes were also identified from a much larger set of genes by experiments designed to find genes whose mRNA products changed in concentration in response to applications of different herbicides to plants. Viability genes are characteristically differentially transcribed in response to fluctuating herbicide levels or concentrations, whether internal or external to an organism or cell. The MA_diff Table reports the changes in transcript levels of various viability genes.

Early Seedling-Phase Specific Responsive Genes, Gene Components and Products

One of the more active stages of the plant life cycle is a few days after germination is complete, also referred to as the early seedling phase. During this period the plant begins development and growth of the first leaves, roots, and other organs not found in the embryo. Generally this stage begins when germination ends. The first sign that germination has been completed is usually that there is an increase in length and fresh weight of the radicle. Such genes and gene products can regulate a number of plant traits to modulate yield. For example, these genes are active or potentially active to a greater extent in developing and rapidly growing cells, tissues and organs, as exemplified by development and growth of a seedling 3 or 4 days after planting a seed.

Rapid, efficient establishment of a seedling is very important in commercial agriculture and horticulture. It is also vital that resources are approximately partitioned between shoot and root to facilitate adaptive growth. Phototropism and geotropism need to be established. All these require post-germination process to be sustained to ensure that vigorous seedlings are produced. Early seedling phase genes, gene components and products are useful to manipulate these and other processes.

Guard Cell Genes, Gene Components and Products

Scattered throughout the epidermis of the shoot are minute pores called stomata. Each stomal pore is surrounded by two guard cells. The guard cells control the size of the stomal pore, which is critical since the stomata control the exchange of carbon dioxide, oxygen, and water vapor between the interior of the plant and the outside atmosphere. Stomata open and close through turgor changes driven by ion fluxes, which occur mainly through the guard cell plasma membrane and tonoplast. Guard cells are known to respond to a number of external stimuli such as changes in light intensity, carbon dioxide and water vapor, for example. Guard cells can also sense and rapidly respond to internal stimuli including changes in ABA, auxin and calcium ion flux.

Thus, genes, gene products, and fragments thereof differentially transcribed and/or translated in guard cells can be useful to modulate ABA responses, drought tolerance, respiration, water potential, and water management as examples. All of which can in turn affect plant yield including seed yield, harvest index, fruit yield, etc.

To identify such guard cell genes, gene products, and fragments thereof, Applicants have performed a microarray experiment comparing the transcript levels of genes in guard cells versus leaves. Experimental data is shown below.

Nitric Oxide Responsive Genes, Gene Components and Products

The rate-limiting element in plant growth and yield is often its ability to tolerate suboptimal or stress conditions, including pathogen attack conditions, wounding and the presence of various other factors. To combat such conditions, plant cells deploy a battery of inducible defense responses, including synergistic interactions between nitric oxide (NO), reactive oxygen intermediates (ROS), and salicylic acid (SA). NO has been shown to play a critical role in the activation of innate immune and inflammatory responses in animals. At least part of this mammalian signaling pathway is present in plants, where NO is known to potentiate the hypersensitive response (HR). In addition, NO is a stimulator molecule in plant photomorphogenesis.

Changes in nitric oxide concentration in the internal or surrounding environment, or in contact with a plant, results in modulation of many genes and gene products.

In addition, the combination of a nitric oxide responsive polynucleotide and/or gene product with other environmentally responsive polynucleotides is also useful because of the interactions that exist between hormone regulated pathways, stress pathways, pathogen stimulated pathways, nutritional pathways and development.

Nitric oxide responsive genes and gene products can function either to increase or dampen the above phenotypes or activities either in response to changes in nitric oxide concentration or in the absence of nitric oxide fluctuations. More specifically, these genes and gene products can modulate stress responses in an organism. In plants, these genes and gene products are useful for modulating yield under stress conditions. Measurements of yield include seed yield, seed size, fruit yield, fruit size, etc.

Shoot-Apical Meristem Genes, Gene Components and Products

New organs, stems, leaves, branches and inflorescences develop from the stem apical meristem (SAM). The growth structure and architecture of the plant therefore depends on the behavior of SAMs. Shoot apical meristems (SAMs) are comprised of a number of morphologically undifferentiated, dividing cells located at the tips of shoots. SAM genes elucidated here are capable of modifying the activity of SAMs and thereby many traits of economic interest from ornamental leaf shape to organ number to responses to plant density.

In addition, a key attribute of the SAM is its capacity for self-renewal. Thus, SAM genes of the instant invention are useful for modulating one or more processes of SAM structure and/or function including (I) cell size and division; (II) cell differentiation and organ primordia. The genes and gene components of this invention are useful for modulating any one or all of these cell division processes generally, as in timing and rate, for example. In addition, the polynucleotides and polypeptides of the invention can control the response of these processes to the internal plant programs associated with embryogenesis, and hormone responses, for example.

Because SAMs determine the architecture of the plant, modified plants will be useful in many agricultural, horticultural, forestry and other industrial sectors. Plants with a different shape, numbers of flowers and seed and fruits will have altered yields of plant parts. For example, plants with more branches can produce more flowers, seed or fruits. Trees without lateral branches will produce long lengths of clean timber. Plants with greater yields of specific plant parts will be useful sources of constituent chemicals.

GFP Experimental Procedures and Results

Procedures

The polynucleotide sequences of the present invention were tested for promoter activity using Green Fluorescent Protein (GFP) assays in the following manner.

Approximately 1-2 kb of genomic sequence occurring immediately upstream of the ATG translational start site of the gene of interest was isolated using appropriate primers tailed with BstXI restriction sites. Standard PCR reactions using these primers and genomic DNA were conducted. The resulting product was isolated, cleaved with BstXI and cloned into the BstXI site of an appropriate vector, such as pNew-Bin4-HAP1-GFP (see FIG. 1).

Transformation

The following procedure was used for transformation of plants

1. Stratification of WS-2 Seed.
    Add 0.5 ml WS-2 (CS2360) seed to 50 ml of 0.2% Phytagar in a 50 ml Corning tube and vortex until seeds and Phytagar form a homogenous mixture.
    Cover tube with foil and stratify at 4° C. for 3 days.

2. Preparation of Seed Mixture.
    Obtain stratified seed from cooler.
    Add seed mixture to a 1000 ml beaker.
    Add an additional 950 ml of 0.2% Phytagar and mix to homogenize.

3. Preparation of Soil Mixture.
    Mix 24 L SunshineMix #5 soil with 16 L Therm-O-Rock vermiculite in cement mixer to make a 60:40 soil mixture.
    Amend soil mixture by adding 2 Tbsp Marathon and 3 Tbsp Osmocote and mix contents thoroughly.
    Add 1 Tbsp Peters fertilizer to 3 gallons of water and add to soil mixture and mix thoroughly.
    Fill 4-inch pots with soil mixture and round the surface to create a slight dome.
    Cover pots with 8-inch squares of nylon netting and fasten using rubber bands.
    Place 14 4-inch pots into each no-hole utility flat.

4. Planting.
    Using a 60 ml syringe, aspirate 35 ml of the seed mixture.
    Exude 25 drops of the seed mixture onto each pot.
    Repeat until all pots have been seeded.
    Place flats on greenhouse bench, cover flat with clear propagation domes, place 55% shade cloth on top of flats and subirrigate by adding 1 inch of water to bottom of each flat.

5. Plant Maintenance.
    3 to 4 days after planting, remove clear lids and shade cloth.
    Subirrigate flats with water as needed.
    After 7-10 days, thin pots to 20 plants per pot using forceps.
    After 2 weeks, subirrigate all plants with Peters fertilizer at a rate of 1 Tsp per gallon water.
    When bolts are about 5-10 cm long, clip them between the first node and the base of stem to induce secondary bolts.
    6 to 7 days after clipping, perform dipping infiltration.

6. Preparation of *Agrobacterium*.
    Add 150 ml fresh YEB to 250 ml centrifuge bottles and cap each with a foam plug (Identi-Plug).
    Autoclave for 40 min at 121° C.
    After cooling to room temperature, uncap and add 0.1 ml each of carbenicillin, spectinomycin and rifampicin stock solutions to each culture vessel.
    Obtain *Agrobacterium* starter block (96-well block with *Agrobacterium* cultures grown to an $OD_{600}$ of approximately 1.0) and inoculate one culture vessel per construct by transferring 1 ml from appropriate well in the starter block.
    Cap culture vessels and place on Lab-Line incubator shaker set at 27° C. and 250 RPM.
    Remove after *Agrobacterium* cultures reach an $OD_{600}$ of approximately 1.0 (about 24 hours), cap culture vessels with plastic caps, place in Sorvall SLA 1500 rotor and centrifuge at 8000 RPM for 8 min at 4° C.
    Pour out supernatant and put bottles on ice until ready to use.
    Add 200 ml Infiltration Media (1M) to each bottle, resuspend *Agrobacterium* pellets and store on ice.

7. Dipping Infiltration.
    Pour resuspended *Agrobacterium* into 16 oz polypropylene containers.
    Invert 4-inch pots and submerge the aerial portion of the plants into the *Agrobacterium* suspension and let stand for 5 min.
    Pour out *Agrobacterium* suspension into waste bucket while keeping polypropylene container in place and return the plants to the upright position.
    Place 10 covered pots per flat.
    Fill each flat with 1-inch of water and cover with shade cloth.
    Keep covered for 24 hr and then remove shade cloth and polypropylene containers.
    Resume normal plant maintenance.
    When plants have finished flowering cover each pot with a ciber plant sleeve.

After plants are completely dry, collect seed and place into 2.0 ml micro tubes and store in 100-place cryogenic boxes.

Recipes:

0.2% Phytagar
  2 g Phytagar
  1 L nanopure water
  Shake until Phytagar suspended
  Autoclave 20 min YEB (for 1 L)
  5 g extract of meat
  5 g Bacto peptone
  1 g yeast extract
  5 g sucrose
  0.24 g magnesium sulfate
  While stiffing, add ingredients, in order, to 900 ml nanopure water
  When dissolved, adjust pH to 7.2
  Fill to 1 L with nanopure water
  Autoclave 35 min Infiltration Medium (IM) (for 1 L)
  2.2 g MS salts
  50 g sucrose
  5 ul BAP solution (stock is 2 mg/ml)
  While stiffing, add ingredients in order listed to 900 ml nanopure water
  When dissolved, adjust pH to 5.8.
  Volume up to 1 L with nanopure water.
  Add 0.02% Silwet L-77 just prior to resuspending *Agrobacterium*

High Throughput Screening—T1 Generation

1. Soil Preparation. Wear Gloves at all Times.
   In a large container, mix 60% autoclaved SunshineMix #5 with 40% vermiculite.
   Add 2.5 Tbsp of Osmocote, and 2.5 Tbsp of 1% granular Marathon per 25 L of soil.
   Mix thoroughly.

2. Fill Com-Packs With Soil.
   Loosely fill D601 Com-Packs level to the rim with the prepared soil.
   Place filled pot into utility flat with holes, within a no-hole utility flat.
   Repeat as necessary for planting. One flat set should contain 6 pots.

3. Saturate Soil.
   Evenly water all pots until the soil is saturated and water is collecting in the bottom of the flats.
   After the soil is completely saturated, dump out the excess water.

4. Plant the Seed.

5. Stratify the Seeds.
   After sowing the seed for all the flats, place them into a dark 4° C. cooler.
   Keep the flats in the cooler for 2 nights for WS seed. Other ecotypes may take longer. This cold treatment will help promote uniform germination of the seed.

6. Remove Flats from Cooler and Cover with Shade Cloth. (Shade Cloth is Only Needed in the Greenhouse)
   After the appropriate time, remove the flats from the cooler and place onto growth racks or benches.
   Cover the entire set of flats with 55% shade cloth. The cloth is necessary to cut down the light intensity during the delicate germination period.
   The cloth and domes should remain on the flats until the cotyledons have fully expanded. This usually takes about 4-5 days under standard greenhouse conditions.

7. Remove 55% Shade Cloth and Propagation Domes.
   After the cotyledons have fully expanded, remove both the 55% shade cloth and propagation domes.

8. Spray Plants with Finale Mixture. Wear Gloves and Protective Clothing at all Times.
   Prepare working Finale mixture by mixing 3 ml concentrated Finale in 48 oz of water in the Poly-TEK sprayer.
   Completely and evenly spray plants with a fine mist of the Finale mixture.
   Repeat Finale spraying every 3-4 days until only transformants remain. (Approximately 3 applications are necessary.)
   When satisfied that only transformants remain, discontinue Finale spraying.

9. Weed Out Excess Transformants.

Weed out excess transformants such that a maximum number of five plants per pot exist evenly spaced throughout the pot.

GFP Assay

Tissues are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

| | |
|---|---|
| Flower | pedicel receptacle nectary sepal petal filament anther pollen carpel style papillae vascular epidermis stomata trichome |
| Silique | stigma style carpel septum placentae transmitting tissue vascular epidermis stomata abscission zone ovule |
| Ovule | Pre-fertilization: inner integument outer integument embryo sac funiculus chalaza micropyle gametophyte |
| Embryo | Post-fertilization: zygote inner integument outer integument seed coat primordia chalaza micropyle early endosperm mature endosperm embryo suspensor preglobular globular heart torpedo late mature provascular hypophysis radicle cotyledons hypocotyl |
| Stem | epidermis cortex vascular xylem phloem pith stomata trichome |
| Leaf | petiole mesophyll vascular epidermis trichome primordia stomata stipule margin |

T1 Mature: These are the T1 plants resulting from independent transformation events. These are screened between stage 6.50-6.90 (means the plant is flowering and that 50-90% of the flowers that the plant will make have developed) which is 4-6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal micsrocopy.

T2 Seedling: Progeny are collected from the T1 plants giving the same expression pattern and the progeny (T2) are sterilized and plated on agar-solidified medium containing M&S salts. In the event that there was no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings were screened until two seedlings were observed to have the same pattern. Generally found the same expression pattern was found in the first two seedlings. However, up to 6 seedlings were screened before "no expression pattern" was recorded. All constructs are screened as T2 seedlings even if they did not have an expression pattern in the T1 generation.

T2 Mature: The T2 mature plants were screened in a similar manner to the T1 plants. The T2 seeds were planted in the greenhouse, exposed to selection and at least one plant screened to confirm the T1 expression pattern. In instances where there were any subtle changes in expression, multiple plants were examined and the changes noted in the tables.

T3 Seedling: This was done similar to the T2 seedlings except that only the plants for which we are trying to confirm the pattern are planted.

Image Data:

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Instrumentation:

Microscope

Inverted Leica DM IRB

Fluorescence Filter Blocks:

Blue excitation BP 450-490; long pass emission LP 515.

Green excitation BP 515-560; long pass emission LP 590

Objectives

HCPL FLUOTAR 5×/0.5

HCPL APO 10×/0.4 IMM water/glycerol/oil

HCPL APO 20×/0.7 IMM water/glycerol/oil

HCXL APO 63×/1.2 IMM water/glycerol/oil

Leica TCS SP2 Confocal Scanner

Spectral range of detector optics 400-850 nm.

Variable computer controlled pinhole diameter.

Optical zoom 1-32×.

Four Simultaneous Detectors:

Three channels for collection of fluorescence or reflected light.

One channel for transmitted light detector.

Laser Sources:

Blue Ar 458/5 mW, 476 nm/5 mW, 488 nm/20 mW, 514 nm/20 mW.

Green HeNe 543 nm/1.2 mW

Red HeNe 633 nm/10 mW

Results

Table 2 presents the results of the GFP assays as reported by their corresponding cDNA ID number, construct number and line number. Unlike the microarray results, which measure the difference in expression of the endogenous cDNA under various conditions, the GFP data gives the location of expression that is visible under the imaging parameters.

The invention being thus described, it will be apparent to one of ordinary skill in the art that various modifications of the materials and methods for practicing the invention can be made.

Such modifications are to be considered within the scope of the invention as defined by the following claims.

Each of the references from the patent and periodical literature cited herein is hereby expressly incorporated in its entirety by such citation.

TABLE 1

```
>SEQ_ID_NO_1_construct_YP0001
ctgcattcacacatattttgggctctcacgtgtttgtgaatttaatatatttgactacacgatctttcaacgtatgaa aaagttttatactactattttcgtttgagtgggaaataaacaaatgatagctacagttatctatatggtataatttta cacttttataactaataatgatgagtgatgacaatcgagtgtcggatataacaggccaacaagtggaatggacttatg taacttttaatcacgggattaaatcacgtaacccaatgtcctaattggtatttaattttgattatctcgatgctaca tattgtcataggactcatatctttgatcacgtgccgctaccaatccagacattttagtatacaaaaaaaagaagata caaacttaagatatggaatatatatcagaactatcagttttagactttaataattcgaattgaataactacgatcaat atataaattggcaaatagattggtcaattgtagtgcaagaaatttgtgaactttattacagtacgaagagagtaagag aagcaagatccggttttaggcaacaagtaacattttgagttcagagagtttgcttcttactttaagttacgtcact acaaaagccaagttcctacttcttaggtctaaagtcaattttcgaatattcagaaaaattgtactctactagatcgaa tagttttcaccggtgaaacgatatataaatgaagactacaatattttttaattttttttaagcgtatgagttctagacc tttggcacgtaaatttctccggtacctgggaccaatcgttgataatatcacgtttaagatttaatcatccatcccaag tagagttgaactagtaaccttgagcacttttctcgagacaactaaaccatcatccacttagtgcaataaagcgtcat
```

TABLE 1-continued tcttttttttctttcaaaaattcgtatttaattttaatttattaaaaatatttcttttgttttaaattgggacagaa
ttatcatttaacatatttaaaatttatattttaattaaaaataggggtaaaatatatttttcaaacaaaaattcaaaa
atagggcaattttcaaaatcatccattcttaaatctaaagtcggctacagtcttttcgttgttttgttgctaatttca
atttatatacatgcaaattacaaaatataatgttttggggataattatcttcttgcgccttttttattaaattaat
atgctcatatagcagttcttacaattaatataactagggttttaaatttcaatatcgagttgacaaaatgaattgttt
acaagttttttctttcaatatgcattgttcatcacgtattcgtagtgatgcaaaaacaaactataaattataattg
cactagtgagattagcaagaagtgttataaattagaataaacggaactatcaaactgtgttatgtacaccatttattt
ttgttaaagaatatgtgtagtagttagaaaactgatcaaattaaactgaaaattcacattacggagatcaagttacat
tgtctattgatgaaaaaaacaaaataaatccaaatggcactaaaagttgtagaaattgaaagaagaaaatagattttt
gtctaggaataaaagtcaaaatgggaaagacaaaaaaaagagaggcaaataagcagtgatggagctaaagcaacgctt
tactcttttaattatgaattatttgatttgacctccactcgcctggctttttttggttgttcttatagaaaagtaaa
ataacacaattagcacataacatgagttatcgagaaaccaattctctttgtggtgttttagttaatttctataactta
tgaaaccatttctcagtttatcatgataattgatcctctatttaaaaccctaaagtttatattttgtttgttcaaac
ac >SEQ_ID_NO_2_construct_YP0007
agcagaacaactatatttattgtgtcacataaatctgagatcatttataaccaccaaagaacctatacacagtaaatg
acaaatgtatctccctctatctctattgcccatatgtagatgctaaagtaagatttctcttttttttaatgtacttt
ttttgtataaagtatattccataagaaaaaggaaaagcttgtttatggatcaattgaccccaaaaaaagttttagat
caaagcccaatataaaaaaaaaacacagtagtgacacaaaggaacttaaataaaccatgaattgatctataaacagta
gagatcgataaggcgaacattttccatgtgaagtgtcttctttcatctataatatttttgacatccaataatttcctc
tataatatcattcacataattgatagaaacattatgttagaattgtccacatcatttgagctgtaatatattctgttt
taacaaattatatggtagttgcttaatcttatgtccatcttcttctatgcatcgttttcgcgcctagttgtccagtcc
atttcaactacctacctctaattcttatcttaaaacaacatttttttaatttaagtattatgctcaaagactaactaga
tagaaaaccgttattaaacattaaacgaattaaaagtcttacatggaaaatgtaggtttataaaccacgagttatgat
tgacaataaaaaaaatgcaaatcatcaatcaaaagagacttgagtgcgactctatatcaaccattgcaattaaaatta
tctatcacaaaaattttagacagattaagttaatttagtctaaattcactaatttattttctataattagtaattaac
tatatttattttatttacacatttttctgataatttagaaatttgcatgaataacaaatataagattttggaaattagta
gcaaatttaattaataattattttttgcctaaatgaaccaaacTATAAAcctccacatacaccagtcatcaaatttac
agagacaacaaactaaagt >SEQ_ID_NO_3_construct_G0013
atcttgtgatacacaatttattactatttggtacattttgaagtatttgttttgcatgatatatgacgttaatttga
actgatattagtcaatttatgggtacaaaagttgaaagtttagagcactatgttggatttattaaaaatgatatcata
caatggttcaatatatatattttttttccacgttttaataacattttttgtaaacaagtcttctactattgtcttta
ttgttaatgagtttctagtacctaattaggaattttgaggatatacgatacattaatgagttacattatcccgaaaac
aaaatcttgaaaacgaacaaagataatttggacattactcgttatgtatacgtatggaattggatagagccgttgaac
catcaagtgggtcttcaagtcaacgaactgaatttgattttacactcatgtacatcggccacaatttttattcacacac
tactaacacctctggtgtccactttttctttctctagattgatgtgttaagattttttgttgcaattcatttattcag
gtattttatatatatatatataaattagaataaactaatttaaagaaagatatagcaattatgtttcacatttta
acattctcaatcatttataaaactaatgtggtgatgaatggtatatatatatatatatatatatatatatatatat
tttgttgtgaactaatggtaaatatttaaaataagacatacgtacataaatccacggactcttaaagtcatgatgcgg
ttaataaaatgttcacataacggtaaccaagtggctcaaaatcatgaaacaacgtcacataattttatcttataatgtgg TABLE 1-continued ataattagtaccgcattatttgtaagaaaattaaattaattatagattcacagctaagaaaatacgaaaagacagctc aacacttttccacttctattccccactgtctataaactctgataaataatctctgatctctcc >SEQ_ID_NO_4_construct_YP0097
ttcatctttatatttaagagtttaaaaactgcaacttttgttttctttcactaagtcttatggccacagttaattaa aagcagatgaaaggtggtccaatggaaaaggagaatgtgattgggctagttgggagagttctgatgtctagtgttggg tacacgtgtccgtcagttacacatagcattaaatcagacggcatgtcattattcaaatctagttcacatagtacgact aatagctgataaattaatgattatacagcatatgaattatgaattcaaaaaaaaaaaaaattgaaaatgttaaggag atgctatattttacaaaattcatcgcaatgctttctactaatttgctaagtggtcttctccagttagtcttgtcgatt ccaagcgatattattaaatcttgaagcatcgctcaaagcattatagcttaagataaccaaattgttattaaaaacacc tagtgaaattttaaattaaaacaattttgatatctttgtaatatctaatactactctttctgtgtctaaaaggatta atttcaaaaatttcacacatattaaaaaaaaaaaaaattactagctaaacaattttcaataatcataaaacaatag taacttaataatttttttttattttcaaaatagtccttcaagtttacaattcattttagtattataatcaacaaaatt tgtattaaaaagttggaaaattaatctttgtggaacaaaaaaatctagaaatcattttttagaattagagagaggttt gataaaaaaaataaaaaaaaatagagagaggtagtacatactaaacgatgtgatactactattgacaaaatcttaat tctcagtttagtagaataaactagaaggaatgaatgaagtaaatgcgaatccaactactaacaaaccctacttagtca tcatattttcccatatgaaatcccTATATAAacccatcatcatctcccactttttttcatatcca >SEQ_ID_NO_5_construct_YP0111
tatatagttttatgcattctcctcttgtgtaatacataaaccaaatatgagataggttaatctgtatttcagataat attaaattccaaacaatattttacttgttataagaaggcaattaatatctctctgttaatggcaagtggtaccaagt agtattaaactattaatgcaatggaagagtactgttggaaattataatcctctatcacacattcaaacagatctcctg aaatcttctcttccaaacttgtacttctctgatccaaatgtaggctccaaaatatagacatttaccatttactaagtc cacaactcctttcttgtctccttcaaaaatgactcttgtgtaaccatcatatgactccgacagttcggcattgccatg atgagagcttaaaaattcaccttcctgagcatttcaagtcttcactcccttagcttgacctgaaccaagataaaatgc ctttgtcgtcccgtaatatccatcctgctttggacggcatcatagttacattcgatccatcctatttacaatgttatt ttagtattaaaaacatgacaataaatttgttgttaaacatattcaaatacaatatgattggatttataagtaattgta atatgaaatgtccttagtaatatgttaaaaaatacatagatacacacgtactaaaagaggcaacgcgggagatgtc attagaggaagaactaggaagcagagcgttcatgcaaaatgctaccaaaaacgttaatgcaatatctcaactaatcag cacagtccatttcatactgagaatgtaaaaaccaatcagcatcgtccattttttcatctaattatttgttaactctta attggccacaacttccaaccacatgacgctctttctattcccttatatattcccatctcaaatgttcttggagacac aaaatatcataaacatataaacataaacgccaatcgcagcttttgtacttttggcggtttaca >SEQ_ID_NO_6_construct_YP0104
tttattttattttttgaatgaaaatgtcttctttattcgtaattttaaactcactggtggtggatatattgttatgtc cccaattcgtctggcaactctcgtatattagtgagaaaatttgtccattatttactgcactattaccctgtgttaat tttttgtattgaaattgttttttagtaattcacgtcatatagcgaatgattctttaattttaaaaattcagtcttaag tttacaaattaaataacgctactgtaaccaactctgtacgaccaacatgttcgagttttgtatatacggccatatat gtacatattttactataaagcgaaaaaatccataaattatttaattaatatataaaggtgccattctatttccaatgt gcttaggaaaatgcagaacctcgtgctatatctctgtcgccacgtgcaaatataacaatatgaaatagaactagcaaa tcttgaaatctaactcttaagactaattcaagcacatacgtagagaaagttgaccaacggttatcagcattttaacat ggaccttatcaacatttttaacaaagtccacaaacaaccagtcttacaatcgcattggtacaagataatcgaattcatc ttccatataacaaaacctaaaccttggtgtgaaaaggagaagatatgtatgttaaaggccgcctatgcctctggtttg gggtatatgattctaagattagggtttgaatattttcgttagcctgccatgagatatatttatgtgataattagagcc TABLE 1-continued tcttatgcattaatgcataaccgactagatcatgtggtattcagctaatcagtacacacaagacaaagtagtaaatga
gtttgatgaagactgtggtctgataattcctatcaacgttaaatctgtcggggccaggcagccagcaacattttgcct
aacaacgctctgaattcaattgaacctaggctatataatagcaggctaacttaactaagagtt >SEQ_ID_NO_7_construct_YP0075
tggattacaaatcattaagctaatatcttcgatgaattaagaagataagtggataacaagtacctaaccgcaatagtc
cataaattaaaacattaatgtatttgtcgttgaaaatttggccgacttttatttgttattctagtttccacatcaaaa
atgtttgtacttcgtagcaatccatccacctaaaccccaaatcttaatttatatttgttgcgtttaaatttgggtgag
atttgattctaagtagttgagataaattgatattctattcattagtaaaatgatagagaaattggtttataataattt
taccctagaacatgacatgatattggtaaccattaatcaaagaaagagcaaagcatttaatttaccctactctccaac
cactccagcctttattagttgcagttgggaatcatttctttatgattcttatgtcattgtctcctaaatcaatgaagt
gccttgaccttgttactaattcgaacatagcaaagccaactacatagatcctttacaaagttctaaaaacaggttgtt
taggcgtctagacaaacaaaaccattttgtacgattcaacaaattggtccatagaatgttattgatcttcttgttta
ggcattcgataaatcggctaatacattattttttgttttgcttttccttattaaaaatatgcaaagtattatgatg
tttaacctgaactgaattttacatttaactggatataggaaaatattgggttgaatttaataattaagcaattgtcac
gtaaatcaaattgggcttaatatatattgttgatttcagcaaagacaaagttgggccgtttcaatagtcttcacgcga
tgtaagcgttcactaaccaactagagaagacaatcaaatgaatacgttccacgtgacgcttacgaacttgtcagtcac
tttggtaatatgacagacagtaaccagtaaactactaatctctttcgctaacgaacacacaaaa >SEQ_ID_NO_8_construct_YP0016
aaacatgttttatgtaactactttgcttatgtgattgcctgaggatactattattctctgtctttattctcttcacac
cacatttaaatagtttaagagcatagaaattaattattttcaaaaaggtgattatatgcatgcaaaatagcacaccat
ttatgtttatattttcaaattatttaatacatttcaatatttcataagtgtgatttttttttttttgtcaatttcat
aagtgtgatttgtcatttgtattaaacaattgtatcgcgcagtacaaataaacagtgggagaggtgaaaatgcagtta
taaaactgtccaataatttactaacacatttaaatatctaaaaagagtgtttcaaaaaaaattcttttgaaataagaa
aagtgatagatattttttacgctttcgtctgaaaataaaacaataatagtttattagaaaaatgttatcaccgaaaatt
attctagtgccactcgctcggatcgaaattcgaagttatattctttctcttacctaatataaaaatcacaagaaaa
atcaatccgaatatatctatcaacatagtatatgcccttacatattgtttctgacttttctctatccgaatttctcgc
ttcatggttttttttttaacatattctcatttaattttcattactattatataactaaagatggaaataaaataaagt
gtctttgagaatcgaacgtccatatcagtaagatagtttgtgtgaaggtaaaatctaaaagatttaagttccaaaaac
agaaaataatatattacgctaaaaaagaagaaaataattaaatacaaacagaaaaaaataatatacgacagacacgt
gtcacgaagatacctacgctatagacacagctctgttttctcttttctatgcctcaaggctctcttaacttcactgt
ctcctcttcggataatcctatccttctcttcctataaatacctctccactcttcctcttcctcc >SEQ_ID_NO_9_construct_YP0094
taaagatcagaagaggaaggtttcgccgcggcggttgcatcttcaccgtcgatttcatcgttacagcgacgccggtaa
ttcctaggttgcttagttcccattctctctctaaaattagggctcgaaatgaattgttgaacaagatagagatctttt
tctgatccccgtcgaacatttattcaaggccaaaaaagcacacgggaatttagagtaccaatacatatcaaaaccta
atgggctttgaatggttgcatgtgtgtgtttattctgatatgcaaagcgatcgatagtcttttccatacaagtgtaa
actgtaaacaacgtaattaagcataacaatacaactctttcttctctttttttttgtaaacacaaaataaaattacat
caattcatgctttcctagttcatctgacattttccaaaattcatgttccattgagtccctaatacttgttcatattc
atattagggtacatgaataaaagttatcattcttgaaactactaaattttcatagtttatttttcttcttttcgtttc
actttcgaacaaaaacactacgcgtggcatttgcaatgaattccacattatatggaataacaccatgatgaacattcta
catatataattattatgtttaagcacttagacagcataaaattctttctaattatataaatctaaccttgttacattgt TABLE 1-continued acatctataaattacttgaagaaataacgagttctatttcttttttaaaaattaaaaatactataccatatctcagtga ttaagttgaaccaaaaggtacggaggagaaacaagcatttgattcttccttattttattttattcatctctcactaat gatggtggagaaaaaagaaaatacctaacaaacaaatatatattgtcatacaaaaatatttctatattttttagttaa ttagtttatattcctcacttttcagggcttatataagaaagtgagcaaacacaaatcaaatgc >SEQ_ID_NO_10_construct_YP0033
aaacttccaaatttctaaacggatgcaataagaacttacatattctctttcattagtcatttattggccagatttatt aaaaaagttttactcaatgaccaaggattagagttaaagataatatagattattacatatattattcgaaaaaatat acgcatgtccgacttttaaacctcaaaaatatcaaaaccagaaaagatgataccacacaaaaaaacaataaaataat aagtggaagagatatcatcggacaacagtacaagtacagcaccagctctgccaaaagccaaaaccatttgtcaattac agaaagatactattgtttgcaattactaaattacccctcggactttacaaaagcatctctaacttatccacgtgtcag tcatctattgattgtttcaataccaccttgtattaacgccccacgattcgtggtgggtacacctgatagtccgagga tatttaaatctcacgcgctcgtgtctataattcgactgtactcgcttttcttgtcgtgatttagcaatttacgaagt caaatgtttgactcaatcagacttgcgcataagagagcgagtataaatgtttactatactcacgcaagtggggcttta ttgaaactactcttttgtaataaaaccagcagtggttttgttctgaatccgctctcttgccatatataccacaaacag aaaccacagaagatatcttttgagaaggaaaaaaaaaaagaagcttctcctcttcctctgccttcttctttccattta ttgcaaaccctgatcaagtaagtcaaatcttcacgaacacatatgtatataaattcaatccaagaaactaggagaaat ctatgaaagaggacaaatctaagtcaagtttgaatcaggaagattatctagatttgatcattttgacatttacgatgt gcttacttattcttgataaactttgatgcagttggttttggtgttagtcttttggggagagag >SEQ_ID_NO_11_construct_YP0049
acatcaatttgcctgcttgtagggtgattcgtcaaatctattatcaggttttaaatatactcgaattgacttccaaat tcttagtctctagtgtaatgattttgagaatcacttaactccaaaaatataatccacgatcccgtgttaattattgaa gaatcaatcgttttttaatttctcaccaatagatgttgctcttattacttaaaacaaattgtttagacaaatgtagcaa gtgtgatacttagtgggatcttaaagacgatttctcctataacagaggacaaacaggtcggtcaattacaatgtcatc cctctttacccctgtcttttttttttcttcttaaaacctaaccatttgattgtttctaaaggtatttcaagaatatatga tcaatctagatgaatactataccgacgatgactacacacacaaggaaatatatatatcagctttcttttcacctaaaa gtggtcccggtttagaatctaattccttttatctctcatttttcttctgcttcacattcccgctagtcaaatgttaataa gtgcacacaacgttttctcgaagcattagaatgtcctcctcttaattaatctccttctgattagattctcaatagagt ttaaatttgttaatggagagatatattgggaccctcaaggcttctaattataccacgtttggcataattctctatcgt ttggggccacatctttcacacttcattaccttatcaccaaaacataaaatcaatcaacttttttttgccttattgatt gtgttggatccctccaaaattaaaacttgtgttccccacaaaagcttacccaatttcacttcaatcttaacaaatagg accaccactaccacgtacggtttgcatcatacaaaccacaaactccttcttcattac >SEQ_ID_NO_12_construct_YP0060
tggagctttattgaaatgcaagaaagtaaacaaaggaagatctttagattgtcaccaagagtggtctgaaactctcat aacactcaatcctcctcctcctcatcaccaccactacaaaatattatattctctatctctcaatctatgaggagatgt attctatcaagcatttgaaatgataagaaactggcgatcatcctctacgtcaccatcactccaaaattatcctctttc taggtttaagttttgtaatgatcgcctttattgttgagatctctaacttctcgcatttccaaaatgttaagtccaat aactgcattggttaagttggggcgttactagtcggcttaaatccaaatatggatttgattccatatgtatgtgacagt ttcttaacgttcatattacaatgaatgatggatccttgactagacaaagagaaaatggattgtcacttcgtaggaaaa atagaaattctccacgaaggctggtctcctttatttaacgacaaattcactcatagtctcattcacaatttgaacttg tctaacacaatgtgttatatactcgcgaaaagaagcataataggctcttaagggtaatccacgaaaccaaaacacata taaaacattaatattttttctctaaatttattcatatcaataataaagtttacaaaaaatataaaacaataatccatac TABLE 1-continued ttagcccatagcttcgtgtggaagaagacttgattttttgactagtcaacgaaaatgagtaaatgacgtattcagctat agtaaaagggatcataagcggaaattacaaagaagctttgagggtaaaatagtcaaaaagcataatcagaaataactt aggcccaaagcaaaaaggaaaggactctggatccagccgcaaatcagaatctggtaagttcgaacgccacgtcatcac ctaaatatctgaaatatctaattaagacttgtcTATATAtaaaggcttctcctttcacaatccc >SEQ_ID_NO_13_construct_YP0092
aaagattgagttgagagagatggtggagacgcagaacagacaaagggagtttaccatatagtgctctaaagggcaatg agattgcagtgatgtggctatccggggaatcatcgcaggttattccttcccatgagcaacaatcaatggatgggttcc aattcagaggagaaacagaagaagaaacgtttccagagaaccacagtagggattctcgatcttgcgagttgcagagag cctctgaaactgcaatagaaaggacactgatgaaaagaacacactgaaggagtatgccaatcatgtgaaaactcagag cttgtattggtcttgtggttgatgaagttctcacaaaacctttggctttgaatctcccctcattagtcatggtgagaa caagaacaagacgagaaacagacaaagaagatgaaaaaacttgttggccagtgttgactaaggggggaatagcccagac ataacaaaattagacttgtcgtacatcttttaatatttttttttatctgtttctttgtcctgacgctttcattattcctg tgatcaattttctcataccattggtccatcgttaatcctttctcaatttcattttctacgtaacatgagaggagacca agtcctatgagaacagttgacgtaacagtggttgttaagttaagttaaaaagaggaagctagtgagagtgaccgttag gtagagaagtgagatctttaaccactcttctttctctctctctgcttttttcgtcgtctttcacatctactgttcg caaactctcttatgcttccaataatggtgataccaattgagacttgcaggagaatctcctcttctccacactctatca actggtcagccatggaatggtcgtttcagtttcaatattcctggattctttttaaggattcctgtttctcttctgttc ctggtatattcttaacgacgaaattagtatcggatcctggtaatacattttgaagcttttaagt >SEQ_ID_NO_14_construct_YP0113
tatgaagaaattataatagactctcataaaaatagtgttacaacttacattctcttatatagaaattaggataaacag aaatgtaaataatatatttcgaaataatgttaaatttcctaaattctaatattaatatttataaatggtcatttaact ttttcgtaccggttcgatgggacatgtgttatattcagttaaggttaccaccatgcgccaacttggcctctaccaagt caacatggatatggaccttatggttacatgccgcctccgcctccaccgctaccgggatatggatacagaggtccgcca cctcagcaaccgacgaggaatgaaacaaggcaataatatattgatgctattgtggatttagttactgataattagtgc cttagtgacagttcaaaaatgttgttcatcaataatctacaatttaaggtttgtgttgtggaatgtttcatgatttta tgaagtcttgcttatcaaaaagtatgatgattaagaatttgacttcatggcatattcatttgagttagcaaaactttt ttgtgttgcaccttcaaatttataaatttatgattttttaaccatcgaaattatatatttgaaaagactatctctacaa gccaaacccactgggccaccaatatgggtttatctgcgaaatctgtgaaccttagaaaatcaaagcccatatccactt tgctggaactttgctggaatgtaggttagacaaaaccttaagacgcagctacaagtctcttatgtggcagatgtcaaa attaatgagcacgtataatttacccaagaggagcaaaataagattagcagcttaaattaattgtgttggattaaatga aacttgcactatgaatggcaaaaaagaggttacaatctagcaaccacctcataaaccctcattaatgagatactgact cgtgaaccaatcaaatctcaagtttcgtagtttaaataagtagtaaacacctcctgatcaaagc >SEQ_ID_NO_15_construct_YP0095
ttcctcgaccatgccgttgccggaaccggctagcgcggccggccggcggcggcggggaggccgcagtgggacgacggg tgaaggatcctccagctgcggaaggaggtggtcctcgaggccgaaggggagaggctacggagatggagggaagccgaa gagaagggaggctgctgctgctgctgcatttgggagacgagaactcgactcgagccatggcggcagattggtgtttca cggcggaatgctaactagatccagcatctccatagcaaaggtagaatggtagattgaggtgagtttttttttcccctct tctgcagttttgatgtattattactgcccctcatctgatctgggtaacatatttctgagctcagtagaactgttaaaaa aaggcagaaatgcacaaactcttctcacaaaacaacatacaaatgcttatattttggagcggaggcaatacatggtat attttttaaagtgaaaaaaacaatcagacacatggtattgagtgatagcaaagctgggtgaccacagaaaatacctcc tgctttaaatactttatacctgggctgtcaatcctcggagttcctcccaatgtaatgtctgaggaagaagtattgcag TABLE 1-continued ctaaattttaagggtttcttgtacgaaacagggacaatcagagattaagaaactctatgtggaaaaggccatgcgcat tttgttatgtgattcaacaaataagatgaggaggcaaagtcatggttctgttctaattaacaaatctactatggggc cgttgctccctattgtccacgctccttttcttcatttctctcctgcaggatatcttgtcttttgattcttcattttag gtcttataaatatcacgtggttcaggcctccaatgtcaaattatcattacgtggaactctcttagatgcttgagaaaa gttagctcttacctgtccatagaagctccaaggaagcgagaatagtagatactttggttggcc >SEQ_ID_NO_16_construct_YP0102
atttggttgataacgttttcactcgactaattatatacttcagaaggatagtaatagaataccaaaataattaaatga ttggttagtgccttagtggagacttttttaaccgattctaatagactaatgatgtagctaagcatttatttgggatcat cactgtttgaaaacgtgaaatgtgataaaagttatgaaacgattaaaatataaaataaccgtacaaaacattatgtac cgttttttctctgttcttttggcgatttggtttagttcgttacactctaaatgttattgcagatatatataataatga tgcatttgcatctgaggaacatataattccggttaacacttccaaatcttatatccgtctaggtagggattttataaa tcatttgtgtcatcatgcgttatgcttgtcggctttgaccataacgcagagatatagaactagcttttacttaactttt tagatttattatttgatctagagttaagtggagatatatagtgttttttgttagattattggtggatgtgagagtttgt ctttagtttcaagttgagaatataaggcaagaggagactctgaggcaatcagaggttttgattggcaaaatatccaaa aggcccaaaccaagtcgaagcccatctcgtacaaaaaagaaagagatctgtaagaaaaaatattctttgatattctt acaaaaataagtgtaaaacttttattagtcaaaatcttcaatcttttaaaaactctcatcactcctacgaaagcgcgtg agagttatgagacattccttaatagcattactcacaagtcacaagttcaaaacgtctgactgaaacagaaacaagcct ttgttgaagtcttgaagaagagacattagtactcgtcgtatagccataaaaggtaatatacgaaatttcttcgctaat ctcttcaccttcctctacgcgtttcacttttcactttataaatccaaatctcccttcgaaaacat >SEQ_ID_NO_17_construct_YP0103
gttttgaagaacaatctggatcgaaatctaacataaggtcatcgtattcaagttacgcagtcaaggacttgacatcat cctactctggtctgaggttaccacttccaaagatgggattttttcgactcggtatgcttcctaagaaattcgtttatt gaacctagcaaaatatcttgtaatgtaagattcctgagatgatgaagaaaaaacaaactttttgttacagcaggagaacg gagagaaagaaaacagagaaccaaatgctcttgaagcaaacagaagaagaagacacaaatccaaacttgagacttctt ctacaccagaaaaccgcagcattctgggacaacgcaaaacacgaaagtgaaacgggcaatgatatatatgtcttgggt gcgttacaaggcatcgtttgcatgttgagttggataagtcaactgtcttcttttcttttggttgtagtagctgccttt ttttttcctttgttgctttaagaaatagcccgaaaaaaagaatgttctacatttcggagcagaaaactaaccgaatgag tttttggtcggatcatcggatcgatcagatatattttgagttacgaactgttataaaaaaagccataattttgtgttg agtttgcaaaataccttataacttgttatttgagattgcacctccatatatattaattcgtaagagtatttattaagt aagctttagtataaatcctttttttcctttaaagtaagttaatgttctactaaataatagtaaagttgaagaaccgctc cgttttacaccatgcacgtgttatctaacaaagaaaatatggtacacctaatggctaatgcaaaggacaacacaatga aactaacttgactctgtgttatacaaacccatagacatctgcatacatcctagtatttgTATAAAttggactcaaatt cctgaggacaatcatagcaaacaatcacatcatcgcaatatacataaacaaaagaggaagaaaaa >SEQ_ID_NO_18_construct_YP0107
taacaatccttgggaacattgcatccatagatatccggttaagatcgatctttgaactcataaaaactagtagattgg ttggttggtttccatgtaccagaaggcttaccctattagttgaaagttgaaactttgttccctactcaattcctagtt gtgtaaatgtatgtatatgtaatgtgtataaaacgtagtacttaaatgactaggagtggttcttgagaccgatgagag atgggagcagaactaaagatgatgacataattaagaacgaatttgaaaggctcttaggtttgaatcctattcgagaat gttttttgtcaaagatagtggcgattttgaaccaaagaaaacatttaaaaaaatcagtatccggttacgttcatgcaaat agaaagtggtctaggatctgattgtaattttagacttaaagagtctcttaagattcaatcctggctgtgtacaaaact acaaataatatattttagactatttggccttaactaaacttccactcattatttactgaggttagagaatagacttgc TABLE 1-continued gaataaacacattcccgagaaatactcatgatcccataattagtcagagggtatgccaatcagatctaagaacacaca ttccctcaaattttaatgcacatgtaatcatagtttagcacaattcaaaaataatgtagtattaaagacagaaatttg tagacttttttttggcgttaaaagaagactaagtttatacgtacattttatttttaagtggaaaaccgaaattttccat cgaaatatatgaatttagtatatatatttctgcaatgtactattttgctattttggcaactttcagtggactactact ttattacaatgtgtatggatgcatgagtttgagtatacacatgtctaaatgcatgctttgtaaaacgtaacggaccac aaaagaggatccatacaaatacatctcatagcttcctccattattttccgacacaaacagagca >SEQ_ID_NO_19_construct_YP0110
tcatctgctaggcgattaggtttcatacacacatgagtaaactgcactatctagttcatatacactccatcttattga tgatatttcaattttaaatagtaactcatatactttttcagtatttaatttattatttccttaaaccaaatttcaatct tacaatttcgaatttgcaatacaatttaaatatctattttatgataataaaaataaaatttaatttgattgtataaaa ttcaaatacaattcgattttgcaatagaaaacaatttaattctatacactccatctactattaattttccattatagt tataaattagtatatgtaaatttgttttatttttttttaggttttttctcttctaagagaaaaaaaaaagttaaaatct tttccgatacatgtcaaaatataagatcgatagatttgccatgtgttacgatcgtatgagttattaactttgaaaatc atactttatataatacaaaacatgtaaatacatgtttatacatatatttacaactaaaaacatgtgtaaaatctaatg gattttaaatacatgcttttagctcgaaaaaaatttgatacggagaaaaaaatttgacgggaaataacatacgtaaa tatctgatcaaattatctatagtacgattttgacgggaaaaaaaattattttaaaggaagagcttaactttgaatctc actaaaccagatcatacataatcaatcctttcttttatcttttttttttcttttcattacgtgtaatcgtgttgtgtct aatatatcagtttgatttgtaataatttgaataaaaaagggagtgttgttatctttaagtttgcccaaaatctatagt catgttcgatgtaaacgtatcttaaacaaaattattaaatgttaaagatagtaacatacaattattaatgaataaatg tttaactaattaaatatcatttagtgattgtccTATAAAatctcttgttttcttgtttcatatc >SEQ_ID_NO_20_construct_YP0112
ttatgtgccctgatgtcctatgcagatggtgcaactactgcttttggtgagaagcttcgcgaacaagttgaggaaagg ctagaatttatgacaaaggtgttgccccacgcaagaacgtggatgtaatgaaggaggtgatagagaatctaaagcaa ggtatttcttgtagctgtttttttttggttgtaatcagagtcctctttatgatggcaaactcagtgttttttatctg ttcctcctttagaagaggaagggaaggagccagttgatgcctcggtgaagaaaagcaagaagaagaaggcaaagggtg aagaagaagaagaggtggtggcaatggaggaggacaagtcagagaaaaagaagaagaaagagaagaggaagatggaga ctgcagaggagaacgagaaatcagagaagaagaagacaaagaagagtaaagctggaggagaagaggagactgatgatg gtcacagcaccaagaagaagaagaagaagtctaagagcgctgaatagaaagggatgcaacattaacaaaccctgtatt gtatttttttttgagctaaattaatgtcgtctgtttttcgtagtgaacatcggagaattttgttttggtctggaaa cgattcaaggtttggcaatatcttaagtttgtttaggttttcactattttgacgtttgcaaccgtgaaggaggctcct ccattttataaaatacaattaccaattccagtgctttgcaaatgtttcaataatagctaaactaactaccaaattgga aaactagcttaacaagtttgtgaaaatgaatttggagccatatgatttattattttacccaaatggagtaatagaaga agagcagctcgcgtttgaatggtcagttaacattaacaaaaggtaaaattgaatagatgttaaaacttgtgtaagtaa acaatagagctacctccttttgagaaggatagataaactcgtgaccaaccacattcccagtccc >SEQ_ID_NO_21_construct_YP0116
aaacgcctcttcggtccacgctgtcgttttattgaaggaattatattttatttttaattgggcctgcaggctaaactat aagtccgtctgatatgggtcgggttgggcttatgagttatgggtctggtaggggtcaattagcttaatttcgatatgt gccctactctcgacctaacgttttgaacacgtaagagagagtttctaatattgagttgtctaattaactcgataggct tatacaaagtgtttccgcatttttaccttcttaataactcatcattcactaactaagaaaagttttactcagaccatat cttccgcttcttgattattgtcaatttgttgtcactcaatttatctcttgcaaaatttagttgaaatcatttggtttc atctttggctcttgaatagttgcatgtgtgtatttagtaagttcttttcaattaagaaggaagaataaaacaaattgt

TABLE 1-continued ggccagaaacaattatgttgagttttatctcatacgttggctcattcatcccatctctctgcttttgaatcattcta
ctcctcccatttttgatcgtccttttctgcttctgaacatggatcattgtgcatgttcggatgttcctcgatcgt
gctgaaactcaaagtctgaatcgattaccatagactctcaacccatctttgatatataaaaagagccttaaccatc
tcttctactctccctctctagaaacaaacacatcacgtgatgatctgtttccccccatacttacgggatgatcagaat
gtggcatgaggaaaaagccaagaaataagttgataaatttaaggtttaatttaacaaaaatgagagattaatcttttc
attttagggtcgcacgcggtgttttgtgcaaccgcagaaacttccTATAAAtaccgatacaatgtgcatgctttcta >SEQ_ID_NO_22_construct_YP0117
aatcacagtcctttatgataaaacgaactcataattattccaccgacaacatgcgttttaaattattttttcttaaat
tatattatattatattgatatcaacctagctaaaataattcggatggcgaaatcggacaattttaatagaaaaaatg
ggtatgaagatagtctatgattccgttcttagcgactagagggacctgctcaaatctcccgggtgatacgcgatgtca
agctcaatagaaccccacaaccgacgagaccgagaaatccttgatttgggctagaagattttgaaatgaatttaatat
attctaagtaacttgcttaaattttttttcaaactctaaagacataactaacataaagtaaaaaaaaaaagttaatac
atgggaagaaaaaattaaactaatgattagctctctaacgtgtttaatctcgtatcaagttttttttttaaaaattat
attgctattaaaacattgtactattgtttctattttgtttagctattattcttgtgaaatgaaaagttgtgtttattc
aattactaaatggcaatatttatcttggaaaactatacctctaattggattaggccctagacatcctctttagcttat
tgacgttaaaattattcccaaaactattaaagtttagtagtttgaaagatgcatcaagacctactcagataggtaaaa
gtagaaaactacagttagtgtgattatattttaaaatatataaaacaatcttattaaactaaatattcaagatatata
ctcaaatggaagataaaaacatttagtctgttaccactaccagcctagctagtcactaatagtcactttggaactgag
tagatatttgcatcttgagttaccatggactcaaaagtccaaaaagagaccccgagtgaaaatgctaccaacttaata
acaaagaagcatttacagcggtcaaaaagtatcTATAAAtgtttacacaacagtagtcataagc >SEQ_ID_NO_23_construct_YP0118
aattgagaaaggtgcctcaatttcagtagaacctgacgcaaaatttcgcgatcatgcatgactcaaattggtttattc
acttaaataaaaaagttgtttccctatctagttgaagttctcaattcaaacgcaacttcttacttttttctttttattt
atactggaatgaattttttcgtcaatgctagacctcaatatttggtgattaagtccaaaaaattatagcaatattcatt
agttaaatcataataatatttgttatttctgctaaatatattagttttaaattggtaaatatatcagtcatcatactt
tatatatgtgcacaagaaaaagaggaaaaaaaactaacttttaataaaattgaacgctatcctctatatctcgtcctgg
tccaaatgtaaacttcaatatccttttgatttttattgctgattgctttaaaaaatttcacaaacacttttatcattct
tttattccaccaaaatctacagacataatactttgtaattttatgtaaaaatcttcaaaatttgggaaaagaaaaatc
atttaaaatcaatttgcattaactggatttatttccaaaggtgtggtattgtgtttatatatgtggagttgttggcta
gtaatataataaggaaaagagtgaaacatatgtagtataacgtatttctagtttttttctctgtattaatgaatcact
aattaagtagtatgcattaattgaattatcagaagctggtcacaaaagtctaccaaaaaaacaaaaaaattggtcag
aagaaaatgaaaataatgagaataaaaaagggaaaaaaaataagaagctagcaaacaaagcaattaacatttcaaggc
agttaattcatcatgcaaggtgcttatgtgtgacaacgtcatgcgttacttttttgcgtctacactcatctctctaacg
caatccactaattctggtaatggattctgctatttagaccagccagtttcttcgtctctcaatc >SEQ_ID_NO_24_construct_YP0126
cattgtatctgagatgtgactgtgaagaacaaagattcatgacatggtattgttaagccgcccattggatgatcataa
ccaaactcttcctcagatttactcaacagttgttgaaacaaaggctggtttaagtatgaaaccggcaccacatatctc
ttcttcttctgatcattctctcctacatagaccgccatgaatcctcttggtgtcgacgatgattcccttcgaataatt
tgcttagcacccaagaaactcctcaaaaaagccatattttcccttatgttttcctgaagcttaaatgtttcttagtct
tggagaaagctttgagattttaaaattggatcttctttagtttgtgaatctaaaggggtttagttacttgttatataa
acgaacgtatgaaagaaatgattaagtattttgaggttttcttttaattacagagcacatggctttgggttgtag

TABLE 1-continued atactaaaccaagaacaaatcaataaatggtgtctgagaagttagtgtctaatgatgtcctacatgataacttcattg gggcttatttgtctcaaagacatcacatgccaaatctctctatagattatgtagggacatgaagttgtgtacctaatg aaccacaagtctctatcactgattaagtcataccttcttctcaatgatattcaaaagacaggaccacatgatttgatt atatactgacaaagtcacaaaagccttcaaaaaaattctgtggcaagaaaggaaaatttgactagttatagtgtctat ctaacaaacaagtggtcatattgatttctgtcttcacatcagaaatcatgaagattgatcactatagggcccttactt atcatgccgtggtccggcaaagccatgtgcttgcttgttggtgtaaaaatttatgagctgaaacttttgaaaccaata aagggttatctacaagtaatgttcttatcTATATAtactcatcactgactcctttctgctctgc >SEQ_ID_NO_25_construct_YP0127
acgtttaaagttgagacataaaacagtgatttcaaatttgtattagggtggtcttattgtgtgtctagctactagcta gagaatactagaagaagaatacgtagcaagatacgcacaacatttggtcctctcttttttttactttcttttaacaca ttgtcctcttatgatttgcttattgatttcagtatctttttgtatcaataattccctccaaatgattaaaccctaaaa aaatgtgattcattcaccacccgaagattagcatcatcaagtaacacacaataactaccaataacctagttttcattt ttctatactaaaatcctaaacatcccataaaaatacaaacaactctgaaccaataatttcctctaatccacgtgcacc ccatcgtctcctgacgtaagatttgtctataacttatcaaatcccaaattcagctttgttttcattatatagtacgta ctcttataaaaagagaagagtacacatctttaatactttaacttaaaagaagaaagtaatactaatataagaggagt ctgagtcagcgacaagtgttcgcggagaaacggaaacgctctctttctctctcttccccaacgccaatacctttgga atccctccctaactctgtcctgtcctttcgtcctcactttctctcttttacattttctacacaccaataaaattgaa accagcaacttataaatcaactcaagtttgaattaatgatcgaaaaactagtttatttgtgtcaatatgacccattct ttattcacataagtattttaacttttcaaaatgttatctcaatctcctttgagtttctgtcttccccataataaattt caaataattaatacacatggttttttaattagaaataatggaaaagaaaggacaaaggaataaaaaagaaacacaagt tggcacactctctttattattcactccctcTATAAAtctcatactatcttctctcatcttcttaaatattggatata tttcttttcaaatttcggaaaagaaa >SEQ_ID_NO_26_construct_YP0128
gataaactgataatggaaaagaacaaagaaaccagttttttaactatttgcatatgtaatttatttgttgcaaattata tttagttaaaatgtttcctctatttatatatatatcagtcaagcactatgtataagaaatgtcaatttataaattttt acatgtcctttaacagaaagaaaatgaattttttacatgtcattcatagagagtcactcgtttatttcttatatagaga ataacacactcacatgcatatgcatgcaatatgatacatttttatgacaaagataatcaacggaaacggtcaagacata atttgataaacaacttgcacgatgcacagatctgatcaaatatataactctttaacatatccaaaatattcaaaagaa aaaactcgatccaaactagcaacatcacgctcacgcgtaggctaaaaatttattaatctccaaaagtctttcttatga acactgcaaacacaacaacttgaaaagtcatataggtttagatgatgacgcgtattggctatcgcttaccggagtggc tcataaatacaataaacaatacgtaaaagtcaaagtcaaatatatttagtcaactataaccattaatcgggcaaaacc tttagctgtcaaaacaacgtgaaaacgatatttgtatatatcatcaagaatcagtagataagagaatgatttaatccc ctgactattacaattttggtgtaataaacagtctctattggtttttattctttgttttaatttctcatgacctataga gagaattaggtagtttcgaaaattggctaatcaacttttgaaaactactgtctactttgcttaaattctctacactta gtttcggataagataattgtcggactaatagttaatcccttgacaatcttttgatattataaaagggtttagttaatctc ttctctatataaatattcatacaccagcttttcaaaaaTA >SEQ_ID_NO_27_construct_YP0020
cagagcagtgcatatttttttttttttttttttggtgttagtgcatatctatatatatagtactattataatatattt caatatatatattttaagaaaatatctgattcttaagtttggacttatttgtcaacaatagccagtaaaaaacaaaag cgaagtttcactaacttaaaaaataaccacatttgtatatttcgaatacatactataaattaataaatttatcaaaac aactatagaaactgttatttccaatcaatttctttatcaagattatatctgaaatatatttattaaaattaatagtta TABLE 1-continued tttacaagaactattttatgaaagtgtaagaactctctgaaaacttgataagtcaatattttttctaacatcgtaaa cataaactagattcaaattcgaatctagttattcaaaaacttataaaaacataaaaatgaaatactgttacttcaaca aaaaaacattattattattttgtttaaatatctaaatttattcatcaacagcaaaatatttaaaagagtgggaaacaa ataaaaattaaactctgttttggtatgataaaattatttactaaactaaactcaatttttttttagtatcacggttata actataacaataatcgaactttgttattttcttggtactggttttagtagtatagatagatattttagtcataactca taagatacatgtacaaatatttgctatatatgatcagtgataactgaatttcgtgctgaaaattgccatagtttgctt attttactcttgaaacaataacgatatggtcgttacttaaaacaacattttaaaaacgaagaaaattaaacagagttt gttaaaataaattaaataccataaatttctctttgactcttcctatatagtaaaatctctcatccccttctctctctc tctcatagcatgttggtctttaggttcctatataaacaacgccacacacacccatttagtccc >SEQ_ID_NO_28_construct_YP0022
tagttccattacaatttccaaatgatttgttacaaagctacaagattattcgaaataggatttcatccataagagaga atggtgtggtcgacgctacaatgttgatttattggttgtggtttgcatcttggggatgtcaaatcctaagtttcaagt tcttgtaaaaacgttttcaggtttctttaatatattttaatattaatgtaaaaagaaaagatatagcttttgtacaaa aaaatttgtttaatcactatgtaggaggatgcgatcaaattcatggaatgatgtattattagcttttctatcctcact ctaaaaacaatactatagtgagttaaataaatttgatcatttcaatgtagattaaaattttattaaaagaagaaaatt taaaagcctataacaaaataaaaaaggaggctcgaggtatgatgggtgtagcagaagagctggcaacagctatcgact gagtgattacgaactcagtactcagtgttctcagctcacacactctttttttgttctctttcttttggacagctttca ttttctcttttctttttctattttgtttcaaaattccatccatattaaaataggcctgatcatgagaataaaggaaa tactaatgatgagtttctcaataatgcaataagatgcaattattatgagctatttactattgaaaatgagcaaataaa tgtcaaaacacaatctggttaagttagagcaactccattgtataggattcatgtagtttctaagaaaacaaaatgtat taatattttacttttacatccaaaaaaccaacttatatgagtaatagaaacgatcctaatattaggaattttagagat tttctctcatctgtttcttaacttttcaatattttttattttttaaaattgtatgagtttctactaagaaactactgct ggagttggtcttagcttcccaatgcttctccacctatatatatgcatatctccttcttaaaac >SEQ_ID_NO_29_construct_YP0024
tgttaagggaaggtttgcacctaagaattttgaaggaattttgcggcgatatatcagtaagtaactttcttcttagtc tcaaaatttaagttgccataaaagtatatcagtttggagttgttaacctcttgttttattatttctcagctgactacg tcatttgccttggttgcaagagcccagacaccattctctccaaggagaaccgtctcttctttctgagatgtgaaaagg tataagttaatctaattagtcctgatcttgatatgcattcctttgtttctgttttacagttttactttctgcgcaaca aagtaataaagtattttgtgtgtttgaatttgctaatgtgattaacgagtgggctacatggttttttgcagtgtggatc tcaacgatctgtggctccgatcaaaacagggtttgttgctcgtgttagtcgcaggaagacttgagaaattagaaggtg aagtgaccttggtatggagtttggagctattctactgcttctgtatgagtttatgagttgaagaaatacttgtcttgt tttttttattttgttttggaatatgattatgacttgacttttaaaatgggataggatcaaaaccttttactctgtcag gttcatgtggtcaccttgaaggttgatttagtaaatccatggacttctttttttgtgttaagattattcttagttcaaa attaatagactaatgatattaacgtccacaggcattgcgttcaacatctcaaattaaagcgtggaaggctcagaaagt ccaatatacactatgtttatctacagttacaatcatactacaaaaaacaaataatgtatacggtttggtctaatatag ccgcatacgatttagtatttaccaacaaaaaattggtctcaaaccaaaccgaacaattggtaattaacaattgttctt ttggtcttgaaccgaaccaaaccgaactgaactatattaaccgaccgacttcgtcctttcctc >SEQ_ID_NO_30_construct_YP0028
tagtacttgaaacacttggttggtttcatgtatttggcctatatatataaacaaacatcgtaattatatacggatttttt tcggaattttacgcccatatctgtaagtatatataacatgcatgtcgttttcaaattcatatgatgaacgatccacgta agtgctactactcctacaatattgcatgagagagatatgtatttataaattttatttttgaagaagaaataagagggaa TABLE 1-continued ggttacttgggtggatcgatgtgaaaacaaaagaagaaaaagcgaaacccactaagccattacatgatatcgaccttc
ttatcttttcctcttatttatttttctcaggactttttctacttaatgaaacctccaaactatctaactaatac
actcccatgtagaataaagaaaattatataagatattgttgatattttgtaactagaaatatatttgctctgtaatt
tttcgtaagttaaatcaacatttttcagtagaaacaaatattactgcaaaaagtaggatcattattttgtccaaaat
ctcagttagctataggttgtagtaaaaacaaaacacattcttgattgccccaaaaaataaagagagagaagaatat
tgttcaaaagtggtctcttctctctaattatgttttcactaaacccaattagattcaaacagtctacaaagtccaa
aagataaacatgggacaacaattcgatgcaaaaaatcctcttttcatgctctttttttattctctagtcttttaaatt
actaataaaaactcacaaatccaccaaacccattctctacaactcaccttcatctagatttacccactcccaccgaga
aacacaagaaaaaaatatacatatataaatatacaagacaacacatgatgctgatgcaatatacacaacaaagtatt
aaatcttagatattgtgggtctcccttcttctattcattttcttattcattaaaaaaaaaaa >SEQ_ID_NO_31_construct_YP0030
tacttgcctcatgtgtttggatacgagattactgaacgttgtggtgtattttatagtcatgggtttgttaattgttat
catgcttgcctacttaactagcgtaattatgtttttttgtactacctcggaagtagctattttgtcgcttattgacaa
cgagatactttaagatgttccacatccacgtcgtaatcggttgatcgaatggtgcctaatagatcaaagttatcctca
acaaatatcgatgtgtagtatatacgtgaatatatagtagtctcttgcatgcatatcatatacaacttaaatactctt
tttgtttcaaaataaataatgttttaggaaaaagattattgtgtcaaattaagtgttggtctattcatccaaacaaga
aagaaaaaaaatacgaatttgttttatatatcattgacgaacaatgtttagctaataataaataattatttatttata
aaaattaaaagttagatagtttcttaatttaggtgcatataagttctttaacaaaaaaaacatttaggtgcataagtc
ttaaatatcaaatattttggaacagtaattttatgtataactttttcgtacctatcttcacaccgcataaattgcca
aagtcaacctttgatatttcattcctcacaaaaccatattaatttatacacctcaatattgtttaatagtattatca
tgttggctttcgctgaatttatcaaagtgcaacatgttttatcttacaaaaaaataaaaagaaattcacgttgtgtga
tcttgagagttgacttttaaatatatcacaacttatataaatacgcagcaacattccaatctctcaagaaaatctaca
gttcctccaaataataataccctccctctaaggtttaaaactatacctcattaacacattaagaagctagtcattact
tcatttctatattttaaataatgtttattgataacaattgcaggcaactaattttcagcaatc >SEQ_ID_NO_32_construct_YP0054
agcttattttgttctattctatcgtatttgattcttctttcgtttttttttgtttgacttaagaaaccgattgttta
tagtagtaaacatttgtttttaatgttgctcgattccagtgcacatgtccaggctagacacttgtcgttataaaggtt
gctttggttcaatattgatccactagagatgttacaactattgttgacatctgagattgtgtgataagaaaatatgaa
actggatttagtgaaagttacaatatataatcatacatcatagataggaaataaggaaatgtcagatatacttgaaga
atacatcaaatagacaaggtcctttttcttattgtcgactattatagagccgtacagaacctttcacgtctttagta
attagtacattctccatttcggctctctcttatttttttttccatctcttttacttctccaaataataacaataaaagc
ttcgatttgtgtgtgtttgtatttacatcttgacatcgatattcttttcatcaatttttttaccaaaaatgtaataaa
aacaaaaaaaaaccaacgctgaacacagacatggtttctccatccgtttatattcatcgtttgtatgtttacttaaca
acttatttcaaaatagtacatatcatggttgtgttttaaaaaaagtatacagaacagaaaagcacatggtagacaaa
ataatgaagccaaaattaatacaaagaagaagttcaacttgtatttattaacacattttctttccttgtcaaagacat
gcaaattggttttgttttcttattcccattttttttttataataaaaagaagaagagtaaaacaaaaaaactatcatt
tcttcttatcgcaaaactcttatctaagcaagaaaccgacaaaacctatatctacatatattctcatcaacatctctt
gagacatattcattttggttaaagcaaaagatttaagagagaaaggggggagaagtgagagag >SEQ_ID_NO_34_construct_YP0050
tacttgagggaaacatcatatttttaaaccttgtctcagtaagctaacacacaccccttgtgattacttatccatgtt
tatccacaagaatgcagttggattgagatattttcttcttgtgttgaaatcaggcctcaaggtgttcatgtggtctgca TABLE 1-continued

```
aaaaaattcccaaaaataaagatagtgacatctgaaatcgataatggattagacgaagagtttcgtgttattccttgg
tatgggcgggtttggggacagatattttggcacagacgaggactaggccactgtggtcctgcagcattaggtgtccct
tccatgtcctgcattacatttattgatggattcatcaccctatctactacaacggctacacaaactatgaagagttt
tgtttactaataaatgcccaagtgaggggtcgatcgaacccgggacacgttttcagtttaccatatagaattatcct
tggaacccttgatactccataaaacatcaccacctctgttgtcatctcatgaatccaggttcaaacctagtctctctc
tccctagtgggaggtatatggccactgggccaatgatgacaaaatgcaaaaaaataaaatacatttgggttcattat
ctaaaatatctcttgtgtttgtaagttttggttgcacactcgtgtggttgaagtgtgtgtgagaggtactatacaata
cactctgcttttgttttgtacctatctctttctcttctccacatatccaagactttggggataaagctgagatcattg
gttgccatttggttgtgtagaagcaatcacccatttgctttatccgaggttgataaatttcctcgggttctccttctg
acacgtatgacaaattctaatagtatattcctcgtagatattacctatatattctcaatagttgcaggtacttaaggc
tttgtcttggcatcctcgtcctcttcagcaaaactcgtctctcttgcactccaaaaagcaacc
```

>SEQ_ID_NO_35_construct_YP0040
```
cccatcacatgtaacatcattgggctatccaaaagtctaaccaataatgtcaatctataaaccacattaagtagttca
ttttttttgtagtcgtgtttagcttgttaaacctcataaaatatgttttcacttacgttaacaaaacaaatatcttca
cgaaaaaaataaaataaaatatcttttgataccgaaaaaataaaataaaataattttcccttcgatcataaaatg
cgtagataagagaaactgtgtttgaggctccatttcatgttcacctaccagtctaccacgtcatttctcaaagacgca
aattttctaattagggatgtgctcttttacatatagatcaatatcctaaaaaaatttaagatattcatattttcgta
catatatatcgagtttcccgaaaaatccataaaatgggtataatgatagtccttttttcacctttaataataattctg
aacaaaattatatcataataaacttgtgattttatacaaaatttatttgtatatataattttactaaccaacgtgaac
gataaaaataatattctcataaaatgttgattaaaaattacttaaaataaataattatttaggattatgtattagtag
tactcgaaccatttttttagttatctgcatgaagaccctaatttttcacatatatcgaaactaaaactttggatatac
actgtaatttgaaaacgcttggaacggataatgtagttacctcacaagattttgtacatccctgacattttatattca
ttaaagtgtgttttttttcttcagaaaagaaaacacttttttttttttgtgcttttagtttaaattaacaaaaaatgga
caccatgagattccactaactcatgtgtatataacattagggaagcagtcaattcatttcagcatccacacacacttt
gaatgctcaatcaaagcttcttcatagttaaacttccacacaacgtcaaaactcgagaagaag
```

>SEQ_ID_NO_37_construct_YP0056
```
ataggaatctgcttcggtagaagattcgagagaggagaggaagcatcggtggttttggagttccttattcttctcttc
tttccaaagttttgtcattcgccaagattccttaaaaacttgttcacacatcataattatgcaccaataggttataaa
tcataatccaacaagttagtcattggctttaatttttaaaaaatcccataagagtaaaatcttttagaaagttaatcaa
cccacacatgggctagaaaaccaaaaaccccacgaacattgagattacaagaaacattttttaagtcctaaatgagccc
aagagcattgcttaatgaagaagaactgatattaattaactaatattaggacacataaaaaaatacgaaaacaccaat
cttcatgccacaaaatcaaacaaaaacgaaaaaatcaattttcatgaaatggataaagagagagcgtaattatcagga
atttgattgagtacggttgttatgatgatcattcacaattatctttgatcttgagatttagcaatagttaattttcgg
atgttttttttgttacttgctgctcacttcttgtatgcagattaatttataagagagaccagttacaactctttcttat
ttgaataagattttataagatgtagtgtggccatgtgggtttattgcatgcagctctctgcgttggtcccaagtccac
gacaatagagagtttctgcacttcacggtatcgtcgtcgtcacaagttctttaccttatcattggcacaagttagcca
ccgtctttgcgcaagttagcatgttgtgctacatacgtgtcatgaactgattggtcaaatttggatatattttattcc
cgtcggttatgtttggataaaaatataaaacggaaatttctgtttcagccttccttggtcccaaagaaaaatacgcac
acctactcccttcattctctatcctctccactcataatatatacatctaaatgcaatctctcc
```

>SEQ_ID_NO_38_construct_YP0068
```
aaattggggagtggggagatgtttggttatattcccttctcatcgatggtctagatgtgcgaggtgactctcatgag
```

TABLE 1-continued

```
gtaaagaacaatggtgattttgtgaagaacccaacgtaatggtaattcctaaaaaggttagaagttttttcagcttgt tgtattgctaaaatggggttgatgtactcaacgacatccaagtgtacttgagtgagcttttttggggttgagtacctc gacccattattcaaactaatgtaaatggtgaatgcagcagtgactttgttgccttttgcaagaactaaagaagacaga aacaggttgtaaaagagagccaagtgtgtgtttatggtagaaagagcaaagtgaacgaaaggtgtacctttttgactt gttgtcactggttttctcccacttcatccgtttcatgctgcatcagaaaacaacataaggaatgaatgacgtaacgcg aagcattaggagttgcttgtaaattaatacattgccattactaacgtaattcagtagattctaactacaaatgaagtc aatgtatctatttgtctactttagccaatgtatgataagaccaaatagtcttctctttttcagaaactctctaggat taaaaagtttgtgggtgaaagaaatattatcgtgtggatgataagaataattgatcttgtgttagtaaattaggaata gatatacaagtaggtttctctctaaataaaaaataaaagagtttaaattgcatgcgtataaaagaaaaaagtaagaag aaaatatgttccggttaatggttgggtgcatccgaatcgaaccggcgcaaaccaaaaaatctaaaggagatttgaggt gataaaggaaatcagacattgaaccaaaaaacaaaagcgagacggtggaaagaaaaaactggaaaagacagtttta gcccctcctaaaagcaaagaaaaaaagataataaatagcttcgtcgtcgtgatcgacctct
```

>SEQ_ID_NO_39_construct_YP0082
```
tgtccttaagactcttatagtaaagctggaattatatggttcaaggaatcgtctagtctatatacactggtttgaaca attgtgatatataatatagttaggggtatattatatttaatctgttagataacggttggggtacttgaagatctgtag gagttgacagcacgtagaggcagaggtaagaacacttctgcatgtagtgtgtctacataataaaatatagagtgtatt ttttacacacaccaaaaagagagattataattaatgtattatgtcaaagcatatatgaaggtcagcttagctagagac acgtcttttgtttatctctcgactaaacaacatggcgttttaataaaatcaaaacttaaaaggtccaattcagaacgg ccccatagtatatagtctacgttgaataaataaacctcaagatagcgtcaaactctttagtctttacccaaaaatatt ttttttaaataacgtcaaaactctaagtcttgacctcaacaccaatatatatttgccttctccaatatctgatttt ttaattgtttatccgagtcttcttggtcttttcgaatgtttgcccgaaccagaccttcccacgttcggtggttggtgg ccgcctcggcctttggttgatttctgtccacattttggtccttttcattcatgtaccatgttctagggtcatttgact tgttgaccataaatctactaaaacaggcctaataccgatgggccgtagcccgttaataaacaagacaatttatatttg tttcacttagcttgggagccacggatctctagaaacatccagagaaatatcaatctcccacttctccagaacattca ctcactgacaatatcccaccttcaacacttaactcctgtatatagtcctccctgtctccagtttcgtcgcacacagt tctcagataaatactaaactcactgttaaaactttctcaacaaagcttcctgtttctctacaa
```

>SEQ_ID_NO_40_construct_YP0019
```
ttacgcggcgctacactcttatcaaagtttgaagattttcaagagacacaacagattcaagattttctggtggctaa acttacaatgacagtacatggaggatctccgcgaatggacttctgcaatgtactagcgtagaacaaacactttttgtt aaagtcatcaaccaacatagcatagagttgtttatctgaacagaacactgaaagtcttggtttgtttgtgttccagt aaactgtttcaaaatgaaagaaaatacttattaacaagttcggcaaaaaaaattcaaacttttgtgcattattatatg aaagcacttctagaaagctaccttcttcctgctcctcctgttcctagttttcggactctccactcgagtgttccctct cgcttcaatcacaaacggctttactacagacatagctgataaaagggtcgaaaaatcatgaaccaagtaagcgaaaca gaggataataaacatggaagaagaacagagtaagacgaattataccactcacttgttattcgaattggaaactgggga taaggtttcaaacgagttccgagaatgtcagagactctaaactgaacagtagaaagagaagtcaaagcagccatgcca agtatcattcgtaaagcatcgaaagtcagaacattaccctcagcggaatttaatcaaacaccttctgtgcaggaataa tctctgggggttttatcaacactccaaaaaaactggaactttgtaaataaaattataaatgttcgtacctttatgcaa aatttctcacagcgtaattatctattctttttgtccttatgaaagaggataaggttttaaataatataactaa attgttttaaaagaaactaaaaataaatggaaagtcttaagcgtcgtcaatggttctagagtcttctgcaactttct tttcatgaaactactgtaatcttctgctaacatatataatctcaaacactatcttctccaatt
```

TABLE 1-continued

>SEQ_ID_NO_42_construct_YP0087
tgaattgagtaaaatgtgttttcaaacagttaggtggtagaaggtaaaggtaataacatcatgatcttactaaagaa
ttgttgcatactaactatcaatattctcaacaacataatataatgttttttaggtaattttccattttaattttttg
tgattaaacaattaaacaactcgaatgatgatgataaaaaaaaaaaattaacaactcgaataagttaaagtagcaata
cacatgtcgttcaattcaaccaataaagtaagacttatattttttaagaagttgactaatagcttaataagttggaaaa
cttgtgtagtttcttaattcccacgtgcagtaagaaataaaaatgaaaaaaattattatatccttcccactctgcgac
ttttcttttattttatcaaatattaaaaagattcatatcacagtttacacattgaaatcataaacgataattatgtat
tttgtaataaaaagttagttctgaagctcatactttggatagtcgctagtcgctaatatgctccttgtaataattaaa
gtcactacgacgcacgtcaaagccgatatttagggcttaattgatgcgtgttttcttttcatataatagtaatataa
attagtactaataaagtatgatggatggttgagacagaaaagaaaaaagatgactgtatggtcatcattacaaagaag
aatgtattcttcatgttcttaagaataataaaatgtcacttgtaaatcaagttggtaagcattttgagaactttgttc
gatgcaacgtatgatgatttatgtagacaaaagataaaaccgtatcttcaactattgccaagaaaagataaaacctaa
tctagtcagtctctcaacataaatacaacccaatagccaaactgtgtccaattcggagagaaactaaactaaaacaaa
acacaaaagcccaacataagcccaataaaacccattttataaacagaacattactaacactca >SEQ_ID_NO_43_construct_YP0180
ttattgttgaaacggatggtatccagattcatagagttatagttgttgacctcgtaaggatgaattcattatcttctt
cttcttttgcagcatggaggtgatcgatggtatgactttgatgatagccatgtccaccaaatcagccaagaaaagatc
aagacctcggctgcttacgttctgttctataaacgccttgtagactaaagaaactgaagcggaaaagacaagaaagtg
gtatttgcattttttgccggggtttggcttatttaaaaacatcattggcttgattctaattcactacaagatcaagatga
aagcagctctgcgttgaggctaatttacagaagagagagagagagttgggaagaagagcaaaagaccgagaggacatg
ttgcggggaattttattttattcttacaaaaattggtatctgattattttattaaccatattcaattagagaatagaag
aatagagaaaagccctttttgtgggatatggttctaaattgttgtttagttcttgtgtgtcagttttggctctcgtcga
ccaaagaagattaaagaaacctctaccttattttaactcaattcttttgtttttgcaatgtcctttgctttccaaaat
tgttagtcttacttttcactactttgatagacattgcctttgcgtttccctgattaataagccagagtacttaaatca
aaattgactgttttgtgcatcctgcatcacgtttccaatcagaaccatagtgttgtcgttgtgtcattatccgaattt
aagtggagacattggtaagttatttataaactaattacaatctattttttctaattatttcaaataacatatttaagct
ctgtagcttccactagacggtgaagatttgaagtgagagctctcttttgcattgctcacccaccaatggatctacctac
ccttcttcttcttctcctccttttaaaccctaaaagtttctctttccttcaaca >SEQ_ID_NO_44_construct_YP0186
tggacaattactcttgtgtgtatccttggagttgctgtttcatatgtaagtggacaattactcttgtgtgtagccttg
gagttttttttatttacgttattttggtcagcctttaattattttgcaaaaaatgtatctgttttttgccacatgcccac
ataatacatttcgcaaatttgatacattatgctttggcccttgtatattcggtaaaaaaaaaagctcaggctactctc
aaaaccggctctgagtattcgtaggccacaatcgaagaaaaaaagtgccgatttacatattttttcatacaaaaaatta
aaactgttatgtattattcaaaagctatttacatatgttttactaacacgttttcaatattttcttaatccttttcaa
aatttaactaagtataatactttttttgtgtgttatttcgttgttttggttaaagaaaaacgaaaaaaagagagagtt
attcatccttgcagataaggctagggttggttgaataaagatgtgcatatcttataccactagaccaaagaaacagtc
acaagtaaaaggccgaatccttttttataaaatataaacagacgaaagctaatgcttcatgggcttggcccaagtgcag
gctctcgctagtcgctacgctacaactatcccatatttaattagtgaagagtattttattattttggtcaacgggcta
tctttgttgacaaaactatcccattggtaaagaaatagcaaaataggcgtttcattctctatatttaaacttgattt
atgaagagttgaatagctgaaccaggaagatatttaagaagcccgtacttcacgctttaactgtcaatcgatagatca
taataaatgactatctatggataggaactataactgaattcagaaagaatctactactactataaatactaaaagagt

TABLE 1-continued attaatacaacggaaaaaacaaaacaaaaaaaaggggggaacaagggagtttcatgttaaaaag >SEQ_ID_NO_45_construct_YP0121
ttggattttttttttgttgagtcagcagaccatctaatctctcttttttccaccacagcctgctttctatgaagcattt
gggcttacggttgtggaatcaatgacttgtgcactcccaacgtttgctacctgtcatggtggacccgcagagattatc
gaaaacggagtttctgggttccacattgacccatatcatccagaccaggttgcagctaccttggtcagcttctttgag
acctgtaacaccaatccaaatcattgggttaaaatctctgaaggagggctcaagcgaatctatgaaaggttggcccat
tctccttgacaggcttaacaatacaacttgtatcgcttcaacaagatgatggcttaataaggattttttgcatgtatag
gtacacatggaagaagtactcagagagactgcttaccctggctggagtctatgcattctggaaacatgtgtctaagct
cgaaaggagagaaacacgacgttacctagagatgttttactcattgaaatttcgtgatttggttagtgtaacccactg
ttattcttttgatgtctacatctactttacttacattattcttttcttcggtttgcaggccaattcaatcccgctggc
aacagatgagaactgatcatgacagggtaggattttattccctgcactttctttagatcttttgtttgtgttatcttg
aataaaaattgttgggttttgtttccttcagtggtttgattttggacttatttgtgttaatgttgttttggctgttct
cttaatatcaataacaaataaatttactggttggtatctaagatctaacaatagttactatttttagaggtaaagaca
ccaaccttgttatattggtcagagagctaaaaccttgacttgttgggaaaacaaaactctaatgacagaaaatctgac
atgatgccttataattagcctcatgttctacataaatcctaacaatagcactttgtttct >SEQ_ID_NO_46_construct_YP0096
tgcaaaattgaaaaattgaagggtgagacaaatttaaagataatatctattaaatcctctaattttaaaaatttagca
aaaattgtattttcttatggatcagttagttcacacgtatcttagttagtatcaaatcatatctaatgattagtgata
aaactagttagatatctatatgtgtctttaccatttaacttgaatccttcttcttttttttacgtaaacaacttgaatc
cttcgttaatatataaatttaaagcatttttttctttaattctattgatcggtatatatttactataagttttagctca
tatgcaatttcaaatgatatgcttttaaattttgtctaggtgtgatagttgtatcttaacataaatcttatagcaaa
actatacttgatattctaaatttatctatttgctcttgtgaacctcatattagtctagagaaactttgaaatcctttc
aattagttgtatgtccaatacatttttactaacatttattagtcttttttaattaagattattgttagaaaaaaaaga
ttttttaaaaataaataatatgttttagatacaatgtgagttaggcttcttatattttaaaaaataaatttatttcat
acttaaaaatagtttggaatttcaatttatttggctgaataccataaaatatgtcaatttgaaccttatacccattga
ctatttggtgttagaaaccctttaacaaaaaaaaactatttggtgttagatatcaaaataaaaaaaaattaaccattg
gtttcttatattgaattggatattgttacatgtattaaagtttttttggtttaattttgaaacgttgatagaaactat
taagtttaagtttggtagtatatttatttgtggaaaatttaattgccattaaatataacgtcaacttttttttgtttt
ttttgagaagttacgttgtgattttgatttcctatataaaagttagattacgtcatttttaa >SEQ_ID_NO_47_construct_YP0098
tattttttataaaattatcttagtaaaagtatgtattttctaatagatctgttagttcatacatatcttaattagtgtta
aattagatctaatgattagtgataaagtttttagatatcgatataggtgtctttaccatttaacttgaatcctttgtt
aatgtaaaattttaaaatattttgctttgattctacttattggtatataattttaacatatcaatccaatgccactct
taaattatcatgtacttttcgatatatgttatgactcacttgttatgaaacgatggattttcaccaattttggttatt
tattaactagaagtttagctctagtgcaattttaaataatatgcttttaaaattggtctagttataatagttgtatc
tataacataaaacttataacaaaactatacttgatattcaaaaattattgattttctcttgtgaacttcatattagcc
tagagaaactttgaaaacctttcaataaattgtatgtcgaataaagttttacaaacatttattagccatttcgattaa
gactattgtgagcaaaagttttttttattataaaataaatatttgtttaagataaattgtgaattaggcttcttata
ttttaaaaattatataaatttatactgaaaaattgttagaattttcaaattttaaatttatttggcttaagaacataa
atatgtcaatttgaaccttatacccactaaatattccatgttagatatctaaataaaagaaaattaactattgatttc
ttatattgaattggatattgttacttgtatttatgttttttgtttcattttaaacgttgataaaatcattaaactaa TABLE 1-continued agttttgtagtatatttatttgtcgaaaatttattcccattaaatataacgttaaatttatttgtctttattaaaaaa gttactttgtgattttgatttcctatataaaatttagataacttcaattttcaaataaaaaat >SEQ_ID_NO_48_construct_YP0108
ttagctgaaccaggaaattgatctcttataccagtttccgggtttagattggtttgatggcgatttgattaaaccccc gaaattttatgtcgtagttgtgcatagtattattattcttttgcggacaatagacgtatcgggaccaagttctgtagca aaattgtataagcttaagtttgatgaaatttaaaggtaatcactaaaacccaaatgggacaataaaccggtgaagatt tagagttttttaattttgactcatgaatctggagaaagagccctcgttaaaaggagtgaatcaatccataggggaaaaa gttttgtcttttaaaaactaaagaaccaaaccttaatagaagcagctcaatgtgtgacaactttccactggcactaa gataaagtgactagcgatgagtgcaattattgaaatagtagatggtaaatattacatacaagagtaaaaatatcttta tgtcaatgcttaattcagtgtttctggttaacaagagaaacttctctaactttcgtaattgggtcttataaaattttta tgcaattatgattttacccttttactacttttcattagctttcacgaatctattttgacaagagaaatcattagaggt aaacatgcttttggtcaagggccttaacagttccaccaatcaagctcaaaagttgtacttaaccgacatcttctgtg aaaacatataattacatgtacaaatcaaaactaccttatgaaataaatagaaatattgcagttcatttctaatttaac ctcttcaacttttaaaactatttacatttctttatgtcatttctagtcattttgatgcaaattgtaccatttatggat tatcttcacaaattttttaagttggtgaaaacttttttggtgggtagttaaaacttgaaatagaaatttactttaccaaa ataaactaatgaaaagtaatcactccactccctataataagatttccaacgttcccactaagc >SEQ_ID_NO_49_construct_YP0134
cctactttaggcttaaacaagaagaaaatgactgctaagtcatattttttcaactctcatgagcaaccgtaaagttg caccgcaatatccaacaaatgacattcgtgttatctacaatctaatgttgaaaatttggctcatctaataaaggagac aaaagttatatctctttcacacacacgttaatggaagtgtaaaggcggtgagagtgtgggagagacttggggaacaag aagaaggacgcggtcaaaaagtgacggtgggctacggcttttcttggtagcagttggaaattccattaatgacttaaa aagtgtaaatcttatcttcttttttattttgtgatttgatatgcacattcatttcatgaaaatatttgtatagtttgat gatcatacgacaaacttatagggttcacaaagtagatgcaatagttgcatacctctgtttaaatgttcttgttaatat tatacttgatgatgaaactcgtgaatgttattcaaaatgtccatgtaatacaagatcatgcactataataagtaatct atcaatttcagcacaacaattttgacaaaaagtaaaaataaaataaaataaactgatatcatatttccgaattatatg taaacgttttctgtttctcaatggtctctttcactcttgtgttttctaatatttcatttaaacctatttctaaactaa gcacatctttgttgattgattgcatttcaaccaaaatcgataaccgaatcattgtttttttatgttttatttcagctt accacacacgtttagaattttaaaaataaaacaaaaaaaagttaactcgttacaaatgaaaatgatatttttaattgg actcgatggaaaggaccaatttattcaacactattgtttagtccgaacacttgccgcgtaagttttccaactcccccc attgacctttcgcactttcacaaactccgtatatataatggatacactctctctttgatct >SEQ_ID_NO_50_construct_YP0138
tgtgtgtcctaaatagtttctttttaaaatttgtaaataccaagacgcgtatttaagagtattttgaaaagatatttg attataaaagaaagaaaaagagaaggctgaggattaactgcaacgtctaccgttggaaaagaaaaacgatcagaaaa cacagaaattaataaaaagagagaaaaaaaatagagtatgagagatgcacatgggtgcctgcaaaaaaaaggtagaa gaaatttgtctgaaagtgtcacaggcacactctctcgaaccacatttaacaacactccaaacactcttcttctactt gtacccttcagtacattactctttccaaagtccgtgatttacgctcttcgatgacacctctcaacagagagagactac atgtgtacattttcttctaccattaaattttgaagattttcgatgattcaatttagtatatatatggaagataaaatt ttcattgtctttctacatgatagtaacggtttagaagggtggttatcacttatagtatttgagttaagaaatataaa aatatacgtgactgtttttccttgtaaactattttaggcccttattttattcaagtagtcacatacgtgtttgaag tgtatttaactaagaaaaagaaagtaggaaatgaaaggatatgtatttatggtgtaatcttggtaaggaccaggag atcagaaggggccacaatgtcacaaagaggaccaacaatgaaattaaatcctcagctggcctttaacattttggctcc TABLE 1-continued caccatctccttccacacatatgcacatgtcttcatgtctctctctctatacgttacctacacaaatatgtacaga caaatagcccattacaaaatctttatttataaatatatactcctcaactccctcaatatccacccatctccttctcca taactctctctctctccctaaacacaaccaaagacttttatctctcaggaaccccaaaaac >SEQ_ID_NO_52_construct_YP0192
tcctcctactgtctgctacgtcaacaagtggattgcaatcagacggtgattgtgtctcttttcattctctctcttta ctaatttctctgataattaaactgagaatgtatattaagaaaaaaaacaaaaacaagagaggaattttcatacacac taacttaagactctttgtaagttttcccaaatatggattttctagtataaatatgagttcattagtttcaccaagcct acaagcatctctccatctcaaatcatattcacctaaaaatcaggtccctctctttatatctctaacattcttatatc agatcatattttttggatttcttgttaagtaacaccaatcttttaaaagtgttttcaggttaatataaaagaataatg atgttttcggtgacggttgcgatccttgtttgtcttattggctacatttaccgatcatttaagcctccaccaccgcga atctgcggccatcctaacggtcctccggttacttctccgagaatcaagctcagtgatggaagatatcttgcttataga gaatctggggttgatagagacaatgctaactacaagatcattgtcgttcatggcttcaacagctccaaagacactgaa tttcccatccctaaggttcactcttattctcaatattaactctcgtacatgtcacatgcccatttcaccattttaga tatacagttttgatactttactttgcatttattttgctatatgtaattgaggatattgtttaatttctttgggtttt tttttggctaaatgagaattcagtgtctttggttcttaaaaaaaaagtatttgttaatggtaaacgctaaacgctat ttgagtttatgttttttcaagaactgaaaacgttttattgaaaatatacactttttttgctatttatagaaaggcata tcacatctagacgcaaacgcaaaattgacttttgaagcaaccacaatcttaaatgcaatgaaa >SEQ_ID_NO_53_construct_YP0204
aactaattaggtcgttaattgtccaagggttttcatagttgatatagttctgttcaaatatagccatccttaatcga ttcatgggatcgtaaattactacttcgagtgttgtaaaaaaaatgaaacttctacattacaaactcgaatttaatgc atctggagtgatactataaaagtagggatgctctcaggtcgcatttgagagacacagaaatgattttaatggaattaa tatattttcagttttcacaaaaaaaaattgtgtttataacaactgcagattcaatgctgattttatgagtctcacct atagaatttatatttctatattcatagaggcagtataggtgttgacccaacatcgaaagaacacttcgtaaaaaattc tttggaacaaggctgaaaatttactcccaaatttagctatccgatgaagataaatcatttaccgtttattaaagaatt atcgagattttagtccaaaccaaaagagattatgagcctaagattttgaatttgtattggtaaaagaaattgaacgaa aatttcagaaaaaaatattaataaattgaacgatagagttcacttactacatagtcaactagtgcctagctataatag tttcaaaagacaaaaaaaaacaaaatcggttaactacttccgtgacataattctcatttgattttgaatccagtct aatttgaaaagtatattcaaaatcttaaatccattaatgataacttttataatacgttgacacacgcaattgtatat acaatattcttgaattttaaatgtaaattctagaatatattgcgatcaccacactaatcaaaatctttgggacaactt gaacccacatttgacttttcttggtcaaatattttggcatcatgcatgatcttctctataaaaccaaaaggcctcaa cgacattcataaactcagtcattatatttattttgttgtatttcaacgttcaatctctgaaa >SEQ_ID_NO_54_construct_BIN2A2/28716-HY2
gtctcttaaaaaggatgaacaaacacgaaactggtggattatacaaatgtcgccttatacatatatcggttattggcc aaaagagctattttaccttatggataatggtgctactatggttggagttggaggtgtagttcaggcttcaccttctgg tttaagccctccaatgggtaatggtaaatttccggcaaaaggtcctttgagatcagccatgttttccaatgttgatgt cttatattccaagtatgagaaaggtaaaataaatgcgtttcctatagtggagttgctagatagtagtagatgttatgg gctacgaattggtaagagagttcgattttggactagtccactcggatacttttcaattatggtggtcctggaggaat ctcttgtggagtttgatatttgcgagtataatctttgaacttgtgtagattgtacccaaaaccgaaaacatatcctat ataaatttcattatgagagtaaaattgtttgtttatgtatcatttctcaactgtgattgagttgactattgaaaaca tatcttagataagtttcgttatgagagttaatgatgattgatgacatacacactcctttatgatggtgattcaacgtt ttggagaaaatttatttataatctctcataaattctccgttattagttgaataaaatcttaaatgtctccttaacca TABLE 1-continued

```
tagcaaaccaacttaaaaatttagattttaaagttaagatggatattgtgattcaacgattaattatcgtaatgcata
ttgattatgtaaaataaaatctaactaccggaatttattcaataactccattgtgtgactgcatttaaatatatgttt
tatgtcccattaattaggctgtaatttcgatttatcaatttatatactagtattaatttaattccatagatttatcaa
agccaactcatgacggctagggttttccgtcaccttttcgatcatcaagagagttttttttataaaaaaatttatacaa
ttatacaatttcttaaccaaacaacacataattataagctatttaacatttcaaattgaaaaaaaaatgtatgagaa
ttttgtggatccattttttgtaattcttttgttgggtaaattcacaaccaaaaaaatagaaaggcccaaaacgcgtaagg
gcaaattagtaaaagtagaaccacaaagagaaagcgaaaaccctagacacctcgtagctataagtaccctcgagtcga
ccaggattagggtgcgctctcatatttctcacattttcgtagccgcaagactcctttcagattcttacttgcaggtta
gatattttctctctttagtgtctccgatcttcatcttcttatgattattgtagctgtttaggggtttagattcttagtt
ttagctctatattgactgtgattatcgcttattctttgctgttgttatactgcttttgattctctagctttagatccg
tttactcgtcgatcaatattgttcctattgagtctgatgtataatcctctgattaattgatagcgtttagttttgata
tcgtcttcgcatgttttttatcatgtcgatctgtatctgctctggttatagttgattctgatgtatttggttggtgat
gttccttagatttgatatacctgttgtctcgtggtttgatatgatagctcaactggtgatatgtggttttgtttcagt
ggatctgtgtttgattatattgttgacgttttggttgttgtatagttgatggttgatgtatttttgttgattctgatg
tttcgatttttgttttgttttgacagct
```

>SEQ_ID_NO_55_construct_BINA1-34414-HY2
```
aagcttatgtcaaaaatatttaattaaaatatatgtaatttatatgttgattgagttatgagtatcaagtaaaaaccc
taatccgttattaaaatatcaatgattataacgtatttataaacgaaaaaaaaaagaacatctagaattttcgatatt
tgatcctcaagttaaacttggaaaaatttggatgtatgaaatattttgtcgtccacttatacaataaagtatgaaaca
tggatgcatgaaggctagacatccaatgtctaaaaatactatatataatgcttttggtagggtcttttctttatcatg
tctcacttctgtttctatccctcattttaaatagccaatataatttcactctttactataaaattattatatataaacat
cattttgattgaactacctaaaaggaagaaacgtataggaattttttggagcctcaagattgtaataatgtctcatagt
ttgacttgcaaaagctaaattaaacgcctaaatcattaccattaaatgaattttttgtacgcaattgattcagac
acaaggaccgaccaattcgaaaacaatgaatggatatgattcatccttatgaaagcttgacaacaaactcggttttgg
ctggttaacctagactcggtttatttaaaccagacaataatttctttcgtcgtcgtttttatttgaataggtgcgtcaa
aaataaaagctgaaattcttggttgcaaaagcccaacaggcctgtggagatagcttttttagattgattaaatgggccg
aattgggctgacacatgacgagaatgtggctatagaaattgttagtgagaggggtccgggtccaaaaatgttgcagaag
tgatatagtatttatttaattaaaaacatattattcgacgtattttttaacgctcactggatttataagtagagatttt
ttgtgtctcacaaaaacaaaaaaatcatcgtgaaacgttcgaaggccattttctttggacgaccatcggcgttaagga
gagagcttagatctcgtgccgtcgtgcgacgttgttttccggtacgtttattcctgttgattccttctctgtctctct
cgattcactgctacttctgtttggattcctttcgcgcgatctctggatccgtgcgttattcattggctcgtcgttttc
agatctgttgcgtttcttctgttttctgttatgagtggatgcgttttcttgtgattcgcttgtttgtaatgctggatc
tgtatctgcgtcgtgggaattcaaagtgatagtagttgatatttttttccagatcaggcatgttctcgtataatcaggt
ctaatggttgatgattctgcggaattatagatctaagatcttgattgatttagatttgaggatatgaatgagattcgt
aggtccacaaaggtcttgttatctctgctgctagatagatgattatccaattgcgtttcgtagttatttttatggatt
caaggaattgcgtgtaattgagagttttactctgttttgtgaacaggcttgatcaaa
```

>SEQ_ID_NO_56_construct_CR13 (GFP-ER)/CR14 (H-YFP)
```
gtgggtaaaagtatcctttcttgtgcatttggtatttttaagcatgtaataagaaaaaccaaaatagacggctggtat
ttaataaaaggagactaatgtatgtatagtatatgatttgtgtggaatataataaagttgtaaaatatagatgtgaag
cgagtatctatcttttgactttcaaaggtgatcgatcgtgttctttgtgatagttttggtcgtcggtctacaagtcaa
caaccaccttgaagttttcgcgtctcggtttcctcttcgcatctggtatccaatagcatacatataccagtgcggaaa
```

TABLE 1-continued atggcgaagactagtgggcttgaaccataaggtttggccccaatacggattccaaacaacaagcctagcgcagtctttt
gggatgcataagactaaactgtcgcagtgatagacgtaagatatatcgacttgattggaatcgtctaagctaataag
tttaccttgaccgtttatagttgcgtcaacgtccttatggagattgatgcccatcaaataaacctgaaaatccatcac
catgaccaccataaactcccttgctgccgctgctttggcttgagcaaggtgtttccttgtaaagctccgatctttgga
taaagtgttccacttttttgcaagtagctctgacccctctcagagatgtcaccggaatcttagacagaacctcctctgc
caaatcacttggaagatcggacaatgtcatcattttttgcaggtaatttctccttcgttgctgctttggcttgagcacg
gtgcttcttgtaaagctccgatctttggataagagcggatcggaatcctctaggaggtgccagtcccttgacctatt
aatttatagaaggttttagtgtattttgttccaatttcttctctaacttaacaaataacaactgcctcatagtcatgg
gcttcaaattttatcgcttggtgtatttcgttatttgcaaggccttggcccattttgagcccaataactaaatctagc
cttttcagaccggacatgaacttcgcatattggcgtaactgtgcagttttacctttttcggatcagacaagatcagat
ttagaccacccaacaatagtcagtcatatttgacaacctaagctagccgacactactaaaaagcaaacaaaagaagaa
ttctatgttgtcattttaccggtggcaagtggacccttctataaaagagtaaagagacagcctgtgtgtgtataatct
ctaattatgttcaccgacacaatcacacaaacccttctctaatcacacaacttcttcatgatttacgacattaattat
cattaactctttaaattcactttacatgctcaaaaatatctaatttgcagcattaatttgagtaccgataactattat
tataatcgtcgtgattcgcaatcttcttcattagatgctgtcaagttgtactcgcacgcggtggtccagtgaagcaaa
tccaacggtttaaaaccttcttacatttctagatctaatctgaaccgtcagatatctagatctcattgtctgaacaca
gttagatgaaactgggaatgaatctggacgaaattacgatcttacaccaaccccctcgacgagctcgtatatataaag
cttatacgctcctccttcaccttcgtactactactaccaccacatttctttagctcaaccttcattactaatctcctt
ttaaggtatgttcacttttcttcgattcatactttctcaagattcctgcatttctgtagaatttgaaccaagtgtcga
tttttgtttgagagaagtgttgatttatagatctggttattgaatctagattccaattttttaattgattcgagtttgt
tatgtgtgtttatactacttctcattgatcttgtttgatttctctgctctgtattaggtttctttcgtgaatcagatc
ggaa >SEQ ID NO:_57_construct_YP0018
tagaaacctcaacttgaatataatagtttgtttgtttgcttgaagttaatctctctcttttttatcagctaaagctgc
atttataaaaattctagtttaacttttaccatttgctataatttagagattttaacaagaaatctggcctagtccgca
aaacttatagaataaatcaaacattcttcaatattttacacatccacaatacccaatccaagaaatggattgcagttg
caccagagattacatgtctcgttttagtttgctagtcactcaaactcacaaagcataaattgtaatagaaaatagaac
tttatttaaatctgaagaaagatatatataaaaaaaaaaaaaaagaagaagcaggctccagttttgatgggagaaga
aaagagagctggcaacagctattcactgatagaccgatcactctcttctgtcccgcactcttttcttcttttgtttct
ttcttttcgacagctttcattttcctccattttaaattgaattattttacagtcataaaagtacttcaaacgtat
atgtaaataacgagcaacaaaacaattaactacaacaaaactagttctagctaagagaattagttagaaattttatt
ataatagttagtatatgtttattcataacacaattaattaacacacaaaatacatgtaatttcctctataccctcttc
acatataattagagtagtgcttaatttaagattaattatcgatttacatcattaatgatcatctagtcttacacaga
gagtttcagtatctgcatgagattatataaaggaatgtattcatgttttttacttcttttttattcatggttaaggatga
tacattataattataaatccataatctatgaactcaactattcttTATAaaaaaggaattaaattctgaaaataaaca
actgtagttggcttcccaaggctgctgcttcacctataaatacctatcctcttttgaaaactc >SEQ ID NO:_58_construct_YP0071
ataggccctacttctaattaaagcccatttacttctctccttgtcttcttattcctcttttctccccatcacgtgacg
acgatgctataaacgccgtcggattatataactggtgccgttgacaagacggcgacagaagaaagaagaagaaacca
caggctctagggaacgtaacgttatgtcctgtctatagcatttataacggtcagatcaacgccgtttagataaagatc TABLE 1-continued tgtcaatgttaaagaagagatgcatctctacaccgttaaatttaaaacgccgtgaacctcttatctattgattttgt
ttgatgaagccaaaacaaatcgtgtcagaagacttatcagagaagaagaaaacgacgacgttcccgtttctccatgtc
taataagtgtagtagtggcggctactaaaaactctaaagtttgactccagtaaaactgccttctagtgtaattccag
tgattttagagtttgaatagtgtgtgaccaaatttgaaagtacaatctcagcaatattattgatcactcgttataaaa
gaatcgaatgtaaaaatagccaatgagagactgagacgtatgtgtttgaccataagtcgtatagtttgtatctatcta
cctgcaagatcagcagatggttctctgatcaattgtaccttaattatcttttatttttcgtaaaatttctctattcaca
aatgataaatctacttaagacagtaaccataacaagatttacaagataaatttgaaaaatgaacacataaaagtatttt
ggcgcattatttttaataataacaatatttatgtaaagtcacataaaagtaTATAttcgctcacaaagtcttacggta
tttagaacagtagtaccacatcgattctcttcatcttcttcttcataatatgccattgttcatgtctctgtgtcctat
cgcataacactcacgctatcttattattttctctcgctctttctcactgagaggacactaaaa >SEQ ID NO:_59_construct_YP0080
aagcggcaatttagtaagaagtactcaaagtatcatttaccaaaagtatatggttttgggaagagttgttagggatgt
attctttctaaacagatgatatgacgatgttcttgaaaactaatgttaaagacggaatctctggcatcttcactcggg
agatatattaaaccgttgattgtagttagccatgtacttagcttagtgcacaaataatctgctgcaagaaatctttt
ctattataatatctctcatttaaacattagaacatattgtttaacttgttcttctagaaataaaactgctaatttctt
atggtaaactattttccttagattgcacaatcgaactcgaaaatctagtggagactatgtgactatgtttatatata
tgaaacctaaatcaaattatcccaataattgggagacacaaaagaaaaattacgaaagaaaacaggaaatcaaatcaa
aagataaagagaaggtaaaaaaaggcaagaagcactaatgtttaatatttatagttttctccattaaagaaaaagcga
tgatgtgtgttctcatcttttgtgaaagtatatatattgcttttgcttttctcaaaagcaaaagactcatccaacaag
aacaaaaaaaaaaactaaagctcaatccaaaagacgaagaatgcattggatactacaacttcttttttcacttttcttt
caaatttacaattatgattttcacaatacagtttattcaaaaataaataaaaaaacgaggcatgaaaataatgattat
cctcttcacttattaagccactcacTATAagcagagcaactccagaacatagtgagcccccaaaacattaaagcatga
tgatgtctaatgatgatgatcttcttcgttccatttctctaaattttttgggattctgcgaagaccttcttctcttt
ctcttctctgaacttcaagattcgtgtcggacaaattttgttttattttctgatgttaca >SEQ ID NO:_60_construct_YP0120
tagttttgatttaatctacgttttctcttaatcataaatgggtaattattagttttgcaaaatcaaaatccaaaaat
tgttctaaacactgcaaccatttaaggcctatatcactcagaaaattctggtgggagaactaatcgtttgtcctttc
taaatctcacatattagaatttagaattagtgtgctacataaaatattagttcagctcggaacaactatttttggt
aaaacagagaacttaaacaaatgcattattttatcaacatgcattttgaattgaatataaaatttcataattgtaaag
acataaattacataaaattttacatgaaaaaatagatatagaaagaaaatgaaactaactgatgatatgctctctaaa
tttttaatctcataacaagaattcaaattaattagttcatattttggttaatataacatttacctgtctaagttgg
aactttcatttttttctgtttttgtttagtcagtattcttaatgtgaaacggaaagttgaatttattcaaacttaaat
tcaatagcattaattaaaggcgaaagctattatctctacatgtggttcaaactagacatccaatttaattagcttatt
gacgttgaaatgttttccaaaactactatagtttggcaatttgaaagatgcatcagaactactcagacaggtaaagt
agaacctctagctgtgtgaattgtatgttagtccataaagaacatcttgtaaacttcatacttaagatatatattaca
atatatacttgaatggtagataaaaacgattagtctgattgctagcatactcaactatttggaaatgagtaagata
ttggcatctagagttactactatggagacaaaagtcgaataaaagagacctcacgtgaaaatgttacgagctagtaac
taaagcatttacactaacggtaaaaaaagtatcTATAaatgtttacacaaggtagtagtcatt >SEQ ID NO:_61_construct_YP0122
agtttaattatttgttatctatccaatcaattttttttctaaactgtttggaccaatgtacgtacgtaccatcctttt
tgattttttttgtaaactaaattttcgaattagcaggttcttaataattgaacgaagaaaataaagaatagaggtaga

TABLE 1-continued cacctgtagtattttcttggtcagaccaataatttataattcaacgtcaaagaagaagaaaaatataaaccattattt cattatgacttacgtataccaaaatacacaaattaaatgtataattgtgaggcatttttatatgcgggaaaaaataaaa taaaaagaatattaatatttcttttgaaaattgtaaagcattttgacccacttgtgatatatatatatatatagatat atatagagagagagattaaaacattgatggctagctatagagtctatggcagggtcatgatcacctgtcttctgatct ctgaagagataccaatctgatttttctcttcctaggtttaattttattttaccattttataattctttattttttgcc tgtagtacaatttacagacccatactaaaagaaaaattaaattttgtcaaagtacaaaacaaagagagaggtgaagcc acacaatctcttttcttctctctctctctgttatatctcttctgtttaattcttttattcttcttcgtctatcttctc cTATAatctcttctctctccctcttcacctaaagaataagaagaaaaataattcacatctttatgcaaactactttct tgtagggttttaggagctatctctattgtcttggttctgatacaaagttttgtaattttcatggtatgagaagatttg cctttctattttgtttattggttcttttttaacttttttcttggagatgggttcttgtagatcttaatgaaacttctgtt tttgtcccaaaaagagttttcttttttcttctcttcttttgggttttcaattcttgagagac >SEQ ID NO:_62_construct_YP0216
Ttttgtttctaatagtttgatgtttatatcaacattattatttactttcatttgttaccgatagaaagaggagaaaat tgttgacaaaaacaaagaaaaaagtaaaattaatattattaaattaataaaaataacaaactgtaaaagctatttta aaaattttctcttgtaaaacatctaaaaattattcttgtagaaacagaggaatatcattgaagataatagtgtgaaatt atatatatatatagaaatatataaagtaggattttttttctgtatacaaatatacgtttccaattttatcaaaaactgt aaagatttttttctttgtcagtacctgctaaacttgttaattttttttattaaaaaaaaatcaaattacaattcttcta taatcattttaaattccatttcttttataccacaaaagattatattgcctttatcgtctttggtatgtatgcgtgaata tatttatttattttcttttcttcattttcttttaaagaactttataaatgaaataaggaacaaacaatatacacat gtactaacgtatatataaataatatcatcaatatctatccaaaacttggatttcatggttgacgtggcccaaccaaaatc tcaagttctctgcggatgacgaaccatctcaccatctcttttttctctctcttttttttttttaatatcatcagcac ggttacataaaattcgtgatccatgaagttggctttcttgtcgttttacttcatcaccccatttttttaaagtctcca tctttatacttcttcaactctccaccaccaccattgtcaccaccacatttaaacacacactttcacttgtagtgggat tcgaaagtgcgttttattcatttgttttactgttttttgataacctcaaaatttgcctaaattttattctcTATAaatc cttatatgttttacttacattcctaaagttttcaactttcttgagcttcaaaaagtacctcca >SEQ ID NO:_63_construct_YP0230
ataaaattatctataaatcattaaatctttgatgagaaatatccaatctactaatgtatatcgatgatttaaatgaaa ttacttatttgaacacaaaaataaatgaatttactaataaataaatagcgtagttgggagcaagtggctaaaaaaatta caaatctagtttccattctcagcgtcggctgcttggaacgtcaccgttttctggaaaacgcaatcttctcccttccgt gacgtctcaccggaattttctcgcttttgtctactctcctccatctccgaggttctccaagctcagctcctcttccca tcattcatccgaccgccttatccggtcagatcctttacgtatttctattttcctgatcgtcgattttttgagaaatgta aaaacagatcgTATAaggcctcgaagttttttaatttgaaagtggtatcgaaattttttggtcttgattaggttaggg caccgtagctctgggtattgaatttgtaggttttcctctggttattggtctttggagcttggtaatttctgctgaat tgattgatcccttttccatcttttgaagtaaagtctcgagctttcgtgtctcgatgtagatgaattctattttgaata tgagatttgataagacgtcaattgctgataatttggagtctttgtgtctgaatttgttcatatgaagttttctgaggg atgtgaattttattgtctgctaattttgaaacgttccttttggaatttggtttgtgaggagtcctagatcttttctg tgaagtttcttgcttgtaagttttctggatcacttgattgagtctagaatctagatagattacatgtacggtttgatt cctttggctgattttccaaagttttgttcaaatttcaggagaactacaaagagggaaaccaagattgttttgttttgtt agactctaccccttttccgattcacatggtaaggacattgaggtagagaataatactaaaaag >SEQ ID NO:_64_construct_YP0261
gtcgattggttgtaaattagttttatcgtagaagtaccaaatcaagtgattcaatggttaaattaaggtattaagtta TABLE 1-continued catttgatatttaaaagtatccagaccttcattatagctcataagggttaaaattttgtcgttcttttgtatattcat
ggcaagctctaattcatgactaagtcacattttcaaatatgttttagttttacttatgttggtaattagtggatt
tatagttaagttaaaaagttggcgagttctagctttgaaactcatttagaaatatatatatatatatatattcaat
tttagtaaattgttaatctattctaatggtgtaactgtaacaaatgagaatgaaaaaaatatactattgtgaataaaa
ccccacacaacacattactataataagttaaacttctttttttataggcgcctggaaaaaaaagaaaagcaacaagag
ggstgtgaggacgcatcaccnggtttcgtagcacacatgtgcatttgtctctttgcttttcggtttttttcttgcca
atcaattattttgttcctcagaaaaagaaaatctaaaaccaaaatatatattataaccctcatttaataaacaacaa
aaatgtttgttgaaaaaaaaaagtttttatttatcttgaccttatttctttgaagaaaataaagcttggttattaaa
gaagtccaagttagttgccaccatcagtggcataacggtaaattaaagccaacttcctctaactaaagttttcTATAa
attcaaccactcacctcccactctaaaacccaacaacataatttcacatatctctctttctttctcttgaaggaaaga
cgaagatctccaagtcccaagtacgtaactactttctccatctacattcaattgtttctccttaatttctctagtaca
tatttacttgtgctataagtaattgattttatatcacccatgtgcaggttgttaacacaaga >SEQ ID NO:_65_construct_YP0263
tattatatatacgattaaataaataaaaaaattgtaatgtgaaaatatcatagtcgagagggg aactgacaagtgtac
atatgtatctagctgtggattccaccaaaattctggcagggccatgatctaaaaactgagactgcgcgtgttgttttg
cagtgatttgtatttcatatttgcaccatcctacacagtccacttggtatcgtaaccaaacataaggagaacctaatt
acattattgttttaatttcgtcaaactggtttttacctttagttacatagttgattcttcatttgttttagtagtta
tggagcacaataatgtgcaacaaagaaagatcatagtggattaatatgttgagaggtcagaaattcttggttaacaaa
aaaaaaaagttacaaggactgagattttgggtgggagaaagccatagcttttaaaacatgattgaacttaaaagtga
tgttatggtttgaggggaaaaaggttgatgtcaactaagatagttgaagtaatgtcttaaactaaagtaaaccaccgg
tccaaacgtggtccggaagcatctctggtatgatttatcctaaaaatcaaaatagtagaaacatactttaaatatata
cattgatcggacgaaaattgtaaactagtatagtttcaaaaactagttgaacaggttatgtaccttaaacatttattt
caaacttaaacactaaagaacatatatgaatagaagtttatataaattactatatatctaccataaatctcttataat
tatgatgtcacgatgaggaagtgttgaaacgttaaaatgccaaaatataagcatgcgacggaattttggcagaagatt
gtagagttgtaatctgtcgcaatcattactcatgctagcattttcattttcccttcatttgtggataacgcacgata
taacattctacacaccaacaagattcTATAaaaacgcaaaggttgtctccatagaatatcgtc >SEQ ID NO:_66_construct_YP0271
atctctgatttttttatcaggaacaagtaaataaatagctttgagttttgttttttttctacattcttcgcccaaa
agatgtaagaaaataaaggatttgaaaccttgttctgttgttactcctttaaattcttaaaaactataaatcattata
tctttgatctgtttcacaaactaatcatattcgttgcaaagtgagaattcgtcccacttactctttacaccgatact
agtattatgatgtacagcatagtattccatatctagttatttagtcaaaactctatatattaagagggtaggttaatt
aattaaggagtaattgaagattatagaaagaataaaaaataccatttaatggacagaaccaaagataactaactatca
tactataatgttgaatttcttccacgatccaatgcatggataacaacatcaatcaaatcatacattcatgctatataa
catagttttcagttacaaactctctttttatttatttcagttgttccttttcatgaccatattaacatcaaataatg
catttttttcaacgtctcttgacttacacccactaatattgacaaattgaacatctatacgactatacacacataagt
taaaaatgcatgcaagtgctaagggaattatataacatctaaggttaataagactaagaaagtataaaataagaatacg
tattatgaatttatgatatactttactaatcttttgaaaaatactttaatttaatctactatagggggtaaaaagta
aaaagaaataaagatacgtttatccgcatatagtacctggaaataacagaaaataaaaacacaggtaagtactttgc
ctgagctagTATAtgaacactaaagagatacacacacacaaaaagagagcagaaacaaaacacacacacacttaaagctt
tcgtctttaccttcttcccttctctctctctatctaaaaagagttccgagaagaagatcatcat TABLE 1-continued >SEQ ID NO:_67_construct_YP0279
cgctttattataggtttaacaattgatttttcattattttgttttcaatctccaaatcatttctcaataactctcaaa cattgtttaaagcttttttttcttaattaacattataacaaaaaaataaatagagaaatttactttgattcaaacacca gtcattgtagattagccaagagttttcagtaacaaaatttaccttataaacctttttgaatggctatttctgaaatgga atagaaatctttagtcgtggaagtatctctatccataagaaaactcgttttacaaagtaattttaaatcaatacaaaa agtgaaaaaatccactggtggaccccattcattccagaattgccgattacgagctatcttgtcccttcttcaccattc gctcactctctctctctctctcgtcttcttcttcccaccactctctctgtttctccacaacttctcttctcaaagt taaaattacccctaaaccaaaaaaaaaaaaaacgctcttcactatttatttactaaactctcctttgtttgttactaa gctctcactaaaaccctaatctttctcctcttaTATActcgtgactcttctttctcctccaatctctctctccctct tcacaaaccaattagcttctttctgtaaaacctcactcgttggccaattcttttggttttcatacacataaatctcag attccaaatgggttttcttagctctttctttcaaatgatgaacatttgttagcagaatcttcctcttcccctaaagtt ttgatcttttttccccttcaattttgtattttctcaccaaataaaaaaaggtttcttcagtgggtttaagggttt attattatcttaaaattaaacacaattctttaatcaaaaggcaaaaatcttaatttcatcactctcttctcactcaca aaagttcttacaatcttcaaagttttggtcttgtttcttttccgatttcaccggacaaaaaaa >SEQ ID NO:_68_construct_YP0285
gggattatatatgatagacgattgtatttgcgggacattgagatgtttccgaaaatagtcatcaaatatcaaaccaga atttgatgtgaaaacactaattaaaacatataattgacaactagactatatcatttgttaagttgagcgttgaaagaa aatgaaagagtgtagactgtagtatgtatgagtttcccaaaggatggtgcttgaatattattgggaagagactttggt tggttcggttgaatgaagattttttacctgccatgttgatagagaaaggcaaataaatgtaggggtcgatgtctaacgt aaagactggatcaaccaagagtcctcctcctcgtcttcaccaaaaaaaaagagtcctcctcgtggaaacttatttctt ctccagccaagatctcatctcatctcttcactctatgaaatataaaggaatcttatggttttctaaaaactatagta cgtctatataccaaaggaaacaatataaaatcagttaatctgataaattttgagtaaataataaagttaactttgtac ttacctatatcaaactaattcacaaaataaagtaataataacaaagaattttttagtagatccacaatatacacacaca ctatgagaaatcataatagagaattttaatgattttgtctaactcatagcaacaagtcgctttggccgagtggttaag gcgtgtgcctgctaagtacatgggctctgcccgcgagagttcgaatctctcaggcgacgtttcttttgttttcggcca taaaggaaaaagcccaattaacacgtctcgcttataagcccataaagcaaacaatgggctgtctctgtctcactcaca cacgcgttttcctacttttttgactattttTATAaccggcgggtctgacttaattagggttttctttaataatcagaca ctctctcactcgtttcgtcaacattgaacacagacaaaaccgcgtcacaaaacaaaactcgct >SEQ ID NO:_69_construct_YP0003
tggatctgctagatatgagaacggaaagaaccagaagctattagaggcgggaggagatatgtggggatgatttcag tgcaattccacgacgcaccatttccactttcgtaacacctaaacgaccgcttcggccgtataaaatcgcaaatgtttg gtctcagtgtattttttccaatttccaaatacatcaattcaaattatataatatctagtggcaattataagtatatcat atattttcaaaattaattaaaaagattactaaattatgtttgactacaactattataatagttaaaaacataaacaaa aacaaagaaactattttaataaaaaaatcaagtaaacattaaaacataagcaaaaataatgttaaagaaattattaa ttattaatttactaataattaatacctctataaattaattgttagaggtttaacgtaatttataaggaaaactaaaga agactttaacccataaagaaaaaaacaaagactgaattgaaggcccatatttagaagaagagaaagaagacccaaata tgatataaaatccagcccatttatatattttttattttgtttctggaaggaaaataagaaaatggcaaaaacgaaataa tctgaaaaagtaaggtcttttaccaaaaaggatatttttttTATAaacagagcataaagttttcacttttcttctgct cctttctcgtctctgtcttcttcgtcctcattcgttttaaagcatcaaaatttcatcacccaaaatagattaaaaaa atctgtagctttcgcatgtaaatctctctcttgaaggttcctaactcgttaatcgtaactcacagtgactcgttcgagt caaagtctctgtctttagctcaaa

TABLE 1-continued

>SEQ ID NO:_70_construct_YP0015
Ttgagccttattgttgttattgacttttagccaatagaaagagatggaaattcaataattatccacaaaattccaaat cattggtgtacaaaaagatctaaggctgttatattttcaaaaaagaaagaaaagaaatgcaacaaatatggattaaac tgtggtttgtaaattgagctttgcatgaaaactttatcactatgatttcactactccatatttattgactaaagtggc actaatgaatttcttaatcatgaaatcttgtatcaaaaagtactaaaataaacatgacattggcaattaggaaaattc taaattagaaattagtaaaaatgaaaggtgaaagggaaagatgatgatatgaattggttggtgaccaggagaaatgta tcccgattttgcagacactttcagtgtccccattcatataattatggcccacctcgttaagattttcattccaccac cataacaagatctaagcttagatttcatgtaattaaacatataatatacttgccaatactatctaataaagtatactt aagcaaaaattattactctagtgtaaggcgatgaaatataagtttagttgaaaatttatgtcgatataacaaagtata atgaattaagaccttggttttcgattaacaaactaattaaacactagttttgcctaataaaaccgggaatcgtattca aaaccgaacgacaaaacaagggacaagttgagagacaaaaccaaatcagcatctttcttccagaaatgtcatgaccac atgacgtcatcttgaccttcttcattgtgatatctgtggataaagcgcacgtgtttaattcacgaaccttcgtagta acgaaaaatccacaactttcatattttttaattacccactaaactaaaacaaatttggaaaaacatgaaaaacttttt cttttttccaggttcgtgaacctcgtaccctctaTATAaacctcttaaccaccttccacata

TABLE 2

Promoter Expression Report # 1

Report Date: Jan. 31, 2003; Revised Aug. 15, 2003
Promoter Tested In: *Arabidopsis thaliana*, WS ecotype
Spatial expression summary:
Flower        (M)upper part of receptacle, (M)base of ovary
Flower        (M)pedicel, (M)receptacle, silique, (M)carpel
Stem         (H)cortex, (H)pith
Hypocotyl       (M)cortex
Primary Root      (H)vascular, (M)cap
Observed expression pattern: T1 mature: Expression was specific to the top of the receptacle and base of gynoecium of immature flowers. Not detected in any other organs. T2 seedlings: No expression observed. T2 mature: In addition to the original expression observed in T1 mature plants, expression is observed in pith cells near the apex of the inflorescence meristem and stem-pedicel junctions. T3 seedling: Expressed at cotyledon-hypocotyl junction, root vascular, and root tip epidermis. This expression is similar to the original 2-component line CS9107.
Expected expression pattern: The candidate was selected from a 2-component line with multiple inserts. The target expression pattern was lateral root cap and older vascular cells, especially in hypocotyls.
Selection Criteria: *Arabidopsis* 2-component line CS9107 (J1911) was selected to test promoter reconstitution and validation. T-DNA flanking sequences were isolated by TAIL-PCR and the fragment cloned into pNewBin4-HAP1-GFP vector to validate expression.
Gene: 2 kb seq. is in 7 kb repeat region on Chr.2 where no genes are annotated.
GenBank: NM_127894 *Arabidopsis thaliana* leucine-rich repeat transmembrane protein kinase, putative (At2g23300) mRNA, complete cds gi|18400232|ref|NM_127894.1|[18400232]
Source Promoter Organism: *Arabidopsis thaliana* WS
Vector:       pNewBin4-HAP1-GFP
Marker Type:     X GFP-ER
Generation Screened:   X T1 Mature  X T2 Seedling  X T2 Mature  X T3 Seedling
Bidirectionality: NO  Exons: NO  Repeats: none noted
Promoter utility
Trait-Subtrait Area: Among other uses this promoter sequence could be useful to improve:
PG&D- abscission, plant size
Nutrients- nitrogen utilization
Utility: Promoter may be useful in fruit abscission but as it appears the expression overlaps the base of the gynoecium, it may be useful to overexpress genes thought to be important in supplying nutrients to the gynoecium or genes important in development of carpel primordia.
Construct:       YP0001
Promoter Candidate I.D:  13148168 (Old ID: CS9107-1)
cDNA I.D:       12736079
T1 lines expressing (T2 seed): SR00375-01, -02, -03, -04, -05

TABLE 2-continued

Promoter Expression Report # 2

Report Date: Jan. 31, 2003
Promoter Tested In: *Arabidopsis thaliana*, WS ecotype
Spatial expression summary:

| | |
|---|---|
| Ovule | Pre-fertilization: (H)inner integument |
| | Post-fertilization: (M)seed coat, (M)endothelium |
| Root | (H)epidermis, (H)atrichoblast |
| Cotyledons | (L)epidermis |

Observed expression pattern: T1 mature: GFP expression exists in the inner integument of ovules. T2 seedling: Expression exists in root epidermal atrichoblast cells. T2 mature: Same expression exists as T1 mature. T3 seedlings: Same expression, plus additional weak epidermal expression was observed in cotyledons.
Expected expression pattern: flower buds, ovules, mature flower, and silique
Selection Criteria: *Arabidopsis* 2-component line CS9180(J2592).
Gene: water channel-like protein" major intrinsic protein (MIP) family
GenBank: NM_118469 *Arabidopsis thaliana* major intrinsic protein
(MIP) family (At4g23400) mRNA, complete cds gi|30686182|ref|NM_118469.2|[30686182]
Source Promoter Organism: *Arabidopsis thaliana* WS

| | |
|---|---|
| Vector: | pNewBin4-HAP1-GFP |
| Marker Type: | X GFP-ER |
| Generation Screened: | X T1 Mature   X T2 Seedling   X T2 Mature   X T3 Seedling |
| Bidirectionality: NO   Exons: NO   Repeats: None Noted | |

Promoter utility
Utility: Promoter could be used to misexpress any genes playing a role in seed size. It will also have utility in misexpressing genes important in root hair initiation to try to get the plant to generate more or fewer root hairs to enhance nutrient utilization and drought tolerance.

| | |
|---|---|
| Construct: | YP0007 |
| Promoter Candidate I.D: | 13148318 (Old ID: CS9180-3) |
| cDNA I.D: | 12703041 (Old I.D: 12332468) |
| T1 lines expressing (T2 seed): | SR00408-01, -02, -05 |

Promoter Expression Report # 3

Report Date: Jan. 31, 2003
Promoter Tested In: *Arabidopsis thaliana*, WS ecotype
Spatial expression summary:

| | |
|---|---|
| Leaf | (L)vascular |
| Hypocotyl | (L)epidermis |
| Primary Root | (H)epidermis, (H)cap |
| Lateral root | (H)epidermis, (H)cap |

Observed expression pattern: T1 mature: Low GFP expression was detected throughout the vasculature of leaves of mature plants. T2 seedling: No expression was detected in the vasculature of seedlings. T2 mature: Transformation events which expressed as T1 plants were screened as T2 plants and no expression was detected. This line was re-screened as T1 plants and leaf expression was not detected in 3 independent events. T3 seedling: New expression was observed in T3 seedlings which was not observed in T2 seedlings. Strong primary and lateral root tip expression and weak hypocotyl epidermal expression exists.
Expected expression pattern: High in leaves. Low in tissues like roots or flowers
Selection Criteria: *Arabidopsis* Public; Sauer N. EMBO J 1990 9:3045-3050
Gene: Glucose transporter (Sugar carrier) STP1
GenBank: NM_100998 *Arabidopsis thaliana* glucose transporter
(At1g11260) mRNA, complete cds, gi|30682126|ref|NM_100998.2|[30682126]
Source Promoter Organism: *Arabidopsis thaliana* WS

| | |
|---|---|
| Vector: | pNewBin4-GFP Direct fusion construct |
| Marker Type: | X GFP-ER |
| Generation Screened: | X T1 Mature   X T2 Seedling   X T2 Mature   XT3 Seedling |
| Bidirectionality: NO   Exons: NO   Repeats: None Noted | |

Promoter utility
Trait-subtrait Area: Among other uses this promoter sequence could be useful to improve:
Source- C/N partitioning, transport of amino acids, source enhancement
Yield- Total yield
Quality- Amino acids, carbohydrates, Optimize C3-C4 transition
Utility: Sequence most useful to overexpress genes important in vascular maintenance and transport in and out of the phloem and xylem.

| | |
|---|---|
| Construct: | G0013 |
| Promoter Candidate I.D.: | 1768610 (Old ID: 35139302) |
| cDNA ID: | 12679922 (Old IDs: 12328210, 4937586.) |
| T1 lines expressing (T2 seed): | SR00423-01, -02, -03, -04, -05 |

Promoter Expression Report # 4

Report Date: Mar. 6, 2003
Promoter Tested In: *Arabidopsis thaliana*, WS ecotype
Spatial expression Summary:

| | |
|---|---|
| Flower | (H)sepal, (L)epidermis |
| Embryo | (H)suspensor, (H)preglobular, (H)globular, (M)heart, (M)torpedo, (L)late, (L)mature, (L)hypophysis |
| Ovule | Pre fertilization: (M)outer integument, (H)funiculus |
| | Post fertilization: (M)outer integument, (H)zygote |

TABLE 2-continued

| | |
|---|---|
| Embryo | (H)hypocotyl, (H)epidermis, (H)cortex, (H)stipules, (L)lateral root, (H)initials, (H)lateral root cap |
| Stem | (L)epidermis |

Observed expression patterns: T1 Mature: Strong expression was seen in 4-cell through heart stage embryo with decreasing expression in the torpedo stage; preferential expression in the root and shoot meristems of the mature embryo. Strong expression was seen in the outer integument and funiculus of developing seed. T2 Seedling: Strong expression was seen in epidermal and cortical cells at the base of the hypocotyl. Strong expression was seen in stipules flanking rosette leaves. Low expression was seen in lateral root initials with increasing expression in the emerging lateral root cap. T2 Mature- Same expression patterns were seen as T1 mature plants with weaker outer integument expression in second event. Both lines show additional epidermal expression at the inflorescence meristem, pedicels and tips of sepals in developing flowers. T3 seedling expression - same expression
Expected expression pattern: Expression in ovules
Selection Criteria: Greater than 50x up in pi ovule microarray
Gene: Lipid transfer protein-like
GenBank: NM_125323 *Arabidopsis thaliana* lipid transfer protein 3 (LTP 3)
(At5g59320) mRNA, complete cds, gi|30697205|ref|NM_125323.2|[30697205]
Source Promoter Organism: *Arabidopsis thaliana* WS

| | |
|---|---|
| Vector: | pNewbin4-HAP1-GFP |
| Marker Type: | X GFP-ER |
| Generation Screened: | X T1 Mature   X T2 Seedling   X T2 Mature   X T3 Seedling |
| Bidirectionality: NO   Exons: NO   Repeats: None noted | |

Promoter utility
Trait-subtrait Area: Among other uses this promoter sequence could be useful to improve:
Water use efficiency - Moisture stress, water use efficiency, ovule/seed abortion
Seed - test weight, seed size
Yield - harvest index, total yield
Quality - amino acids, carbohydrate, protein total oil, total seed composition

| | |
|---|---|
| Construct: | YP0097 |
| Promoter Candidate I.D: | 11768657 (Old ID: 35139702) |
| cDNA_ID | 12692181 (Old IDs: 12334169, 1021642) |
| T1 lines expressing (T2 seed): | SR00706-01, -02 |

Promoter Expression Report # 5

Report Date: Mar. 6, 2003
Promoter Tested In: *Arabidopsis thaliana*, WS ecotype
Spatial expression summary:

| | |
|---|---|
| Ovule | Pre-fertilization: (L)inner integument |
| | Post-fertilization: (H)inner integument, (M)endothelium |
| Primary Root | (H)endodermis |

Observed expression pattern: GFP is expressed in the endosperm of developing seeds and pericycle cells of seedling roots. GFP level rapidly increases following fertilization, through mature endosperm cellularization. GFP is also expressed in individual pericycle cells. T1 and T2 mature: Same expression pattern was observed in T1 and T2 mature plants. Closer examination of the images reveals that GFP is expressed in the endothelium of ovules which is derived from the inner most layer of the inner integuments. Lower levels of expression can be seen in the maturing seeds which is consistent with disintegration of the endothelium layer as the embryo enters maturity. T2 seedling: Expression appears to be localized to the endodermis which is the third cell layer of seedling root not pericycle as previously noted. T3 seedlings: Low germination. No expression was observed in the few surviving seedlings.
Expected expression pattern: Expression in ovules
Selection Criteria: Greater than 50x up in pi ovule microarray
Gene: palmitoyl-protein thioesterase
GenBank: NM_124106 *Arabidopsis thaliana* palmitoyl protein thioesterase
precursor, putative (At5g47350) mRNA, complete cds gi|30695161|ref|NM_124106.2|[30695161]
Source Promoter Organism: *Arabidopsis thaliana* WS

| | |
|---|---|
| Vector: | pNewbin4-HAP1-GFP. |
| Marker Type: | (X) GFP-ER |
| Generation Screened: | (X) T1 Mature   (X) T2 Seedling   (X) T3 Mature   (X) T3 Seedling |
| Marker Intensity: | (X) High   ☐ Med   ☐ Low |
| Bidirectionality: NO   Exons: NO   Repeats: None Noted | |

Promoter utility
Trait - Sub-trait Area: Among other uses this promoter sequence could be useful to improve:
Seed - ovule/seed abortion, seed size, test weight, total seed
Composition - amino acids, carbohydrate, protein to oil composition
Utility: Promoter useful for increasing endosperm production or affecting compositional changes in the developing seed. Should also have utility in helping to control seed size.

| | |
|---|---|
| Construct: | YP0111 |
| Promoter Candidate I.D: | 11768845 (Old ID: 4772159) |
| cDNA ID | 13619323 (Old IDs: 12396169, 4772159) |
| T1 lines expressing (T2 seed): | SR00690-01, -02 |

Promoter Expression Report # 6

Report Date: Mar. 6, 2003
Promoter Tested In: *Arabidopsis thaliana*, WS ecotype
Spatial expression summary:

| | |
|---|---|
| Stem | (H)epidermis, (H)cortex |
| Hypocotyl | (H)epidermis, (H)cortex |

TABLE 2-continued

Silique (H)style, (H)carpel, (H)septum, (H)epidermis
Leaf (M)mesophyll, (M)epidermis
Observed expression patterns: Strong GFP expression exists throughout stem epidermal and cortical cells in T1 mature plants. GFP expression exhibits polarity in T2 seedling epidermal cells. First, it appears in the upper part of the hypocotyl near cotyledonary petioles, increasing toward the root, and in the abaxial epidermal cells of the petiole. An optical section of the seedling reveals GFP expression in the cortical cells of the hypocotyl. T2 mature: Same expression pattern was seen as in T1 mature with extension of cortex and epidermal expression through to siliques. No expression was seen in placental tissues and ovules. Additional expression was observed in epidermis and mesophyll of cauline leaves. T3 seedling: Same as T2.
Expected expression pattern: Expression in ovules
Selection Criteria: Greater than 50x up in pi ovule microarray
Gene: cytochrome P450 homolog
GenBank: NM_104570 *Arabidopsis thaliana* cytochrome P450, putative
(At1g57750) mRNA, complete cds, gi|30696174|ref|NM_104570.2|[30696174]
Source Promoter Organism: *Arabidopsis thaliana* WS
Vector: pNewbin4-HAP1-GFP
Marker Type: X GFP-ER
Generation Screened: X T1 Mature  X T2 Seedling  X T3 Mature  X T3 Seedling
Bidirectionality: NO   Exons: NO   Repeats: None Noted
Promoter utility
Trait - Sub-trait Area: Among other uses this promoter sequence could be useful to improve:
Water use efficiency - moisture stress, water use efficiency, ovule/seed abortion
Seed - test weight, seed size
Yield - harvest index, total yield
Composition - amino acids, carbohydrate, protein total oil, total seed
Utility: Useful when expression is predominantly desired in stems, in particular, the epidermis.
Construct: YP0104
Promoter Candidate ID: 11768842
cDNA ID: 13612879 (Old IDs: 12371683, 1393104)
T1 lines expressing (T2 seed): SR00644-01, -02, -03

Promoter Expression Report # 7

Report Date: Mar. 6, 2003
Promoter Tested In: *Arabidopsis thaliana*, WS ecotype
Spatial expression summary:
Flower (L)sepal, (L)petal, (L)silique, (L)vascular, (H)stomata, (L)pedicel
Silique (L)vascular, (L)epidermis
Cotyledon (H)stomata, (L)root hair
Observed expression patterns: GFP expressed in the vasculature and guard cells of sepals and pedicels in mature plants. GFP expressed in the guard cells of seedling cotyledons.
T2 mature: Stronger expression extended into epidermal tissue of siliques in proximal-distal fashion.
T3 seedling: Weak root hair expression was observed which was not observed in T2 seedlings; no guard cell expression observed. All epidermal tissue type expression was seen with the exception of weak vasculature in siliques.
Expected expression pattern: Drought induced
Selection Criteria: Expression data (cDNAChip), >10 fold induction under drought condition. Screened under non-induced condition.
Gene: Unknown protein; At5g43750
GenBank: NM_123742 *Arabidopsis thaliana* expressed protein (At5g43750)
mRNA, complete cds, gi|30694366|ref|NM_123742.2|[30694366]
Source Promoter Organism: *Arabidopsis thaliana* WS
Vector: pNewbin4-HAP1-GFP
Marker Type: X GFP-ER
Generation Screened: X T1 Mature  X T2 Seedling  X T3 Mature  X T3 Seedling
Bidirectionality: NO   Exons: NO   Repeats: None noted
Promoter utility
Trait - Subtrait Area: Among other uses this promoter sequence could be useful to improve:
Water use efficiency - Heat
Construct: YP0075
Promoter Candidate I.D: 11768626 (Old ID: 35139358)
cDNA ID: 13612919 (Old IDs: 12694633, 5672796)
T1 lines expressing (T2 seed): SR00554-01, -02

Promoter Expression Report # 8

Report Date: Mar. 6, 2003
Promoter Tested In: *Arabidopsis thaliana*, WS ecotype
Spatial expression summary:
Flower (L)receptacle, (L)vascular
Leaf (H)vascular, (H)epidermis
Root (M)phloem
Cotyledon (M)vascular, (M)hydathode
Primary Root (L)epidermis, (M)vascular
Observed expression patterns: Expression was seen at the receptacle and vasculature of immature flower and leaf, and phloem of seedling root. T2 mature: Similar to T1 expression. Strong expression was seen in vascular tissues on mature leaves. Vascular expression in flowers was not observed as in T1.
T3 seedling: Similar to T2 seedling expression.
Expected expression pattern: Vascular tissues; The SUC2 promoter directed expression of GUS activity with

TABLE 2-continued high specificity to the phloem of all green tissues of *Arabidopsis* such as rosette leaves, stems, and sepals.
Selection Criteria: *Arabidopsis* public; Planta 1995; 196:564-70
Gene: "Sugar Transport" SUC2
GenBank: NM_102118 *Arabidopsis thaliana* sucrose transporter SUC2
(sucrose-proton transporter) (At1g22710) mRNA, complete cds, gi|30688004|ref|NM_102118.2|[30688004]
Source Promoter Organism: *Arabidopsis thaliana* WS
Vector: Newbin4-HAP1-GFP
Marker Type: X GFP-ER
Generation Screened: X T1 Mature   X T2 Seedling   X T3 Mature   X T3 Seedling
Bidirectionality: NO   Exons: NO   Repeats: None Noted
Promoter utility
Trait - Sub-trait Area: Among other uses this promoter sequence could be useful to improve:
Source - Source enhancement, C/N partitioning
Utility: Useful for loading and unloading phloem.
Construct: YP0016
Promoter Candidate I.D: 11768612 (Old ID: 35139304)
cDNA ID 13491988 (Old IDs: 6434453, 12340314)
T1 lines expressing (T2 seed): SR00416-01, -02, -03, -04, -05

Promoter Expression Report # 9

Report Date: Mar. 6, 2003
Promoter Tested In: *Arabidopsis thaliana*, WS ecotype
Spatial expression summary:
Flower          (L)inflorescence, (H)pedicel, (H)vascular
Stem            (L)phloem
Leaf            (L)vascular
Ovule           Pre fertilization: (H)chalaza end of embryo sac
Hypocotyl       (M)vascular, (M)phloem
Cotyledon       (M)vascular, (M)phloem
Root            (H)vascular, (H)pericycle, (H)phloem
Observed expression patterns: GFP expressed in the stem, pedicels and leaf vasculature of mature plants and in
seedling hypocotyl, cotyledon, petiole, primary leaf and root.
Expected expression pattern: Phloem of the stem, xylem-to-phloem transfer tissues, veins of supplying seeds,
vascular strands of siliques and in funiculi. Also expressed in the vascular system of the cotyledons in developing
seedlings. T2 mature: Same as T1 mature. T3 seedling: Same as T2 seedling.
Selection Criteria: *Arabidopsis* public PNAS 92, 12036-12040 (1995)
Gene: AAP2 (X95623)
GenBank: NM_120958 *Arabidopsis thaliana* amino acid permease 2 (AAP2)
(At5g09220) mRNA, complete cds, gi|30682579|ref|NM_120958.2|[30682579]
Source Promoter Organism: *Arabidopsis thaliana* WS
Vector: pNewbin4-HAP1-GFP
Marker Type: X GFP-ER
Generation Screened: X T1 Mature   X T2 Seedling   X T3 Mature   X T3 Seedling
Bidirectionality: FAILS   Exons: FAILS   Repeats: None Noted
Promoter Utility
Trait - Sub-trait Area: Among other uses this promoter sequence could be useful to improve:
Trait Area: Seed - Seed enhancement
Source - transport amino acids
Yield - harvest index, test weight, seed size,
Quality - amino acids, carbohydrate, protein, total seed composition
Utility:
Construct: YP0094
Promoter Candidate I.D: 11768636 (Old ID: 35139638)
cDNA ID: 13609817 (Old IDs: 7076261, 12680497)
T1 lines expressing (T2 seed): SR00641-01, -02

Promoter Expression Report # 10

Report Date: Mar. 6, 2003
Promoter Tested In: *Arabidopsis thaliana*, WS ecotype
Spatial expression summary:
Flower          (L)sepal, (L)pedicel, (L)vascular
Silique         (H)stomata
Hypocotyl       (M)epidermis
Primary Leaf    (H)stomata
Root            (H)epidermis, (H)root hairs
Observed expression pattern: T1 mature: GFP expression was seen in the guard cells of pedicles and mature
siliques. Weak expression was seen in floral vasculature.T2 seedling: Strong expression observed in epidermis and
root hairs of seedling roots (not in lateral roots) and guard cells of primary leaves. T2 mature: Similar to T1 plants.
T3 seedling: Similar to T2 seedling. Screened under non-induced conditions.
Expected expression pattern: As described by literature. Expressed preferentially in the root, not in mature stems or
leaves of adult plants (much like AGL 17); induced by KNO3 at 0.5 hr with max at 3.5 hr
Selection Criteria: *Arabidopsis* Public; Science 279, 407-409 (1998)
Gene: ANR1, putative nitrate inducible MADS-box protein;
GenBank: NM_126990 *Arabidopsis thaliana* MADS-box protein ANR1
(At2g14210) mRNA, complete cds gi|22325672|ref|NM_126990.2|[22325672]
Source Promoter Organism: *Arabidopsis thaliana* WS

TABLE 2-continued

Vector: pNewbin4-HAP1-GFP
Marker Type: X GFP-ER
Generation Screened:  X T1 Mature   X T2 Seedling   X T2 Mature   X T3 Seedling
Bidirectionality: NO   Exons: NO   Repeats: None Noted
Promoter Utility
Trait - Sub-trait Area: Among other uses this promoter sequence could be useful to improve:
Yield - Heterosis, general combining ability, specific combining ability
Construct: YP0033
Promoter Candidate I.D: 13148205 (Old ID: 35139684)
cDNA ID: 12370148 (Old IDs: 7088230, 12729537)
T1 lines expressing (T2 seed): SRXXXXX-01,

Promoter Expression Report # 11

Report Date: Mar. 6, 2003
Promoter Tested In: *Arabidopsis thaliana*, WS ecotype
Spatial expression summary:
Flower          (H)epidermis, (H)sepal, (H)petal, (H)vascular
Stem            (L)vascular
Hypocotyl       (L)epidermis, (H)phloem
Cotyledon       (L)epidermis, (M)stomata, (L)vascular
Root            (H)phloem
Observed expression pattern: Strong GFP expression was seen in the epidermal layer and vasculature of the
sepals and petals of developing flowers in mature plants and seedlings. T2 mature: Expression was similar to T1
mature plants. Vascular expression in the stem was not observed in T1 mature. T3 Seedling: Same expression
seen as T2 seedling expression
Expected expression pattern: Predominantly expressed in the phloem.
Selection Criteria: *Arabidopsis* public: Deeken, R. The Plant J. (2000) 23(2), 285-290
Geiger, D. Plant Cell (2002) 14, 1859-1868
Gene: potassium channel protein AKT3
GenBank: NM_118342 *Arabidopsis thaliana* potassium channel (K+ transporter 2)(AKT2) (At4g22200) mRNA,
complete cds, gi|30685723|ref|NM_118342.2|[30685723]
Source Promoter Organism: *Arabidopsis thaliana* WS
Vector: pNewbin4-HAP1-GFP
Marker Type: X GFP-ER
Generation Screened:  X T1 Mature   X T2 Seedling   X T3 Mature   X T3 Seedling
Bidirectionality: NO   Exons: NO   Repeats: None Noted
Trait - Sub-trait Area: Among other uses this promoter sequence could be useful to improve:
Nutrient - Low nitrogen tolerance; Nitrogen use efficiency; Nitrogen utilization
Utility:
Construct: YP0049
Promoter Candidate I.D: 11768643 (Old ID: 6452796)
cDNA ID: 12660077 (Old IDs: 7095446, 6452796)
T1 lines expressing (T2 seed): SR00548-01, -02, -03

Promoter Expression Report # 12

Report Date: Mar. 6, 2003
Promoter Tested In: *Arabidopsis thaliana*, WS ecotype
Spatial expression summary:
Flower          (L)pedicel, (L)sepal, (L)vascular
Leaf            (M)petiole, (M)vascular
Cotyledon       (H)stomata, (M)petiole, (H)vascular
Primary Leaf    (L)vascular, (L)petiole
Root            (H)root hair
Observed expression pattern: GFP expression was detected in the vasculature of sepals, pedicel, and leaf petiole of
immature flowers. Also weak guard cell expression existed in sepals. Strong GFP expression was seen in guard cells
and phloem of cotyledons, and upper root hairs at hypocotyl root transition zone. T2 mature: Same as T1 mature.
T3 seedling: Same as T2 seedling.
Expected expression pattern: Shoot apical meristems
Selection Criteria: Greater than 5x down in stm microarray
Gene: AP2 domain transcription factor
GenBank: NM_129594 *Arabidopsis thaliana* AP2 domain transcription factor,
putative(DRE2B) (At2g40340) mRNA, complete cds, gi|30688235|ref|NM_129594.2|[30688235]
Source Promoter Organism: *Arabidopsis thaliana* WS
Vector: pNewbin4-HAP1-GFP
Marker Type: X GFP-ER
Generation Screened:  X T1 Mature   X T2 Seedling   X T3 Mature   X T3 Seedling
Bidirectionality: NO   Exons: FAILS   Repeats: None Noted
Promoter Utility
Trait Area: Among other uses this promoter sequence could be useful to improve:
Cold, PG&D,
Sub-trait Area: Cold germination & vigor, plant size, growth rate, plant development
Utility:
Construct: YP0060
Promoter Candidate I.D: 11768797 (Old ID: 35139885)
cDNA ID: 13613553 (Old IDs: 4282588, 12421894)
T1 lines expressing (T2 seed): SR00552-02, -03

TABLE 2-continued

Promoter Expression Report # 13

Report Date: Mar. 6, 2003
Promoter Tested In: *Arabidopsis thaliana*, WS ecotype
Spatial expression summary:
Ovule                        Post-fertilization: (H)endothelium, (H)micropyle, (H)chalaza
Observed expression pattern: T1 and T2 mature: Strong expression was seen in the mature inner integument
cell layer, endothelium, micropyle and chalaza ends of maturing ovules.
Expression was not detected in earlier stage ovules. T2 and T3 seedling expression: None
Expected expression pattern: Primarily in developing seeds
Selection Criteria: *Arabidopsis* public; Mol. Gen. Genet. 244, 572-587 (1994)
Gene: plasma membrane H(+)-ATPase isoform AHA10;
GenBank: NM_101587 *Arabidopsis thaliana* ATPase 10, plasma membrane-
type (proton pump 10) (proton-exporting ATPase), putative (At1g17260) mRNA, complete cds, gi|18394459|
Source Promoter Organism: *Arabidopsis thaliana* WS
Vector:                     pNewbin4-HAP1-GFP.
Marker Type:           X GFP-ER
Generation Screened:     X T1 Mature   X T2 Seedling   X T3 Mature   X T3 Seedling
Bidirectionality: FAILS    Exons: FAILS    Repeats: None Note
Trait Area: Among other uses this promoter sequence could be useful to improve:
Seed - Endosperm cell number and size, endosperm granule number/size, seed enhancement
Yield - harvest index, test weight, seed size
Quality - protein, total oil, total seed composition, composition
Utility:
Construct:                YP0092
Promoter Candidate I.D:    13148193 (Old ID: 35139598)
cDNA ID               12661844 (Old ID: 4993117)
T1 lines expressing (T2 seed):   SR00639-01, -02, -03

Promoter Expression Report # 14

Report Date: Mar. 6, 2003
Promoter Tested In: *Arabidopsis thaliana*, WS ecotype
Spatial expression summary:
Flower                    (L)silique
Silique                  (L)medial vasculature, (L)lateral vasculature
Observed expression pattern: GFP expressed in the medial and lateral vasculature of pre-fertilized siliques.
Expression was not detected in the older siliques or in T2 seedlings. T2 mature: Weak silique vasculature
expression was seen in one of two events. T3 seedling: Same as T2 seedling, no expression was seen.
Expected expression pattern: Expression in ovules
Selection Criteria: Greater than 50x up in pi ovule microarray
Gene: expressed protein; protein id: At4g15750.1, hypothetical protein
GenBank: NM_117666 *Arabidopsis thaliana* expressed protein (At4g15750) mRNA,
complete cds gi|18414516|ref|NM_117666.1|[18414516]
Source Promoter Organism: *Arabidopsis thaliana* WS
Vector:                    pNewbin4-HAP1-GFP
Marker Type:          X GFP-ER
Lines Screened:        n = 3
Lines Expressing:      n = 3
Generation Screened:     X T1 Mature   X T2 Seedling   X T3 Mature   X T3 Seedling
Bidirectionality: NO    Exons: NO    Repeats: None Noted
Promoter utility
Trait - Sub-trait Area: Among other uses this promoter sequence could be useful to improve:
Water use efficiency - Moisture stress at seed set, Moisture stress at seed fill, water use efficiency,
Ovule/seed abortion
Seed - test weight, seed size
Yield - harvest index, total yield
Quality - amino acids, carbohydrate, protein, total oil, total seed composition
Construct:                YP0113
Promoter Candidate I.D:    13148162 (Old ID: 35139698)
cDNA ID:              12332135 (Old ID: 5663809)
T1 lines expressing (T2 seed):   SR00691-01, -03

Promoter Expression Report # 15

Report Date: Mar. 6, 2003
Promoter Tested In: *Arabidopsis thaliana*, WS ecotype
Spatial expression summary:
Flower                    (L)silique
Silique                  (L)medial vasculature, (L)lateral vasculature, (H)guard cells
Rosette leaf            (H)guard cell
Observed expression pattern: GFP expressed in the medial and lateral vasculature of pre-fertilized siliques.
Expression was not detected in older siliques. Guard cell expression was seen throughout pre-fertilized and
fertilized siliques. T2 seedling: No expression was seen. T2 mature expression: Similar to T1 mature
expression. T3 seedling: Guard cell expression not seen in T2 seedlings, however it is in the same
tissue type observed in mature plants of previous generation.
Expected expression pattern: Strong activity in the inner endosperm tissue of developing seeds and weak
activity in root tips.
Selection Criteria: *Arabidopsis* public; Plant Mol. Biol. 39, 149-159 (1999)

TABLE 2-continued

Gene: Alanine aminotransferase, AlaAT
GenBank: NM_103859 *Arabidopsis thaliana* abscisic acid responsive elements-binding factor (At1g49720) mRNA, complete cds gi|30694628|ref|NM_103859.2|[30694628]
INCORRECT (L. M. 10/14/03)
AAK92629 - CORRECT (L. M 10/14/03)
Putative alanine aminotransferase [*Oryza sativa*]
gi|15217285|gb|AAK92629.1|AC079633_9[15217285]
Source Promoter Organism: Rice
Vector: pNewbin4-HAP1-GFP.
Marker Type: X GFP-ER
Generation Screened: X T1 Mature   X T2 Seedling   X T3 Mature   X T3 Seedling
Bidirectionality: NO   Exons: NO   Repeats: None Noted
Promoter utility
Trait Area: Among other uses this promoter sequence could be useful to improve:
Seed, source, yield, quality
Sub-trait Area: Seed enhancement, transport amino acids, harvest index, test weight, seed size, amino acids, carbohydrate, protein, total seed composition
Construct: YP0095
Promoter Candidate ID: 13148198 (Old ID: 35139658)
cDNA ID: 6795099 in rice
T1 lines expressing (T2 seed): SR00642-02, -03

Promoter Expression Report # 16

Report Date: Mar. 6, 2003
Promoter Tested In: *Arabidopsis thaliana*, WS ecotype
Spatial expression summary:
Ovule                Pre-fertilization: (M)gametophyte, (M)embryo sac
Root                 (H)epidermis, (M)pericycle, (H)root hairs
Lateral root         (H)flanking cells
Observed expression patterns: GFP expressed in the egg cell and synergid cell of female gametophyte in early ovule development. It expressed in polarizing embryo sac in later stages of pre-fertilized ovule development. No expression was seen in fertilized ovules. GFP expressed throughout the epidermal cells of seedling roots. It also expressed in flanking cells of lateral root primordia.
T2 mature: Same as T1 mature. T3 seedling: Same as T2 seedling
Expected expression pattern: Expression in ovules
Selection Criteria: Greater than 50x up in pi ovule microarray
Gene: Senescence-associated protein homolog
GenBank: NM_119189 *Arabidopsis thaliana* senescence-associated protein family (At4g30430) mRNA, complete cds, gi|18417592|ref|NM_119189.1|[18417592]
Source Promoter Organism: *Arabidopsis thaliana* WS
Vector: pNewbin4-HAP1-GFP
Marker Type: X GFP-ER
Generation Screened: XT1 Mature   X T2 Seedling   X T3 Mature   X T3 Seedling
Bidirectionality: NO   Exons: NO   Repeats: None Noted
Promoter utility
Trait Area: Among other uses this promoter sequence could be useful to improve:
Water use efficiency, seed, yield
Sub-trait Area: Moisture stress, water use efficiency, ovule/seed abortion, harvest index, test weight, seed size, total yield, amino acids, carbohydrate, proteintotail oil, total seed composition
Construct: YP0102
Promoter Candidate I.D: 11768651 (Old ID: 35139696)
cDNA ID: 13613954 (Old IDs: 12329268, 1382001)
T1 lines expressing (T2 seed): SR00643-01, -02

Promoter Expression Report # 17

Report Date: Mar. 6, 2003
Promoter Tested In: *Arabidopsis thaliana*, WS ecotype
Spatial expression summary:
Ovule                Pre-fertilization: (H)inner integument
                     Post-fertilization: (H)inner integument, (M)outer integument,
                     (M)seed coat
Primary Root         (L)root hair
Observed expression pattern: GFP expressed in the inner integuments of pre-fertilized and fertilized ovules. Female gametophyte vacuole seen as dark oval. T2 mature: Same expression was seen as T1 with additional expression observed in similar tissue. GFP expressed in the outer integument and seed coat of developing ovules and seed. T3 seedling expression: GFP expression was seen in a few root hairs.
Expected expression pattern: Expression in ovules
Selection Criteria: Greater than 50x up in pi ovule microarray
Gene: putative protease inhibitor
GenBank: NM_129447 *Arabidopsis thaliana* protease inhibitor - related (At2g38900) mRNA, complete cds, gi|30687699|ref|NM_129447.2|[30687699]
Source Promoter Organism: *Arabidopsis thaliana* WS
Vector: pNewbin4-HAP1-GFP
Marker Type: X GFP-ER
Generation Screened: X T1 Mature   X T2 Seedling   X T3 Mature   X T3 Seedling
Bidirectionality: NO   Exons: FAILS   Repeats: None Noted
Promoter utility TABLE 2-continued Trait Area: Among other uses this promoter sequence could be useful to improve:
Water use efficency, seed, yield
Sub-trait Area: Moisture stress, water use efficiency, ovule/seed abortion, harvest index, test weight, seed size,
total yield, amino acids, carbohydrate, proteintotail oil, total seed composition.
Construct: YP0103
Promoter Candidate I.D: 13148199 (Old ID: 35139718)
cDNA ID: 4905097 (Old ID: 12322121, 1387372)
T1 lines expressing (T2 seed): SR00709-01, -02, -03

Promoter Expression Report # 18

Report Date: Mar. 6, 2003
Promoter Tested In: *Arabidopsis thaliana*, WS ecotype
Spatial expression summary:
Embryo (H)mature, (H)late
Ovule (H)endothelium
Primary root (L)root hair
Observed expression pattern: Low levels of GFP expression were detected in late torpedo stage with highest
levels in the mature and late embryo. High GFP expression was detected in late endosperm stage in endothelium
layer of developing seed. T2 mature: Same as T1 mature. T3 seedling: GFP was detected in a few
root hairs not observed in T2 seedlings.
Expected expression pattern: Embryo and seed
Selection Criteria: *Arabidopsis* public; Rossak, M. Plant Mol. Bio. 2001.46:717
Gene: fatty acid elongase 1; FAE1
GenBank: NM_119617 *Arabidopsis thaliana* fatty acid elongase 1 (FAE1)
(At4g34520) mRNA, complete cds, gi|30690063|ref|NM_119617.2|[30690063]
Source Promoter Organism: *Arabidopsis thaliana* WS
Vector: pNewbin4-HAP1-GFP
Marker Type: X GFP-ER
Generation Screened: X T1 Mature X T2 Seedling X T2 Mature X T3 Seedling
Bidirectionality: NO Exons: NO Repeats: Not Done
Promoter utility
Trait - Sub-trait Area: Among other uses this promoter sequence could be useful to improve:
Seed - Ovule/seed abortion, seed enhancement, seed size
Yield
Construct: YP0107
Promoter Candidate I.D: 13148252 (Old ID: 35139824)
cDNA ID: 12656458 (Old ID: 1815714)
T1 lines expressing (T2 seed): SR00646-01, -02

Promoter Expression Report # 19

Report Date: Mar. 6, 2003
Promoter Tested In: *Arabidopsis thaliana*, WS ecotype
Spatial expression summary:
Ovule Pre-fertilization: (M)gametophyte, (M)embryo sac
Post-fertilization: (H)zygote
Observed expression pattern: GFP expressed in the developing female gametophyte of unfertilized ovules and the
degenerated synergid cell of the fertilized ovule hours after fertilization. No expression was observed in T2
seedlings. T2 mature: Similar expression as T1 mature. T3 seedling: Root expression in one of two events was not
observed in T2 seedlings. No expression was observed in the second line which is consistent with T2 seedling expression.
Expected expression pattern: Expression in ovules
Selection Criteria: Greater than 50x up in pi ovule microarray
Gene: Hypothetical protein
GenBank: NM_112033 *Arabidopsis thaliana* expressed protein (At3g11990)
mRNA, complete cds gi|18399438|ref|NM_112033.1|[18399438]
Source Promoter Organism: *Arabidopsis thaliana* WS
Vector: pNewbin4-HAP1-GFP
Marker Type: X GFP-ER
Generation Screened: X T1 Mature X T2 Seedling X T3 Mature X T3 Seedling
Bidirectionality: NO Exons: FAILS Repeats: None Noted
Promoter utility
Trait Area: Among other uses this promoter sequence could be useful to improve:
Water use efficiency, seed, yield
Sub-trait Area: Moisture stress, water use efficiency, ovule/seed abortion, harvest index, test weight,
seed size, total yield, amino acids, carbohydrate, proteintotail oil, total seed composition.
Construct: YP0110
Promoter Candidate I.D: 13148212 (Old ID: 35139697)
cDNA ID: 13604221 (Old IDs: 12395818, 4772042)
T1 lines expressing (T2 seed): SR00689-02, -03

Promoter Expression Report # 20

Report Date: Mar. 6, 2003
Promoter Tested In: *Arabidopsis thaliana*, WS ecotype
Spatial expression summary:
Flower (L)silique
Silique (M)medial vasculature, (M)lateral vasculature, (M)guard cells
Observed expression pattern: GFP expressed in the medial and lateral vasculature of pre-fertilized siliques.

TABLE 2-continued

Expression was not detected in older siliques. Guard cell expression was seen throughout pre-fertilized and fertilized siliques. T2 Mature: Same as T1 Mature. T2 seedling: Same as T2 seedling.
Expected expression pattern: Expression in ovules
Selection Criteria: Greater than 50x up in pi ovule microarray
Gene: hypothetical protein
GenBank: NM_104488 *Arabidopsis thaliana* hypothetical protein
(At1g56100) mRNA, complete cds gi|18405686|ref|NM_104488.1|[18405686]
Source Promoter Organism: *Arabidopsis thaliana* WS
Vector:                  pNewbin4-HAP1-GFP
Marker Type:             X GFP-ER
Generation Screened:     X T1 Mature    X T2 Seedling    X T2 Mature    X T3 Seedling
Bidirectionality: NO   Exons: FAILS   Repeats: None Noted
Promoter Utility
Trait Area: Among other uses this promoter sequence could be useful to improve:
Water use efficiency, seed, yield
Sub-trait Area: Moisture stress at seed set, moisture stress at seed fill, water use efficiency, ovule/seed abortion, harvest index, test weight, seed size, total yield, amino acids, carbohydrate, protein, total oil, total seed composition, composition
Utility:
Construct:               YP0112
Promoter Candidate I.D:  13148226 (Old ID: 35139719)
cDNA ID:                 12321680 (Old ID: 5662775)
T1 lines expressing (T2 seed):   SR00710-01, -02, -03

Promoter Expression Report # 21

Report Date: Mar. 6, 2003
Promoter Tested In: *Arabidopsis thaliana*, WS ecotype
Spatial expression summary:
Silique                  (H)stigma, (H)transmitting tissue
Observed expression pattern: GFP expression was seen in the stigma and pollen transmitting tract spanning the entire silique. No expression was detected in the T2 seedlings.
T2 Mature: Same as T1. T3 seedlings: No data
Expected expression pattern: Expression in ovules
Selection Criteria: Greater than 50x up in pi ovule microarray
Gene: putative drought induced protein
GenBank: NM_105888 *Arabidopsis thaliana* drought induced protein - related (At1g72290) mRNA, complete cds
gi|18410044|ref|NM_105888.1|[18410044]
Source Promoter Organism: *Arabidopsis thaliana* WS
Vector:                  pNewbin4-HAP1-GFP
Marker Type:             X GFP-ER
Generation Screened:     X T1 Mature    X T2 Seedling    X T3 Mature    X T3 Seedling
Bidirectionality: NO   Exons: NO   Repeats: None Noted
Promoter utility
Trait - Sub-trait Area: Among other uses, this promoter sequence could be useful to improve:
Water use efficiency - Moisture stress at seed set, Moisture stress at seed fill, water use efficiency, Ovule/seed abortion
Utility: Interesting to think about using this promoter to drive a gene that would select against a specific pollen type in a hybrid situation.
Construct:               YP0116
Promoter Candidate I.D:  13148262 (Old ID: 35139699)
cDNA ID:                 12325134 (Old ID: 6403538)
T1 lines expressing (T2 seed):   SR00693-02, -03

Promoter Expression Report # 22

Report Date: Mar. 8, 2003
Promoter Tested In: *Arabidopsis thaliana*, WS ecotype
Spatial expression summary:
Flower                   (H)pedicle
Silique                  (M)vascular
Stem                     (H)cortex
Ovule                    Pre-fertilization: (H)outer integument, (M)chalaza
Hypocotyl                (H)cortex
Root                     (H)epidermis, (H)atrichoblast, (H)cortex
Observed expression pattern:
Strong GFP expression was seen in the adaxial surface of the pedicel and secondary inflorescence meristem internodes. High magnification reveals expression in 2-3 cell layers of the cortex. GFP expressed in the vasculature of silique, inner integuments, and chalazal region of ovule. Expression was highest in the outer integuments of pre-fertilized ovules decreasing to a few cells at the micropylar pole at maturity. Specific expression was in the chalazal bulb region where mineral deposits are thought to be accumulated for seed storage. GFP expressed in 2 cortical cell layers of the hypocotyl from root transition zone to apex. At the apex, GFP is expressed at the base of the leaf primordial and cotyledon. Root expression is specific to the epidermis and cortex. T2 Mature: Same as T1 mature. T3 seedling: Same expression as in T2 seedlings. Expression is different in one seedling which has with weak root epidermal, weak hypocotyl and stronger lateral root expression. This expression is variable within siblings in this family.
Expected expression pattern: Expressed in ovules and different parts of seeds
Selection Criteria: Greater than 50x up in pi ovule microarray
Gene: hypothetical protein T20K18.24
GenBank: NM_117358 *Arabidopsis thaliana* expressed protein (At4g12890)

TABLE 2-continued mRNA, complete cds gi|30682271|ref|NM_117358.2|[30682271]
Source Promoter Organism: *Arabidopsis thaliana* WS
Vector:                        pNewbin4-HAP1-GFP
Marker Type:                   X GFP-ER
Generation Screened:           X T1 Mature    X T2 Seedling    X T2 Mature    X T3 Seedling
Bidirectionality: NO    Exons: NO    Repeats: NO
Promoter utility
Trait - Sub-trait Area: Among other uses this promoter sequence could be useful to improve:
Water use efficiency - Moisture stress at seed set, Moisture stress at seed fill, water use efficiency, ovule/seed abortion
Seed - harvest index, test weight, seed size
Yield - total yield
Quality - amino acids, carbohydrate, protein, total oil, total seed composition
Construct:                     YP0117
Promoter Candidate I.D:        11768655 (Old ID: 35139700)
cDNA I.D:                      13617054 (Old IDs: 12322571, 7074452)
T1 lines expressing (T2 seed): SR00694-01, -02

Promoter Expression Report # 23

Report Date: Mar. 8, 2003
Promoter Tested In: *Arabidopsis thaliana*, WS ecotype
Spatial expression summary:
Flower                         (L)silique
Silique                        (L)carpel, (L)vascular
Observed expression pattern: Low levels of GFP expressed in the medial and lateral vasculature of developing
pre-fertilized siliques.
T2 mature: No Expression. T3 seedling: No Expression.
Expected expression pattern: Expressed in ovules and different parts of seeds.
Selection Criteria: Greater than 50x up in pi ovule microarray
Gene: Putative vacuolar processing enzyme
GenBank: NM_112912 *Arabidopsis thaliana* vacuolar processing enzyme/asparaginyl endopeptidase - related
(At3g20210) mRNA, complete cds gi|30685671|ref|NM_112912.2|[30685671]
Source Promoter Organism: *Arabidopsis thaliana* WS
Vector:                        pNewbin4-HAP1-GFP
Marker Type:                   X GFP-ER
Generation Screened:           X T1 Mature    X T2 Seedling    X T2 Mature    X T3 Seedling
Bidirectionality: NO    Exons: NO    Repeats: None Noted
Promoter utility
Trait Area: Among other uses this promoter sequence could be useful to improve:
Water use efficiency - Moisture stress at seed set, Moisture stress at seed fill, water use efficiency, ovule/seed abortion
Seed - harvest index, test weight, seed size
Yield - total yield
Quality - amino acids, carbohydrate, protein, total oil, total seed composition
Construct:                     YP0118
Promoter Candidate I.D:        11768691 (Old ID: 35139754)
cDNA I.D:                      12329827 (Old ID: 4908806)
T1 lines expressing (T2 seed): SR00711-01, -02, -03

Promoter Expression Report # 24

Report Date: Mar. 9, 2003
Promoter Tested In: *Arabidopsis thaliana*, WS ecotype
Spatial expression summary:
Flower                         sepal, petal, silique
Silique                        epidermis
Leaf                           mesophyll, vascular, epidermis, margin
Hypocotyl                      epidermis
Cotyledon                      mesophyll, vascular epidermis
Observed expression pattern: Screened under non-induced conditions. Strong GFP expression was seen in
epidermal and vasculature tissue of mature floral organs and leaves including photosynthetic cells. GFP is expressed
in two cell layers of the margin and throughout mesophyll cells of mature leaf. GFP expressed in the epidermal cells
of hypocotyl and cotyledons and mesophyll cells. GFP expression in the leaf is non guard cell, epidermal specific.
Expected expression pattern: N induced, source tissue.
Selection Criteria: *arabidopsis* microarray-nitrogen
Gene: hypothetical protein, auxin-induced protein-like
GenBank: NM_120044 *Arabidopsis thaliana* auxin-induced (indole-3-acetic acid induced) protein,
putative (At4g38840) mRNA, complete cds gi|18420319|ref|NM_120044.1|[18420319]
Source Promoter Organism: *Arabidopsis thaliana* WS
Vector:                        pNewbin4-Hap1-GFP
Marker Type:                   X GFP-ER
Generation Screened:           XT1 Mature    X T2 Seedling    X T3 Mature    X T3 Seedling
Bidirectionality: FAILS    Exons: FAILS    Repeats: None Noted
Promoter utility
Trait - Sub-trait Area: Among other uses this promoter sequence could be useful to improve:
Source - Photosynthetic efficiency
Yield - seed size TABLE 2-continued Construct: YP0126
Promoter Candidate I.D: 11768662 (Old ID: 35139721)
cDNA ID: 12713856 (Old IDs: 12580379, 4767659)
T1 lines expressing (T2 seed): SR00715-01, -02

Promoter Expression Report # 25

Report date: Mar. 23, 2003
Promoter Tested In: *Arabidopsis thaliana*, WS ecotype
Spatial expression summary:
Flower (H)sepal, (H)anther
Silique (M)vascular
Ovule Post-fertilization: (M)inner integument, (M)chalaza, (M)micropyle
Stem (H)Pith
Hypocotyl (H)phloem
Cotyledon (M)epidermis
Rosette Leaf (H)hydathode
Primary Root (H)phloem, (H)pericycle
Lateral root (H)phloem
Observed expression pattern: Expressed in the vasculature of sepal and connective tissue of anthers in pre-fertilized flowers, inner integuments restricted to micropyle region, and chalazal bulb of post-fertilized ovules. GFP expressed throughout the phloem of hypocotyl and root and in pericycle cells in root differentiation zone. Screened under non-induced conditions.
T2 mature: Same expression as observed in T1 mature. In addition, silique vascular expression was not observed in T1 mature.T3 seedling: Same expression as observed in T2 seedlings. In addition, expression was observed in cotyledon epidermal and rosette leaf hydathode secretory gland cells.
Expected expression pattern: nitrogen induced
Selection Criteria: *Arabidopsis* microarray
Gene: probable auxin-induced protein
GenBank: NM_119918 *Arabidopsis thaliana* lateral organ boundaries (LOB)
domain family (At4g37540) mRNA, complete cds gi|18420067|ref|NM_119918.1|[18420067]
Source Promoter Organism: *Arabidopsis thaliana* WS
Vector: pNewBin4-HAP1-GFP
Marker Type: X GFP-ER
Generation Screened: X T1 Mature   X T2 Seedling   X T2 Mature   X T3 Seedling
Bidirectionality: NO   Exons: NO   Repeats: None Noted
Promoter Utility
Trait - Sub-trait Area: Among other uses this promoter sequence could be useful to improve:
Source - Photosynthetic efficiency
Yield - seed size
Utility:
Construct: YP0127
Promoter Candidate I.D: 13148197 (Old ID: 11768663)
cDNA I.D: 13617784 (Old IDs: 12712729, 4771741)
T1 lines expressing (T2 seed): SR00716-01, -02

Promoter Expression Report # 26

Report Date: Mar. 17, 2003
Promoter Tested In: *Arabidopsis thaliana*, WS ecotype
Spatial expression summary:
Silique (L)vascular
Rosette Leaf (H)stipule
Primary Root (H)trichoblast, (H)atrichoblast
Cotyledon (L)hydathode
Observed expression pattern: Weak expression in vasculature of pre-fertilized siliques. Expressed throughout epidermal cells of seedling root. T2 mature: Expression not confirmed. T3 seedlings: Same expression as observed in T2 seedlings. In addition, expression was observed in cotyledon epidermal and hydathode secretory gland cells.
Expected expression pattern: Inducible promoter - induced by different forms of stress (e.g., drought, heat, cold).
Selection Criteria: *Arabidopsis* microarray-Nitrogen
Gene: similar to SP|P30986 reticuline oxidase precursor (Berberine-bridge-forming enzyme; Tetrahydroprotoberberine synthase) contains PF01565 FAD binding domain"
product = "FAD-linked oxidoreductase family"
GenBank: NM_102808 *Arabidopsis thaliana* FAD-linked oxidoreductase family
(At1g30720) mRNA, complete cds gi|30692034|ref|NM_102808.2|[30692034]
Source Promoter Organism: *Arabidopsis thaliana* WS
Vector: pNewBin4-HAP1-GFP
Marker Type: X GFP-ER
Generation Screened: XT1 Mature   X T2 Seedling   X T2 Mature   X T3 Seedling
Bidirectionality: NO   Exons: NO   Repeats: NO
Promoter utility
Trait - Sub-trait Area: Among other uses this promoter sequence could be useful to improve:
Water use efficiency - Heat
Utility: This promoter is useful for root nutrient uptake.
Construct: YP0128
Promoter Candidate I.D: 13148257 (Old ID: 11769664)
cDNA I.D: 13610584 (Old IDs: 12327909, 4807730)
T1 lines expressing (T2 seed): SR00717-01, -02

TABLE 2-continued

Promoter Expression Report # 27

Report Date: Mar. 23, 2003
Promoter Tested In: *Arabidopsis thaliana*, WS ecotype
Spatial expression summary:
Flower                    (L)stomata
Silique                   (M)stomata
Stem                      (L)stomata
Cotyledon                 (L)mesophyll, (L)vascular, (M)hydathode
Rosette Leaf              (H)stomata, (H)hydathode
Primary Root              (L)root hairs
Observed expression pattern: Expression specific to upper root hairs at hypocotyl root transition zone and
hydathode secretory cells of the distal cotyledon.
T1 mature: No T1 mature expression by old screening protocol
T2 mature: Guard cell and Hydathode expression same as T1 mature expression (new protocol), T2 and T3 seedling expression.
Expected expression pattern: Shoot and root meristem
Selection Criteria: Literature. Plant Cell 1998 10 231-243
Gene: CYP90B1, *Arabidopsis* steroid 22-alpha-hydroxylase (DWF4)
GenBank: NM_113917 *Arabidopsis thaliana* cytochrome p450, putative (At3g30180) mRNA, complete cds
gi|30689806|ref|NM_113917.2|[30689806]
Source Promoter Organism: *Arabidopsis thaliana* WS
Vector:                   pNewBin4-HAP1-GFP
Marker Type:              X GFP-ER
Generation Screened:      XT1 Mature    XT2 Seedling    X T2 Mature    X T3 Seedling
Bidirectionality: NO    Exons: NO    Repeats: None Noted
Promoter utility
Trait - Sub-trait Area: Among other uses, this promoter sequence could be useful to improve:
PG&D - Plant size, growth rate
Utility: Useful to increase biomass, root mass, growth rate, seed set
Construct:                YP0020
Promoter Candidate I.D:   11768639 (Old ID: 11768639)
cDNA I.D:                 12576899 (Old ID: 7104529)
T1 lines expressing (T2 seed): SR00490-01, -02, -03, -04

Promoter Expression Report # 28

Report Date: Mar. 23, 2003
Promoter Tested In: *Arabidopsis thaliana*, WS ecotype
Spatial expression summary:
Flower                    (L)pedicel, (M)vascular
Stem                      (H)vascular, (H)pith
Silique                   (H)septum, (H)vascular
Cotyledon                 (H)vascular, (H)epidermis
Rosette Leaf              (H)vascular, (H)phloem
Primary Root              (H)vascular; (H)phloem
Lateral root              (H)vascular
Observed expression pattern: T1 mature (old protocol - screened target tissue): No expression observed. T2
seedling: Strong expression throughout phloem of hypocotyl, cotyledons, primary rosette leaves and roots. Also
found in epidermal cells of upper root hairs at root transition zone. GFP expressed in a few epidermal cells of distal cotyledon.
T1 mature: (new protocol - screened all tissues): High expression found in silique vasculature. T2 mature: Strong
expression detected in inflorescence meristem and silique medial vasculature. T3 seedling: Same expression as T2
seedlings, however no cotyledon vascular expression was detected.
Expected expression pattern: Shoot and root meristem
Selection Criteria: Plant Physiol. 2002 129:1241-51
Gene: brassinosteroid-regulated protein (xyloglucan endotransglycosylase related protein
GenBank: NM_117490 *Arabidopsis thaliana* xyloglucan endotransglycosylase (XTR7)
(At4g14130) mRNA, complete cds gi|30682721|ref|NM_117490.2|[30682721]
Source Promoter Organism: *Arabidopsis thaliana* WS
Vector:                   pNewBin4-HAP1-GFP
Marker Type:              X GFP-ER
Generation Screened:      X T1 Mature    XT2 Seedling    X T2 Mature    X T3 Seedling
Bidirectionality: NO    Exons: NO    Repeats: None Noted
Promoter utility
Trait Area: Among other uses this promoter sequence could be useful to improve:
PG&D - Plant size, growth rate
Utility: Useful to increase biomass, root mass, growth rate
Construct:                YP0022
Promoter Candidate I.D:   11768614
cDNA I.D:                 12711515 (Old ID: 5674312)
T1 lines expressing (T2 seed): SR00492-02, -03

Promoter Expression Report # 29

Report Date: Mar. 23, 2003
Promoter Tested In: *Arabidopsis thaliana*, WS ecotype
Spatial expression summary:
Flower                    (M)sepal, (L)stomata
Silique                   (M)stomata

TABLE 2-continued

Rosette Leaf (H)stomata
Primary Root (H)epidermis, (H)trichoblast, (H)root hair
Observed expression pattern: Strong GFP expression in stomata of primary rosette leaves and epidermal root hair trichoblast cells of seedlings. T1 mature: No expression observed. T2 seedling: Same as T2 seedling expression. T2 mature: Guard cell and weak vascular expression in flowers.
Expected expression pattern: embryo
Selection Criteria: Plant J 2000 21:143-55
Gene: ABI3 - interacting protein 2. AIP2 [*Arabidopsis thaliana*]
GenBank: NM_122099 *Arabidopsis thaliana* zinc finger (C3HC4-type
RING finger) protein family (At5g20910) mRNA, complete cds gi|30688046|ref|NM_122099.2|[30688046]
Source Promoter Organism: *Arabidopsis thaliana*, WS
Vector: pNewBin4-HAP1-GFP
Marker Type: X GFP-ER
Generation Screened: X T1 Mature   X T2 Seedling   X T2 Mature   X T3 Seedling
Bidirectionality: NO   Exons: FAILS   Repeats: None Noted
Promoter utility
Trait - Sub-trait Area: Among other uses this promoter sequence could be useful to improve:
Water use efficiency - Drought, heat
Utility: This promoter might be useful for enhancing recovery after growth under water deprivation
Also could be useful for nutrition uptake
Construct: YP0024
Promoter Candidate I.D: 11768616
cDNA I.D: 13614559 (Old IDs: 12324998, 5675795)
T1 lines expressing (T2 seed): SR00494-01, -03

Promoter Expression Report # 30

Report Date: Mar. 17, 2003
Promoter Tested In: *Arabidopsis thaliana*, WS ecotype
Spatial expression summary:
Silique (H)ovule
Ovule Pre-fertilization: (H)outer integument, (H)funiculus
 Post-fertilization: (H)outer integument, (H)funiculus
Rosette Leaf (H)vascular
Primary Root (H)epidermis, (H)trichoblast, (H)root hair
Lateral root (H)pericycle
Observed expression pattern: Strong GFP expression in upper root hairs at root transition zone and in distal vascular bundle of cotyledon. Low expression in pericycle cells of seedling root. T1 mature: No expression observed. T3 seedling: Same as T2 seedling expression. T2 mature: GFP expression in funiculus of ovules as in connective tissue between locules of anther.
Expected expression pattern: Root vasculature
Selection Criteria: Helariutta, et al. 2000 Cell 101:555-567
Gene: SHR (Short-root gene)
GenBank: NM_119928 *Arabidopsis thaliana* short-root transcription factor (SHR) (At4g37650) mRNA, complete cds gi|30691190|ref|NM_119928.2|[30691190]
Source Promoter Organism: *Arabidopsis thaliana* WS
Vector: pNewBin4-HAP1-GFP
Marker Type: X GFP-ER
Generation Screened: X T1 Mature   X T2 Seedling   X T2 Mature   X T3 Seedling
Bidirectionality: NO   Exons: NO   Repeats: None Noted
Promoter utility
Trait - Sub-trait Area: Among other uses this promoter sequence could be useful to improve:
Water use efficiency - Increase leaf water potential
PG&D - increase root biomass, plant size
Nutrient - nitrogen use efficiency, nitrogen utilization, low nitrogen tolerance
Construct: YP0028
Promoter Candidate I.D: 11768648
cDNA I.D: 12561142 (Old ID: 7093615)
T1 lines expressing (T2 seed): SR00586-03, -04
Utility: This promoter might be a good promoter for root nutrition uptake, root biomass.

Promoter Expression Report # 31

Report Date: Mar. 23, 2003
Promoter Tested In: *Arabidopsis thaliana*, WS ecotype
Spatial expression summary:
Flower (L)stomata
Primary Root (H)epidermis, (H)trichoblast, (H)atrichoblast, (H)root hairs
Observed expression pattern: Strong GFP expression specific to epidermal root hair trichoblast and atrichoblast cells throughout seedling root. Not expressed in lateral root.
T1 mature: No expression observed. T2 mature: Low guard cell expression in flower not observed in T1 mature.
T3 seedling expression: Same as T2 seedlings.
Expected expression pattern: localized to the lateral root cap, root hairs, epidermis and cortex of roots.
Selection Criteria: *Arabidopsis* public; The roles of three functional sulfate transporters involved in uptake and translocation of sulfate in *Arabidopsis thaliana*. Plant J. 2000 23:171-82
Gene: Sulfate transporter
GenBank: NM_116931 *Arabidopsis thaliana* sulfate transporter - related
(At4g08620) mRNA, complete cds gi|30680813|ref|NM_116931.2|[30680813]
Source Promoter Organism: *Arabidopsis thaliana* WS

TABLE 2-continued

Vector: pNewBin4-HAP1-GFP
Marker Type: X GFP-ER
Generation Screened: XT1 Mature   XT2 Seedling   X T2 Mature   X T3 Seedling
Bidirectionality: NO   Exons: NO   Repeats: None Noted
Promoter utility
Sub-trait Area: Among other uses this promoter sequence could be useful to improve:
Water use efficiency - Water potential, drought, moisture stress at seed set and seed fill, water use efficiency
Nutrient - nitrogen use efficiency
Utility: This is good promoter root nutrient uptake, increase root mass and water use efficiency
Construct: YP0030
Promoter Candidate I.D: 11768642
cDNA I.D: 12664333 (Old ID: 7079065)
T1 lines expressing (T2 seed): SR00545-01, -02

Promoter Expression Report # 32

Report Date: Mar. 24, 2003
Promoter Tested In: *Arabidopsis thaliana*, WS ecotype
Spatial expression summary:
Cotyledon              (L)epidermis
Primary Root           (H)epidermis, (H)trichoblast, (H)atrichoblast
Observed expression pattern: High GFP expression in epidermal cells of seedling root from hypocotyl root
transition to differentiation zone. Not observed in root tip. Low GFP expression in epidermal cells of distal cotyledon.
T1 mature: No expression detected. T2 mature: Guard cell expression in stem, pedicles. Low silique vascular
expression. T3 seedling: Same as T2 seedlings.
Expected expression pattern: predominantly expressed in the phloem
Selection Criteria: Ceres microarray data
Gene: putative glucosyltransferase [*Arabidopsis thaliana*]
GenBank: BT010327 *Arabidopsis thaliana* At2g43820 mRNA, complete cds gi|33942050|gb|BT010327.1|[33942050]
Source Promoter Organism: *Arabidopsis thaliana* WS
Vector: pNewBin4-HAP1-GFP
Marker Type: X GFP-ER
Generation Screened: X T1 Mature   XT2 Seedling   X T2 Mature   X T3 Seedling
Bidirectionality: NO   Exons: NO   Repeats: None Noted
Promoter utility
Trait - Sub-trait Area: Among other uses this promoter sequence could be useful to improve:
Nutrient - nitrogen and phosphate uptake and transport
Growth and Development - plant size, growth rate
Utility: Promoter should be useful where expression in the root epidermis is important. Expression
appears to be in expanded or differentiated epidermal cells.
Construct: YP0054
Promoter I.D: 13148233 (Old ID: 11768644)
cDNA I.D: 12348737 (Old ID: 1609253)
T1 lines expressing (T2 seed): SR00549-01, -02

Promoter Expression Report # 34

Report Date: Jan. 31, 2003
Promoter Tested In: *Arabidopsis thaliana*, WS ecotype
Spatial expression summary:
Flower                 (M)sepal, (M)style, (M)epidermis
Stem                   (M)epidermis, (H)endodermis, (H)cortex
Leaf                   (H)mesophyll, (H)epidermis
Hypocotyl              (H)epidermis, (H)vascular
Cotyledon              (H)epidermis, (H)mesophyll
Primary Root           (H)epidermis, (H)trichoblast, (H)atrichoblast, (H)vascular phloem,
                       (H)Root cap, (H)root hairs
Lateral root           (H)vascular, (H)cap
Observed expression pattern: GFP expressed in sepals, style of silique in immature flowers, mesophyll,
and epidermis of mature leaves. GFP expressed throughout epidermal layers of seedling including root
tissue. Also expressed in mesophyll and epidermal tissue in distal primary leaf, and vasculature of root.
Specific expression in meristematic zone of primary and lateral root.
T2 Mature: Same expression as
T1 mature: Additional images taken of stem expression.
T3 Seedling expression: Same as T2 seedling expression.
Expected expression pattern: Shoot apical meristem
Selection Criteria: Greater than 5x down in stm microarray
Gene: Fructose-bisphosphate aldolase
GenBank: NM_118786 *Arabidopsis thaliana* fructose-bisphosphate aldolase,
putative (At4g26530) mRNA, complete cds gi|30687252|ref|NM_118786.2|[30687252]
Source Promoter Organism: *Arabidopsis thaliana* WS
Vector: pNewBin4-HAP1-GFP
Marker Type: X GFP-ER
Generation Screened: X T1 Mature   X T2 Seedling   X T2 Mature   X T3 Seedling
Bidirectionality: NO??   Exons: NO??   Repeats: None Noted
Promoter Utility
Trait - Sub-trait Area: Among other uses this promoter sequence could be useful to improve:
PG&D - Plant size, growth rate, plant development
Water use efficiency -

TABLE 2-continued

Utility:
Construct: YP0050
Promoter Candidate I.D: 13148170 (Old ID: 11768794)
cDNA I.D: 4909806 (Old IDs: 12340148, 1017738)
T1 lines expressing (T2 seed): SR00543-01, -02

Promoter Expression Report # 35

Report Date: Mar. 24, 2003
Promoter Tested In: *Arabidopsis thaliana*, WS ecotype
Spatial expression summary:
Flower            (H)pedicel, (H)anther, (H)pollen, (H)vascular, (H)epidermis
Stem              (H)cortex, (L)vascular
Hypocotyl         (H)epidermis, (H)vascular, (H)phloem
Cotyledon         (H)vascular
Primary Root      (H)vascular, (H)phloem, (H)pericycle
Observed expression pattern: High GFP expression throughout seedling vasculature including root. Low
Expression at the base of hypocotyls. Not detected in rosette leaves. T1 mature: No expression observed. T3
seedling: Same as T2 seedling expression. T2 mature: Strong vascular and epidermal expression in floral pedicels
and in developing pollen sacs of anthers.
Expected expression pattern: xylem parenchyma cells of roots and leaves and in the root pericycles and leaf phloem.
Selection Criteria: *Arabidopsis* public; The roles of three functional sulfate transporters involved in uptake and
translocation of sulfate in *Arabidopsis thaliana*. Plant J. 2000 23:171-82
Gene: Sulfate transport
GenBank: NM_121056 *Arabidopsis thaliana* sulfate transporter (At5g10180) mRNA,
complete cds gi|30683048|ref|NM_121056.2|[30683048]
Source Promoter Organism: *Arabidopsis thaliana* WS
Vector:           pNewBin4-HAP1-GFP
Marker Type:      X GFP-ER
Generation Screened:    XT1 Mature   X T2 Seedling   X T2 Mature   X T3 Seedling
Bidirectionality: NO   Exons: NO   Repeats: None Noted
Promoter utility
Trait Area: Among other uses this promoter sequence could be useful to improve:
Water use efficiency -
Nutrient - nitrogen use, Nutrient efficiency
Plant Growth and Development - growth rate
Utility: Useful for root nutrient uptake and metabolism manipulation
Construct: YP0040
Promoter Candidate I.D: 11768694
cDNA I.D: 12670159 (Old ID: 11020088)
T1 lines expressing (T2 seed): SR00588-01, -02, -03

Promoter Expression Report # 37

Report Date: Jan. 31, 2003
Promoter Tested In: *Arabidopsis thaliana*, WS ecotype
Spatial expression summary:
Flower            (L)pedicel, (L)stomata
Stem              (L)stomata
Leaf              (L)vascular, (L)stomata
Cotyledon         (H)mesophyll, (H)vascular, (H)epidermis
Primary Root      (H)root hairs
Observed expression pattern: Low GFP expression in stomatal cells of stem, pedicels, and vasculature of leaves
in mature plants. High GFP expression in root hairs, epidermis and mesophyll cells of seedling cotyledon. Not seen in rosette leaves.
T2 mature: Same as T1 mature expression.
T3 seedling: Same as T2 seedling expression.
Expected expression pattern: Constitutively expressed in all green tissues
Selection Criteria: *Arabidopsis* microarray
Gene: Expressed protein [*Arabidopsis thaliana*]
GenBank: NM_119524 *Arabidopsis thaliana* expressed protein (At4g33666) mRNA,
complete cds gi|30689773|ref|NM_119524.2|[30689773]
Source Promoter Organism: *Arabidopsis thaliana* WS
Vector:           pNewBin4-HAP1-GFP
Marker Type:      X GFP-ER
Generation Screened:    X T1 Mature   X T2 Seedling   XT2 Mature   X T3 Seedling
Bidirectionality:   Exons:   Repeats:
Promoter utility
Trait Area: Among other uses this promoter sequence could be useful to improve:
PG&D
Sub-trait Area: Plant size, growth rate, stay green,
Utility: Useful for C/N partitioning, photosynthetic efficiency, source enhancement and seedling establishment
Construct: YP0056
Promoter Candidate I.D: 11768645
cDNA I.D: 12396394 (Old ID: 7083850)
T1 lines expressing (T2 seed): SR00550-01

TABLE 2-continued

Promoter Expression Report # 38

Report Date: Mar. 24, 2003
Promoter Tested In: *Arabidopsis thaliana*, WS ecotype
Spatial expression summary:
Primary root                    (H)root hairs
Observed expression pattern: GFP expression specific to epidermal root hairs at hypocotyl root transition zone.
This line was not screened in T2 mature and T3 seedlings.
Expected expression pattern: Shoot apical meristem
Selection Criteria: Greater than 5x down in stm microarray
Gene: hypothetical protein
GenBank: NM_118575 *Arabidopsis thaliana* RNA recognition motif (RRM)-containing protein (At4g24420) mRNA, complete cds gi|18416342|ref|NM_118575.1|[18416342]
Source Promoter Organism: *Arabidopsis thaliana* WS
Vector:                         pNewBin4-HAP1-GFP
Marker Type:                    X GFP-ER
Generation Screened:            X T1 Mature    X T2 Seedling    T2 Mature    T3 Seedling
Bidirectionality:    Exons:    Fail Repeats:
Promoter utility
Trait Area: Among other uses this promoter sequence could be useful to improve:
Water use efficiency; Nutrient
Sub-trait Area: Plant size, growth rate, drought, water use efficiency, nitrogen utilization
Utility: early establishment of *Rhizobium* infection by increasing expression of elicitors
Construct:                      YP0068
Promoter Candidate I.D:         11768798
cDNA I.D:                       12678173 (Old ID: 1022896)
T1 lines expressing (T2 seed):  SR00598-01, -02

Promoter Expression Report # 39

Report Date: Mar. 24, 2003
Promoter Tested In: *Arabidopsis thaliana*, WS ecotype
Spatial expression summary:
Primary root                    (H)root hairs
Observed expression pattern: High GFP expression specific to epidermal root hair at hypocotyls root transition zone. Screened under non-induced condition.
T1 mature: No expression detected.
T2 mature: No expression detected.
T3 seedling: Same expression as T2 seedlings. GFP specific to root hairs.
Expected expression pattern: Heat inducible.
Selection Criteria: Expression data (full_chip) >30 fold induction at 42 C. at 1 h and 6
Gene: LMW heat shock protein - mitochondrial
GenBank: NM_118652 *Arabidopsis thaliana* mitochondrion-localized small heat shock protein (At4g25200) mRNA, complete cds gi|30686795|ref|NM_118652.2|[30686795]
Source Promoter Organism: *Arabidopsis thaliana* WS
Vector:                         pNewBin4-HAP1-GFP
Marker Type:                    X GFP-ER
Generation Screened:            X T1 Mature    X T2 Seedling    X T2 Mature    X T3 Seedling
Bidirectionality: NO    Exons: NO    Repeats: NO
Promoter utility
Trait Area: Among other uses this promoter sequence could be useful to improve:
Water use efficiency; Nutrient
Sub-trait Area: Increase plant growth or seed yield under heat stress conditions, nitrogen utilization, low N tolerance
Utility: Useful for root nutrient uptake
Construct:                      YP0082
Promoter Candidate I.D:         13148250 (Old ID: 11768604)
cDNA I.D:                       13609100 (Old IDs: 12678209, 6462494)
T1 lines expressing (T2 seed):  SR00606-01, -02, -03

Promoter Expression Report # 40

Report Date: Mar. 24, 2003
Promoter Tested In: *Arabidopsis thaliana*, WS ecotype
Spatial expression summary:
Hypocotyl                       (H)epidermis
Primary Root                    (H)epidermis, (H)trichoblast, (H)root hairs
Observed expression pattern: High GFP expression throughout epidermal layer of hypocotyl and upper root including root hairs. Not detected in lower root. No expression observed in T1 mature plants. T2 mature: No expression observed. T3 seedling: Same expression as T2 seedlings.
Expected expression pattern: Root
Selection Criteria: Genome annotation
Gene: ABI3-interacting protein 2 homolog (but recent annotation changed as hypothetical protein and promoter position is opposite orientation in the hypothetical protein, see map below); unknown protein
GenBank: NM_101286 *Arabidopsis thaliana* zinc finger (C3HC4-type RING finger) protein family (At1g14200) mRNA, complete cds gi|30683647|ref|NM_101286.2|[30683647]
Source Promoter Organism: *Arabidopsis thaliana* WS
Vector:                         pNewBin4-HAP1-GFP
Marker Type:                    X GFP-ER TABLE 2-continued Generation Screened: X T1 Mature   X T2 Seedling   X T2 Mature   X T3 Seedling
Bidirectionality: Fail   Exons: Fail   Repeats: NO
Promoter utility
Trait Area: Among other uses this promoter sequence could be useful to improve:
PG&D
Sub-trait Area: Nitrogen utilization; plant size, growth rate
Utility: Useful for nutrient uptake e.g., root hairs root epidermis
Construct: YP0019
Promoter Candidate I.D: 11768613
cDNA I.D: 4909291
T1 lines expressing (T2 seed): SR00489-01, -02

Promoter Expression Report # 42

Report Date: Mar. 22, 2003
Promoter Tested In: *Arabidopsis thaliana*, WS ecotype
Spatial expression summary:
Flower                (L)receptacle, (L)vascular
Silique               (L)vascular
Stem                  (L)vascular, (L)phloem
Primary root:         (H)phloem
Observed expression pattern: High GFP expression specific to the seedling root phloem tissue. T1 mature:
No expression was observed. T2 mature: Low expression in flower and stem vascular tissues was not observed in
T1 mature. T3 seedlings: Same vascular expression exists as T2 seedlings.
Expected expression pattern: Constitutive in all green tissues
Selection Criteria: cDNA cluster
Gene: 40S ribosomal protein S5
GenBank: NM_129283 *Arabidopsis thaliana* 40S ribosomal protein
S5 (RPS5A) (At2g37270) mRNA, complete cds gi|30687090|ref|NM_129283.2|[30687090]
Source Promoter Organism: *Arabidopsis thaliana* WS
Vector:               pNewBin4-HAP1-GFP
Marker Type:          X GFP-ER
Generation Screened:  X T1 Mature   X T2 Seedling   X T2 Mature   X T3 Seedling
Bidirectionality: NO   Exons: NO   Repeats: NO
Promoter utility
Trait Area: Among other uses this promoter sequence could be useful to improve:
PG&D, Nutrient economy
Sub-trait Area: Plant size, growth rate, low nitrogen tolerance, NUE
Utility: Useful for root nutrient uptake, source/sink relationships, root growth
Construct: YP0087
Promoter Candidate I.D: 12748731
cDNA I.D: 13580795 (Old IDs: 11006078, 12581302 )
T1 lines expressing (T2 seed): SR00583-01, -02

Promoter Expression Report # 43

Report Date: Mar. 25, 2003
Promoter Tested In: *Arabidopsis thaliana*, WS ecotype
Spatial expression summary: Screened under non-induced conditions
Flower                (H)petal, (H)epidermis, (H)anther
Stem                  (H)epidermis
Cotyledon             (H)epidermis
Hypocotyl             (L)epidermis, (L)stomata
Rosette Leaf          (L)petiole, (L)stomata
Primary Root          (H)phloem, (H)vascular
Observed expression pattern: T1 mature: High GFP expression in petals of developing to mature flowers and in
and pollen nutritive lipid rich ameboid tapetum cells in developing anthers. T2 seedling: High GFP expression in
root phloem with weak expression in epidermal tissues of seedlings. T2 mature: Same as T1 mature with
additional stem epidermal expression was not observed in T1 mature plants. T3 seedling: Same as T2 seedling,
however, no expression was seen in epidermal cells of hypocotyls as in T2 seedlings.
Expected expression pattern: : Inducible promoter - was induced by different forms of stress (e.g., drought, heat, cold)
Selection Criteria *Arabidopsis* microarray
Gene: Putative strictosidine synthase
GenBank: NM_147884 *Arabidopsis thaliana* strictosidine synthase family
(At5g22020) mRNA, complete cds gi|30688266|ref|NM_147884.2|[30688266]
Source Promoter Organism: *Arabidopsis thaliana* WS
Vector:               pNewBin4-HAP1-GFP
Marker Type:          X GFP-ER
Generation Screened:  XT1 Mature   X T2 Seedling   XT2 Mature   X T3 Seedling
Bidirectionality: NO   Exons: FAILS   Repeats: NO
Promoter utility
Trait Area: PD&G, Nutrient, seed, water use efficiency
Sub-trait Area: Nutrient uptake, C/N partitioning, Source enhancement, source/sink
Utility: Useful for nutrient uptake and transport in root, transport or mobilization of steroid reserves
Construct: YP0180
Promoter Candidate I.D: 11768712
cDNA I.D: 5787483 (Old IDs: 2918666, 12367001)
T1 lines expressing (T2 seed): SR00902-01, -02, -03

TABLE 2-continued

Promoter Expression Report # 44

Report Date: Mar. 22, 2003
Promoter Tested In: *Arabidopsis thaliana*, WS ecotype
Spatial expression summary:
Hypocotyl                      (L)epidermis
Observed expression pattern: Low GFP expression in the epidermal cells of hypocotyl. Screened under non-
induced conditions. No T1 mature expression was observed. T2 mature: No expression was observed. T3
seedling: Same expression as the T2 seedling seen in one of two events. Guard cell expression was observed in second event.
Expected expression pattern: Induced by different forms of stress (e.g., drought, heat, cold).
Selection Criteria: *Arabidopsis* microarray. Induced by different forms of stress (e.g., drought, heat, cold)
Gene: Berberine bridge enzyme
GenBank: NM_100078 *Arabidopsis thaliana* FAD-linked oxidoreductase family
(At1g01980) mRNA, complete cds gi|18378905|ref|NM_100078.1|[18378905]
Source Promoter Organism: *Arabidopsis thaliana* WS
Vector:                        pNewBin4-HAP1-GFP
Marker Type:                   X GFP-ER
Generation Screened:           X T1 Mature    X T2 Seedling    X T2 Mature    X T3 Seedling
Bidirectionality: NO    Exons: NO    Repeats: NO
Promoter utility
Trait Area: Among other uses this promoter sequence could be useful to improve:
Water use efficiency; PG&D
Sub-trait Area: Heat
Utility: Seedling establishment,
Construct:                     YP0186
Promoter Candidate I.D:        11768854
cDNA I.D:                      13647840 (Old IDs: 12689527, 11437778)
T1 lines expressing (T2 seed): SR00906-02, -03

Promoter Expression Report # 45

Report Date: Mar. 25, 2003
Promoter Tested In: *Arabidopsis thaliana*, WS ecotype
Spatial expression summary:
Ovule                          Pre-fertilization: (H)inner integument
                               Post-fertilization: (H)inner integument, (H)outer integument
Observed expression pattern: High GFP expression specific to the inner integuments of developing pre-
fertilized ovules and outer integuments at the mycropylar end of post fertilized ovules. GFP detected throughout
inner integument of developing seed at mature embryo stage. T2 seedling: No expression observed. T2 Mature:
Same expression as observed in T1 mature. T3 seedling: Not screened.
Expected expression pattern: Expressed in ovules and different parts of seeds
Selection Criteria: Greater than 50x up in pi ovule microarray
Gene: pectin methylesterase [*Arabidopsis thaliana*].
GenBank: NM_124295 *Arabidopsis thaliana* pectinesterase family (At5g49180) mRNA,
complete cds gi|30695612|ref|NM_124295.2|[30695612]
Source Promoter Organism: *Arabidopsis thaliana* WS
Vector:                        pNewBin4-HAP1-GFP
Marker Type:                   X GFP-ER
Generation Screened:           XT1 Mature    X T2 Seedling    X T2 Mature    T3 Seedling
Bidirectionality: NO    Exons: FAILS    Repeats: NO
Promoter utility
Trait Area: Seed, Yield, Nutrient, cold, water use efficiency
Sub-trait Area: Ovule/seed abortion, seed enhamcement, seed number, seed size, total yield, seed nitrogen, cold germination and vigor
Utility: Useful for improvement for seed yield, composition, moisture stress at seed set, moisture stress during seed fill
Construct:                     YP0121
Promoter Candidate I.D:        11768686
cDNA I.D:                      12646933 (Old IDs: 12370661, 7080188)
T1 lines expressing (T2 seed): SR00805-01, -02, -03

Promoter Expression Report # 46

Report Date: Mar. 25, 2003
Promoter Tested In: *Arabidopsis thaliana*, WS ecotype
Spatial expression summary:
Silique                        (H)ovule
Ovule                          Pre-fertilization: (H)embryo sac, (H)gametophyte
                               Post-fertilization: (H)zygote
Observed expression pattern: GFP expression is specific to female gametophyte and surrounding sporophytic
tissue of pre-fertilized ovules and zygote of fertilized ovule 0-5 hours after fertilization (HAF). Not detected in
developing embryos. T2 mature: Did not germinate. T3 seedlings: No seeds available.
Expected expression pattern: Expressed in ovules and different parts of seeds
Selection Criteria: Greater than 50x up in pi ovule microarray
Gene: hypothetical protein
GenBank: NM_123661 *Arabidopsis thaliana* expressed protein (At5g42955) mRNA,
complete cds gi|18422274|ref|NM_123661.1|[18422274]
Source Promoter Organism: *Arabidopsis thaliana* WS
Vector:                        pNewBin4-HAP1-GFP
Marker Type:                   X GFP-ER

TABLE 2-continued

Generation Screened: XT1 Mature  X T2 Seedling  T2 Mature  T3 Seedling
Bidirectionality: NO   Exons: NO   Repeats: NO
Promoter utility
Trait Area: Among other uses this promoter sequence could be useful to improve:
Seed, yield, quality
Sub-trait Area: Ovule/seed abortion, harvest index, test weight, seed size, total yield, amino
acid, protein, total oil, total seed composition
Utility: This is promoter is useful for enhance of seed composition, seed size, seed number and yield, etc.
Construct: YP0096
Promoter Candidate I.D: 13148242 (Old ID: 11768682)
cDNA I.D: 4949423 (Old IDs: 12325608, 1007532)
T1 lines expressing (T2 seed): SR00775-01, -02

Promoter Expression Report # 47

Report Date: Mar. 25, 2003
Promoter Tested In: *Arabidopsis thaliana*, WS ecotype
Spatial expression summary:
Flower                 (H)pedicel, (H)stomata
Silique                (M)stomata
Stem                   (M)stomata
Rosette Leaf           (L)stomata
Primary Root           (H)root hairs
Observed expression pattern: Guard cell expression throughout stem, pedicels, and siliques.
High GFP preferential expression to root hairs of seedlings and medium to low expression in primary rosette leaves
and petioles and stems.
T2 mature: Same expression as T1 mature.
T3 seedlings: Same expression as T2 seedlings.
Expected expression pattern: Expressed in ovules and different parts of seeds
Selection Criteria: Greater than 50x up in pi ovule microarray
Gene: hypothetical protein
GenBank: NM_122878 *Arabidopsis thaliana* expressed protein (At5g34885)
mRNA, complete cds gi|30692647|ref|NM_122878.2|[30692647]
Source Promoter Organism: *Arabidopsis thaliana* WS
Vector:                pNewBin4-HAP1-GFP
Marker Type:           X GFP-ER
Generation Screened:   XT1 Mature  X T2 Seedling  X T2 Mature  X T3 Seedling
Bidirectionality: NO   Exons: NO   Repeats: NO
Promoter utility
Trait Area: Among other uses this promoter sequence could be useful to improve:
Water use efficiency, PG&D, nutrient
Sub-trait Area: Drought, heat, water use efficiency, plant size, low nitrogen utilization
Utility: Useful for root nutrient uptake, plant growth under drought, heat
Construct: YP0098
Promoter Candidate I.D: 12758479
cDNA I.D: 4906343 (Old IDs: 12662283, 1024001)
T1 lines expressing (T2 seed): SR00896-01, -02

Promoter Expression Report # 48

Report Date: Mar. 25, 2003
Promoter Tested In: *Arabidopsis thaliana*, WS ecotype
Spatial expression summary:
Flower                 (H)pedicel, (H)sepal, (H)vascular
Silique                (H)septum, (H)vascular
Stem                   (H)vascular
Leaf                   (H)petiole, (H)vascular, (H)phloem
Hypocotyl              (H)vascular
Primary Root           (H)vascular, (H)phloem
Observed expression pattern: High GFP expression throughout mature and seedling vascular tissue. T2 mature
and T3 seedling: Not screened.
Expected expression pattern: Expressed in ovules and different parts of seeds
Selection Criteria: Greater than 50x up in pi ovule microarray
Gene: unknown protein; expressed protein
GenBank: NM_129068 *Arabidopsis thaliana* expressed protein (At2g35150)
mRNA, complete cds gi|30686319|ref|NM_129068.2|[30686319]
Source Promoter Organism: *Arabidopsis thaliana* WS
Vector:                pNewBin4-HAP1-GFP
Marker Type:           X GFP-ER
Generation Screened:   XT1 Mature  X T2 Seedling  T2 Mature  T3 Seedling
Bidirectionality: NO   Exons: FAILS   Repeats: NO
Promoter utility
Trait Area: Among other uses this promoter sequence could be useful to improve:
PG&D, nutrient, seed
Sub-trait Area: Growth rate, plant size, low nitrogen use efficiency, nitrogen utilization, seed size and yield
Utility: Useful for root nutrient uptake and transport, enhance plant growth rate under low nitrogen
condition. Enhance plant to use water efficiently. Might be also useful for seed program. Source/sink
Construct: YP0108
Promoter Candidate I.D: 11768683

TABLE 2-continued cDNA I.D: 13601936 (Old IDs: 12339941, 4768517)
T1 lines expressing (T2 seed): SR00778-01, -02

Promoter Expression Report # 49

Report Date: Mar. 25, 2003
Promoter Tested In: *Arabidopsis thaliana*, WS ecotype
Spatial expression summary: Screened under non-induced conditions.
Flower                  (H)septum, (H)epidermis
Silique                 (L)carpel, (H)septum, (H)epidermis, (M)vascular
Stem                    (M)epidermis
Hypocotyl               (L)epidermis, (L)stomata
Cotyledon               (L)epidermis, (L)guard cell
Primary Root            (H)epidermis, (H)trichoblast, (H)atrichoblast, (H)root hairs
Observed expression pattern: High preferential GFP expression in septum epidermal cells in siliques and root
hair cells of seedlings. Low expression in cotyledon and hypocotyl epidermal cells. T2 mature: Stem epidermal
and silique vascular expression observed in addition to expression observed in T1 mature. Expression in stem
epidermal cells appears variable. T3 seedling: Same expression as T2 seedlings with additional guard cell expression in siliques.
Expected expression pattern: Root
Selection Criteria: Greater than 10x induced by Roundup. Induced in *Arabidopsis* microarray at 4 hours
Gene: Hypothetical protein
GenBank: NM_111930 *Arabidopsis thaliana* expressed protein (At3g10930) mRNA,
complete cds gi|30681550|ref|NM_111930.2|[30681550]
Source Promoter Organism: *Arabidopsis thaliana* WS
Vector:                 pNewBin4-HAP1-GFP
Marker Type:            X GFP-ER
Generation Screened:    XT1 Mature   X T2 Seedling   X T2 Mature   X T3 Seedling
Bidirectionality: NO   Exons: NO   Repeats: NO
Promoter utility
Trait Area: Among other uses this promoter sequence could be useful to improve:
Water use efficiency, PG&D, nutrient, yield
Sub-trait Area: Drought, growth rate, plant size, low nitrogen use efficiency, nitrogen utilization; seed yield
Utility: Useful for root nutrient uptake, enhance plant growth rate under low nitrogen
condition. Enhance plant to use water efficiency, useful for pod shatter
Construct:              YP0134
Promoter Candidate I.D: 11768684
cDNA I.D:               13489977 (Old IDs: 12332605, 6403797)
T1 lines expressing (T2 seed): SR00780-02, -03

Promoter Expression Report # 50

Report Date: Mar. 25, 2003
Promoter Tested In: *Arabidopsis thaliana*, WS ecotype
Spatial expression summary: Screened under non-induced conditions
Flower                  (H)pedicel, (L)petal, (H)silique
Silique                 (H)carpel, (H)cortex, (H)epidermis
Ovule                   Post-fertilization: (L)outer integument
Embryo                  (L)mature
Stem                    (M)epidermis, (H)cortex, (H)endodermis
Leaf                    (H)petiole, (H)mesophyll, (H)epidermis
Cotyledon               (H)mesophyll, (H)epidermis
Rosette Leaf            (H)mesophyll, (L)vascular, (H)epidermis
Primary Root            (H)cortex
Lateral root            (H)cortex, (H)flanking cells
Observed expression pattern: High preferential GFP expression in photosynthetic, cortical and epidermal tissues
in mature plants and seedlings. T2 mature: Weak outer integument expression in mature ovules and mature
embryo in addition to expression observed in T1 mature plants. T3 seedling: Same expression observed as T2
seedlings (seen in one event). Weak epidermal and high lateral root flanking cell expression observed in second event.
Expected expression pattern: Root hairs
Selection Criteria: Ceres Microarray 2.5-5X down in rhl (root hair less) mutant
Gene: probable auxin-induced protein
GenBank: NM_119642 *Arabidopsis thaliana* auxin-induced (indole-3-acetic acid induced) protein family
(At4g34760) mRNA, complete cds gi|30690121|ref|NM_119642.2|[30690121]
Source Promoter Organism: *Arabidopsis thaliana* WS
Vector:                 pNewBin4-HAP1-GFP
Marker Type:            X GFP-ER
Generation Screened:    XT1 Mature   X T2 Seedling   X T2 Mature   X T3 Seedling
Bidirectionality: NO   Exons: NO   Repeats: NO
Promoter utility
Trait Area: Among other uses this promoter sequence could be useful to improve:
PG&D, Nutrient; C3-C4 optimization
Sub-trait Area: Low nitrogen use efficiency, nitrogen utilization, low nitrogen tolerance, plant
size, growth rate, water use efficiency; manipulate expression of C3-C4 enzymes in leaves
Utility: Useful for root nutrient uptake and transport, enhance plant growth rate, also for
enhance of plant water use efficiency
Construct:              YP0138
Promoter Candidate I.D: 13148247 (Old ID: 11768685)

TABLE 2-continued cDNA I.D:  12333534 (Old ID: 7077536)
T1 lines expressing (T2 seed):  SR00781-01, -02, -03

---

Promoter Expression Report # 52

Report Date: Mar. 25, 2003
Promoter Tested In: *Arabidopsis thaliana*, WS ecotype
Spatial expression summary:
Flower  (L)sepal, (L)vascular
Rosette Leaf  (L)vascular, (L)stomata
Observed expression pattern: Weak GFP expression in sepal vasculature of developing flower buds. Weak expression in vasculature and guard cells of rosette leaves. Not detected in mature flowers. T2 mature: Same expression as T1 mature detected in one of two events. Vascular expression in pedicels of developing flowers. T3 seedlings: No expression detected.
Expected expression pattern: Shoot apex including leaf primordia and parts of leaves
Selection Criteria: Greater than 5x up in stm microarray
Gene: unknown protein
GenBank: NM_122151 *Arabidopsis thaliana* esterase/lipase/thioesterase family
(At5g22460) mRNA, complete cds gi|30688485|ref|NM_122151.2|[30688485]
Source Promoter Organism: *Arabidopsis thaliana* WS
Vector:  pNewBin4-HAP1-GFP
Marker Type:  X GFP-ER
Generation Screened:  XT1 Mature  X T2 Seedling  X T2 Mature  X T3 Seedling
Bidirectionality: NO  Exons: FAILS  Repeats: NO
Promoter utility
Trait Area: Among other uses this promoter sequence could be useful to improve:
Water use efficiency
Sub-trait Area: Water use efficiency
Construct:  YP0192
Promoter Candidate ID:  11768715
cDNA I.D:  12688453 (Old IDs: 12384618, 3434328)
T1 lines expressing (T2 seed):  SR00908-01, -02
Utility: This is weak promoter expressed in guard cell and flower. Might be useful for water use efficiency

---

Promoter Expression Report # 53

Report Date: Mar. 25, 2003
Promoter Tested In: *Arabidopsis thaliana*, WS ecotype
Spatial expression summary:
Flower  (H)pedicel, (H)vascular
Primary Root  (H)epidermis, (H)trichoblast, (H)atrichoblast, (L)root hair
Observed expression pattern: High GFP expression specific in floral pedicel vascular tissue of developing flowers. Not detected in pedicels and stems of mature plants. High GFP expression throughout epidermal layers of primary seedling root. T2 mature: No expression in 3 plants observed . T3 seedling: Same as T2 seedling expression.
Expected expression pattern: Inducible promoter - induced by different forms of stress (e.g., drought, heat, cold).
Selection Criteria: *Arabidopsis* microarray
Gene: Reticuline oxidase; berberine bridge enzyme
GenBank: NM_102806 *Arabidopsis thaliana* FAD-linked oxidoreductase family (At1g30700) mRNA,
complete cds gi|30692021|ref|NM_102806.2|[30692021]
Source Promoter Organism: *Arabidopsis thaliana* WS
Vector:  pNewBin4-HAP1-GFP
Marker Type:  X GFP-ER
Generation Screened:  XT1 Mature  X T2 Seedling  X T2 Mature  X T3 Seedling
Bidirectionality: NO  Exons: NO  Repeats: NO
Promoter utility
Trait Area: PG&D, Nutrient. Seed development, yield
Sub-trait Area: Plant size, growth rate, nitrogen use efficiency and utilization
Utility: Very useful for root nutrient uptake, enhancement for plant growth under low nitrogen condition
Construct:  YP0204
Promoter Candidate I.D:  11768721
cDNA I.D:  12669615 (Old ID: 7089815)
T1 lines expressing (T2 seed):  SR00914-02, -03, -04

---

Promoter Expression Report # 54

Report Date: Mar. 31, 2003
Promoter Tested In:  I. *Arabidopsis thaliana*, WS ecotype
  II. *Oryza sativa*
  III. *Lycopersicon esculentum*.
Spatial expression summary:
I. *Arabidopsis thaliana*
Flower  (H)pedicel, (H)receptacle, (H)nectary, (H)sepal, (H)petal, (H)filament, (H)anther,
  (H)carpel, (H)style, (H)stigma, (H)epidermis
Silique  (H)stigma, (H)style, (H)carpel, (H)septum, (H)placentae, (H)epidermis, (H)ovule
Ovule  Pre-fertilization: (H)inner integument, (H)outer integument, (H)embryo sac,
  (H)funiculus, (H)chalaza, (H)micropyle
  Post-fertilization: (H)inner integument, (H)outer integument, (H)seed coat,
  (H)chalaza, (H)micropyle, (H)embryo
Embryo  (H)late, (H)mature

TABLE 2-continued

| | |
|---|---|
| Stem | (H)epidermis, (H)cortex, (H)vascular |
| Leaf | (H)petiole, (H)mesophyll, (H)epidermis |
| Hypocotyl | (M)epidermis |
| Cotyledon | (H)mesophyll, (H)epidermis |
| Primary Root | (H)epidermis, (H)atrichoblas, (H)vascular, (H)cap |
| Lateral root | (H)epidermis, (H)initials, (H)cap |
| II. *Oryza sativa* | |
| Leaf sheath | epidermis, vascular, cortex |
| Leaf | mesophyll, vascular |
| Lateral root | initials, cap |
| Primary root | cap |
| Embryo | 5 day |
| III. *Lycopersicon esculentum* | |
| Leaf | mesophyll |
| Flower | ovules, stamen, pollen |
| Root | epidermis |
| Fruit | peel tissue |

Observed expression patterns: T2 mature and T2 seedling: Expressed throughout mature and seedling tissues. High expression in L1, L2, and L3 layers of shoot apical meristem.
Expected expression pattern: Constitutive
Selection Criteria: cDNA cluster
Gene: *Arabidopsis* Elongation Factor 1-α
GenBank: NM_125432 *Arabidopsis thaliana* elongation factor 1-alpha (EF-1-alpha) (At5g60390) mRNA, complete cds gi|30697365|ref|NM_125432.2|[30697365]
Source Promoter Organism: *Arabidopsis thaliana* WS
Vector: CRS-BIN2A2
Marker Type: Histone-YFP
Generation Screened:

| | | | | | |
|---|---|---|---|---|---|
| I. *Arabidopsis thaliana* | | T1 Mature | X T2 Seedling | X T2 Mature | T3 Seedling |
| II. *Oryza sativa* | | X T1 Mature | T2 Seedling | T2 Mature | T3 Seedling |
| III. *Lycopersicon esculentum* | | X T1 Mature | T2 Seedling | T2 Mature | T3 Seedling |

Criteria: Bidirectionality: NO    Exons: NO    Repeats: NO
Trait Area: Among other uses, this promoter sequence could be useful to improve:
Water use efficiency, PG&D, Seed, Nutrient, Yield
Construct: BIN2A2/28716-HY2
Promoter Candidate I.D: 12786308
cDNA I.D: 12739224 (Old ID: 12731344)

---

Promoter Expression Report # 55

Report Date: Mar. 23, 2003
Promoter Tested In:    I. *Arabidopsis thaliana*, WS ecotype
                      II. *Oryza sativa*
Spatial expression summary:
I. *Arabidopsis thaliana*, WS ecotype

| | |
|---|---|
| Flower | (H)pedicel, (H)receptacle, (H)nectary, (H)sepal, (H)petal, (H)filament, (H)anther, (H)pollen, (H)carpel, (H)style, (H)papillae, (H)epidermis, (H)SAM |
| Silique | (H)stigma, (H)style, (H)carpel, (H)septum, (H)placentae, (H)transmitting (H)tissue, (H)epidermis, (H)ovule |
| Ovule | Pre-fertilization: (H)inner integument, (H)outer integument, (H)embryo sac, (H)funiculus, (H)chalaza, (H)micropyle<br>Post-fertilization: (H)zygote, (H)inner integument, (H)outer integument, (H)seed coat, (H)chalaza, (H)micropyle, (H)early endosperm, (H)mature endosperm, (H)embryo |
| Embryo | (H)suspensor, (H)preglobular, (H)globular, (H)heart, (H)torpedo, (H)late, (H)mature, (H)hypophysis, (H)radicle, (H)cotyledons, (H)hypocotyl |
| Stem | (H)epidermis, (H)cortex, (H)vascular, (H)pith |
| Leaf | (H)petiole, (H)mesophyll, (H)epidermis |
| Hypocotyl | (L)epidermis, (L)cortex, (L)vascular |
| Rosette Leaf | (H)mesophyll, (H)epidermis, (H)petiole |
| Primary Root | (H)epidermis, (H)trichoblast, (H)atrichoblast, (H)cortex, (H)cap, (H)root hairs |
| Lateral Root | (H)epidermis, (H)initials, (H)cap |
| II. *Oryza sativa* | |
| Flower | |
| Pollen | |
| Leaf sheath | |

Observed expression patterns: Constitutive. Expression observed throughout mature and seedling plants.
Expected expression pattern: Constitutive
Selection Criteria: cDNA cluster
Gene: *Arabidopsis* ADP-Ribosylation Factor 1
GenBank: NM_130285 *Arabidopsis thaliana* ADP-ribosylation factor 1 (ARF1) (At2g47170) mRNA, complete cds gi|18407284|ref|NM_130285.1|[18407284]
Source Promoter Organism: *Arabidopsis thaliana* WS
Vector: CRS-Bin1A1
Marker Type: X Histone-YFP
Generation Screened:

| | | | | | |
|---|---|---|---|---|---|
| I. *Arabidopsis thaliana* | | T1 Mature | X T2 Seedling | X T2 Mature | T3 Seedling |
| II. *Oryza sativa* | | X T1 Mature | T2 Seedling | T2 Mature | T3 Seedling |

TABLE 2-continued

Bidirectionality: NO    Exons: NO    Repeats: NO
Promoter utility
Trait Area: Among other uses, this promoter sequence could be useful to improve:
Water use efficiency, PG&D, Seed, Nutrient, Yield
Construct:                BINA1-34414-HY2
Promoter Candidate I.D:   12786307
cDNA I.D:                 13609583 (Old ID: 12394813)

Promoter Expression Report # 56

Report Date: Mar. 23, 2003
Promoter Tested In:       I. *Arabidopsis thaliana*, WS ecotype
                          II. *Oryza sativa*
Spatial expression summary:
I. *Arabidopsis thaliana*
Flower                    (H)pedicel, (H)receptacle, (H)nectary, (H)sepal, (H)anther, (H)phloem,
                          (H)cap, (H)root hairs, (H)pollen, (H)carpel, (H)style, (H)epidermis
Silique                   (H)style, (H)carpel, (H)septum, (H)placentae, (H)vascular, (H)epidermis, (H)ovule
Ovule                     Pre-fertilization: (H)outer integument, (H)funiculus
                          Post-fertilization: (H)outer integument, (H)seed coat
Stem                      (H)epidermis, (H)cortex, (H)vascular, (H)xylem, (H)phloem, (H)pith
Leaf                      (M)mesophyll, (H)vascular
Hypocotyl                 (H)epidermis, (H)vascular
Cotyledon                 (H)mesophyll, (H)epidermis
Primary Root              (H)epidermis, (H)trichoblast, (H)atrichoblast, (H)vascular, (H)xylem,
                          (H)phloem, (H)cap, (H)root hairs
II. *Oryza sativa*
Flower                    (L)vascular
Sheath                    (H)all cells
Leaf tip                  (H)all cells
Leaf lower blade          (H)vascular
Root                      (M)vascular, (L)epidermis
Lateral root              (H)epidermis
Ovule                     (H)all structures
Immature seed             (M)connective tissue
Observed expression patterns:
I. *Arabidopsis thaliana*: Expressed throughout most mature tissues screened. Not detected in shoot apical meristem
and stage 1 and 2 flower buds. Not detected in stamen and siliques of stage 4 flowers. Not detected in the stigma,
which has abnormal development. Aborted embryos. Not detected in developing embryos. High Expression in
epidermal, vascular and photosynthetic tissue of seedling. Lines characterized have gone through several
generations. Not screened in successive generation.
II. *Oryza sativa*: High expression throughout leaf sheath, leaf, root, lateral root tip, anther filament, ovule, stem
and connection point between seed and pedicel. Not detectable in developing seeds. Not expressed in organs of developing flowers.
Expected expression pattern: Constitutive expression
Selection Criteria: From Ceres, Inc. and Stanford microarray data. Selected for constitutive expression.
Gene: S-Adenosylmethionine Synthetase 2
GenBank: NM_112618 *Arabidopsis thaliana* s-adenosylmethionine synthetase - related (At3g17390) mRNA,
complete cds gi|30684501|ref|NM_112618.2|[30684501]
Source Promoter Organism: *Arabidopsis thaliana* WS
Vector:                   I. *Arabidopsis*- CRS-HT1 (Construct: CR13-GFP-ER)
                          II. *Oryza sativa*- CRS-HT1 (Construct: CR13-GFP-ER),
                          CRS-BIN1A (Construct: CR14-hYFP)
Marker Type:              I. *Arabidopsis*- GFP-ER
                          II. *Oryza sativa*- GFP-ER, hYFP
Generation Screened:
I. *Arabidopsis*-         ☐ T1 Mature    X T2 Seedling    X T2 Mature    ☐ T3 Seedling
II. *Oryza sativa*-       X T1 Mature    X T2 Seedling    ☐ T2 Mature    ☐ T3 Seedling
Bidirectionality: FAILS??    Exons: FAILS??    Repeats: NO
Promoter utility
Trait Area: Among other uses this, promoter sequence could be useful to improve:
Water use efficiency, PG&D, seeds; nutrients
Sub-trait Area: Drought, water use efficiency, growth rate, plant size, low nitrogen
tolerance, nitrogen use efficiency, seed enhancement
Utility: Useful for root nutrient uptake and transport, water use efficiency, and
improvement of seed size, yield, etc.
Construct:                CR13 (GFP-ER)
                          CR14 (H-YFP)
Promoter I.D:             12786306
cDNA I.D:                 13614841 (Old ID: 12331556)

Promoter Expression Report # 98

Report Date: Dec. 3, 2003
Promoter Tested In: *Arabidopsis thaliana*, WS ecotype
Spatial expression summary:
Flower                    H pedicel, H receptacle, H sepal, H epidermis, H endodermis
Silique                   H placenta
Stem                      H endodermis
Leaf                      H endodermis TABLE 2-continued

| | |
|---|---|
| Hypocotyl | M epidermis, L vascular |
| Cotyledon | L vascular |
| Rosette Leaf | H vascular, H epidermis, H mid rib |
| Primary Root | H pericycle, H endodermis, L root hairs |
| Lateral root | H initials |

Observed expression pattern:
T1 mature: Strong GFP expression in rib vein support tissue in flowers, leaves and endodermis of stems. Appears not to be expressed within vascular tissue.
T2 seedling: Expressed throughout epidermal and vascular tissues of seedling. Expressed in both mid-vein ground tissue and vasculature of developing leaves. Expression in ground tissues of roots. Not observed in root vascular.
Expected expression pattern: Shoot meristem
Selection Criteria: *Arabidopsis* public
Gene: Xyloglucan endotransglycosylase.
GenBank: NM_113277 *Arabidopsis thaliana* xyloglucan endotransglycosylase,
putative (At3g23730) mRNA, complete cds gi|18403866|ref|NM_113277.1|[18403866]
Source Promoter Organism: *Arabidopsis thaliana* WS

| | |
|---|---|
| Vector: | pNewbin4-HAP1-GFP |
| Marker Type: | GFP-ER |
| Generation Screened: | X T1 Mature   X T2 Seedling   T2 Mature   T3 Seedling |
| Criteria: Bidirectional: PASS   Exons: PASS   Repeats: PASS | |
| Table 3. | Promoter utility |

Utility: Translocation, seed fill. Improved loading of phloem, increased source capacity. Increased seed yield.
Notes: The polysaccharide xyloglucan is thought to play an important structural role in the primary cell wall of dicotyledons. Endodermis: Recent studies have implicated these cell types in gravity perception by sedimentation of starch within these cells. Gravity perception by dicot organs involves primarily the sedimentation of amyloplasts within specialized cells (statocytes) located in the columella region of the root cap and in the starch sheath, which constitutes the endodermis of hypocotyls and inflorescence stems (Kiss et al., 1996; Kuznetsov and Hasenstein, 1996; Blancaflor et al., 1998; Weise et al., 2000). In shoots, sedimentable amyloplasts and the curvature response to gravistimulation occur along the elongation zone (for review, see Masson et al., 2002). After amyloplast sedimentation, signals are likely transduced within the endodermal cells, and physiological signals are transported laterally to affect elongation of cortical and epidermal cells. In roots, sites of gravity perception and curvature response may be physically separated (Poff and Martin, 1989).

| | |
|---|---|
| Construct: | YP0018 |
| Promoter candidate I.D: | 11768673 |
| cDNA I.D: | 12647555 |
| Lines expressing: | YP0018-01; YP0018-02 plant date 7/28/03 |

Promoter Expression Report # 99

Report Date: Dec. 3, 2003
Promoter Tested In: *Arabidopsis thaliana*, WS ecotype
Spatial expression summary:

| | |
|---|---|
| Flower | L pedicel, L receptacle, L sepal, L petal, L filament, L epidermis |
| Stem | L vascular |
| Leaf | M vascular, L rib |
| Hypocotyl | L epidermis, L cortex, H vascular |
| Cotyledon | L mesophyll, L epidermis |
| Rosette Leaf | L mesophyll, L vascular, L epidermis, H petiole |
| Primary Root | H vascular |

Observed expression pattern:
T1 mature: Weak vascular expression throughout inflorescence meristem and flowers. Variable levels of expression in cells at receptacle of flowers. Expressed in both vascular and supporting ground tissue in leaves. T2 seedling: Strong expression observed throughout vasculature of root and hypocotyl. Expression in a few epidermal and cortex cells of hypocotyl at cotyledon junction. Weak epidermis and mesophyll expression in developing leaves.
Expected expression pattern: Stem cell population in center of shoot apical, inflorescence and floral meristem.
Selection Criteria: *Arabidopsis* public. Clark S E, Williams R W, Meyerowitz E M, The CLAVATA1 gene encodes a putative receptor kinase that controls shoot and floral meristem size in *Arabidopsis*. Cell. 1997 May 16; 89(4):575-85.
Gene: CLAVATA1 receptor kinase (CLV1)
GenBank: NM_106232 *Arabidopsis thaliana* CLAVATA1 receptor kinase (CLV1) (At1g75820) mRNA, complete cds gi|30699119|ref|NM_106232.2|[30699119]
Source Promoter Organism: *Arabidopsis thaliana* WS

| | |
|---|---|
| Vector: | pNewbin4-HAP1-GFP |
| Marker Type: | GFP-ER |
| Generation Screened: | X T1 Mature   X T2 Seedling   T2 Mature   T3 Seedling |
| Criteria: Bidirectionality: PASS   Exons: PASS   Repeats: PASS | |
| Table 3. | Promoter utility |

Utility: Translocation, seed fill. Improved loading of phloem, increased source capacity. Increased seed yield. Cotyledon angle, improved seedling survival.
Notes: Extensive studies on plant signaling molecules over the past decade indicate that plant cell-to-cell communication, as is the case with animal systems, makes use of small peptide signals and specific receptors. To date, four peptide-ligand-receptor pairs have been identified and shown to be involved in a variety of processes. Matsubayashi . Ligand-receptor pairs in plant peptide signaling. J Cell Sci. 2003 Oct 1; 116(Pt 19):3863-70.

| | |
|---|---|
| Construct: | YP0071 |
| Promoter candidate I.D: | 11768674 |

TABLE 2-continued

| | |
|---|---|
| cDNA I.D: | 12721583 (OCKHAM3-C) |
| Lines expressing: | YP0071-01, YP0071-02 plant date 7/28/03 |

Promoter Expression Report # 101

Report Date: Dec. 3, 2003
Promoter Tested In: *Arabidopsis thaliana*, WS ecotype
Spatial expression summary:

| | |
|---|---|
| Flower | H pedicel, H receptacle |
| Silique | H placentae |
| Stem | H epidermis H cortex H vascular, L pith |
| Hypocotyl | H epidermis, H vascular |
| Cotyledon | H mesophyll, H vascular, H epidermis, H hydathode |
| Rosette Leaf | H mesophyll, H vascular, H epidermis, H primordia |
| Primary Root | H epidermis, H cortex, H vascular |
| Lateral root | H epidermis, H cortex |

Observed expression pattern:
T1 mature: High expression in epidermis and cortical cells of stem and pedicles near inflorescence shoot apex.
Weakens near floral organs except in the placenta where GFP is also highly expressed. Not expressed in ovules or embryos. High GFP expression in vasculature of stem. T2 seedling: High expression throughout leaves and epidermis of hypocotyl. No expression observed in ground tissues of hypocotyl. High epidermal, cortex and vascular expression in root.
Expected expression pattern: Enzyme located in chloroplasts, >4 old high in seedlings
Selection Criteria: Ceres *Arabidopsis* microarray
Gene: product = "DEF (CLA1) protein" CLA1 (for "cloroplastos alterados', or "altered chloroplasts') CLA1 encodes 1-deoxy-d-xylulose 5-phosphate synthase, which catalyses the first step of the non-mevalonate isoprenoid biosynthetic pathway.
GenBank: NM__117647 *Arabidopsis thaliana* DEF (CLA1) protein (At4g15560) mRNA, complete cds gi|30683316|ref|NM__117647.2|[30683316]
Source Promoter Organism: *Arabidopsis thaliana* WS

| | |
|---|---|
| Vector: | pNewbin4-HAP1-GFP |
| Marker Type: | GFP-ER |
| Generation Screened: | X T1 Mature    X T2 Seedling    T2 Mature    T3 Seedling |
| Criteria: Bidirectionality: PASS | Exons: PASS    Repeats: PASS |
| Table 3. | Promoter utility |

Utility: Increased photosynthetic capacity and source capacity. Larger plants. Altered plant morphology. Altered plant metabolism. Increased seed loading and seed yield.
Notes: CLA1 encodes 1-deoxy-d-xylulose 5-phosphate synthase, which catalyses the first step of the non-mevalonate isoprenoid biosynthetic pathway. Crowell D N, Packard C E, Pierson C A, Giner J L, Downes B P, Chary S N. Identification of an allele of CLA1 associated with variegation in *Arabidopsis thaliana*. Physiol Plant. 2003 May; 118(1):29-37.

| | |
|---|---|
| Construct: | YP0216 |
| Promoter candidate I.D: | 13148171 |
| cDNA I.D: | 12575820 |
| Lines expressing: | YP0216-01, -02, -03, -04 plant date 05/05/03; |

Promoter Expression Report # 102

Report Date: Oct. 30, 2003
Promoter Tested In: *Arabidopsis thaliana*, WS ecotype
Spatial expression summary:

| | |
|---|---|
| Ovule | Pre-fertilization: L primordia L inner integument L outer integument |
| | Post-fertilization: H suspensor |

Observed expression pattern:
T1 mature: Weak expression observed throughout ovule primordia including mother megaspore cell. Post-fertilization expression specific to suspensor cells of embryo. Degeneration of expression in suspensor at torpedo stage.
T2 Seedling: No expression.
Expected expression pattern: Nucellus and megaspore mother cell
Selection Criteria: Literature. Yang W C, Ye D, Xu J, Sundaresan V. The SPOROCYTELESS gene of *Arabidopsis* is required for initiation of sporogenesis and encodes a novel nuclear protein.
Genes Dev. 1999 Aug 15; 13(16):2108-17.
Gene: Nozzle Sporocyteles
GenBank: NM__118867 *Arabidopsis thaliana* NOZZLE SPOROCYTELESS (At4g27330) RNA, complete cds gi|18416968|ref|NM__118867.1|[18416968]
Source Promoter Organism: *Arabidopsis thaliana* WS

| | |
|---|---|
| Vector: | pNewbin4-HAP1-GFP |
| Marker Type: | GFP-ER |
| Generation Screened: | XT1 Mature    XT2 Seedling    T2 Mature    T3 Seedling |
| Criteria: Bidirectionality: | Exons:    Repeats: |
| Table 5. | Promoter utility |

Utility: Better embryo fill, larger embryo and seed. Altered seed composition. Increased seed weight and yield. Better performing seedlings. Seedlings tolerant to stress. Altered source-sink balance.
Notes: Balasubramanian S, Schneitz K. NOZZLE links proximal-distal and adaxial-abaxial pattern formation during ovule development in *Arabidopsis thaliana*. Development. 2002 Sep; 129(18):4291-

| | |
|---|---|
| Construct: | YP0271 |
| Promoter candidate I.D: | 11768757 |
| cDNA I.D: | 12658070 |
| Lines expressing: | YP0271-01, -02 plant date 4/14/03 |

TABLE 2-continued

Promoter Expression Report # 103

Report Date: Oct. 30, 2003
Promoter Tested In: *Arabidopsis thaliana*, WS ecotype
Spatial expression summary:

| | |
|---|---|
| Silique | L ovule |
| Ovule | Post-fertilization: M zygote L embryo sac L embryo |
| Embryo | M suspensor L torpedo L radicle |
| Rosette Leaf | M mesophyll H epidermis H stomata |
| Primary Root | H pericycle |
| Lateral root | H initials H flanking cells H primordia |

Observed expression pattern:
T1 mature: High expression throughout mature female gametophyte at fertilization and in embryo from zygote to torpedo stage embryo. Expression in embryo restricted to radicle. Not observed in leaf, however this may coincide with severe yellowing of leaves in plants screened during this time. T2 seedling: High GFP expression in mesophyll and epidermal cells of rosette leaves. Expression in root is specific to pericycle cells and lateral root primordia.
Expected expression pattern: Leaf
Selection Criteria: Literature. Leaf-Specific Upregulation of Chloroplast Translocon Genes by a CCT Motif-Containing Protein, CIA 2. Sun C W, Chen L J, Lin L C, Li H M. Plant Cell. 2001 Sep; 13(9): 2053-2062, PMCID: 139451 [Abstract] [Full Text][PDF]
Gene: CIA2
GenBank: NM_125100 *Arabidopsis thaliana* CIA2 (CIA2) (At5g57180) mRNA, complete cds gi|30696839|ref|NM_125100.2|[30696839]
Source Promoter Organism: *Arabidopsis thaliana* WS

| | |
|---|---|
| Vector: | pNewbin4-HAP1-GFP |
| Marker Type: | GFP-ER |
| Generation Screened: | XT1 Mature   XT2 Seedling   T2 Mature   T3 Seedling |
| Criteria: Bidirectionality: | Exons:   Repeats: |
| Table 5. | Promoter utility |

Utility: Nutrition. Imprint modulation through female, heavier seed, lighter seed, seedless fruits. Increased lateral root growth. More lateral roots, larger lateral roots. Improved drought tolerance. Improved performance in low-nitrogen soil, improved source capacity.
Notes:

| | |
|---|---|
| Construct: | YP0279 |
| Promoter candidate I.D: | 11768839 |
| cDNA I.D: | 12600234 (OCKHAM3-C) |
| Lines expressing: | YP00279-01, -02, -03 plant date 4/14/03 |

Promoter Expression Report # 105

Report Date: Dec. 3, 2003
Promoter Tested In: *Arabidopsis thaliana*, WS ecotype
Spatial expression summary:

| | |
|---|---|
| Silique | L ovule |
| Ovule | M embryo sac |
| Leaf | L vascular |
| Hypocotyl | L vascular |
| Cotyledon | L vascular, M hydathode |
| Primary Root | L epidermis, M vascular, M pericycle |

Observed expression pattern:
T1 mature: GFP expression decreasing in female gametophyte. Low expression in leaf vasculature. T2 seedling: Low expression in cotyledon and hypocotyl vasculature. Low expression in root vasculature and pericycle cells.
Expected expression pattern: PEG-inducible
Selection Criteria: Ceres, Inc. *Arabidopsis* Expression data
Gene: *Arabidopsis thaliana* mitochondrial carrier protein family
GenBank: NM_118590 *Arabidopsis thaliana* mitochondrial carrier protein family (At4g24570) mRNA, complete cds gi|30686585|ref|NM_118590.2|[30686585]
Source Promoter Organism: *Arabidopsis thaliana* WS

| | |
|---|---|
| Vector: | pNewbin4-HAP1-GFP |
| Marker Type: | GFP-ER |
| Generation Screened: | X T1 Mature   X T2 Seedling   T2 Mature   T3 Seedling |
| Criteria: Bidirectionality: PASS | Exons: PASS   Repeats: PASS |
| Table 3. | Promoter utility |

Utility: Imprint modulation through female, larger (heavier) seeds, smaller (lighter) seeds, seedless fruits. Altered endosperm and seed composition, improved drought tolerance. Improved performance in low-nitrogen soil.
Notes:

| | |
|---|---|
| Construct: | YP0285 |
| Promoter candidate I.D: | 11768588 |
| cDNA I.D: | 13609092 |
| Lines expressing: | YP0285-01, -02, -04 plant date 6/04/03 |

Promoter Expression Report # 106

Report Date: Oct. 31, 2003
Promoter Tested In: *Arabidopsis thaliana*, WS ecotype
Spatial expression summary:

| | |
|---|---|
| Flower | H vascular |
| Silique | H vascular |
| Stem | H vascular |

TABLE 2-continued

| | |
|---|---|
| Leaf | H vascular |
| Hypocotyl | H vascular |
| Cotyledon | H vascular |
| Rosette Leaf | H vascular |
| Primary Root | H vascular, H pericycle |
| Lateral root | H pericycle H vascular |

Observed expression pattern:
T1 mature: Very high expression in vasculature of flowers, stems, and leaves. Not detected in reproductive tissues in silique. T2 seedling: Very high expression throughout seedling vasculature. Expression in root extending into pericycle cells.
Expected expression pattern: Shoot apical meristem
Selection Criteria: Greater than 5x down in stm microarray
Gene: Leucine-rich repeat transmembrane protein kinase
GenBank: NM_118146 *Arabidopsis thaliana* leucine-rich repeat transmembrane protein kinase, putative (At4g20270) mRNA, complete cds gi|30685044|ref|NM_118146.2|[30685044]
Source Promoter Organism: *Arabidopsis thaliana* WS

| | |
|---|---|
| Vector: | pNewbin4-HAP1-GFP |
| Marker Type: | GFP-ER |
| Generation Screened: | XT1 Mature   XT2 Seedling   ? T2 Mature   ? T3 Seedling |
| Criteria: Bidirectionality: | Exons:   Repeats: |
| Table 5. | Promoter utility |

Utility: Improved translocation, improved source capacity and seed fill. Heavier seeds. More seeds. Larger siliques. Improved seed yield. Moderate nitrate and/or amino acid transport. Increased transport to floorsink.
Notes:

| | |
|---|---|
| Construct: | YP0080 |
| Promoter candidate I.D: | 11768676 |
| cDNA I.D: | 12603755 (OCKHAM3-C) |
| Lines expressing: | YP0080-01, -02, -03 plant date 7/28/03 |

Promoter Expression Report # 107

Report Date: Oct. 31, 2003
Promoter Tested In: *Arabidopsis thaliana*, WS ecotype
Spatial expression summary:

| | |
|---|---|
| Rosette Leaf | L vascular M epidermis |
| Primary Root | H epidermis M root hairs |

Observed expression pattern:
T1 mature: No expression observed. Predicted expression in ovule primordium.
T2 seedling: High expression throughout root epidermal cells. Low epidermal and vasculature expression at leaf margins.
Expected expression pattern: Integument.
Selection Criteria: *Arabidopsis* public: The BELL1 gene encodes a homeodomain protein involved in pattern formation in the *Arabidopsis* ovule primordium.
Gene: = "homeodomain protein, BELL1 (BEL1)"
GenBank: NM_123506 *Arabidopsis thaliana* homeodomain protein, BELL1 (BEL1) (At5g41410) mRNA, complete cds gi|30693794|ref|NM_123506.2|[30693794]
Source Promoter Organism: *Arabidopsis thaliana* WS

| | |
|---|---|
| Vector: | pNewbin4-HAP1-GFP |
| Marker Type: | GFP-ER |
| Generation Screened: | XT1 Mature   XT2 Seedling   ? T2 Mature   ? T3 Seedling |
| Criteria: Bidirectionality: | Exons:   Repeats: |
| Table 5. | Promoter utility |

Utility: Improve ion uptake in roots.
Notes:

| | |
|---|---|
| Construct: | YP0122 |
| Promoter candidate I.D: | 11768849 |
| cDNA I.D: | 13593439 (OCKHAM3-C) |
| Lines expressing: | YP0122-01, -02 plant date 1/17/03 |

Promoter Expression Report # 116

Report Date: Nov. 4, 2003
Promoter Tested In: *Arabidopsis thaliana*, WS ecotype
Spatial expression summary:

| | |
|---|---|
| Flower | L pedicel, L sepal, H carpel, H epidermis, L stomata, H silique |
| Silique | H carpel, H epidermis, L stomata, L abscission zone |
| Leaf | H mesophyll, L vascular, H epidermis |
| Primary Root | L root hairs |

Observed expression pattern:
T1 mature: GFP expression at the base of sepals at abscission zone of developing and mature flowers. High expression specific to carpels of developing and mature siliques. T2 seedling: Weak root hair expression at hypocotyl transition zone observed in 1 in 6 seedlings and in only 1 of 2 events screened.
Expected expression pattern: Flowers, seed, roots.
Selection Criteria: *Arabidopsis* public; containing AP2 DNA binding domain.
Gene: EREBP-2
GenBank: NM_124093 *Arabidopsis thaliana* ethylene responsive element binding factor 2 (EREBP-2) (At5g47220) mRNA, complete cds gi|30695135|ref|NM_124093.2|[30695135]
Source Promoter Organism: *Arabidopsis thaliana* WS TABLE 2-continued Vector: pNewbin4-HAP1-GFP
Marker Type: GFP-ER
Generation Screened: X T1 Mature   XT2 Seedling   ? T2 Mature   ? T3 Seedling
Criteria: Bidirectionality: PASS   Exons: PASS   Repeats:
Table 5.   Promoter utility
Utility: Increased leaf size and volume, increased source capacity. Tolerance to drought. Improved performance in low nitrogen conditions. Larger siliques, increased seed number. Increased seed yield. Altered dehiscence and seed scatter.
Notes:
Construct: YP0015
Promoter candidate I.D: 11768611
cDNA I.D: 13612380
Lines expressing: YP0015-03, -04 plant date 9/8/03

Promoter Expression Report # 118

Report Date: Nov. 4, 2003
Promoter Tested In: *Arabidopsis thaliana*, WS ecotype
Spatial expression summary:

| | |
|---|---|
| Flower | H anther H pollen L vascular H stomata |
| Silique | M ovule |
| Ovule | Pre-fertilization: H outer integument H embryo sac H gametophyte |
| | Post-fertilization: M outer integument H seed coat H embryo |
| Embryo | H suspensor H heart H late H mature L radicle L cotyledons |
| Stem | H epidermis H stomata H trichome |
| Leaf | H stomata |
| Hypocotyl | H epidermis L cortex H stomata |
| Cotyledon | H mesophyll H vascular H epidermis H stomata |
| Rosette Leaf | H stomata |
| Primary Root | H cortex |

Observed expression pattern:
T1 mature: Expressed in pollen cells throughout development. Expression visible during pollination when dehisced pollen attaches to stigma resulting in extension of the cell wall to establish an attachment site or "foot". Once attached, pollen is hydrated and germination of pollen tubes follows through the stigma at the attachment site. These processes are likely targets in regulation of self-incompatibility and species-specific pollen recognition. No expression is observed after hydration. Expressed in egg sac of pre-fertilized ovules, inner integument, endosperm, heart stage embryo and suspensor cells of developing ovules. High specific expression in and epidermal cell files flanking trichomes of stem and guard cells throughout mature plant. T2 seedling: High expression in epidermal and guard cells throughout seedling. High expression epidermal, vascular, and mesophyll cells of cotyledons. Not observed in leaf primordia. High expression specific to cortical cells of root.
Expected expression pattern: Induced prior to cell division and usually associated with dividing cells.
Selection Criteria: Ceres BLAST search homology; CDC2-like protein
Gene: putative protein kinase/note = "similar to cyclin-dependent kinase cdc2MsE [*Medicago sativa*]
GenBank: NM_125756 *Arabidopsis thaliana* protein kinase, putative (At5g63610) mRNA, complete cds gi|30697871|ref|NM_125756.2|[30697871]
Source Promoter Organism: *Arabidopsis thaliana* WS
Vector: pNewbin4-HAP1-GFP
Marker Type: GFP-ER
Generation Screened: XT1 Mature   XT2 Seedling   T2 Mature   T3 Seedling
Criteria: Bidirectionality:   Exons:   Repeats:
Table 5.   Promoter utility
Utility: Imprint modulation through male, larger (heavier) seeds, smaller (lighter) seeds. Male sterility and altered breeding barriers. Altered pollen composition. Altered fertility. Resistance to drought.
Notes: Abstracts; Elucidating the complete molecular determination of a self-incompatibility (SI) system in plants has grown significantly with recent investigations of the sporophytic incompatibility system in the genus *Brassica*. Male (pollen) and female (stigma) components of the recognition/incompatibility reaction appear to be controlled by separate genes that reside in a small genomic region (the S-locus; see YU et al. 1996 ↓ ; SCHOPFER et al. 1999 ↓). The interaction between male and female components is not completely understood, but it is thought that a pollen surface protein acts as a ligand that is recognized by a transmembrane protein in the papillary cells on the surface of the stigma. When the pollen and pistil specificities are from the same S-allele, pollen tube growth is inhibited. The stigma component of this recognition system is now thought to be the S-locus receptor kinase, encoded by the SRK gene. This protein has an extracellular glycoprotein domain and an intracellular serine-threonine protein kinase (STEIN et al. 1991 ↓) and has been shown to be necessary, and perhaps sufficient, for determining specificity (CUI et al. 2000 ↓ ; TAKASAKI et al. 2000 ↓). A second protein, S-locus glycoprotein, encoded by the closely linked SLG gene, is not in itself sufficient for determining specificity, although it may be necessary for proper rejection of incompatible pollen (SHIBA et al. 2000 ↓; TAKASAKI et al. 2000 ↓). SLG sequences show homology to those of the first exon of SRK (the S-domain). A pollen coat protein, encoded by the linked SCR gene, has recently been shown to be necessary and sufficient for determination of the pollen specificity (SCHOPFER et al. 1999 ↓; TAKAYAMA et al. 2000 ↓). Genetics, Vol. 158, 387-399, May 2001, Copyright © 2001
SCHIERUP, M. H., B. K. MABLE, P. AWADALLA, and D. CHARLESWORTH, 2001 Identification and characterization of a polymorphic receptor kinase gene linked to the self-incompatibility locus of *Arabidopsis lyrata*.. Genetics 158:387-399. [Abstract/Free Full Text]
SCHOPFER, C. R., M. E. NASRALLAH, and J. B. NASRALLAH, 1999 The male determinant of self-incompatibility in *Brassica*. Science 286:1697-1700[Abstract/Full Text] . STEIN, J., B. HOWLETT, D. C. BOYES, M. E. NASRALLAH, and J. B. NASRALLAH, 1991 Molecular cloning of a putative receptor protein kinase gene encoded at the self-incompatibility locus of *Brassica oleracea*. Proc. Natl. Acad. Sci. USA 88:8816-8820[Abstract].

TABLE 2-continued

| | |
|---|---|
| Construct: | YP0230 |
| Promoter candidate I.D: | 13148201 |
| cDNA I.D: | 12676237 |
| Lines expressing: | YP0230-02, -03 (9/08/03) |

Promoter Expression Report # 119

Report Date: Dec. 3, 2003
Promoter Tested In: *Arabidopsis thaliana*, WS ecotype
Spatial expression summary:

| | |
|---|---|
| Silique | H ovule |
| Ovule | Pre-fertilization: H outer integument |
| | Post-fertilization: H outer integument, H seed coat |

Observed expression pattern:
T1 Mature: GFP expressed in outer integument early in ovule development through seed coat of mature seeds. T2 Seedling: No expression observed.
Expected expression pattern: Expressed in ovules and different parts of seeds
Selection Criteria: Greater than 50x up in pi ovule microarray
Gene: "hypothetical protein /product = "expressed protein"
GenBank: NM_117365 *Arabidopsis thaliana* expressed protein (At4g12960) mRNA, complete cds gi|30682287|ref|NM_117365.2|[30682287]
Source Promoter Organism: *Arabidopsis thaliana* WS

| | |
|---|---|
| Vector: | pNewbin4-HAP1-GFP |
| Marker Type: | GFP-ER |
| Generation Screened: | XT1 Mature   XT2 Seedling   T2 Mature   T3 Seedling |
| Criteria: Bidirectionality: PASS   Exons: PASS   Repeats: PASS | |
| Table 3. | Promoter utility |

Utility: Seed size determination. Increased seed size. Altered seed composition. Tolerance of seeds to desiccation. Resistance of seeds to abortion. Increase sink strength by expression of A.A. transporters

| | |
|---|---|
| Construct: | YP0120 |
| Promoter candidate I.D: | 11768656 |
| cDNA I.D: | 12370095 |
| Lines expressing: | YP0120-01, -02 Plant date 9/8/03 |

Promoter Expression Report # 120

Report Date: Nov. 4, 2003
Promoter Tested In: *Arabidopsis thaliana*, WS ecotype
Spatial expression summary:

| | |
|---|---|
| Flower | H sepal |
| Rosette Leaf | H epidermis H stomata |

Observed expression pattern:
T1 Mature: High epidermal expression in petals of developing and mature flowers.
Not detected in other organs. T2 Seedlings: High expression in epidermal cells of initial leaf primordia.
Expected expression pattern: Emerging true leaves.
Selection Criteria: Literature; Cho H T, Cosgrove D J Altered expression of expansin modulates leaf growth and pedicel abscission in *Arabidopsis thaliana*. Proc Natl Acad Sci USA. 2000 Aug 15; 97(17):9783-8.
Gene: product = "expansin, putative (EXP10)"
GenBank: NM_102440 *Arabidopsis thaliana* expansin, putative (EXP10) (At1g26770) mRNA, complete cds gi|30689629|ref|NM_102440.2|[30689629]
Source Promoter Organism: *Arabidopsis thaliana* WS

| | |
|---|---|
| Vector: | pNewbin4-HAP1-GFP |
| Marker Type: | GFP-ER |
| Generation Screened: | XT1 Mature   XT2 Seedling   ? T2 Mature   ? T3 Seedling |
| Criteria: Bidirectionality:   Exons:   Repeats: | |
| Table 5. | Promoter utility |

Utility: Leaf size and photosynthetic capacity. Increased source strength. Increased sucrose loading.
Increased leaf expansion, resulting in improved seedling stress tolerance. Modulate size of organs, young leaf specific exp.
Notes:

| | |
|---|---|
| Construct: | YP0261 |
| Promoter candidate I.D: | 11768750 |
| cDNA I.D: | 12385291 |
| Lines expressing: | YP0261-01, -03 plant date 09/08/03 |

Promoter Expression Report # 121

Report Date: Nov. 5, 2003
Promoter Tested In: *Arabidopsis thaliana*, WS ecotype
Spatial expression summary:

| | |
|---|---|
| Flower | H pedicel H receptacle H filament H anther H carpel H vascular H silique |
| Silique | H vascular |
| Stem | H vascular |
| Leaf | H vascular |
| Hypocotyl | L epidermis H vascular |
| Cotyledon | H vascular L epidermis |
| Rosette Leaf | H epidermis |
| Primary Root | H cortex H root cap |

TABLE 2-continued

Observed expression pattern:
T1 Mature: High GFP expression in vasculature of stem and leaves, also pedicles, siliques and stamen of flowers.
Not detected in sepals and petals. Expression in silique specific to medial vasculature. T2 Seedling: High GFP
expression in hypocotyl and cotyledon vasculature and cortex of root. Not observed in root vasculature.
Expected expression pattern: Stem and root elongation zones.
Selection Criteria: Hanzawa Y, Takahashi T, Michael A J, Burtin D, Long D, Pineiro M, Coupland G, Komeda Y,
ACAULIS5, an *Arabidopsis* gene required for stem elongation, encodes a spermine synthase. EMBO J. 2000 Aug 15; 19(16):4248-56.
Gene: *Arabidopsis* ACAULIS5 (ACL5)
GenBank: NM__121958 *Arabidopsis thaliana* spermine synthase (ACL5)(At5g19530) mRNA, complete cds
gi|30687363|ref|NM__121958.2|[30687363]
Source Promoter Organism: *Arabidopsis thaliana* WS
Vector: pNewbin4-HAP1-GFP
Marker Type: GFP-ER
Generation Screened: XT1 Mature  XT2 Seedling  T2 Mature  T3 Seedling
Criteria: Bidirectionality:  Exons:  Repeats:
Table 5.  Promoter utility
Utility: Translocation to the flower, seed fill. Sucrose loading and transport. Improved source capacity, lending
to larger plant organs, larger plants, Increased biomass, increased yield. Improved root growth and soil penetration.
Resistance to drought, improved uptake of nitrogen and phosphate. Modify nitrate uptake and translocation to Xylem.
Construct: YP0263
Promoter candidate I.D: 11768752
cDNA I.D: 12640578
Lines expressing: YP0263-10, -11, -12 plant date 9/8/03

Promoter Expression Report # 123

Report Date: Nov. 5, 2003
Promoter Tested In: *Arabidopsis thaliana*, WS ecotype
Spatial expression summary:
Flower           M stomata
Silique          M stomata
Ovule            Post-fertilization: L embryo
Embryo           L provascular, L cotyledons
Primary Root     L epidermis, L xylem
Observed expression pattern:
T1 mature: Strong expression in embryonic vascular tissue of cotyledons.
Weak guard cell expression in flower pedicle and silique. T2 seedling: Weak
degrading root epidermis expression near transition zone. Weak root vascular
expression in elongation zone. Expression in very thin cell layer appears to be xylem.
Expected expression pattern: root, flowers, ovules, young silique
Selection Criteria: *Arabidopsis* Two component line CS9135 (see notes).
Gene: Hypothetical protein containing helix-loop-helix DNA binding domain.
GenBank: NM__116493 *Arabidopsis thaliana* bHLH protein (At4g02590) mRNA,
complete cds gi|30679204|ref|NM __116493.2|[30679204]
Source Promoter Organism: *Arabidopsis thaliana* WS
Vector: pNewbin4-HAP1-GFP
Marker Type: GFP-ER
Generation Screened: XT1 Mature  XT2 Seedling  ? T2 Mature  ? T3 Seedling Criteria: Bidirectionality:  Exons:  Repeats:
Table 5.  Promoter utility
Utility: Translocation to cotyledons, seed fill. Increased embryo and seed weight. Altered embryo
and seed composition. Improved seedling vigor, seedling resistance to drought, cold, cold/wet conditions.
Construct: YP0003
Promoter candidate I.D: 13148213
cDNA I.D: 12649228
Lines expressing: YP0003-04, -06 plant date 9/8/03

TABLE 3

Optional Promoter Fragments

| SEQ ID NO. | CONSTRUCT NO | EXON | UTR | INTERVENING SEQUENCE |
|---|---|---|---|---|
| 1 | | | | |
| 2 | YP0007 | | 1013-1033 | |
| 3 | | | | |
| 5 | YP0111 | | 935-999 | |
| 6 | | | | |
| 7 | | | | |
| 8 | YP0016 | 746-1000 | 935-1000 | |
| 9 | YP0094 | 1-28; 1-101 | | |
| 10 | | | | |
| 11 | YP0049 | | | 395-915 |
| 12 | YP0060 | 265-343 | | 1-264 |
| 13 | YP0092 | 1-764 | | |
| 14 | | | | |
| 15 | YP0095 | 1-214 | | |
| 16 | | | | |
| 17 | YP0103 | 224-362; 1-128 | 950-1001 | 129-223 |
| 18 | YP0107 | | 1-55 | |
| 19 | | | | |

TABLE 3-continued

Optional Promoter Fragments

| SEQ ID NO. | CONSTRUCT NO | EXON | UTR | INTERVENING SEQUENCE |
|---|---|---|---|---|
| 20 | YP0112 | 245-640 | | 1-245 |
| 21 | | | | |
| 22 | | | | |
| 23 | | | | |
| 24 | YP0126 | 1-355 | | |
| 25 | YP0024 | 1-56; 148-233; 381-670 | | 57-147; 234-280 |
| 26 | | | | |
| 27 | | | | |
| 28 | | | | |
| 29 | | | | |
| 30 | | | | |
| 31 | | | | |
| 32 | YP0054 | | 948-999 | |
| 33 | | | | |
| 34 | YP0050 | 1-44; 131-339 | 940-999 | 45-130 |
| 35 | YP0040 | | 933-999 | |
| 36 | | | | |
| 37 | | | | |
| 38 | YP0068 | 1-119; 271-725 | 932-999 | 120-270 |
| 39 | YP0082 | | | |
| 40 | | | | |
| 41 | | | | |
| 42 | | | | |
| 43 | YP0180 | 91-234; 302-656 | | 1-90; 235-301 |
| 44 | | | | |
| 45 | YP0121 | 55-294; 389-530; 604-640 | | 1-54; 295-388; 531-603 |
| 46 | | | | |
| 47 | | | | |
| 48 | YP0108 | 1-216 | | |
| 49 | | | | |
| 50 | | | | |
| 51 | | | | |
| 52 | YP0192 | | 257-640 | 641- |
| 53 | YP0204 | | 947-999 | |
| 54 | BIN2A2-28716-HY2 | 14-406 | 1260-1322 | 1-14 |
| 55 | BIN1-34414-HY2 | | 900-1056 | |
| 56 | CR13(GFP-ER) | 178-735; 761-813 | 1660-1723; 1928-1954 | 1-177; 736-760; 1724-1927 |
| 57 | | | | |
| 58 | | | | |
| 59 | | | | |
| 60 | | | | |
| 61 | YP0122 | | 709-999 | |
| 62 | YP0216 | | 925-999 | |
| 63 | | | | |
| 64 | YP0261 | | 806-880 | |
| 65 | | | | |
| 66 | YP0271 | | 983-999 | |
| 67 | | | | |
| 68 | | | | |
| 69 | YP0003 | | 700-882 | |
| 70 | | | | |

TABLE 4

| _cDNA_ID | Expt_Rep_ID | Short_Name | Differential |
|---|---|---|---|
| 13610584 | 20000264 | At_Open_Flower | − |
| 12656458 | 20000708 | At_Fis1_Siliques | − |
| 4909806 | 20000439 | At_Roots | − |
| 4909806 | 20000185 | At_Roots_YF | − |
| 12669615 | 20000264 | At_Open_Flower | − |
| 4909806 | 20000794 | At_Petals | − |
| 12711515 | 20000794 | At_Petals | − |
| 12669615 | 20000265 | At_Open_Flower | − |

TABLE 4-continued

| _cDNA_ID | Expt_Rep_ID | Short_Name | Differential |
|---|---|---|---|
| 4909291 | 20000092 | At_42deg_Heat | − |
| 13612879 | 20000185 | At_Roots | − |
| 13489977 | 20000234 | At_Siliques | − |
| 13610584 | 20000794 | At_Petals | − |
| 13612879 | 20000438 | At_Shoots | − |
| 12669615 | 20000234 | At_Siliques | − |
| 13489977 | 20000264 | At_Open_Flower | − |
| 12669615 | 20000286 | At_Open_Flower | − |
| 12329827 | 20000439 | At_Roots | − |
| 13610584 | 20000286 | At_Open_Flower | − |
| 13610584 | 20000234 | At_Siliques | − |
| 13612879 | 20000439 | At_Roots | − |
| 12688453 | 20000439 | At_Roots | − |
| 12669615 | 20000794 | At_Petals | − |
| 12688453 | 20000185 | At_Roots | − |
| 12329827 | 20000185 | At_Roots | − |
| 12692181 | 20000314 | At_14day_Shoots-Roots | − |
| 13489977 | 20000286 | At_Open_Flower | − |
| 4909291 | 20000457 | At_42deg_Heat | − |
| 12370148 | 20000234 | At_Siliques | − |
| 13489977 | 20000265 | At_Open_Flower | − |
| 13609817 | 108434 | At_Root_Tips | − |
| 12348737 | 20000794 | At_Petals | − |
| 12713856 | 20000439 | At_Roots | − |
| 12333534 | 20000794 | At_Petals | − |
| 13612879 | 20000184 | At_Shoots | − |
| 13489977 | 20000438 | At_Shoots | − |
| 12692181 | 108457 | At_Diversity_Expt | − |
| 13489977 | 20000235 | At_Siliques | − |
| 12669615 | 20000235 | At_Siliques | − |
| 13489977 | 20000326 | At_Pollen | − |
| 13489977 | 20000236 | At_Siliques | − |
| 12713856 | 20000185 | At_Roots | − |
| 13612879 | 20000527 | At_10%_PEG | − |
| 13612879 | 20000794 | At_Petals | − |
| 4909806 | 108435 | At_stm_Mutants | − |
| 13610584 | 20000235 | At_Siliques | − |
| 12370148 | 20000235 | At_Siliques | − |
| 12669615 | 20000438 | At_Shoots | − |
| 12322657 | 20000438 | At_Shoots | − |
| 12692181 | 20000315 | At_14day_Shoots-Roots | − |
| 12370148 | 20000265 | At_Open_Flower | − |
| 12679922 | 20000439 | At_Roots | − |
| 12678173 | 20001654 | At_Interploidy_Crosses | − |
| 13612919 | 108595 | At_Ler-pi_Ovule | − |
| 12370148 | 20000286 | At_Open_Flower | − |
| 12670159 | 20000185 | At_Roots | − |
| 12333534 | 20001654 | At_Interploidy_Crosses | − |
| 12713856 | 20000071 | At_100uM_ABA_Mutants | − |
| 12711515 | 20000214 | At_4deg_Cold | − |
| 12322657 | 20000326 | At_Pollen | − |
| 12679922 | 20000234 | At_Siliques | − |
| 12679922 | 20000185 | At_Roots | − |
| 12370148 | 20000236 | At_Siliques | − |
| 12660077 | 20001248 | At_Far-red-induction | − |
| 12713856 | 108595 | At_Ler-pi_Ovule_cDNA_P | − |
| 13612919 | 20000326 | At_Pollen | − |
| 12679922 | 20000265 | At_Open_Flower | − |
| 12348737 | 20000264 | At_Open_Flower | − |
| 12669615 | 20000236 | At_Siliques | − |
| 12679922 | 20001556 | At_Drought_Soil_Dry | − |
| 12711515 | 20001554 | At_Drought_Soil_Dry | − |
| 12711515 | 20000264 | At_Open_Flower | − |
| 12678173 | 20000223 | At_CS6632_Shoots-Roots_cDNA_P | − |
| 12713856 | 20000117 | At_100uM_ABA_Mutants_cDNA_P | − |
| 13612879 | 20000458 | At_42deg_Heat | − |
| 12329827 | 20000245 | At_Caf_Knockout | − |
| 13612919 | 20000439 | At_Roots | − |
| 12322657 | 20000184 | At_Shoots | − |
| 12646933 | 20000185 | At_Roots | − |
| 12646933 | 20000438 | At_Shoots | − |
| 12679922 | 20000286 | At_Open_Flower | − |
| 12576899 | 20000458 | At_42deg_Heat | − |
| 12348737 | 20000235 | At_Siliques | − |
| 12348737 | 108595 | At_Ler-pi_Ovule_cDNA_P | − |

TABLE 4-continued

| _cDNA_ID | Expt_Rep_ID | Short_Name | Differential |
|---|---|---|---|
| 13609817 | 108457 | At_Diversity_Expt_cDNA_P | − |
| 12660077 | 20000185 | At_Roots | − |
| 12664333 | 20000527 | At_10%_PEG | − |
| 13613553 | 20000180 | At_Germinating_Seeds | − |
| 13647840 | 20000438 | At_Shoots | − |
| 12679922 | 20001555 | At_Drought_Soil_Dry | − |
| 12370148 | 20000439 | At_Roots | − |
| 12348737 | 20000708 | At_Fis1_Siliques | − |
| 12711515 | 20001556 | At_Drought_Soil_Dry | − |
| 12333534 | 108577 | At_42deg_Heat_cDNA_P | − |
| 12329827 | 20000438 | At_Shoots | − |
| 12348737 | 108435 | At_stm_Mutants_cDNA_P | − |
| 12679922 | 20000236 | At_Siliques | − |
| 12713856 | 20001248 | At_Far-red-induction | − |
| 4909806 | 20001557 | At_Drought_Soil_Dry | − |
| 12711515 | 20001555 | At_Drought_Soil_Dry | − |
| 13619323 | 20000438 | At_Shoots | − |
| 12679922 | 20000264 | At_Open_Flower | − |
| 13613553 | 20001247 | At_Far-red-induction | − |
| 12455436 | 108462 | At_Germinating_Seeds_cDNA_P | − |
| 13612919 | 20001450 | At_Far-red-induction | − |
| 12332135 | 20000439 | At_Roots | − |
| 12332135 | 20000438 | At_Shoots | − |
| 13647840 | 20000185 | At_Roots | − |
| 12576899 | 20001555 | At_Drought_Soil_Dry | − |
| 12455436 | 108464 | At_Germinating_Seeds_cDNA_P | − |
| 13612919 | 20001248 | At_Far-red-induction | − |
| 13647840 | 20000708 | At_Fis1_Siliques | − |
| 12370148 | 20000264 | At_Open_Flower | − |
| 13609817 | 20001558 | At_Drought_Soil_Dry | − |
| 12329827 | 20000794 | At_Petals | − |
| 13489977 | 20000184 | At_Shoots | − |
| 13489977 | 20000180 | At_Germinating_Seeds | − |
| 13613553 | 108464 | At_Germinating_Seeds_cDNA_P | − |
| 4909806 | 20001560 | At_Drought_Soil_Dry | − |
| 12678173 | 108457 | At_Diversity_Expt_cDNA_P | − |
| 13613553 | 20000438 | At_Shoots | − |
| 12370148 | 20000185 | At_Roots | − |
| 13613553 | 20000185 | At_Roots | − |
| 4909806 | 20001558 | At_Drought_Soil_Dry | − |
| 12576899 | 20000173 | At_42deg_Heat | − |
| 12370148 | 20000438 | At_Shoots | − |
| 12332135 | 20000265 | At_Open_Flower | − |
| 12333534 | 20000185 | At_Roots | − |
| 13489977 | 20000439 | At_Roots | − |
| 13617784 | 20000234 | At_Siliques | − |
| 4909806 | 20000577 | At_42deg_Heat_cDNA_P | − |
| 4909806 | 108595 | At_Ler-pi_Ovule_cDNA_P | − |
| 12455436 | 108463 | At_Germinating_Seeds_cDNA_P | − |
| 12703041 | 20001559 | At_Drought_Soil_Dry | − |
| 12713856 | 20000086 | At_100uM_ABA_Mutants_cDNA_P | − |
| 12711515 | 20000213 | At_4deg_Cold | − |
| 12703041 | 20000234 | At_Siliques | − |
| 13489977 | 20000185 | At_Roots | − |
| 12669615 | 20000527 | At_10%_PEG | − |
| 12679922 | 108501 | At_ap2_floral_buds_cDNA_P | − |
| 13612919 | 108435 | At_stm_Mutants_cDNA_P | − |
| 12333534 | 108579 | At_4deg_Cold_cDNA_P | − |
| 12670159 | 20000265 | At_Open_Flower | − |
| 12396394 | 20001557 | At_Drought_Soil_Dry | − |
| 12646933 | 20000439 | At_Roots | − |
| 12735519 | 20001248 | At_Far-red-induction | − |
| 13609817 | 20001557 | At_Drought_Soil_Dry | − |
| 12348737 | 20000236 | At_Siliques | − |
| 12713856 | 20000069 | At_100uM_ABA_Mutants_cDNA_P | − |
| 12713856 | 108573 | At_Drought_cDNA_P | − |
| 12370148 | 20000184 | At_Shoots | − |
| 13619323 | 20000184 | At_Shoots | − |
| 13610584 | 20000236 | At_Siliques | − |
| 13610584 | 20000437 | At_Drought | − |
| 12713856 | 20000088 | At_100uM_ABA_Mutants_cDNA_P | − |
| 13609817 | 20000265 | At_Open_Flower | − |
| 12711515 | 20000236 | At_Siliques | − |
| 12333534 | 108595 | At_Ler-pi_Ovule_cDNA_P | − |
| 13609817 | 20000227 | At_Root-Tips-vs-Tops | − |
| 12713856 | 20000326 | At_Pollen | − |
| 12679922 | 20001559 | At_Drought_Soil_Dry | − |
| 12679922 | 20000214 | At_4deg_Cold | − |
| 13647840 | 20000245 | At_Caf_Knockout | − |
| 12703041 | 20001556 | At_Drought_Soil_Dry | − |
| 12703041 | 108595 | At_Ler-pi_Ovule_cDNA_P | − |
| 12370148 | 20000573 | At_100uM_ABA_Mutants | − |
| 13612879 | 20000326 | At_Pollen | − |
| 12348737 | 20000234 | At_Siliques | − |
| 4909806 | 108585 | At_5mM_NaNP_cDNA_P | − |
| 12348737 | 20000265 | At_Open_Flower | − |
| 13614559 | 20000180 | At_Germinating_Seeds | − |
| 13612879 | 108668 | At_2mM_SA_cDNA_P | − |
| 13489977 | 20000573 | At_100uM_ABA_Mutants | − |
| 13613553 | 20000184 | At_Shoots | − |
| 12713856 | 20000070 | At_100uM_ABA_Mutants_cDNA_P | − |
| 12670159 | 20000264 | At_Open_Flower | − |
| 13491988 | 20000227 | At_Root-Tips-vs-Tops | − |
| 13609817 | 20000234 | At_Siliques | − |
| 12329827 | 108462 | At_Germinating_Seeds_cDNA_P | − |
| 12703041 | 108434 | At_Root_Tips_cDNA_P | − |
| 13617784 | 20000286 | At_Open_Flower | − |
| 12703041 | 20000437 | At_Drought | − |
| 13653114 | 20000307 | At_Germinating_Seeds | − |
| 12670159 | 20000439 | At_Roots | − |
| 12656458 | 20001653 | At_Interploidy_Crosses | − |
| 12711515 | 20000437 | At_Drought | − |
| 13489977 | 20000179 | At_Germinating_Seeds | − |
| 12396394 | 108595 | At_Ler-pi_Ovule_cDNA_P | − |
| 13491988 | 20000185 | At_Roots | − |
| 12711515 | 108668 | At_2mM_SA_cDNA_P | − |
| 13610584 | 20000495 | At_Guard_Cells | − |
| 13617784 | 20000236 | At_Siliques | − |
| 12348737 | 20000286 | At_Open_Flower | − |
| 12688453 | 20000326 | At_Pollen | − |
| 13617784 | 20000264 | At_Open_Flower | − |
| 12370148 | 20000173 | At_42deg_Heat | − |
| 13617784 | 20000265 | At_Open_Flower | − |
| 12370148 | 20000574 | At_100uM_ABA_Mutants | − |
| 12333534 | 20000111 | At_42deg_Heat_cDNA_P | − |
| 13610584 | 20001557 | At_Drought_Soil_Dry | − |
| 4909291 | 108488 | At_50mM_NH4NO3_L-to-H_Rosette_cDNA_P | − |
| 12333534 | 20000227 | At_Root-Tips-vs-Tops | − |
| 12396394 | 20001248 | At_Far-red-induction | − |
| 12713856 | 20000087 | At_100uM_ABA_Mutants_cDNA_P | − |
| 12332135 | 20000185 | At_Roots | − |
| 13612919 | 20000185 | At_Roots | − |
| 12576899 | 20000214 | At_4deg_Cold | − |
| 13617784 | 20000235 | At_Siliques | − |
| 13489977 | 20000708 | At_Fis1_Siliques | − |
| 12660077 | 20000573 | At_100uM_ABA_Mutants | − |
| 12322657 | 20000185 | At_Roots | − |
| 12370148 | 20000171 | At_42deg_Heat | − |
| 12669615 | 20000458 | At_42deg_Heat | − |
| 13619323 | 108474 | At_Drought_Flowers_cDNA_P | − |
| 12333534 | 20000173 | At_42deg_Heat | − |
| 4909806 | 20001459 | At_50mM_NH4NO3_L-to-H | − |
| 13647840 | 20000439 | At_Roots | − |
| 12329827 | 108463 | At_Germinating_Seeds_cDNA_P | − |
| 12679922 | 108577 | At_42deg_Heat_cDNA_P | − |
| 12679922 | 20000268 | At_100mM_NaCl | − |
| 12370148 | 20000180 | At_Germinating_Seeds | − |
| 12370148 | 108434 | At_Root_Tips_cDNA_P | − |
| 12322657 | 20001247 | At_Far-red-induction | − |
| 13610584 | 20000438 | At_Shoots | − |
| 13647840 | 20000184 | At_Shoots | − |
| 13613553 | 20001451 | At_Far-red-induction | − |
| 4905097 | 20001654 | At_Interploidy_Crosses | − |
| 12703041 | 20000265 | At_Open_Flower | − |
| 12396394 | 108579 | At_4deg_Cold_cDNA_P | − |
| 12713856 | 20000794 | At_Petals | − |
| 12646933 | 20000245 | At_Caf_Knockout | − |
| 12370148 | 20000268 | At_100mM_NaCl | − |
| 12333534 | 20000437 | At_Drought | − |

TABLE 4-continued

| _cDNA_ID | Expt_Rep_ID | Short_Name | Differential |
|---|---|---|---|
| 12713856 | 108499 | At_DMT-II_cDNA_P | – |
| 12678173 | 20000030 | At_CS6630_Roots_cDNA_P | – |
| 12669615 | 20000180 | At_Germinating_Seeds | – |
| 4909806 | 108668 | At_2mM_SA_cDNA_P | – |
| 12703041 | 20001555 | At_Drought_Soil_Dry | – |
| 13491988 | 20000439 | At_Roots | – |
| 13610584 | 20000451 | At_CS6879_Shoots-Roots | – |
| 12711515 | 108499 | At_DMT-II_cDNA_P | – |
| 13612879 | 20001556 | At_Drought_Soil_Dry | – |
| 12332135 | 20000184 | At_Shoots | – |
| 12670159 | 20000794 | At_Petals | – |
| 12646933 | 20001654 | At_Interploidy_Crosses | – |
| 12348737 | 108579 | At_4deg_Cold_cDNA_P | – |
| 12370148 | 20000111 | At_42deg_Heat_cDNA_P | – |
| 12576899 | 20001556 | At_Drought_Soil_Dry | – |
| 12329827 | 20000184 | At_Shoots | – |
| 12333534 | 20000439 | At_Roots | – |
| 12370148 | 20000708 | At_Fis1_Siliques | – |
| 13613553 | 20000439 | At_Roots | – |
| 12322657 | 20000439 | At_Roots | – |
| 13610584 | 108434 | At_Root_Tips_cDNA_P | – |
| 12713856 | 108584 | At_5mM_NaNP_cDNA_P | – |
| 12333534 | 108499 | At_DMT-II_cDNA_P | – |
| 13609817 | 20001560 | At_Drought_Soil_Dry | – |
| 12670159 | 20000286 | At_Open_Flower | – |
| 4909291 | 20000286 | At_Open_Flower | – |
| 12396394 | 20000070 | At_100uM_ABA_Mutants_cDNA_P | – |
| 12679922 | 20000180 | At_Germinating_Seeds | – |
| 12711515 | 108435 | At_stm_Mutants_cDNA_P | – |
| 4909806 | 108576 | At_42deg_Heat_cDNA_P | – |
| 12332135 | 20000527 | At_10%_PEG | – |
| 4909806 | 20000264 | At_Open_Flower | – |
| 12711515 | 20000235 | At_Siliques | – |
| 12711515 | 108461 | At_Germinating_Seeds_cDNA_P | – |
| 13489977 | 20000574 | At_100uM_ABA_Mutants | – |
| 13614841 | 20000437 | At_Drought | – |
| 12711515 | 20000438 | At_Shoots | – |
| 12703041 | 20000214 | At_4deg_Cold | – |
| 12646933 | 20000184 | At_Shoots | – |
| 13610584 | 20001300 | At_Line_Comparisons | – |
| 12333534 | 20000117 | At_100uM_ABA_Mutants_cDNA_P | – |
| 12656458 | 20001316 | At_Interploidy_Crosses | – |
| 12679922 | 20000308 | At_100mM_NaCl | – |
| 12678173 | 108435 | At_stm_Mutants_cDNA_P | – |
| 12669615 | 20000244 | At_Caf_Knockout | – |
| 12333534 | 20000069 | At_100uM_ABA_Mutants_cDNA_P | – |
| 12329827 | 20000265 | At_Open_Flower | – |
| 13613553 | 108463 | At_Germinating_Seeds_cDNA_P | – |
| 12703041 | 108594 | At_Ler-rhl_Root_cDNA_P | – |
| 13617784 | 20000326 | At_Pollen | – |
| 12333534 | 20001556 | At_Drought_Soil_Dry | – |
| 12396394 | 20001558 | At_Drought_Soil_Dry | – |
| 12329827 | 108461 | At_Germinating_Seeds_cDNA_P | – |
| 12332135 | 20001654 | At_Interploidy_Crosses | – |
| 12711515 | 20000173 | At_42deg_Heat | – |
| 12679922 | 20001560 | At_Drought_Soil_Dry | – |
| 12679922 | 20000438 | At_Shoots | – |
| 13613553 | 108488 | At_50mM_NH4NO3_L-to-H_Rosette_cDNA_P | – |
| 12325134 | 108474 | At_Drought_Flowers_cDNA_P | – |
| 13612919 | 20000070 | At_100uM_ABA_Mutants_cDNA_P | – |
| 12333534 | 108584 | At_5mM_NaNP_cDNA_P | – |
| 13612919 | 20000794 | At_Petals | – |
| 12679922 | 20001300 | At_Line_Comparisons | – |
| 13610584 | 108478 | At_Shoot_Apices_cDNA_P | – |
| 12370148 | 108606 | At_100uM_ABA_cDNA_P | – |
| 13612919 | 20000088 | At_100uM_ABA_Mutants_cDNA_P | – |
| 13613553 | 108435 | At_stm_Mutants_cDNA_P | – |
| 12396394 | 20000088 | At_100uM_ABA_Mutants_cDNA_P | – |
| 12703041 | 108499 | At_DMT-II_cDNA_P | – |
| 12713856 | 108572 | At_Drought_cDNA_P | – |
| 12333534 | 20000436 | At_Drought | – |
| 12711515 | 20000456 | At_100uM_BA | – |
| 13613553 | 108434 | At_Root_Tips_cDNA_P | – |
| 12561142 | 20000794 | At_Petals | – |
| 13613553 | 108462 | At_Germinating_Seeds_cDNA_P | – |
| 12576899 | 20000213 | At_4deg_Cold | – |
| 13601936 | 20001556 | At_Drought_Soil_Dry | – |
| 12396394 | 20000086 | At_100uM_ABA_Mutants_cDNA_P | – |
| 4909291 | 20000265 | At_Open_Flower | – |
| 12711515 | 20000234 | At_Siliques | – |
| 12703041 | 20000087 | At_100uM_ABA_Mutants_cDNA_P | – |
| 12703041 | 20000267 | At_Drought | – |
| 12670159 | 20001451 | At_Far-red-induction | – |
| 12370148 | 20000046 | At_CS237-vs-Columbia_cDNA_P | – |
| 12679922 | 20001558 | At_Drought_Soil_Dry | – |
| 12711515 | 108463 | At_Germinating_Seeds_cDNA_P | – |
| 12332135 | 108474 | At_Drought_Flowers_cDNA_P | – |
| 12370148 | 20000437 | At_Drought | – |
| 13621692 | 20000173 | At_42deg_Heat_ | – |
| 12396394 | 108435 | At_stm_Mutants_cDNA_P | – |
| 12660077 | 20000439 | At_Roots | – |
| 4909291 | 20000234 | At_Siliques | – |
| 12396394 | 20000090 | At_2mM_SA_CS3726-Columbia_cDNA_P | – |
| 12660077 | 20000574 | At_100uM_ABA_Mutants | – |
| 12669615 | 20000179 | At_Germinating_Seeds | – |
| 12396394 | 108589 | At_15mM_NH4NO3_L-to-H_cDNA_P | – |
| 12370148 | 108501 | At_ap2_floral_buds_cDNA_P | – |
| 13617784 | 108457 | At_Diversity_Expt_cDNA_P | – |
| 4909291 | 20000127 | At_50mM_NH4NO3_L-to-H_Siliques_cDNA_P | – |
| 12455436 | 20000326 | At_Pollen | – |
| 12370148 | 108608 | At_100uM_ABA_cDNA_P | – |
| 13612879 | 108667 | At_2mM_SA_cDNA_P | – |
| 12370148 | 20001317 | At_Interploidy_Crosses | – |
| 13489977 | 20000171 | At_42deg_Heat | – |
| 12370148 | 20000166 | At_100uM_ABA | – |
| 13609817 | 20001556 | At_Drought_Soil_Dry | – |
| 12679922 | 20001554 | At_Drought_Soil_Dry | – |
| 13617784 | 20000456 | At_100uM_BA | – |
| 12333534 | 20000088 | At_100uM_ABA_Mutants_cDNA_P | – |
| 4909806 | 20000576 | At_100uM_ABA_Mutants | – |
| 4909806 | 20000573 | At_100uM_ABA_Mutants | – |
| 4909806 | 20000574 | At_100uM_ABA_Mutants | – |
| 12576899 | 20000171 | At_42deg_Heat | – |
| 12679922 | 108462 | At_Germinating_Seeds_cDNA_P | – |
| 13621692 | 20000184 | At_Shoots | – |
| 12396394 | 20001556 | At_Drought_Soil_Dry | – |
| 4909291 | 20000264 | At_Open_Flower | – |
| 12322657 | 108577 | At_42deg_Heat_cDNA_P | – |
| 4909806 | 20000575 | At_100uM_ABA_Mutants_ | – |
| 12333534 | 20000070 | At_100uM_ABA_Mutants_cDNA_P | – |
| 13609817 | 108595 | At_Ler-pi_Ovule_cDNA_P | – |
| 12348737 | 108501 | At_ap2_floral_buds_cDNA_P | – |
| 12396394 | 20000071 | At_100uM_ABA_Mutants_cDNA_P | – |
| 13613553 | 108461 | At_Germinating_Seeds_cDNA_P | – |
| 4909806 | 108607 | At_100uM_ABA_cDNA_P | – |
| 13610584 | 20000267 | At_Drought | – |
| 12713856 | 108579 | At_4deg_Cold_cDNA_P | – |
| 13609817 | 20000708 | At_Fis1_Siliques | – |
| 12688453 | 20000438 | At_Shoots | – |
| 13489977 | 20000506 | At_Wounding | – |
| 12348737 | 20000179 | At_Germinating_Seeds | – |
| 12711515 | 108579 | At_4deg_Cold_cDNA_P | – |
| 12713856 | 108607 | At_100uM_ABA_cDNA_P | – |
| 12679922 | 108461 | At_Germinating_Seeds_cDNA_P | – |
| 13614841 | 20001451 | At_Far-red-induction | – |
| 4909806 | 20000437 | At_Drought | – |
| 12325134 | 108569 | At_0.001%_MeJA_cDNA_P | – |
| 4909291 | 20000235 | At_Siliques | – |
| 12713856 | 108606 | At_100uM_ABA_cDNA_P | – |
| 12321680 | 20000439 | At_Roots | – |
| 13601936 | 20000069 | At_100uM_ABA_Mutants_cDNA_P | – |
| 13610584 | 20000326 | At_Pollen | – |
| 12679922 | 108500 | At_DMT-II_cDNA_P | – |
| 12322657 | 20000111 | At_42deg_Heat_cDNA_P | – |
| 13619323 | 20001654 | At_Interploidy_Crosses | – |
| 12713856 | 108435 | At_stm_Mutants_cDNA_P | – |
| 12348737 | 108488 | At_50mM_NH4NO3_L-to- | – |

TABLE 4-continued

| _cDNA_ID | Expt_Rep_ID | Short_Name | Differential |
|---|---|---|---|
| | | H_Rosette_cDNA_P | |
| 12576899 | 20001554 | At_Drought_Soil_Dry | − |
| 13601936 | 20000438 | At_Shoots | − |
| 13614841 | 20000794 | At_Petals | − |
| 12455436 | 20000794 | At_Petals | − |
| 12333534 | 20001555 | At_Drought_Soil_Dry | − |
| 12370148 | 20000308 | At_100mM_NaCl | − |
| 12713856 | 108577 | At_42deg_Heat_cDNA_P | − |
| 12711515 | 20000171 | At_42deg_Heat | − |
| 12713856 | 20000436 | At_Drought | − |
| 12711515 | 20000046 | At_CS237-vs-Columbia_cDNA_P | − |
| 12333534 | 108478 | At_Shoot_Apices_cDNA_P | − |
| 12703041 | 20000090 | At_2mM_SA_CS3726-Columbia_cDNA_P | − |
| 13509244 | 20000184 | At_Shoots | − |
| 13610584 | 20000709 | At_15mM_NH4NO3_L-to-H | − |
| 12711515 | 20000527 | At_10%_PEG | − |
| 12370148 | 108575 | At_Wounding_cDNA_P | − |
| 13612919 | 20001451 | At_Far-red-induction | − |
| 12333534 | 20001559 | At_Drought_Soil_Dry | − |
| 4905097 | 108461 | At_Germinating_Seeds_cDNA_P | − |
| 12669615 | 20000173 | At_42deg_Heat | − |
| 13491988 | 20000451 | At_CS6879_Shoots-Roots | − |
| 12669615 | 20001555 | At_Drought_Soil_Dry | − |
| 12711515 | 20000111 | At_42deg_Heat_cDNA_P | − |
| 4909291 | 20000213 | At_4deg_Cold | − |
| 12333534 | 20000072 | At_100uM_ABA_Mutants_cDNA_P | − |
| 12713856 | 20000437 | At_Drought | − |
| 13621692 | 20000265 | At_Open_Flower | − |
| 12679922 | 108463 | At_Germinating_Seeds_cDNA_P | − |
| 13491988 | 20001558 | At_Drought_Soil_Dry | − |
| 4909806 | 108512 | At_3642-1_cDNA_P | − |
| 12370148 | 108461 | At_Germinating_Seeds_cDNA_P | − |
| 13617784 | 108595 | At_Ler-pi_Ovule_cDNA_P | − |
| 12332135 | 20001397 | At_Line_Comparisons | − |
| 12711515 | 20000144 | At_42deg_Heat_cDNA_P | − |
| 4909291 | 108579 | At_4deg_Cold_cDNA_P | − |
| 13610584 | 20000184 | At_Shoots | − |
| 12679922 | 20000113 | At_42deg_Heat_cDNA_P | − |
| 12321680 | 20001654 | At_Interploidy_Crosses | − |
| 12713856 | 20000286 | At_Open_Flower | − |
| 13489977 | 20000227 | At_Root-Tips-vs-Tops | − |
| 12711515 | 108464 | At_Germinating_Seeds_cDNA_P | − |
| 12692181 | 108480 | At_Shoot_Apices_cDNA_P | − |
| 12670159 | 20001557 | At_Drought_Soil_Dry | − |
| 12370148 | 20000288 | At_Drought | − |
| 12670159 | 20000708 | At_Fis1_Siliques | − |
| 4905097 | 108474 | At_Drought_Flowers_cDNA_P | − |
| 12396394 | 20000117 | At_100uM_ABA_Mutants_cDNA_P | − |
| 13614559 | 108463 | At_Germinating_Seeds_cDNA_P | − |
| 12670159 | 20001556 | At_Drought_Soil_Dry | − |
| 13509244 | 20000326 | At_Pollen | − |
| 4996264 | 20000286 | At_Open_Flower | − |
| 13614559 | 108461 | At_Germinating_Seeds_cDNA_P | − |
| 12692181 | 108435 | At_stm_Mutants_cDNA_P | − |
| 12333534 | 20000087 | At_100uM_ABA_Mutants_cDNA_P | − |
| 12455436 | 108461 | At_Germinating_Seeds_cDNA_P | − |
| 12670159 | 20000227 | At_Root-Tips-vs-Tops | − |
| 12669615 | 20000171 | At_42deg_Heat | − |
| 12703041 | 20000451 | At_CS6879_Shoots-Roots | − |
| 12333534 | 108561 | At_100uM_ABA_cDNA_P | − |
| 12332135 | 108569 | At_0.001%_MeJA_cDNA_P | − |
| 13621692 | 20000438 | At_Shoots | − |
| 12329827 | 20001654 | At_Interploidy_Crosses | − |
| 12646933 | 20001397 | At_Line_Comparisons | − |
| 12669615 | 20000184 | At_Shoots | − |
| 5787483 | 108576 | At_42deg_Heat_cDNA_P | − |
| 12711515 | 20000286 | At_Open_Flower | − |
| 12678173 | 20000068 | At_CS3824_vs_Landsberg_cDNA_P | − |
| 13612919 | 20001557 | At_Drought_Soil_Dry | − |
| 13612919 | 20000090 | At_2mM_SA_CS3726-Columbia_cDNA_P | − |
| 13614559 | 108462 | At_Germinating_Seeds_cDNA_P | − |
| 12333534 | 20000086 | At_100uM_ABA_Mutants_cDNA_P | − |
| 12711515 | 20000265 | At_Open_Flower | − |
| 13609100 | 20001248 | At_Far-red-induction | − |
| 12370148 | 108579 | At_4deg_Cold_cDNA_P | − |
| 13617784 | 20000269 | At_1mM_KNO3_L-vs-H_Roots | − |
| 12735519 | 20000573 | At_100uM_ABA_Mutants | − |
| 12646933 | 20000794 | At_Petals | − |
| 13489977 | 20000211 | At_0.001%_MeJA | − |
| 12713856 | 108608 | At_100uM_ABA_cDNA_P | − |
| 12348737 | 20000173 | At_42deg_Heat | − |
| 12711515 | 20000267 | At_Drought | − |
| 12703041 | 20001554 | At_Drought_Soil_Dry | − |
| 4996264 | 20000264 | At_Open_Flower | − |
| 13612919 | 20000437 | At_Drought | − |
| 13610584 | 20000268 | At_100mM_NaCl | − |
| 13653114 | 20000306 | At_Germinating_Seeds | − |
| 12322657 | 108434 | At_Root_Tips_cDNA_P | − |
| 12703041 | 108457 | At_Diversity_Expt_cDNA_P | − |
| 4909806 | 20001556 | At_Drought_Soil_Dry | − |
| 12370148 | 20000506 | At_Wounding | − |
| 13489977 | 108434 | At_Root_Tips_cDNA_P | − |
| 13612919 | 108585 | At_5mM_NaNP_cDNA_P | − |
| 12660077 | 20000184 | At_Shoots | − |
| 12679922 | 20000179 | At_Germinating_Seeds | − |
| 13614559 | 108464 | At_Germinating_Seeds_cDNA_P | − |
| 13610584 | 108574 | At_Wounding_cDNA_P | − |
| 12646933 | 20001449 | At_Line_Comparisons | − |
| 13617784 | 20000086 | At_100uM_ABA_Mutants_cDNA_P | − |
| 4909806 | 20001316 | At_Interploidy_Crosses | − |
| 12703041 | 20000268 | At_100mM_NaCl | − |
| 12576899 | 20001557 | At_Drought_Soil_Dry | − |
| 12333534 | 20000093 | At_42deg_Heat_cDNA_P | − |
| 13491988 | 20001560 | At_Drought_Soil_Dry | − |
| 4996264 | 20000265 | At_Open_Flower | − |
| 12679922 | 20000794 | At_Petals | − |
| 4909806 | 20000169 | At_100uM_ABA | − |
| 12688453 | 20000573 | At_100uM_ABA_Mutants | − |
| 4909806 | 20000234 | At_Siliques | − |
| 12711515 | 20000436 | At_Drought | − |
| 13619323 | 108500 | At_DMT-II_cDNA_P | − |
| 12713856 | 20001450 | At_Far-red-induction | − |
| 12333534 | 20000071 | At_100uM_ABA_Mutants_cDNA_P | − |
| 12348737 | 108594 | At_Ler-rhl_Root_cDNA_P | − |
| 4996264 | 20000184 | At_Shoots | − |
| 13609817 | 20000090 | At_2mM_SA_CS3726-Columbia_cDNA_P | − |
| 12321680 | 20000438 | At_Shoots | − |
| 12370148 | 20000227 | At_Root-Tips-vs-Tops | − |
| 4909291 | 20001558 | At_Drought_Soil_Dry | − |
| 4909806 | 20000286 | At_Open_Flower | − |
| 12561142 | 20001556 | At_Drought_Soil_Dry | − |
| 13617784 | 108499 | At_DMT-II_cDNA_P | − |
| 12321680 | 20001397 | At_Line_Comparisons | − |
| 12679922 | 20001449 | At_Line_Comparisons | − |
| 13491988 | 108577 | At_42deg_Heat_cDNA_P | − |
| 12333534 | 108607 | At_100uM_ABA_cDNA_P | − |
| 4909291 | 20000214 | At_4deg_Cold | − |
| 12396394 | 20001555 | At_Drought_Soil_Dry | − |
| 12703041 | 108489 | At_50mM_NH4NO3_L-to-H_Rosette_cDNA_P | − |
| 5787483 | 108577 | At_42deg_Heat_cDNA_P | − |
| 4996264 | 108434 | At_Root_Tips_cDNA_P | − |
| 13612919 | 20000451 | At_CS6879_Shoots-Roots | − |
| 12660077 | 20000460 | At_10%_PEG | − |
| 13612919 | 20000213 | At_4deg_Cold | + |
| 4905097 | 20000113 | At_42deg_Heat_cDNA_P | + |
| 12713856 | 20000066 | At_CS3071_vs_Columbia_cDNA_P | + |
| 12713856 | 108590 | At_15mM_NH4NO3_L-to-H_cDNA_P | + |
| 13489977 | 20000223 | At_CS6632_Shoots-Roots_cDNA_P | + |
| 12576899 | 20000286 | At_Open_Flower | + |
| 12333534 | 20001560 | At_Drought_Soil_Dry | + |
| 4909291 | 20000496 | At_Guard_Cells | + |
| 12713856 | 20001397 | At_Line_Comparisons | + |
| 12739224 | 20001558 | At_Drought_Soil_Dry | + |
| 4949423 | 20000264 | At_Open_Flower | + |
| 12669615 | 20000439 | At_Roots | + |
| 13613553 | 20000573 | At_100uM_ABA_Mutants | + |

TABLE 4-continued

| _cDNA_ID | Expt_Rep_ID | Short_Name | Differential |
|---|---|---|---|
| 12711515 | 108605 | At_100uM_ABA_cDNA_P | + |
| 13614559 | 108583 | At_5mM_H2O2_cDNA_P | + |
| 12656458 | 20001317 | At_Interploidy_Crosses | + |
| 13601936 | 108501 | At_ap2_floral_buds_cDNA_P | + |
| 4906343 | 20001451 | At_Far-red-induction | + |
| 13609583 | 20000227 | At_Root-Tips-vs-Tops | + |
| 13647840 | 20000234 | At_Siliques | + |
| 12669615 | 20001247 | At_Far-red-induction | + |
| 13610584 | 108607 | At_100uM_cDNA_P | + |
| 12660077 | 20001654 | At_Interploidy_Crosses | + |
| 13614841 | 20001560 | At_Drought_Soil_Dry | + |
| 12713856 | 108591 | At_15mM_NH4NO3_L-to-H_cDNA_P | + |
| 12711515 | 20000086 | At_100uM_ABA_Mutants_cDNA_P | + |
| 12688453 | 20000443 | At_1uM_BR-BRZ | + |
| 13614559 | 108668 | At_2mM_SA_YF_cDNA_P | + |
| 4909806 | 20001654 | At_Interploidy_Crosses | + |
| 13619323 | 108589 | At_15mM_NH4NO3_L-to-H_cDNA_P | + |
| 12679922 | 20000496 | At_Guard_Cells | + |
| 13509244 | 20000286 | At_Open_Flower | + |
| 12333534 | 20000184 | At_Shoots | + |
| 13619323 | 20000443 | At_1uM_BR-BRZ | + |
| 13621692 | 20001247 | At_Far-red-induction | + |
| 12713856 | 20000184 | At_Shoots | + |
| 13617784 | 108481 | At_Shoot_Apices_cDNA_P | + |
| 12333534 | 20000444 | At_100uM_NAA | + |
| 12670159 | 20000575 | At_100uM_ABA_Mutants | + |
| 5787483 | 108462 | At_Germinating_Seeds_cDNA_P | + |
| 13614559 | 20000071 | At_100uM_ABA_Mutants_cDNA_P | + |
| 13621692 | 20000573 | At_100uM_ABA_Mutants | + |
| 12711515 | 20001504 | At_Far-red-enriched | + |
| 12711515 | 108610 | At_100uM_ABA_cDNA_P | + |
| 13613553 | 20000087 | At_100uM_ABA_Mutants_cDNA_P | + |
| 13617784 | 20000127 | At_50mM_NH4NO3_L-to-H_Siliques_cDNA_P | + |
| 12679922 | 20000443 | At_1uM_BR-BRZ | + |
| 12735519 | 20000184 | At_Shoots | + |
| 5787483 | 108461 | At_Germinating_Seeds_cDNA_P | + |
| 4905097 | 108457 | At_Diversity_Expt_cDNA_P | + |
| 13609817 | 108499 | At_DMT-II_cDNA_P | + |
| 12713856 | 20000438 | At_Shoots | + |
| 12678173 | 20000070 | At_100uM_ABA_Mutants_cDNA_P | + |
| 12711515 | 20000574 | At_100uM_ABA_Mutants | + |
| 13621692 | 20000179 | At_Germinating_Seeds | + |
| 13617784 | 20001555 | At_Drought_Soil_Dry | + |
| 13610584 | 20001247 | At_Far-red-induction | + |
| 12711515 | 20001316 | At_Interploidy_Crosses | + |
| 13614559 | 20000173 | At_42deg_Heat | + |
| 12711515 | 108455 | At_20uM_KNO3_H-to-L_cDNA_P | + |
| 13619323 | 108473 | At_Drought_Flowers_cDNA_P | + |
| 12735519 | 20000458 | At_42deg_Heat | + |
| 12703041 | 20000113 | At_42deg_Heat_cDNA_P | + |
| 13601936 | 20000264 | At_Open_Flower | + |
| 13619323 | 108573 | At_Drought_cDNA_P | + |
| 12713856 | 20000092 | At_42deg_Heat_cDNA_P | + |
| 13610584 | 108462 | At_Germinating_Seeds_cDNA_P | + |
| 12669615 | 20000460 | At_10%_PEG | + |
| 13614559 | 20000437 | At_Drought | + |
| 12736079 | 20001557 | At_Drought_Soil_Dry | + |
| 12735519 | 20000438 | At_Shoots | + |
| 13489977 | 108480 | At_Shoot_Apices_cDNA_P | + |
| 12329827 | 108478 | At_Shoot_Apices_cDNA_P | + |
| 13489977 | 20000169 | At_100uM_ABA | + |
| 12703041 | 20001654 | At_Interploidy_Crosses | + |
| 12348737 | 20000086 | At_100uM_ABA_Mutants_cDNA_P | + |
| 13609583 | 20000234 | At_Siliques | + |
| 12455436 | 20001560 | At_Drought_Soil_Dry | + |
| 12688453 | 20001504 | At_Far-red-enriched | + |
| 13619323 | 108575 | At_Wounding_cDNA_P | + |
| 13612919 | 108461 | At_Germinating_Seeds_cDNA_P | + |
| 13610584 | 108605 | At_100uM_ABA_cDNA_P | + |
| 13617784 | 108441 | At_1uM_BR-BRZ | + |
| 13489977 | 108481 | At_Shoot_Apices_cDNA_P | + |
| 12669615 | 20000169 | At_100uM_ABA | + |
| 13612879 | 20000286 | At_Open_Flower | + |
| 13489977 | 20000070 | At_100uM_ABA_Mutants_cDNA_P | + |
| 4909291 | 108434 | At_Root_Tips_cDNA_P | + |
| 12688453 | 20000264 | At_Open_Flower | + |
| 13613553 | 20000086 | At_100uM_ABA_Mutants_cDNA_P | + |
| 12679922 | 108512 | At_3642-1_cDNA_P | + |
| 13489977 | 20000117 | At_100uM_ABA_Mutants_cDNA_P | + |
| 12711515 | 108607 | At_100uM_ABA_cDNA_P | + |
| 12333534 | 20000457 | At_42deg_Heat | + |
| 12711515 | 20000070 | At_100uM_ABA_Mutants_cDNA_P | + |
| 13601936 | 20000458 | At_42deg_Heat | + |
| 12348737 | 20000087 | At_100uM_ABA_Mutants_cDNA_P | + |
| 12711515 | 20000495 | At_Guard_Cells | + |
| 13609583 | 108461 | At_Germinating_Seeds_cDNA_P | + |
| 12711515 | 20000455 | At_100uM_ABA | + |
| 12576899 | 20000227 | At_Root-Tips-vs-Tops | + |
| 13619323 | 20000286 | At_Open_Flower | + |
| 13491988 | 20001654 | At_Interploidy_Crosses | + |
| 13609100 | 20001555 | At_Drought_Soil_Dry | + |
| 12688453 | 20001556 | At_Drought_Soil_Dry | + |
| 12348737 | 20000227 | At_Root-Tips-vs-Tops | + |
| 12660077 | 20000438 | At_Shoots | + |
| 12703041 | 108463 | At_Germinating_Seeds_cDNA_P | + |
| 13613553 | 20000436 | At_Drought | + |
| 13613553 | 20000794 | At_Petals | + |
| 13619323 | 108605 | At_100uM_ABA_cDNA_P | + |
| 12692181 | 108560 | At_100uM_ABA_cDNA_P | + |
| 12679922 | 20000573 | At_100uM_ABA_Mutants | + |
| 13617784 | 20001458 | At_50mM_NH4NO3_L-to-H | + |
| 4909806 | 108461 | At_Germinating_Seeds_cDNA_P | + |
| 12576899 | 20000496 | At_Guard_Cells | + |
| 12692181 | 108590 | At_15mM_NH4NO3_L-to-H_cDNA_P | + |
| 13619323 | 20000070 | At_100uM_ABA_Mutants_cDNA_P | + |
| 13613553 | 108579 | At_4deg_Cold_cDNA_P | + |
| 12711515 | 108512 | At_3642-1_cDNA_P | + |
| 13610584 | 20000573 | At_100uM_ABA_Mutants | + |
| 12692181 | 108473 | At_Drought_Flowers_cDNA_P | + |
| 12329827 | 108473 | At_Drought_Flowers_cDNA_P | + |
| 12713856 | 20000457 | At_42deg_Heat | + |
| 12711515 | 108501 | At_ap2_floral_buds_cDNA_P | + |
| 12688453 | 20000234 | At_Siliques | + |
| 12679922 | 108594 | At_Ler_rhl_Root_cDNA_P | + |
| 13613553 | 108576 | At_42deg_Heat_cDNA_P | + |
| 12703041 | 108488 | At_50mM_NH4NO3_L-to-H_Rosette_cDNA_P | + |
| 12711515 | 108474 | At_Drought_Flowers_cDNA_P | + |
| 12736079 | 20000185 | At_Roots | + |
| 13610584 | 20000574 | At_100uM_ABA_Mutants | + |
| 12678173 | 20000236 | At_Siliques | + |
| 13612919 | 20000438 | At_Shoots | + |
| 13619323 | 20001653 | At_Interploidy_Crosses | + |
| 12370148 | 20000069 | At_100uM_ABA_Mutants_cDNA_P | + |
| 12688453 | 20000445 | At_100uM_NAA | + |
| 12370148 | 20001458 | At_50mM_NH4NO3_L-to-H | + |
| 12739224 | 20001557 | At_Drought_Soil_Dry | + |
| 12332135 | 108473 | At_Drought_Flowers_cDNA_P | + |
| 13609817 | 20001654 | At_Interploidy_Crosses | + |
| 12370148 | 20001557 | At_Drought_Soil_Dry | + |
| 12692181 | 20000355 | At_Siliques | + |
| 12322677 | 20000437 | At_Drought | + |
| 12325134 | 108591 | At_15mM_NH4NO3_L-to-H_cDNA_P | + |
| 12713856 | 20001316 | At_Interploidy_Crosses | + |
| 12711515 | 20001503 | At_Far-red-enriched | + |
| 12688453 | 20000794 | At_Petals | + |
| 13617784 | 20001558 | At_Drought_Soil_Dry | + |
| 13614559 | 108561 | At_100uM_ABA_cDNA_P | + |
| 12669615 | 20000185 | At_Roots | + |
| 13614559 | 20000113 | At_42deg_Heat_cDNA_P | + |
| 4909291 | 108464 | At_Germinating_Seeds_cDNA_P | + |
| 12646933 | 20000264 | At_Open_Flower | + |
| 13614841 | 20001247 | At_Far-red-induction | + |
| 12455436 | 108488 | At_50mM_NH4NO3_L-to-H_Rosette_cDNA_P | + |
| 12703041 | 108572 | At_Drought_cDNA_P | + |
| 13614559 | 20000794 | At_Petals | + |
| 13610584 | 108668 | At_2mM_SA_cDNA_P | + |
| 13612879 | 108590 | At_15mM_NH4NO3_L-to-H_cDNA_P | + |

TABLE 4-continued

| _cDNA_ID | Expt_Rep_ID | Short_Name | Differential |
|---|---|---|---|
| 12396394 | 108464 | At_Germinating_Seeds_cDNA_P | + |
| 12370148 | 108584 | At_5mM_NaNP_cDNA_P | + |
| 12660077 | 20000265 | At_Open_Flower | + |
| 13614559 | 108573 | At_Drought_cDNA_P | + |
| 12396394 | 108462 | At_Germinating_Seeds_cDNA_P | + |
| 12332135 | 20000443 | At_1uM_BR-BRZ | + |
| 13617784 | 20001560 | At_Drought_Soil_Dry | + |
| 13613553 | 20000113 | At_42deg_Heat_cDNA_P | + |
| 12711515 | 20000573 | At_100uM_ABA_Mutants | + |
| 12692181 | 108573 | At_Drought_cDNA_P | + |
| 12370148 | 108463 | At_Germinating_Seeds_cDNA_P | + |
| 12333534 | 20000244 | At_Caf_Knockout | + |
| 13489977 | 20000443 | At_1uM_BR-BRZ | + |
| 12713856 | 20000180 | At_Germinating_Seeds | + |
| 12370148 | 108588 | At_15mM_NH4NO3_L-to-H0_cDNA_P | + |
| 13614559 | 20000458 | At_42deg_Heat | + |
| 4909806 | 20000527 | At_10%_PEG | + |
| 13609583 | 20000180 | At_Germinating_Seeds | + |
| 12678173 | 20000234 | At_Siliques | + |
| 4909806 | 108573 | At_Drought_cDNA_P | + |
| 12711515 | 20000227 | At_Root-Tips-vs-Tops | + |
| 12348737 | 20000090 | At_2mM_SA_CS3726-Columbia_cDNA_P | + |
| 12576899 | 20000264 | At_Open_Flower | + |
| 13613553 | 108595 | At_Ler-pi_Ovule_cDNA_P | + |
| 12713856 | 108489 | At_50mM_NH4NO3_L-to-H_Rosette_cDNA_P | + |
| 12688453 | 20000308 | At_100mM_NaCl | + |
| 13619323 | 20000086 | At_100uM_ABA_Mutants_cDNA_P | + |
| 12692181 | 108462 | At_Germinating_Seeds_cDNA_P | + |
| 12678173 | 20000574 | At_100uM_ABA_Mutants | + |
| 12348737 | 20000088 | At_100uM_ABA_Mutants_cDNA_P | + |
| 12348737 | 108667 | At_2mM_SA_cDNA_P | + |
| 12333534 | 20001558 | At_Drought_Soil_Dry | + |
| 12692181 | 108575 | At_Wounding_cDNA_P | + |
| 13609817 | 20000185 | At_Roots | + |
| 12688453 | 20000495 | At_Guard_Cells | + |
| 12348737 | 20000117 | At_100uM_ABA_Mutants_cDNA_P | + |
| 13617784 | 20000113 | At_42deg_Heat_cDNA_P | + |
| 12329827 | 20000437 | At_Drought | + |
| 12329827 | 108590 | At_15mM_NH4NO3_L-to-H_cDNA_P | + |
| 12348737 | 20001560 | At_Drought_Soil_Dry | + |
| 12711515 | 108561 | At_100uM_ABA_cDNA_P | + |
| 13612879 | 20000264 | At_Open_Flower | + |
| 13619323 | 20000069 | At_100uM_ABA_Mutants_cDNA_P | + |
| 13609817 | 20000439 | At_Roots | + |
| 13614841 | 20000213 | At_4deg_Cold | + |
| 4909806 | 20000438 | At_Shoots | + |
| 12348737 | 20000709 | At_15mM_NH4NO3_L-to-H | + |
| 13489977 | 108584 | At_5mM_NaNP_cDNA_P | + |
| 12332135 | 108457 | At_Diversity_Expt_cDNA_P | + |
| 12370148 | 108470 | At_2mM_SA_CS3726-Columbia_cDNA_P | + |
| 12736079 | 20000439 | At_Roots | + |
| 12713856 | 108463 | At_Germinating_Seeds_cDNA_P | + |
| 12396394 | 20000438 | At_Shoots | + |
| 12711515 | 20001560 | At_Drought_Soil_Dry | + |
| 13609817 | 108573 | At_Drought_cDNA_P | + |
| 12370148 | 20000527 | At_10%_PEG | + |
| 13491988 | 108572 | At_Drought_cDNA_P | + |
| 12688453 | 20000437 | At_Drought | + |
| 12688453 | 20000267 | At_Drought | + |
| 12322657 | 20000213 | At_4deg_Cold | + |
| 4909291 | 20000113 | At_42deg_Heat_cDNA_P | + |
| 13489977 | 20001247 | At_Far-red-induction | + |
| 12692181 | 20000046 | At_CS237-vs-Columbia_cDNA_P | + |
| 12692181 | 20000352 | At_Drought | + |
| 12735519 | 20000265 | At_Open_Flower | + |
| 12679922 | 20000441 | At_1uM_BR-BRZ | + |
| 12678173 | 20000794 | At_Petals | + |
| 12688453 | 20001560 | At_Drought_Soil_Dry | + |
| 12660077 | 20000286 | At_Open_Flower | + |
| 12646933 | 20000708 | At_Fis1_Siliques | + |
| 12688453 | 20001316 | At_Interploidy_Crosses | + |
| 12711515 | 20000169 | At_100uM_ABA | + |
| 13647840 | 20000286 | At_Open_Flower | + |
| 13617784 | 108573 | At_Drought_cDNA_P | + |
| 13614841 | 20001558 | At_Drought_Soil_Dry | + |
| 12678173 | 20000573 | At_100uM_ABA_Mutants | + |
| 12370148 | 108454 | At_20uM_KNO3_H-to-L_cDNA_P | + |
| 12322657 | 108579 | At_4deg_Cold_cDNA_P | + |
| 12688453 | 20001554 | At_Drought_Soil_Dry | + |
| 13613553 | 20000111 | At_42deg_Heat_cDNA_P | + |
| 12333534 | 20001247 | At_Far-red-induction | + |
| 12661844 | 20000708 | At_Fis1_Siliques | + |
| 12332135 | 108501 | At_ap2_floral_buds_cDNA_P | + |
| 13491988 | 20000496 | At_Guard_Cells | + |
| 13491988 | 20000179 | At_Germinating_Seeds | + |
| 12348737 | 20000071 | At_100uM_ABA_Mutants_cDNA_P | + |
| 13609583 | 20000235 | At_Siliques | + |
| 12688453 | 20001555 | At_Drought_Soil_Dry | + |
| 12348737 | 108469 | At_2mM_SA_CS3726-Columbia_cDNA_P | + |
| 4909291 | 108585 | At_5mM_NaNP_cDNA_P | + |
| 13613553 | 20000173 | At_42deg_Heat | + |
| 12646933 | 20000286 | At_Open_Flower | + |
| 13489977 | 108455 | At_20uM_KNO3_H-to-L_cDNA_P | + |
| 12678173 | 20000265 | At_Open_Flower | + |
| 12370148 | 20001248 | At_Far-red-induction | + |
| 12679922 | 108480 | At_Shoot_Apices_cDNA_P | + |
| 13612879 | 108573 | At_Drought_cDNA_P | + |
| 12678173 | 20000235 | At_Siliques | + |
| 13617784 | 20000709 | At_15mM_NH4NO3_L-to-H | + |
| 13601936 | 20000111 | At_42deg_Heat_cDNA_P | + |
| 13489977 | 108454 | At_20uM_KNO3_H-to-L_cDNA_P | + |
| 4996264 | 108457 | At_Diversity_Expt_cDNA_P | + |
| 13619323 | 20000071 | At_100uM_ABA_Mutants_cDNA_P | + |
| 12348737 | 20000089 | At_2mM_SA_CS3726-Columbia_cDNA_P | + |
| 12370148 | 20000460 | At_10%_PEG | + |
| 13617784 | 20001557 | At_Drought_Soil_Dry | + |
| 12348737 | 20000072 | At_100uM_ABA_Mutants_cDNA_P | + |
| 13613553 | 108573 | At_Drought_cDNA_P | + |
| 12735519 | 20001653 | At_Interploidy_Crosses | + |
| 12348737 | 20001247 | At_Far-red-induction | + |
| 12329827 | 108589 | At_15mM_NH4NO3_L-to-H_cDNA_P | + |
| 12321680 | 108589 | At_15mM_NH4NO3_L-to-H_cDNA_P | + |
| 13613553 | 20000072 | At_100uM_ABA_Mutants_YF_2-4-02_cDNA_P | + |
| 4909806 | 108463 | At_Germinating_Seeds_cDNA_P | + |
| 12688453 | 20000268 | At_100mM_NaCl | + |
| 13489977 | 20000527 | At_10%_PEG | + |
| 4909291 | 20000458 | At_42deg_Heat | + |
| 12325134 | 108590 | At_15mM_NH4NO3_L-to-H_cDNA_P | + |
| 12322657 | 20000088 | At_100uM_ABA_Mutants_cDNA_P | + |
| 4909291 | 108577 | At_42deg_Heat_cDNA_P | + |
| 12321680 | 20000264 | At_Open_Flower | + |
| 13619323 | 20000072 | At_100uM_ABA_Mutants_cDNA_P | + |
| 12646933 | 108590 | At_15mM_NH4NO3_L-to-H_cDNA_P | + |
| 13610584 | 20001451 | At_Far-red-induction | + |
| 12370148 | 20001308 | At_Line_Comparisons | + |
| 4909291 | 20000173 | At_42deg_Heat | + |
| 12692181 | 20000087 | At_100uM_ABA_Mutants_cDNA_P | + |
| 13610584 | 20000180 | At_Germinating_Seeds | + |
| 12713856 | 108462 | At_Germinating_Seeds_cDNA_P | + |
| 12333534 | 20001451 | At_Far-red-induction | + |
| 12669615 | 20000455 | At_100uM_ABA | + |
| 4906343 | 20000264 | At_Open_Flower | + |
| 13610584 | 20000527 | At_10%_PEG | + |
| 12713856 | 20000495 | At_Guard_Cells | + |
| 12348737 | 20000096 | At_100uM_ABA_Mutants_cDNA_P | + |
| 13613553 | 108668 | At_2mM_SA_cDNA_P | + |
| 13619323 | 20000264 | At_Open_Flower | + |
| 12692181 | 108463 | At_Germinating_Seeds_cDNA_P | + |
| 13610584 | 108457 | At_Diversity_Expt_cDNA_P | + |
| 13612879 | 20000453 | At_100uM_ABA | + |
| 12669615 | 20000453 | At_100uM_ABA | + |
| 13491988 | 20000180 | At_Germinating_Seeds | + |
| 13613553 | 20000458 | At_42deg_Heat | + |
| 12711515 | 20000071 | At_100uM_ABA_Mutants_cDNA_P | + |

TABLE 4-continued

| _cDNA_ID | Expt_Rep_ID | Short_Name | Differential |
|---|---|---|---|
| 12670159 | 20000495 | At_Guard_Cells | + |
| 13489977 | 20000441 | At_1uM_BR-BRZ | + |
| 12370148 | 20000441 | At_1uM_BR-BRZ | + |
| 12646933 | 108591 | At_15mM_NH4NO3_L-to-H_cDNA_P | + |
| 12348737 | 20000070 | At_100uM_ABA_Mutants_cDNA_P | + |
| 13489977 | 20000069 | At_100uM_ABA_Mutants_cDNA_P | + |
| 12348737 | 108470 | At_2mM_SA_CS3726-Columbia_cDNA_P | + |
| 13610584 | 108464 | At_Germinating_Seeds_cDNA_P | + |
| 13613553 | 20001557 | At_Drought_Soil_Dry | + |
| 13614841 | 20001557 | At_Drought_Soil_Dry | + |
| 12370148 | 20000443 | At_1uM_BR-BRZ | + |
| 12322657 | 20000072 | At_100uM_ABA_Mutants_cDNA_P | + |
| 12661844 | 20000236 | At_Siliques | + |
| 4905097 | 20000236 | At_Siliques | + |
| 12711515 | 20000117 | At_100uM_ABA_Mutants_cDNA_P | + |
| 12703041 | 108462 | At_Germinating_Seeds_cDNA_P | + |
| 12322657 | 20000086 | At_100uM_ABA_Mutants_cDNA_P | + |
| 12370148 | 108481 | At_Shoot_Apices_cDNA_P | + |
| 12703041 | 108573 | At_Drought_cDNA_P | + |
| 12692181 | 108608 | At_100uM_ABA_cDNA_P | + |
| 12321680 | 108591 | At_15mM_NH4NO3_L-to-H_cDNA_P | + |
| 12692181 | 108464 | At_Germinating_Seeds_cDNA_P | + |
| 4909291 | 20000111 | At_42deg_Heat_cDNA_P | + |
| 4909806 | 108464 | At_Germinating_Seeds_cDNA_P | + |
| 13613553 | 20000709 | At_15mM_NH4NO3_L-to-H | + |
| 12692181 | 108572 | At_Drought_cDNA_P | + |
| 4909806 | 20000184 | At_Shoots | + |
| 13612879 | 20000234 | At_Siliques | + |
| 4949423 | 20000437 | At_Drought | + |
| 4905097 | 20000235 | At_Siliques | + |
| 12692181 | 20000089 | At_2mM_SA_CS3726-Columbia_cDNA_P | + |
| 12711515 | 108609 | At_100uM_ABA_cDNA_P | + |
| 12688453 | 20000436 | At_Drought | + |
| 13647840 | 20000794 | At_Petals | + |
| 12322657 | 20000090 | At_2mM_SA_CS3726-Columbia_cDNA_P | + |
| 13489977 | 108595 | At_Ler-pi_Ovule_cDNA_P | + |
| 13617784 | 108591 | At_15mM_NH4NO3_L-to-H_cDNA_P | + |
| 4909806 | 108462 | At_Germinating_Seeds_cDNA_P | + |
| 12664333 | 20001451 | At_Far-red-induction | + |
| 12333534 | 20000495 | At_Guard_Cells | + |
| 13612919 | 20000180 | At_Germinating_Seeds | + |
| 13609817 | 108463 | At_Germinating_Seeds_cDNA_P | + |
| 12396394 | 108573 | At_Drought_cDNA_P | + |
| 12332135 | 20000264 | At_Open_Flower | + |
| 12321680 | 20000236 | At_Siliques_YF | + |
| 13647840 | 20000264 | At_Open_Flower | + |
| 4909806 | 20000708 | At_Fis1_Siliques | + |
| 13612879 | 20000708 | At_Fis1_Siliques | + |
| 12332135 | 108589 | At_15mM_NH4NO3_L-to-H_cDNA_P | + |
| 12692181 | 108501 | At_ap2_floral_buds_cDNA_P | + |
| 12678173 | 20000264 | At_Open_Flower | + |
| 13617784 | 20000458 | At_42deg_Heat | + |
| 12329827 | 20000180 | At_Germinating_Seeds | + |
| 13619323 | 20000234 | At_Siliques | + |
| 12348737 | 20001654 | At_Interploidy_Crosses | + |
| 12329827 | 108591 | At_15mM_NH4NO3_L-to-H_cDNA_P | + |
| 12688453 | 20000453 | At_100uM_ABA | + |
| 12713856 | 108464 | At_Germinating_Seeds_cDNA_P | + |
| 13491988 | 108573 | At_Drought | + |
| 12396394 | 20000184 | At_Shoots | + |
| 12348737 | 108572 | At_Drought_cDNA_P | + |
| 12348737 | 108457 | At_Diversity_Expt_cDNA_P | + |
| 13610584 | 20001450 | At_Far-red-induction | + |
| 12660077 | 20000794 | At_Petals | + |
| 13619323 | 108591 | At_15mM_NH4NO3_L-to-H_cDNA_P | + |
| 12692181 | 20000072 | At_100uM_ABA_Mutants_cDNA_P | + |
| 4905097 | 20000708 | At_Fis1_Siliques | + |
| 12321680 | 20000235 | At_Siliques | + |
| 12703041 | 108464 | At_Germinating_Seeds_cDNA_P | + |
| 12661844 | 20000235 | At_SiliquesP | + |
| 12348737 | 108585 | At_5mM_NaNP_cDNA_P | + |
| 13612919 | 108462 | At_Germinating_Seeds_cDNA_P | + |
| 12678173 | 20000286 | At_Open_Flower | + |
| 4905097 | 20000234 | At_Siliques | + |
| 12321680 | 20000234 | At_Siliques | + |
| 13489977 | 20001308 | At_Line_Comparisons | + |
| 12692181 | 20000086 | At_100uM_ABA_MutantscDNA_P | + |
| 12455436 | 108434 | At_Root_TipscDNA_P | + |
| 13617784 | 108588 | At_15mM_NH4NO3_L-to-H_cDNA_P | + |
| 12322657 | 20000070 | At_100uM_ABA_Mutants_cDNA_P | + |
| 13614559 | 108585 | At_5mM_NaNP_cDNA_P | + |
| 13610584 | 20001248 | At_Far-red-induction | + |
| 12711515 | 20000441 | At_1uM_BR-BRZ | + |
| 12329827 | 20000234 | At_Siliques | + |
| 12692181 | 20000069 | At_100uM_ABA_Mutants_cDNA_P | + |
| 13619323 | 20000708 | At_Fis1_Siliques | + |
| 12322657 | 20001248 | At_Far-red-induction | + |
| 12332135 | 20000235 | At_Siliques | + |
| 12692181 | 20000349 | At_100uM_ABA | + |
| 13621692 | 20000326 | At_Pollen | + |
| 13489977 | 20000460 | At_10%_PEG | + |
| 12576899 | 20000794 | At_Petals | + |
| 12711515 | 20000453 | At_100uM_ABA | + |
| 12329827 | 20000179 | At_Germinating_Seeds | + |
| 12322657 | 20000071 | At_100uM_ABA_Mutants_cDNA_P | + |
| 12692181 | 108606 | At_100uM_ABA_cDNA_P | + |
| 12329827 | 20000708 | At_Fis1_Siliques | + |
| 4909291 | 108576 | At_42deg_Heat_cDNA_P | + |
| 12678173 | 20000326 | At_Pollen | + |
| 12348737 | 108668 | At_2mM_SA_cDNA_P | + |
| 12670159 | 20000451 | At_CS6879_Shoots-Roots | + |
| 12692181 | 20000071 | At_100uM_ABA_Mutants_cDNA_P | + |
| 12711515 | 108480 | At_Shoot_Apices_cDNA_P | + |
| 12332135 | 20000236 | At_Siliques | + |
| 13609817 | 108464 | At_Germinating_Seeds_cDNA_P | + |
| 12348737 | 108573 | At_Drought_cDNA_P | + |
| 12692181 | 108610 | At_100uM_ABA_cDNA_P | + |
| 12322657 | 20000117 | At_100uM_ABA_Mutants_cDNA_P | + |
| 12321680 | 20000708 | At_Fis1_Siliques | + |
| 12646933 | 20000235 | At_Siliques | + |
| 12325134 | 108501 | At_ap2_floral_buds_cDNA_P | + |
| 12711515 | 20001451 | At_Far-red-induction | + |
| 13609817 | 108462 | At_Germinating_Seeds_cDNA_P | + |
| 12661844 | 20000234 | At_Siliques | + |
| 13613553 | 108585 | At_5mM_NaNP_cDNA_P | + |
| 12692181 | 108561 | At_100uM_ABA_cDNA_P | + |
| 13609100 | 20000709 | At_15mM_NH4NO3_L-to-H_ | + |
| 4909291 | 20000112 | At_42deg_Heat_cDNA_P | + |
| 12711515 | 108481 | At_Shoot_Apices_cDNA_P | + |
| 12692181 | 108609 | At_100uM_ABA_cDNA_P | + |
| 12679922 | 20001247 | At_Far-red-induction | + |
| 12646933 | 20000236 | At_Siliques | + |
| 12646933 | 20000234 | At_Siliques | + |
| 12322657 | 20000087 | At_100uM_ABA_Mutants_cDNA_P | + |
| 12679922 | 20001248 | At_Far-red-induction | + |
| 12692181 | 20000088 | At_100uM_ABA_Mutants_cDNA_P | + |
| 12646933 | 108501 | At_ap2_floral_buds_cDNA_P | + |
| 4909806 | 108488 | At_50mM_NH4NO3_L-to-H_Rosette_cDNA_P | + |
| 12692181 | 20000070 | At_100uM_ABA_Mutants_cDNA_P | + |
| 4909291 | 20000171 | At_42deg_Heat | + |
| 12396394 | 108572 | At_Drought_cDNA_P | + |
| 12692181 | 108512 | At_3642-1_cDNA_P | + |
| 12322657 | 20000069 | At_100uM_ABA_Mutants_cDNA_P | + |
| 12329827 | 20000236 | At_Siliques | + |
| 13647840 | 20000326 | At_Pollen | + |
| 12332135 | 20000234 | At_Siliques | + |
| 12679922 | 20001450 | At_Far-red-induction | + |
| 12711515 | 20001248 | At_Far-red-induction | + |
| 4909291 | 20000093 | At_42deg_Heat_cDNA_P | + |
| 12692181 | 108605 | At_100uM_ABA_cDNA_P | + |
| 12692181 | 108607 | At_100uM_ABA_cDNA_P | + |
| 4909291 | 20000144 | At_42deg_Heat_cDNA_P | + |
| 13619323 | 108595 | At_Ler-pi_Ovule_cDNA_P | + |
| 12692181 | 20000117 | At_100uM_ABA_Mutants_cDNA_P | + |
| 12321680 | 108501 | At_ap2_floral_buds_cDNA_P | + |
| 12679922 | 20001451 | At_Far-red-induction | + |

TABLE 4-continued

| _cDNA_ID | Expt_Rep_ID | Short_Name | Differential |
|---|---|---|---|
| 12711515 | 20001450 | At_Far-red-induction | + |
| 13612879 | 108595 | At_Ler-pi_Ovule_cDNA_P | + |
| 13609100 | 20000171 | At_42deg_Heat | + |
| 13609100 | 20000173 | At_42deg_Heat | + |
| 12692181 | 108595 | At_Ler-pi_Ovule | + |
| 4949423 | 108595 | At_Ler-pi_Ovule | + |
| 13609100 | 20000458 | At_42deg_Heat | + |
| 12329827 | 108595 | At_Ler-pi_Ovule | + |
| 12332135 | 108595 | At_Ler-pi_Ovule | + |
| 12321680 | 108595 | At_Ler-pi_Ovule | + |
| 12370095 | 108501 | At_ap2_floral_buds_cDNA_P | + |
| 12370095 | 108584 | At_5mM_NaNP_cDNA_P | + |
| 12370095 | 108589 | At_15mM_NH4NO3_L-to-H_cDNA_P | + |
| 12370095 | 108590 | At_15mM_NH4NO3_L-to-H_cDNA_P | + |
| 12370095 | 108591 | At_15mM_NH4NO3_L-to-H_cDNA_P | + |
| 12370095 | 108595 | At_Ler-pi_Ovule_cDNA_P | + |
| 12370095 | 20000234 | At_Siliques_P | + |
| 12370095 | 20000235 | At_Siliques_P | + |
| 12370095 | 20000264 | At_Open_Flower_P | + |
| 12385291 | 108434 | At_Root_Tips_cDNA_P | + |
| 12385291 | 108470 | At_2mM_SA_CS3726-Columbia_cDNA_P | + |
| 12385291 | 108572 | At_Drought_cDNA_P | + |
| 12385291 | 108573 | At_Drought_cDNA_P | + |
| 12385291 | 108574 | At_Wounding_cDNA_P | + |
| 12385291 | 20000184 | At_Shoots_P | + |
| 12385291 | 20000236 | At_Siliques_P | + |
| 12385291 | 20000244 | At_Caf_Knockout_P | + |
| 12385291 | 20000268 | At_100mM_NaCl_P | + |
| 12385291 | 20000456 | At_100uM_BA_P | + |
| 12385291 | 20000496 | At_Guard_Cells_P | + |
| 12385291 | 20001557 | At_Drought_Soil_Dry_P | + |
| 12385291 | 20001558 | At_Drought_Soil_Dry_P | + |
| 12385291 | 20001560 | At_Drought_Soil_Dry_P | + |
| 12385291 | 20001757 | At_50mM_NH4NO3_L-to-H_P | + |
| 12395532 | 108454 | At_20uM_KNO3_H-to-L_cDNA_P | + |
| 12395532 | 108455 | At_20uM_KNO3_H-to-L_cDNA_P | + |
| 12395532 | 108470 | At_2mM_SA_CS3726-Columbia_cDNA_P | + |
| 12395532 | 108480 | At_Shoot_Apices_cDNA_P | + |
| 12395532 | 108481 | At_Shoot_Apices_cDNA_P | + |
| 12395532 | 108574 | At_Wounding_cDNA_P | + |
| 12395532 | 108578 | At_4deg_Cold_cDNA_P | + |
| 12395532 | 108579 | At_4deg_Cold_cDNA_P | + |
| 12395532 | 108584 | At_5mM_NaNP_cDNA_P | + |
| 12395532 | 108585 | At_5mM_NaNP_cDNA_P | + |
| 12395532 | 108588 | At_15mM_NH4NO3_L-to-H_cDNA_P | + |
| 12395532 | 108667 | At_2mM_SA_cDNA_P | + |
| 12395532 | 20000213 | At_4deg_Cold_P | + |
| 12395532 | 20000214 | At_4deg_Cold_P | + |
| 12395532 | 20000441 | At_1uM_BR-BRZ_P | + |
| 12395532 | 20000443 | At_1uM_BR-BRZ_P | + |
| 12395532 | 20000460 | At_10%_PEG_P | + |
| 12395532 | 20000527 | At_10%_PEG_P | + |
| 12395532 | 20001247 | At_Far-red-induction_P | + |
| 12395532 | 20001308 | At_Line_Comparisons_P | + |
| 12395532 | 20001458 | At_50mM_NH4NO3_L-to-H_P | + |
| 12395532 | 20001557 | At_Drought_Soil_Dry_P | + |
| 12395532 | 20001558 | At_Drought_Soil_Dry_P | + |
| 12395532 | 20001560 | At_Drought_Soil_Dry_P | + |
| 12575820 | 108573 | At_Drought_cDNA_P | + |
| 12575820 | 108595 | At_Ler-pi_Ovule_cDNA_P | + |
| 12575820 | 20000112 | At_42deg_Heat_cDNA_P | + |
| 12575820 | 20000179 | At_Germinating_Seeds_P | + |
| 12575820 | 20000180 | At_Germinating_Seeds_P | + |
| 12575820 | 20000438 | At_Shoots_P | + |
| 12600234 | 20000234 | At_Siliques_P | + |
| 12600234 | 20000458 | At_42deg_Heat_P | + |
| 12600234 | 20001556 | At_Drought_Soil_Dry_P | + |
| 12600234 | 20001557 | At_Drought_Soil_Dry_P | + |
| 12600234 | 20001558 | At_Drought_Soil_Dry_P | + |
| 12600234 | 20001756 | At_50mM_NH4NO3_L-to-H_P | + |
| 12600234 | 20001757 | At_50mM_NH4NO3_L-to-H_P | + |
| 12603755 | 20000185 | At_Roots_P | + |
| 12603755 | 20000234 | At_Siliques_P | + |
| 12603755 | 20000439 | At_Roots_P | + |
| 12603755 | 20000495 | At_Guard_Cells_P | + |
| 12603755 | 20000496 | At_Guard_Cells_P | + |
| 12640578 | 108461 | At_Germinating_Seeds_cDNA_P | + |
| 12640578 | 20000180 | At_Germinating_Seeds_P | + |
| 12640578 | 20000495 | At_Guard_Cells_P | + |
| 12640578 | 20001247 | At_Far-red-induction_P | + |
| 12640578 | 20001248 | At_Far-red-induction_P | + |
| 12640578 | 20001450 | At_Far-red-induction_P | + |
| 12647555 | 108455 | At_20uM_KNO3_H-to-L_cDNA_P | + |
| 12647555 | 20000179 | At_Germinating_Seeds_P | + |
| 12647555 | 20000180 | At_Germinating_Seeds_P | + |
| 12647555 | 20000227 | At_Root-Tips-vs-Tops_P | + |
| 12647555 | 20000496 | At_Guard_Cells_P | + |
| 12647555 | 20001557 | At_Drought_Soil_Dry_P | + |
| 12647555 | 20001558 | At_Drought_Soil_Dry_P | + |
| 12647555 | 20001560 | At_Drought_Soil_Dry_P | + |
| 12649228 | 108573 | At_Drought_cDNA_P | + |
| 12649228 | 20000495 | At_Guard_Cells_P | + |
| 12721583 | 20000496 | At_Guard_Cells_P | + |
| 12721583 | 20001248 | At_Far-red-induction_P | + |
| 12721583 | 20001450 | At_Far-red-induction_P | + |
| 13612380 | 108454 | At_20uM_KNO3_H-to-L_cDNA_P | + |
| 13612380 | 108464 | At_Germinating_Seeds_cDNA_P | + |
| 13612380 | 108480 | At_Shoot_Apices_cDNA_P | + |
| 13612380 | 108568 | At_0.001%_MeJA_cDNA_P | + |
| 13612380 | 108574 | At_Wounding_cDNA_P | + |
| 13612380 | 108584 | At_5mM_NaNP_cDNA_P | + |
| 13612380 | 108585 | At_5mM_NaNP_cDNA_P | + |
| 13612380 | 108588 | At_15mM_NH4NO3_L-to-H_cDNA_P | + |
| 13612380 | 108594 | At_Ler-rhl_Root_cDNA_P | + |
| 13612380 | 108595 | At_Ler-pi_Ovule_cDNA_P | + |
| 13612380 | 108667 | At_2mM_SA_cDNA_P | + |
| 13612380 | 20000069 | At_100uM_ABA_Mutants_cDNA_P | + |
| 13612380 | 20000086 | At_100uM_ABA_Mutants_cDNA_P | + |
| 13612380 | 20000090 | At_2mM_SA_CS3726-Columbia_cDNA_P | + |
| 13612380 | 20000213 | At_4deg_Cold_P | + |
| 13612380 | 20000441 | At_1uM_BR-BRZ_P | + |
| 13612380 | 20000443 | At_1uM_BR-BRZ_P | + |
| 13612380 | 20001248 | At_Far-red-induction_P | + |
| 12370095 | 20000184 | At_Shoots_P | − |
| 12370095 | 20000185 | At_Roots_P | − |
| 12370095 | 20000245 | At_Caf_Knockout_P | − |
| 12370095 | 20000438 | At_Shoots_P | − |
| 12370095 | 20000439 | At_Roots_P | − |
| 12370095 | 20000794 | At_Petals_P | − |
| 12385291 | 108461 | At_Germinating_Seeds_cDNA_P | − |
| 12385291 | 108462 | At_Germinating_Seeds_cDNA_P | − |
| 12385291 | 108463 | At_Germinating_Seeds_cDNA_P | − |
| 12385291 | 108464 | At_Germinating_Seeds_cDNA_P | − |
| 12385291 | 108594 | At_Ler-rhl_Root_DNA_P | − |
| 12385291 | 108595 | At_Ler-pi_Ovule_cDNA_P | − |
| 12385291 | 20000069 | At_100uM_ABA_Mutants_cDNA_P | − |
| 12385291 | 20000072 | At_100uM_ABA_Mutants_cDNA_P | − |
| 12385291 | 20000086 | At_100uM_ABA_Mutants_cDNA_P | − |
| 12385291 | 20000087 | At_100uM_ABA_Mutants_cDNA_P | − |
| 12385291 | 20000171 | At_42deg_Heat_P | − |
| 12385291 | 20000179 | At_Germinating_Seeds_P | − |
| 12385291 | 20000180 | At_Germinating_Seeds_P | − |
| 12385291 | 20000185 | At_Roots_P | − |
| 12385291 | 20000326 | At_Pollen_P | − |
| 12385291 | 20000437 | At_Drought_P | − |
| 12385291 | 20000439 | At_Roots_P | − |
| 12385291 | 20000453 | At_100uM_ABA_P | − |
| 12385291 | 20000794 | At_Petals_P | − |
| 12385291 | 20001247 | At_Far-red-induction_P | − |
| 12385291 | 20001248 | At_Far-red-induction_P | − |
| 12385291 | 20001450 | At_Far-red-induction_P | − |
| 12385291 | 20001451 | At_Far-red-induction_P | − |
| 12385291 | 20001554 | At_Drought_Soil_Dry_P | − |
| 12385291 | 20001555 | At_Drought_Soil_Dry_P | − |
| 12385291 | 20001556 | At_Drought_Soil_Dry_P | − |
| 12395532 | 108434 | At_Root_Tips_cDNA_P | − |
| 12395532 | 108461 | At_Germinating_Seeds_cDNA_P | − |

TABLE 4-continued

| _cDNA_ID | Expt_Rep_ID | Short_Name | Differential |
|---|---|---|---|
| 12395532 | 108462 | At_Germinating_Seeds_cDNA_P | – |
| 12395532 | 108561 | At_100uM_ABA_cDNA_P | – |
| 12395532 | 108575 | At_Wounding_cDNA_P | – |
| 12395532 | 108577 | At_42deg_Heat_cDNA_P | – |
| 12395532 | 108606 | At_100uM_ABA_cDNA_P | – |
| 12395532 | 20000046 | At_CS237-vs-Columbia_cDNA_P | – |
| 12395532 | 20000070 | At_100uM_ABA_Mutants_cDNA_P | – |
| 12395532 | 20000089 | At_2mM_SA_CS3726-Columbia_cDNA_P | – |
| 12395532 | 20000144 | At_42deg_Heat_cDNA_P | – |
| 12395532 | 20000171 | At_42deg_Heat_P | – |
| 12395532 | 20000184 | At_Shoots_P | – |
| 12395532 | 20000185 | At_Roots_P | – |
| 12395532 | 20000234 | At_Siliques_P | – |
| 12395532 | 20000236 | At_Siliques_P | – |
| 12395532 | 20000264 | At_Open_Flower_P | – |
| 12395532 | 20000265 | At_Open_Flower_P | – |
| 12395532 | 20000268 | At_100mM_NaCl_P | – |
| 12395532 | 20000286 | At_Open_Flower_P | – |
| 12395532 | 20000326 | At_Pollen_P | – |
| 12395532 | 20000437 | At_Drought_P | – |
| 12395532 | 20000438 | At_Shoots_P | – |
| 12395532 | 20000439 | At_Roots_P | – |
| 12395532 | 20000495 | At_Guard_Cells_P | – |
| 12395532 | 20000506 | At_Wounding_P | – |
| 12395532 | 20000573 | At_100uM_ABA_Mutants_P | – |
| 12395532 | 20000574 | At_100uM_ABA_Mutants2_P | – |
| 12395532 | 20000794 | At_Petals_P | – |
| 12395532 | 20001554 | At_Drought_Soil_Dry_P | – |
| 12395532 | 20001760 | At_50mM_NH4NO3_L-to-H_P | – |
| 12575820 | 108579 | At_4deg_Cold_cDNA_P | – |
| 12575820 | 108590 | At_15mM_NH4NO3_L-to-H_cDNA_P | – |
| 12575820 | 20000326 | At_Pollen_P | – |
| 12575820 | 20000439 | At_Roots_P | – |
| 12575820 | 20000495 | At_Guard_Cells_P | – |
| 12575820 | 20001248 | At_Far-red-induction_P | – |
| 12575820 | 20001557 | At_Drought_Soil_Dry_P | – |
| 12600234 | 20001248 | At_Far-red-induction_P | – |
| 12603755 | 20000326 | At_Pollen_P | – |
| 12640578 | 20000227 | At_Root-Tips-vs-Tops_P | – |
| 12640578 | 20000264 | At_Open_Flower_P | – |
| 12640578 | 20000265 | At_Open_Flower_P | – |
| 12640578 | 20000286 | At_Open_Flower_P | – |
| 12640578 | 20000326 | At_Pollen_P | – |
| 12640578 | 20000451 | At_CS6879_Shoots-Roots_P | – |
| 12640578 | 20000794 | At_Petals_P | – |
| 12647555 | 108473 | At_Drought_Flowers_cDNA_P | – |
| 12647555 | 108572 | At_Drought_cDNA_P | – |
| 12647555 | 108573 | At_Drought_cDNA_P | – |
| 12647555 | 108577 | At_42deg_Heat_P | – |
| 12647555 | 108668 | At_2mM_SA_cDNA_P | – |
| 12647555 | 20000111 | At_42deg_Heat_cDNA_P | – |
| 12647555 | 20000173 | At_42deg_Heat_P | – |
| 12647555 | 20000185 | At_Roots_P | – |
| 12647555 | 20000236 | At_Siliques_P | – |
| 12647555 | 20000268 | At_100mM_NaCl_P | – |
| 12647555 | 20000436 | At_Drought_P | – |
| 12647555 | 20000437 | At_Drought_P | – |
| 12647555 | 20000439 | At_Roots_P | – |
| 12647555 | 20000451 | At_CS6879_Shoots-Roots_P | – |
| 12647555 | 20001554 | At_Drought_Soil_Dry_P | – |
| 12647555 | 20001555 | At_Drought_Soil_Dry_P | – |
| 12647555 | 20001556 | At_Drought_Soil_Dry_P | – |
| 12649228 | 108434 | At_Root_Tips_cDNA_P | – |
| 12649228 | 20000326 | At_Pollen_P | – |
| 12658070 | 20000439 | At_Roots_P | – |
| 12721583 | 20000173 | At_42deg_Heat_P | – |
| 12721583 | 20000265 | At_Open_Flower_P | – |
| 12721583 | 20000458 | At_42deg_Heat_P | – |
| 12721583 | 20000794 | At_Petals_P | – |
| 12721583 | 20001555 | At_Drought_Soil_Dry_P | – |
| 12721583 | 20001556 | At_Drought_Soil_Dry_P | – |
| 12721583 | 20001557 | At_Drought_Soil_Dry_P | – |
| 12721583 | 20001558 | At_Drought_Soil_Dry_P | – |
| 12721583 | 20001559 | At_Drought_Soil_Dry_P | – |
| 12721583 | 20001560 | At_Drought_Soil_Dry_P | – |
| 13593439 | 20000173 | At_42deg_Heat_P | – |
| 13593439 | 20000184 | At_Shoots_P | – |
| 13593439 | 20000185 | At_Roots_P | – |
| 13593439 | 20001247 | At_Far-red-induction_P | – |
| 13593439 | 20001248 | At_Far-red-induction_P | – |
| 13593439 | 20001560 | At_Drought_Soil_Dry_P | – |
| 13612380 | 108434 | At_Root_Tips_cDNA_P | – |
| 13612380 | 108577 | At_42deg_Heat_cDNA_P | – |
| 13612380 | 108606 | At_100uM_ABA_cDNA_P | – |
| 13612380 | 20000046 | At_CS237-vs-Columbia_cDNA_P | – |
| 13612380 | 20000111 | At_42deg_Heat_cDNA_P | – |
| 13612380 | 20000113 | At_42deg_Heat_cDNA_P | – |
| 13612380 | 20000144 | At_42deg_Heat_cDNA_P | – |
| 13612380 | 20000166 | At_100uM_ABA_P | – |
| 13612380 | 20000169 | At_100uM_ABA_P | – |
| 13612380 | 20000173 | At_42deg_Heat_P | – |
| 13612380 | 20000179 | At_Germinating_Seeds_P | – |
| 13612380 | 20000180 | At_Germinating_Seeds_P | – |
| 13612380 | 20000184 | At_Shoots_P | – |
| 13612380 | 20000185 | At_Roots_P | – |
| 13612380 | 20000234 | At_Siliques_P | – |
| 13612380 | 20000236 | At_Siliques_P | – |
| 13612380 | 20000264 | At_Open_Flower_P | – |
| 13612380 | 20000265 | At_Open_Flower_P | – |
| 13612380 | 20000286 | At_Open_Flower_P | – |
| 13612380 | 20000436 | At_Drought_P | – |
| 13612380 | 20000438 | At_Shoots_P | – |
| 13612380 | 20000439 | At_Roots_P | – |
| 13612380 | 20000458 | At_42deg_Heat_P | – |
| 13612380 | 20000495 | At_Guard_Cells_P | – |
| 13612380 | 20000573 | At_100uM_ABA_Mutants_P | – |
| 13612380 | 20000574 | At_100uM_ABA_Mutants_P | – |
| 13612380 | 20000794 | At_Petals_P | – |
| 13612380 | 20001555 | At_Drought_Soil_Dry_P | – |

TABLE 5

| Utility Section | Expt_Rep_ID | Short_Name | Parameter | Value |
|---|---|---|---|---|
| Viability | 107881 | At_Herbicide_v2_cDNA_P | Timepoint (hr) | 4 |
| | 107881 | At_Herbicide_v2_cDNA_P | Treatment | Glean vs. No Treatment |
| | 107891 | At_Herbicide_v2_cDNA_P | Timepoint (hr) | 12 |
| | 107891 | At_Herbicide_v2_cDNA_P | Treatment | Trimec vs. No Treatment |
| Root | 108429 | At_Tissue_Specific_Expression_cDNA_P | Probe Amount | 50 |
| | 108429 | At_Tissue_Specific_Expression_cDNA_P | Probe Method | operon |
| | 108429 | At_Tissue_Specific_Expression_cDNA_P | Tissue | Green Flower vs. Whole Plant |

TABLE 5-continued

| Utility Section | Expt_Rep_ID | Short_Name | Parameter | Value |
|---|---|---|---|---|
| Root | 108434 | At_Root_Tips_cDNA_P | Tissue | Root Tips |
| Shoot Meristem | 108435 | At_stm_Mutants_cDNA_P | Plant Line | wt Landsburg vs stm |
| | 108435 | At_stm_Mutants_cDNA_P | Tissue | Shoot Apical Meristem Region |
| Reproductive and Seed & Fruit Development | 108437 | At_Tissue_Specific_Expression_cDNA_P | Probe Amount | 33 |
| | 108437 | At_Tissue_Specific_Expression_cDNA_P | Probe Method | operon |
| | 108437 | At_Tissue_Specific_Expression_cDNA_P | Tissue | <5 mm Siliques vs. Whole Plant |
| Reproductive and Seed & Fruit Development | 108438 | At_Tissue_Specific_Expression_cDNA_P | Probe Amount | 33 |
| | 108438 | At_Tissue_Specific_Expression_cDNA_P | Probe Method | operon |
| | 108438 | At_Tissue_Specific_Expression_cDNA_P | Tissue | 5 wk Siliques vs. Whole Plant |
| Root | 108439 | At_Tissue_Specific_Expression_cDNA_P | Probe Amount | 33 |
| | 108439 | At_Tissue_Specific_Expression_cDNA_P | Probe Method | operon |
| | 108439 | At_Tissue_Specific_Expression_cDNA_P | Tissue | Roots (2 wk) vs. Whole Plant |
| Imbibition & Germination | 108461 | At_Germinating_Seeds_cDNA_P | Age | 1 vs. 0 |
| | 108461 | At_Germinating_Seeds_cDNA_P | Tissue | Germinating Seeds |
| Imbibition & Germination | 108462 | At_Germinating_Seeds_cDNA_P | Age | 2 vs. 0 |
| | 108462 | At_Germinating_Seeds_cDNA_P | Tissue | Greminating Seeds |
| Early Seedling Phase | 108463 | At_Germinating_Seeds_cDNA_P | Age | 3 vs. 0 |
| | 108463 | At_Germinating_Seeds_cDNA_P | Tissue | Germinating Seeds |
| Early Seedling Phase | 108464 | At_Germinating_Seeds_cDNA_P | Age | 4 vs. 0 |
| | 108464 | At_Germinating_Seeds_cDNA_P | Tissue | Germinating Seeds |
| Viability | 108465 | At_Herbicide_v3_1_cDNA_P | Timepoint (hr) | 12 |
| | 108465 | At_Herbicide_v3_1_cDNA_P | Treatment | Roundup vs. No Treatment |
| Drought and Reproductive | 108473 | At_Drought_Flowers_cDNA_P | Timepoint (hr) | 7 d |
| | 108473 | At_Drought_Flowers_cDNA_P | Tissue | Flowers |
| | 108473 | At_Drought_Flowers_cDNA_P | Treatment | Drought vs. No Drought |
| Shoot Meristem | 108480 | At_Shoot_Apices_cDNA_P | Plant Line | Ws-2 |
| | 108480 | At_Shoot_Apices_cDNA_P | Treatment | 1 uM BR vs. No Treatment |
| Shoot Meristem | 108481 | At_Shoot_Apices_cDNA_P | Plant Line | Ws-2 |
| | 108481 | At_Shoot_Apices_cDNA_P | Treatment | 1 uM BRZ vs. No Treatment |
| Leaves | 108488 | At_50mM_NH4NO3_L-to-H_Rosette_cDNA_P | Timepoint (hr) | 2 |
| Heat | 108523 | Zm_42deg_Heat_P | Temperature | Heat (42 deg C.) |
| | 108523 | Zm_42deg_Heat_P | Timepoint (hr) | 6 |
| | 108523 | Zm_42deg_Heat_P | Tissue | Aerial |
| Imbibition & Germination | 108528 | Zm_Imbibed_Seeds_P | Age | 5 vs. 2 |
| | 108528 | Zm_Imbibed_Seeds_P | Tissue | Aerial vs. Embryo |
| | 108528 | Zm_Imbibed_Seeds_P | Treatment | Imbibition |
| Imbibition & Germination | 108530 | Zm_Imbibed_Seeds_P | Age | 6 vs. 2 |
| | 108530 | Zm_Imbibed_Seeds_P | Tissue | Aerial vs. Embryo |
| | 108530 | Zm_Imbibed_Seeds_P | Treatment | Imbibition |
| Imbibition & Germination, Reproductive | 108543 | Zm_Imbibed_Embryo_Endosperm_P | Age | 2 |

TABLE 5-continued

| Utility Section | Expt_Rep_ID | Short_Name | Parameter | Value |
|---|---|---|---|---|
| | 108543 | Zm_Imbibed_Embryo_Endosperm_P | Tissue | Embryo vs. Whole Plant |
| | 108543 | Zm_Imbibed_Embryo_Endosperm_P | Treatment | Imbibed |
| Imbibition & Germination | 108546 | Zm_Imbibed_Seeds_P | Age | 3 vs. 2 |
| | 108546 | Zm_Imbibed_Seeds_P | Tissue | Roots vs. Embryo |
| | 108546 | Zm_Imbibed_Seeds_P | Treatment | Imbibition |
| Jasmonate | 108569 | At_0.001%_MeJA_cDNA_P | Timepoint (hr) | 6 |
| | 108569 | At_0.001%_MeJA_cDNA_P | Tissue | Aerial |
| | 108569 | At_0.001%_MeJA_cDNA_P | Treatment | 0.001% MeJA vs. No Treatment |
| Heat | 108577 | At_42deg_Heat_cDNA_P | Temperature | 42 vs. 22 |
| | 108577 | At_42deg_Heat_cDNA_P | Timepoint (hr) | 6 |
| | 108577 | At_42deg_Heat_cDNA_P | Tissue | Aerial |
| Cold | 108579 | At_4deg_Cold_cDNA_P | Temperature | 4 vs. 22 |
| | 108579 | At_4deg_Cold_cDNA_P | Timepoint (hr) | 6 |
| | 108579 | At_4deg_Cold_cDNA_P | Tissue | Aerial |
| Root and Root Hairs | 108594 | At_Ler-rhl_Root_cDNA_P | Plant Line | Ler_rhl |
| | 108594 | At_Ler-rhl_Root_cDNA_P | Tissue | Root |
| ABA, Drought, Germination | 108614 | At_100uM_ABA_Mutants_cDNA_P | Plant Line | CS24 |
| | 108614 | At_100uM_ABA_Mutants_cDNA_P | Timepoint (hr) | 6 |
| | 108614 | At_100uM_ABA_Mutants_cDNA_P | Tissue | Aerial |
| | 108614 | At_100uM_ABA_Mutants_cDNA_P | Treatment | 100 uM ABA vs. No Treatment |
| ABA, Drought, Germination | 108622 | At_100uM_ABA_Mutants_cDNA_P | Plant Line | CS22 |
| | 108622 | At_100uM_ABA_Mutants_cDNA_P | Timepoint (hr) | 6 |
| | 108622 | At_100uM_ABA_Mutants_cDNA_P | Tissue | Aerial |
| | 108622 | At_100uM_ABA_Mutants_cDNA_P | Treatment | 100 uM ABA vs. No Treatment |
| Viability | 108629 | At_Herbicide_v3_1_cDNA_P | Timepoint (hr) | 1 |
| | 108629 | At_Herbicide_v3_1_cDNA_P | Treatment | Glean vs. No Treatment |
| Viability | 108630 | At_Herbicide_v3_1_cDNA_P | Timepoint (hr) | 1 |
| | 108630 | At_Herbicide_v3_1_cDNA_P | Treatment | Trimec vs. No Treatment |
| Salicylic Acid | 108668 | At_2mM_SA_cDNA_P | Plant Line | WS |
| | 108668 | At_2mM_SA_cDNA_P | Timepoint (hr) | 6 |
| | 108668 | At_2mM_SA_cDNA_P | Treatment | 2 mM SA vs. No Treatment |
| Reproductive and Seed & Fruit Development | 108687 | Zm_Embryos-Flowers_P | Tissue | Embryo |
| | 108688 | Zm_Embryos-Flowers_P | Tissue | Immature Flowers |
| ABA, Drought, Germination | 20000069 | At_100uM_ABA_Mutants_cDNA_P | Plant Line | CS23 |
| | 20000069 | At_100uM_ABA_Mutants_cDNA_P | Timepoint (hr) | 6 |
| | 20000069 | At_100uM_ABA_Mutants_cDNA_P | Tissue | Aerial |
| | 20000069 | At_100uM_ABA_Mutants_cDNA_P | Treatment | 100 uM ABA vs. No Treatment |
| ABA, Drought, Germination | 20000070 | At_100uM_ABA_Mutants_cDNA_P | Plant Line | CS24 |
| | 20000070 | At_100uM_ABA_Mutants_cDNA_P | Timepoint (hr) | 6 |
| | 20000070 | At_100uM_ABA_Mutants_cDNA_P | Tissue | Aerial |
| | 20000070 | At_100uM_ABA_Mutants_cDNA_P | Treatment | 100 uM ABA vs. No Treatment |
| ABA, Drought, Germination | 20000071 | At_100uM_ABA_Mutants_cDNA_P | Plant Line | CS8104 |
| | 20000071 | At_100uM_ABA_Mutants_cDNA_P | Timepoint (hr) | 6 |
| | 20000071 | At_100uM_ABA_Mutants_cDNA_P | Tissue | Aerial |
| | 20000071 | At_100uM_ABA_Mutants_cDNA_P | Treatment | 100 uM ABA vs. No Treatment |
| ABA, Drought, Germination | 20000072 | At_100uM_ABA_Mutants_cDNA_P | Plant Line | CS8105 |
| | 20000072 | At_100uM_ABA_Mutants_cDNA_P | Timepoint (hr) | 6 |
| | 20000072 | At_100uM_ABA_Mutants_cDNA_P | Tissue | Aerial |

TABLE 5-continued

| Utility Section | Expt_Rep_ID | Short_Name | Parameter | Value |
|---|---|---|---|---|
| | 20000072 | At_100uM_ABA_Mutants_cDNA_P | Treatment | 100 uM ABA vs. No Treatment |
| ABA, Drought, Germination | 20000086 | At_100uM_ABA_Mutants_cDNA_P | Plant Line | CS22 |
| | 20000086 | At_100uM_ABA_Mutants_cDNA_P | Timepoint (hr) | 6 |
| | 20000086 | At_100uM_ABA_Mutants_cDNA_P | Tissue | aeriel |
| | 20000086 | At_100uM_ABA_Mutants_cDNA_P | Treatment | 100 uM ABA vs. No Treatment |
| ABA, Drought, Germination | 20000087 | At_100uM_ABA_Mutants_cDNA_P | Plant Line | WS |
| | 20000087 | At_100uM_ABA_Mutants_cDNA_P | Timepoint (hr) | 6 |
| | 20000087 | At_100uM_ABA_Mutants_cDNA_P | Tissue | aeriel |
| | 20000087 | At_100uM_ABA_Mutants_cDNA_P | Treatment | 100 uM ABA vs. No Treatment |
| ABA, Drought, Germination | 20000088 | At_100uM_ABA_Mutants_cDNA_P | Plant Line | Landsberg |
| | 20000088 | At_100uM_ABA_Mutants_cDNA_P | Timepoint (hr) | 6 |
| | 20000088 | At_100uM_ABA_Mutants_cDNA_P | Tissue | aeriel |
| | 20000088 | At_100uM_ABA_Mutants_cDNA_P | Treatment | 100 uM ABA vs. No Treatment |
| Salicylic Acid | 20000090 | At_2mM_SA_CS3726-Columbia_cDNA_P | Plant Line | Columbia |
| | 20000090 | At_2mM_SA_CS3726-Columbia_cDNA_P | Timepoint (hr) | 6 |
| | 20000090 | At_2mM_SA_CS3726-Columbia_cDNA_P | Tissue | Aerial |
| | 20000090 | At_2mM_SA_CS3726-Columbia_cDNA_P | Treatment | 2 mM SA vs. No Treatment |
| Heat | 20000111 | At_42deg_Heat_cDNA_P | Temperature | 42 vs. 23 |
| | 20000111 | At_42deg_Heat_cDNA_P | Timepoint (hr) | 6 |
| | 20000111 | At_42deg_Heat_cDNA_P | Tissue | Aerial |
| Heat | 20000113 | At_42deg_Heat_cDNA_P | Temperature | 42 vs. 23 |
| | 20000113 | At_42deg_Heat_cDNA_P | Timepoint (hr) | 8 |
| | 20000113 | At_42deg_Heat_cDNA_P | Tissue | Aerial |
| ABA, Drought, Germination | 20000117 | At_100uM_ABA_Mutants_cDNA_P | Plant Line | columbia |
| | 20000117 | At_100uM_ABA_Mutants_cDNA_P | Timepoint (hr) | 6 |
| | 20000117 | At_100uM_ABA_Mutants_cDNA_P | Tissue | aerial |
| | 20000117 | At_100uM_ABA_Mutants_cDNA_P | Treatment | 100 uM ABA vs. No Treatment |
| Heat | 20000171 | At_42deg_Heat_P | Probe Method | mRNA vs. mRNA |
| | 20000171 | At_42deg_Heat_P | Temperature | 42 vs. 22 |
| | 20000171 | At_42deg_Heat_P | Timepoint (hr) | 1 |
| | 20000171 | At_42deg_Heat_P | Tissue | Aerial |
| Heat | 20000173 | At_42deg_Heat_P | Probe Method | mRNA vs. mRNA |
| | 20000173 | At_42deg_Heat_P | Temperature | 42 vs. 22 |
| | 20000173 | At_42deg_Heat_P | Timepoint (hr) | 6 |
| | 20000173 | At_42deg_Heat_P | Tissue | Aerial |
| Early Seedling Phase | 20000179 | At_Germinating_Seeds_P | Age | 6 vs. 0 |
| | 20000179 | At_Germinating_Seeds_P | Tissue | Germinating Seeds |
| Early Seedling Phase | 20000180 | At_Germinating_Seeds_P | Age | 24 vs. 0 |
| | 20000180 | At_Germinating_Seeds_P | Tissue | Germinating Seeds |
| Salicylic Acid | 20000182 | At_2mM_SA_P | Timepoint (hr) | 6 |
| | 20000182 | At_2mM_SA_P | Tissue | Aerial |
| | 20000182 | At_2mM_SA_P | Treatment | 2 mM SA vs. No Treatment |
| Leaves, Shoot Meristem | 20000184 | At_Shoots_P | Age | 7 |
| | 20000184 | At_Shoots_P | Tissue | Shoots vs. Whole Plant |
| Root | 20000185 | At_Roots_P | Age | 7 |
| | 20000185 | At_Roots_P | Tissue | Roots vs. Whole Plant |
| Cold | 20000213 | At_4deg_Cold_P | Temperature | 4 vs. 22 |
| | 20000213 | At_4deg_Cold_P | Timepoint (hr) | 2 |

TABLE 5-continued

| Utility Section | Expt_Rep_ID | Short_Name | Parameter | Value |
|---|---|---|---|---|
| Seed and Fruit Development | 20000234 | At_Siliques_P | Tissue | <5 mm Siliques vs. Whole Plant |
| Seed and Fruit Development | 20000235 | At_Siliques_YF_6-05-02_P | Tissue | 5-10 mm Siliques vs. Whole Plant |
| Seed and Fruit Development | 20000236 | At_Siliques_P | Tissue | >10 mm Siliques vs. Whole Plant |
| Reproductive and Seed & Fruit Development | 20000264 | At_Open_Flower_P | Tissue | Open Flower vs. Whole Plant |
| Reproductive and Seed & Fruit Development | 20000265 | At_Open_Flower_P | Tissue | Closed Bud vs. Whole Plant |
| Reproductive and Seed & Fruit Development | 20000286 | At_Open_Flower_P | Tissue | Half Open vs. Whole Plant |
| Drought | 20000437 | At_Drought_P | Timepoint (hr) | 24 |
|  | 20000437 | At_Drought_P | Tissue | Whole Plant |
|  | 20000437 | At_Drought_P | Treatment | Drought vs. No Drought |
| Leaves, Shoot Meristem | 20000438 | At_Shoots_P | Age | 14 |
|  | 20000438 | At_Shoots_P | Tissue | Shoots vs. Whole Plant |
| Roots | 20000439 | At_Roots_P | Age | 14 |
|  | 20000439 | At_Roots_P | Tissue | Roots vs. Whole Plant |
| Brassinolide | 20000441 | At_1uM_BR-BRZ_P | Tissue | Shoot Apices |
|  | 20000441 | At_1uM_BR-BRZ_P | Treatment | 1 uM BR vs. No Treatment |
|  | 20000443 | At_1uM_BR-BRZ_P | Tissue | Shoot Apices |
|  | 20000443 | At_1uM_BR-BRZ_P | Treatment | 1 uM BRZ vs. No Treatment |
| Salicylic Acid | 20000478 | Zm_5mM_SA_P | Age | 8 |
|  | 20000478 | Zm_5mM_SA_P | Plant Line | Hybrid |
|  | 20000478 | Zm_5mM_SA_P | Timepoint (hr) | 72 |
|  | 20000478 | Zm_5mM_SA_P | Tissue | Aerial |
|  | 20000478 | Zm_5mM_SA_P | Treatment | 5 mM SA vs. No Treatment |
| Reproductive and Seed & Fruit Development | 20000493 | Zm_Hybrid_Seed_Dev_P | DAP | 20 vs. 12 |
|  | 20000493 | Zm_Hybrid_Seed_Dev_P | Plant Line | Hybrid |
|  | 20000493 | Zm_Hybrid_Seed_Dev_P | Tissue | Endosperm vs. Unfert Floret |
| Guard Cells | 20000495 | At_Guard_Cells_P | Harvest Date | Aug. 2, 2002 |
|  | 20000495 | At_Guard_Cells_P | Organism | *A. thaliana* |
|  | 20000495 | At_Guard_Cells_P | Tissue | Guard Cells vs. Leaves |
| PEG | 20000527 | At_10%_PEG_P | Age | 20 |
|  | 20000527 | At_10%_PEG_P | Tissue | Aerial |
|  | 20000527 | At_10%_PEG_P | Treatment | 10% PEG vs. No Treatment |
| ABA, Drought, Germination | 20000573 | At_100uM_ABA_Mutants_P | Organism | *A. thaliana* |
|  | 20000573 | At_100uM_ABA_Mutants_P | Plant Line | CS22 vs. Ler wt |
|  | 20000573 | At_100uM_ABA_Mutants_P | Timepoint (hr) | N/A |
|  | 20000573 | At_100uM_ABA_Mutants_P | Tissue | Whole Plant |
|  | 20000573 | At_100uM_ABA_Mutants_P | Treatment | None |
| Viability | 20000629 | Zm_Herbicide-Treatments_P | Timepoint (hr) | 12 |
|  | 20000629 | Zm_Herbicide-Treatments_P | Tissue | Aerial |
|  | 20000629 | Zm_Herbicide-Treatments_P | Treatment | Trimec vs. No Treatment |
| Drought | 20000638 | At_Drought_cDNA_P | Timepoint (hr) | 144 |
|  | 20000638 | At_Drought_cDNA_P | Tissue | sdf |
| Reproductive | 20000794 | At_Petals_P | Age | 23-25 days |
|  | 20000794 | At_Petals_P | Tissue | Petals vs. Whole plant |
| Shade | 20001247 | At_Far-red-induction_P | Age | 7 |
|  | 20001247 | At_Far-red-induction_P | Light | Far Red vs. White |
|  | 20001247 | At_Far-red-induction_P | Plant Line | Columbia |
|  | 20001247 | At_Far-red-induction_P | Timepoint (hr) | 1 |

TABLE 5-continued

| Utility Section | Expt_Rep_ID | Short_Name | Parameter | Value |
|---|---|---|---|---|
| Shade | 20001248 | At_Far-red-induction_P | Age | 7 |
|  | 20001248 | At_Far-red-induction_P | Light | Far Red vs. White |
|  | 20001248 | At_Far-red-induction_P | Plant Line | Columbia |
|  | 20001248 | At_Far-red-induction_P | Timepoint (hr) | 4 |
| Shade | 20001450 | At_Far-red-induction_P | Age | 7 |
|  | 20001450 | At_Far-red-induction_P | Light | Far Red vs. White |
|  | 20001450 | At_Far-red-induction_P | Plant Line | Columbia |
|  | 20001450 | At_Far-red-induction_P | Timepoint (hr) | 8 |
| Shade | 20001451 | At_Far-red-induction_P | Age | 7 |
|  | 20001451 | At_Far-red-induction_P | Light | Far Red vs. White |
|  | 20001451 | At_Far-red-induction_P | Plant Line | Columbia |
|  | 20001451 | At_Far-red-induction_P | Timepoint (hr) | 24 |
| Nitrogen | 20001459 | At_50mM_NH4NO3_L-to-H_P | Timepoint (hr) | 4 |
|  | 20001459 | At_50mM_NH4NO3_L-to-H_P | Tissue | Siliques |
|  | 20001459 | At_50mM_NH4NO3_L-to-H_P | Treatment | 50 mM NH4NO3 vs. 100 mM Manitol |
| Viability | 20000530 | Zm_2-4D_YF_8-26-02_P | Organism | Zea Mays |
|  | 20000530 | Zm_2-4D_YF_8-26-02_P | Timepoint (hr) | 48 |
|  | 20000530 | Zm_2-4D_YF_8-26-02_P | Tissue | Aerial |
|  | 20000530 | Zm_2-4D_YF_8-26-02_P | Treatment | 2,4-D vs. No Treatment |
| Guard Cells | 20000570 | At_Guard_Cells_JD_9-9-02_cDNA_P | Harvest Date | Jul. 19, 2002 |
|  | 20000570 | At_Guard_Cells_JD_9-9-02_cDNA_P | Organism | Canola |
|  | 20000570 | At_Guard_Cells_JD_9-9-02_cDNA_P | Tissue | Guard Cells vs. Leaves |
| Nitric Oxide Responsive |  | At_5mM NaNP; Zm_5mMNO |  |  |
| Reproductive, fruit and seed development |  | At_ap2_floral_buds |  |  |
| Reproductive |  | At_Ler-pi_Ovule |  |  |
| Root and Root Hairs |  | At_rhl_Mutants |  |  |
| Wounding |  | At_Wounding |  |  |
| Methyl Jasmonate |  | Zm_0.001%MeJA |  |  |
| Shoot Meristem |  | Zm_Meristem |  |  |

What is claimed is:

1. An isolated nucleic acid molecule having promoter activity consisting of SEQ ID NO: 52 or a fragment of SEQ ID NO:52, wherein said fragment has promoter activity.

2. The isolated nucleic acid molecule of claim 1, wherein said nucleic acid molecule modulates transcription in a cell, tissue, or organ.

3. A host cell comprising the isolated nucleic acid molecule according to claim 1, wherein said nucleic acid molecule is flanked by exogenous sequence.

4. A vector construct comprising:
  a) a first nucleic acid having promoter activity that is SEQ ID NO:52 or a fragment of SEQ ID NO:52 that has promoter activity; and
  b) a second nucleic acid to be transcribed,
    wherein said first and second nucleic acid molecules are heterologous to each other and are operably linked together.

5. A host cell comprising a vector construct of claim 4.

6. A plant comprising a vector construct according to claim 4.

7. A plant or plant cell comprising:
  a) the nucleic acid molecule according to claim 1 that is operably linked to a heterologous polynucleotide, or
  b) the vector construct according to claim 4.

8. A seed of a plant according to claim 7.

9. A method of modulating transcription by combining, in an environment suitable for transcription:
  a) a first nucleic acid molecule having promoter activity that is SEQ ID NO:52 or a fragment of SEQ ID NO:52 that has promoter activity; and
  b) a second molecule to be transcribed;
    wherein the first and second nucleic acid molecules are heterologous to each other and are operably linked together.

10. The method according to claim 9, wherein said first nucleic acid molecule modulates transcription in a cell tissue, or organ, wherein said first nucleic acid molecule is inserted into a plant cell and said plant cell is regenerated into a plant.

* * * * *

UNITED STATES PATENT AND TRADEMARK OFFICE
CERTIFICATE OF CORRECTION

PATENT NO.       : 7,868,155 B2
APPLICATION NO.  : 11/603542
DATED            : January 11, 2011
INVENTOR(S)      : Roger Pennell et al.

Page 1 of 1

It is certified that error appears in the above-identified patent and that said Letters Patent is hereby corrected as shown below:

On the Title Page

Please add Item (60)

The following priority applications should be listed as follows: --Divisional of application No. 10/981,334 filed on November 4, 2004 PAT 7,179,904, which claims benefit of application No. 60/518,075 filed on November 6, 2003; and claims benefit of application No. 60/527,611 filed on December 4, 2003.--

Signed and Sealed this
Fourth Day of October, 2011

David J. Kappos
*Director of the United States Patent and Trademark Office*